(12) United States Patent
Shyjan

(10) Patent No.: US 6,506,607 B1
(45) Date of Patent: Jan. 14, 2003

(54) METHODS AND COMPOSITIONS FOR THE IDENTIFICATION AND ASSESSMENT OF PROSTATE CANCER THERAPIES AND THE DIAGNOSIS OF PROSTATE CANCER

(75) Inventor: Andrew W. Shyjan, Nahant, MA (US)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 09/220,132

(22) Filed: Dec. 23, 1998

Related U.S. Application Data

(60) Provisional application No. 60/079,303, filed on Mar. 25, 1998, and provisional application No. 60/068,821, filed on Dec. 24, 1997.

(51) Int. Cl.$^7$ .................. G01N 33/00; G01N 33/48; C12Q 1/68; C12P 19/34; C07H 21/02
(52) U.S. Cl. .................. 436/94; 435/6; 435/91.1; 436/64; 536/23.1
(58) Field of Search .................. 435/6, 91.1, 91.2, 435/183, 91.51; 436/94, 64; 536/23.1, 24.3, 24.33, 25.3

(56) References Cited

FOREIGN PATENT DOCUMENTS

US WO 90/00195 * 1/1990

OTHER PUBLICATIONS

Hsu et al., Structural features of human monoamine oxidase A elucidated from cDNA and peptide sequences. Journal of Neurochemistry, 51, 1321–1324, 1988.*

Ablin, R., "A retrospective and prospective overview of prostate–specific antigen" J. of Cancer Res. and Clinical Oncology 123(11/12):583–594, 1997.

Carducci et al., "Prostate–Specific Antigen and Other Markers of Therapeutic Response" Urologic Clinics of North America 26(2):291–301, 1999.

Daher et al., "Prostate–Specific Antigen and New Related Markers for Prostate Cancer" Clin. Chem. Lab Med. 36(9):671–681, 1998.

Keesee et al., "Utilization of Nuclear Matrix Proteins for Cancer Diagnosis" Critical Rev. in Eukaryotic Gene Expression 6(2–3):189–214, 1996.

Moul, J. "Angiogenesis, p53, bcl02 and Ki–67 in the Progression of Prostate Cancer after Radical Prostatectomy" European Eurology 35:399–407, 1999.

Ross, et al., "Androgen Metabolism and Prostate Cancer: Establishing a Model of Genetic Susceptibility" Cancer Research 58:4497–4504, 1998.

Schalken, J., "Molecular Diagnostics and Therapy of Prostate Cancer: New Avenues" European Urology 34(3):3–6, 1998.

Smith et al., "Future Directions in Tumor Marker Technology for Prostate Cancer" Urologic Clinics of North America 20(4):771–777, 1993.

Young, et al., "Prostate–Specific Human Kallikrein (hK2) as a Novel Marker for Prostate Cancer" The Prostate Supplement 7:17–24, 1996.

* cited by examiner

Primary Examiner—Ethan C. Whisenant
Assistant Examiner—Frank Lu
(74) Attorney, Agent, or Firm—Fish & Richardson, PC

(57) ABSTRACT

The invention concerns two classes of differentially regulated genes: 1) genes that are more highly expressed in prostate cancer cells treated with testosterone than in untreated prostate cancer cells; and 2) genes that are more highly expressed in prostate cancer cells treated with bicalutamide, an anti-androgenic compound, than in untreated prostate cancer cells. Disclosed are methods for selecting and monitoring the effectiveness of therapeutic agents used for the treatment of prostate cancer. Also disclosed are methods for identifying novel therapeutic agents for the treatment of prostate cancer and methods and compositions for preventing, treating, and diagnosing prostate cancer.

4 Claims, 1 Drawing Sheet

```
<400> 1
gaattcctga cacgctcctg ggtcgtaggc acaugagtgg gggccaaagc atggagaatc      60
aagagaaggc gagtatcgcg ggccacatgt tcgacgtagt cgtgatcgga ggtggcattt     120
caggactatc tgctgccaaa ctcttgactg aatatggcgt tagtgttttg gttttagaag     180
ctcgggacag ggttggagga agaacatata ctataaggaa tgagcatgtt gattacgtag     240
atgttggtgg agcttatgtg ggaccaaccc aaaacagaat cttacgcttg tctaaggagc     300
tgggcataga gacttacaaa gtgaaugtca gtgagcgtct cgttcaatat gtcaagggga     360
aaacatatcc atttcggggc gcctttccac cagtatggaa tcccattgca tatttggatt     420
acaataatct gtggaggaca atagataaca tggggaagga gattccaact gatgcaccct     480
gggaggctca acatgctgac aaaugggaca aaatgacrat gaaagagctc attgacaaaa     540
tctgctggac aaagactgct aggcggtttg cttatctttt tgtgaatatc aatgtgacct     600
ctgagcctca cgaagtgtct gccctgtggt tcttgtggta tgtgaagcag tgcgggggca     660
ccactcggat attctctgtc accaatggtg gccaggaacg gaagtttgta ggtggatctg     720
gtcaagtgag cgaacggata atggacctcc tcggagacca agtgaagctg aaccatcctg     780
tcactcacgt tgaccagtca agtgacaaca tcatcataga gacgctgaac catgaacatt     840
atgagtgcaa atacgtaatt aatgcgatcc ctccgacctt gactgccaag attcacttca     900
gaccagagct tccagcagag agaaaccagt taattcagcg tcttccaatg ggagctgtca     960
ttaagtgcat gatgtattac aaggaggcct tctggaagaa gaaggattac tgtggctgca    1020
tgatcattga agatgaagat gctccaattt caataacctt ggatgacacc aagccagatg    1080
ggtcactgcc tgccatcatg ggcttcattc ttgcccggaa agctgatcga cttgctaagc    1140
tacataagga aataaggaag aagaaaatct gtgagctcta tgccaaagtg ctgggatccc    1200
aagaagcttt acatccagtg cattatgaag agaagaactg gtgtgaggag cagtactctg    1260
ggggctgcta cacggcctac ttccctcctg ggatcatgac tcaatatgga agggtgattc    1320
gtcaacccgt gggcaggatt ttctttgcgg gcacagagac tgccacaaag tggagcggct    1380
acatggaagg ggcagttgag gctggagaac gagcagctag ggaggtctta aatggtctcg    1440
ggaaggtgac cgagaaagac atctgggtac aagaacctga atcaaaggac gttccagcgg    1500
tagaaatcac ccacaccttc tgggaaagga acctgccctc tgtttctggc ctgctgaaga    1560
tcattggatt ttccacatca gtaactgccc tggggtttgt gctgtacaaa tacaagctcc    1620
tgccacggtc ttgaagttct gttcttatgc tctctgctca ctggttttca ataccaccaa    1680
gaggaaaata ttgacaagtt taaggctgtg tcattgggc catgtttaag tgtactggat    1740
ttaactacct ttggcttaat tccaatcatt gttaaagtaa aaacaattca aagaatcacc    1800
taattaattt cagtaagatc aagctccatc ttatttgtca gtgtagatca actcatgtta    1860
attgatagaa taaagccttg tgatcacttt ctgaaattca caaagttaaa cgtgatgtgc    1920
tcatcagaaa c                                                         1931
(SEQ ID NO: 1)
```

FIG. 1

METHODS AND COMPOSITIONS FOR THE IDENTIFICATION AND ASSESSMENT OF PROSTATE CANCER THERAPIES AND THE DIAGNOSIS OF PROSTATE CANCER

RELATED APPLICATION INFORMATION

This application claims priority from provisional application Ser. No. 60/079,303, filed Mar. 25, 1998, and from provisional application Ser. No. 60/068,821, filed Dec. 24, 1997.

BACKGROUND OF THE INVENTION

Prostate cancer is the most commonly diagnosed cancer in American men and the second most common cause of death from cancer in American men.

Androgen withdrawal, by castration or through the use of an anti-androgenic drug, is the preferred treatment method for prostate cancer.

Bicalutamide (casodex) is a relatively potent, orally active anti-androgenic drug. Approximately 80% of the prostate cancer patients treated with bicalutamide respond to the treatment; however, most patients eventually relapse.

Prostate cancer, like other cancers, can be viewed as a breakdown in the communication between tumor cells and their environment, including their normal neighboring cells. Growth-stimulatory and growth-inhibitory signals are routinely exchanged between cells within a tissue. Normally, cells do not divide in the absence of stimulatory signals, and, likewise, will cease dividing in the presence of inhibitory signals. In a cancerous or neoplastic state, a cell acquires the ability to "override" these signals and to proliferate under conditions in which a normal cell would not grow.

In general, tumor cells must acquire a number of distinct aberrant traits in order to proliferate in an abnormal maimer. Reflecting this requirement is the fact that the genomes of certain well-studied tumors carry several different independently altered genes, including activated oncogenes and inactivated tumor suppressor genes.

In addition to abnormal cell proliferation, cells must acquire several other traits for tumor progression to occur. For example, early on in tumor progression, cells must evade the host immune system. Further, as tumor mass increases, the tumor must acquire vasculature to supply nourishment and remove metabolic waste. Additionally, cells must acquire an ability to invade adjacent tissue. In many cases cells ultimately acquire the capacity to metastasize to distant sites.

It is apparent that the complex process of tumor development and growth must involve multiple gene products. It is therefore important to define the role of specific genes involved in tumor development and growth and identify those genes and gene products that can serve as targets for the diagnosis, prevention and treatment of cancers.

In the realm of cancer therapy it often happens that a therapeutic agent that is initially effective for a given patient becomes, overtime, ineffective or less effective for that patient. The very same therapeutic agent may continue to be effective over a long period of time for a different patient. Further, a therapeutic agent which is effective, at least initially, for some patients is completely ineffective or even harmful for other patients. Accordingly, it would be useful to identify genes and/or gene products that represent prognostic markers with respect to a given therapeutic agent or class of therapeutic agents. It then may be possible to determine which patients will benefit from particular therapeutic regimen and, importantly, determine when, if ever, the therapeutic regime begins to lose its effectiveness. The ability to make such predictions would make it possible to cease a therapeutic regime which has lost its effectiveness well before its loss of effectiveness becomes apparent by conventional measures.

SUMMARY OF THE INVENTION

The invention features methods for selecting and monitoring the effectiveness of therapeutic agents used for the treatment of prostate cancer. The invention also features methods for identifying novel therapeutic agents for the treatment of prostate cancer. The invention also features methods and compositions diagnosing prostate cancer and methods and compositions for preventing, treating, and diagnosing prostate cancer.

The invention is based, in part, on the identification of two classes of differentially regulated genes: 1) genes that are more highly expressed in prostate cancer cells treated with testosterone than in untreated prostate cancer cells; and 2) genes that are more highly expressed in prostate cancer cells treated with bicalutamide, an anti-androgenic compound, than in untreated prostate cancer cells. Genes which are more highly expressed in testosterone-treated prostate cancer cells than untreated prostate cancer cells are listed in Table 1 (SEQ ID NOS:1–40 and 86–130). Genes which are more highly expressed in bicalutamide-treated prostate cancer cells than untreated prostate cancer cells are listed in Table 2 (SEQ ID NOS:41–85 and 131–191).

By examining the expression of one or more of these identified genes in a sample of prostate cancer cells, it is possible to determine whether a selected compound, e.g., an anti-androgenic compound, can be used to treat the prostate cancer. Importantly, this determination can be made on a patient by patient basis. Thus, one can determine whether or not a particular prostate cancer treatment is likely to benefit a particular patient. The invention also features methods for determining whether a particular prostate cancer has become refractory to treatment with an anti-androgenic compound or other therapeutic agent.

The invention also features diagnostic methods and prognostic methods which can be used to identify patients having or at risk for developing prostate cancer. The identified differentially expressed genes whose expression is increased in the presence of testosterone and/or the products of such genes can be used to identify cells exhibiting or predisposed development of prostate cancer thereby diagnosing individuals having, or at high risk for developing, prostate cancer. The detection of the differential expression of identified genes can be used to select therapies before the benign cells attain a malignant state and to design a preventive intervention in pre-neoplastic cells in individuals at high risk.

In the various methods of the invention, gene expression can be measured at the mRNA or protein level. Alternatively, expression can be measured indirectly by measuring the activity of the protein encoded by the identified gene.

The differentially expressed genes identified herein are potential targets for the development of therapeutic compounds. Genes that are expressed at a higher level in prostate cancer cells in the presence of testosterone than in the absence of testosterone are identified. Because testosterone is required for growth and survival of prostate cancer cells, genes whose expression is increased in the presence of testosterone are potential therapeutic targets. Thus, identifying compounds which reduce the expression of such a gene or reduce the activity of the product of such a gene forms the basis for the development of new therapeutic agents. In addition, as noted above, increased expression of these genes can serve as a prognostic or diagnostic indicator of prostate cancer. Moreover, where increased expression of these genes is observed during the course of a therapy, it can be expected that the therapy is or has become relatively ineffective.

Also identified are genes that are expressed in prostate cancer cells at a high level in the presence of the anti-androgenic drug bicalutamide than in the absence of bicalutamide. Because bicalutamide is known to inhibit the growth of prostate cancer cells, genes whose expression is increased in the presence of bicalutamide are potential therapeutic targets. Thus, identifying compounds which increase the expression of such a gene or increase the activity of the product of such a gene forms the basis for the development of new therapeutic agents. In addition, increased expression of these genes can serve as a indicator that a given therapy is effective.

The invention provides methods for the identification of compounds that modulate the expression of genes or the activity of gene products involved in prostate cancer as well as methods for the treatment of prostate cancer. Such methods can, for example, involve the administration of such modulatory compounds to individuals exhibiting symptoms or markers of prostate cancer.

This invention is based, in part, on systematic search strategies coupled with sensitive and high throughput gene expression assays, to identify genes differentially expressed in prostate tumor cells treated with different drugs. The search strategies and assays used herein permit the identification of all genes, whether known or novel, which are differentially expressed in, e.g., testosterone-treated prostate cancer cells relative to untreated prostate cancer cells.

This comprehensive approach and evaluation permits the discovery of novel genes and gene products, as well as the identification of an array of genes and gene products (whether novel or known) that are influenced by drugs and natural products which are known to influence the growth and survival of prostate cancer cells. Thus, the present invention makes possible the identification and characterization of targets useful for rationale drug design and for the prognosis, diagnosis, monitoring, treatment, and prevention of prostate cancer.

In some respects the differentially expressed genes described herein can be used in the same manner and prostate specfic antigen, a commonly used marker for prostate cancer and pre-cancerous conditions related to prostate cancer.

"Differential expression," as used herein, refers to both quantitative, as well as qualitative, differences in the expression pattern of a gene in tumor cells treated with a particular drug and untreated tumor cells. Differentially expressed genes can represent "fingerprint genes," and/or "target genes."

"Fingerprint gene," as used herein, refers to a differentially expressed gene whose expression pattern can be utilized as part of a prognostic or diagnostic marker for the evaluation of prostate cancer or which, alternatively, can be used in methods for identifying compounds useful for the treatment of prostate cancer or evaluating the effectiveness of a prostate cancer treatment. For example, the effect of the compound on the fingerprint gene expression pattern normally displayed in connection with prostate cancer can be used to evaluate the efficacy of the compound as a treatment for prostate cancer or can, additionally, be used to monitor patients undergoing clinical evaluation for the treatment of prostate cancer.

A "fingerprint pattern," as described herein, is the pattern generated when the expression pattern of a series (which can range from two up to all the fingerprint genes which exist for a given state) of fingerprint genes is determined. A fingerprint pattern can be used in the same diagnostic, prognostic and compound identification methods as the expression of a single fingerprint gene.

A "target gene," as described herein, is a differentially expressed gene involved in prostate cancer such that modulation of the level of target gene expression or of target gene product activity can act to prevent and/or ameliorate symptoms of the prostate cancer. Compounds that modulate the expression of the target gene or the activity of the target gene product can be used in the treatment of prostate cancer. Still further, compounds that modulate the expression of the target gene or activity of the target gene product can be used in treatments to deter benign cells from developing into prostate cancer cells. Still further, compounds that modulate the expression of the target gene or activity of the target gene product can be used to design a preventive intervention in pre-neoplastic cells in individuals at high risk.

DESCRIPTION OF THE FIGURES

FIG. 1 depicts the nucleotide sequence of SEQ ID NO: 1.

DETAILED DESCRIPTION OF THE INVENTION

The invention is based, in part, on the identification of genes that are differentially expressed in prostate cancer cells treated with selected compounds. By evaluating the expression pattern of a variety of genes in the presence and absence of a selected compound it is possible to create a profile of the response of prostate cancer cells to the selected compound.

1. Identification of Differentially Expressed Genes

Described below are examples of methods which can be used to identify differentially expressed genes, i.e., genes whose expression in prostate cancer cells is altered by a selected compound, e.g., testosterone.

Differential expression refers to both quantitative, as well as qualitative differences the expression pattern of a gene or group of genes. Thus, a differentially expressed gene can qualitatively have its expression increased or decreased in, for example, testosterone-treated prostate cancer cells versus untreated prostate cancer cells.

In some cases, the difference in expression between treated and untreated (control) cells may be qualitative rather than quantitative. Thus, the expression of a selected gene might be detectable using a certain assay method in the presence of a given drug and undetectable using the same assay in the absence of the drug.

Alternatively, a differentially expressed gene can exhibit an expression level which differs, i.e., is quantitatively increased or decreased in treated cells versus control cells.

The degree to which expression differs need only be large enough to be visualized via standard characterization techniques, such as, for example, a differential display technique. Other standard, well-known characterization techniques by which expression differences can be visualized include, but are not limited to, quantitative reverse transcriptase (RT)-coupled PCR and Northern analyses and RNase protection techniques and methods which employ arrays of nucleic acid molecules, e.g., cDNAs linked to a solid support, e.g., a Gene Expression Micro-Array™ (Synteni, Inc.; Fremont, Calif.).

a) Approaches to the Identification of Differentially Expressed Genes

There are a variety of approaches (or paradigms) which can be used to identify differentially expressed genes. In all cases, drug-treated and untreated cells (or cells treated with different drugs) are compared. The paradigms differ in the source of the cells that are differentially treated. Thus, the cells can be differentially treated in vitro prostate cancer cells, e.g., a cells of a prostate cancer cell line (an "in vitro paradigm"), differentially treated representatives of an animal model of prostate cancer (an "in vivo paradigm"), or differentially treated prostate cancer patients (a "clinical paradigm").

Once a particular differentially expressed gene has been identified through the use of one paradigm, its expression pattern can be further characterized, for example, by studying its expression in a different paradigm. A gene can, for example, be regulated one way, i.e., can exhibit one differential gene expression pattern, in a given paradigm, but can be regulated differently in another paradigm. The use, therefore, of multiple paradigms can be helpful in distinguishing the roles and relative importance of particular genes in prostate cancer.

In an in vitro paradigm, differentially expressed genes are detected by comparing the pattern of gene expression between the experimental (drug-treated) prostate cancer cells and control (untreated or treated with a different drug) prostate cancer cells.

In an in vivo paradigm, animal models of prostate cancer can be utilized to discover differentially expressed genes. A variety of animal models can be used in an in vivo paradigms. Matched animal are treated with a drug or left untreated (or treated with a different drug).

In a clinical paradigm samples from surgical and biopsy specimens are used. Such specimens can represent normal tissue, primary, secondary or metastasized tumors obtained from patients. Surgical specimens can be procured under standard conditions involving freezing and storing in liquid nitrogen (see, for example, Karmali et al., 1983, Br. J. Cancer 48:689–696.) RNA from specimen cells is isolated by, for example, differential centrifugation of homogenized tissue, and analyzed for differential expression relative to other specimen cells, preferably cells obtained from the same patient at a different time, e.g., before drug treatment, during treatment with a different drug, or at an earlier time during treatment with the same drug.

b) Methods for Identifying Differentially Expressed Genes

In order to identify differentially expressed genes, RNA, either total or mRNA, can be isolated from cells utilized in paradigms such as those described above. Any RNA isolation technique which does not select against the isolation of mRNA can be utilized for the purification of such RNA samples (see, e.g., Ausubel et al., eds., 1987–1997, *Current Protocols in Molecular Biology*, John Wiley & Sons, Inc. New York). Additionally, large numbers of tissue samples can readily be processed using techniques well known to those of skill in the art, such as, for example, the single-step RNA isolation process of Chomczynski (1989, U.S. Pat. No. 4,843,155).

Transcripts within the collected RNA samples which represent RNA produced by differentially expressed genes can be identified by utilizing a variety of methods which are well known to those of skill in the art. For example, differential screening (Tedder et al., 1988, Proc. Natl. Acad. Sci. USA 85:208–212), subtractive hybridization (Hedrick et al., 1984, Nature 308:149–153; Lee et al., 1984, Proc. Natl. Acad. Sci. USA 88:2825), and, preferably, differential display (Liang and Pardee 1993, U.S. Pat. No. 5,262,311), can be utilized to identify nucleic acid sequences derived from genes that are differentially expressed.

Differential screening involves the duplicate screening of a cDNA library in which one copy of the library is screened with a total cell cDNA probe corresponding to the mRNA population of sample while a duplicate copy of the cDNA library is screened with a total cDNA probe corresponding to the mRNA population of a second sample. For example, one cDNA probe can correspond to a total cell cDNA probe of a cell or tissue derived from a control sample, while the second cDNA probe can correspond to a total cell cDNA probe of the same cell type derived from an experimental (e.g, drug-treated) sample. Those clones which hybridize to one probe but not to the other potentially represent clones derived from genes differentially expressed in the cell of interest in control versus experimental samples.

Subtractive hybridization techniques generally involve the isolation of mRNA taken from two different sources, e.g., treated and untreated cells, the hybridization of the mRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed in the two mRNA sources. Such single-stranded cDNAs are then used as the starting material for the construction of a library comprising clones derived from differentially expressed genes.

Differential display is a procedure which, utilizing the well-known polymerase chain reaction (PCR; the experimental embodiment set forth in Mullis 1987, U.S. Pat. No. 4,683,202), allows for the identification of sequences derived from genes which are differentially expressed. First, isolated RNA is reverse-transcribed into single-stranded cDNA, utilizing standard techniques which are well known to those of skill in the art. Primers for the reverse transcriptase reaction can include, but are not limited to, oligo dT-containing primers, preferably of the 3' primer type of oligonucleotide described below. Next, this technique uses pairs of PCR primers, as described below, which allow for the amplification of clones representing a random subset of the RNA transcripts present within any given cell. Utilizing different pairs of primers allows each of the mRNA transcripts present in a cell to be amplified. Among such amplified transcripts can be identified those which have been produced from differentially expressed genes.

The 3' oligonucleotide primer of the primer pairs can contain an oligo dT stretch of 10–13 dT nucleotides at its 5' end, preferably 11, which hybridizes to the poly(A) tail of mRNA or to the complement of a cDNA reverse transcribed from an mRNA poly(A) tail. Second, in order to increase the specificity of the 3' primer, the primer can contain one or more, preferably two, additional nucleotides at its 3' end. Because, statistically, only a subset of the mRNA derived sequences present in the sample of interest will hybridize to such primers, the additional nucleotides allow the primers to amplify only a subset of the mRNA derived sequences present in the sample of interest. This is preferred in that it allows more accurate and complete visualization and characterization of each of the bands representing amplified sequences.

The 5' primer can contain a nucleotide sequence expected, statistically, to have the ability to hybridize to cDNA sequences derived from the tissues of interest. The nucleotide sequence can be an arbitrary one, and the length of the 5' oligonucleotide primer can range from about 9 to about 15 nucleotides, with about 13 nucleotides being preferred.

Additionally, arbitrary primer sequences cause the lengths of the amplified partial cDNAs produced to be variable, thus allowing different clones to be separated by using standard denaturing sequencing gel electrophoresis.

PCR reaction conditions should be chosen which optimize amplified product yield and specificity, and, additionally, produce amplified products of lengths which can be resolved utilizing standard gel electrophoresis techniques. Such reaction conditions are well known to those of skill in the art, and important reaction parameters include, for example, length and nucleotide sequence of oligonucleotide primers as discussed above, and annealing and elongation step temperatures and reaction times.

The pattern of clones resulting from the reverse transcription and amplification of the mRNA of two different cell types is displayed via sequencing gel electrophoresis and compared. Differences in the two banding patterns indicate potentially differentially expressed genes.

Once potentially differentially expressed gene sequences have been identified via bulk techniques such as, for example, those described above, the differential expression of such putatively differentially expressed genes should be corroborated. Corroboration can be accomplished via, for example, such well-known techniques as Northern analysis, quantitative RT-coupled PCR or RNase protection.

Upon corroboration, the differentially expressed genes can be further characterized, and can be identified as target and/or fingerprint genes.

Amplified sequences of differentially expressed genes obtained through differential display can be used to isolate the full length clones of the corresponding gene. The full-length coding portion of the gene can readily be isolated, without undue experimentation, by molecular biological techniques well known in the art. For example, the isolated differentially expressed amplified fragment can be labeled and used to screen a cDNA library. Alternatively, the labeled fragment can be used to screen a genomic library.

PCR technology can also be utilized to isolate full-length cDNA sequences. Thus, the isolated amplified gene fragments (of about at least 10 nucleotides, preferably longer, of about 15 nucleotides) obtained through differential display have their 5' terminal end at some random point within the gene and have 3' terminal ends at a position corresponding to the 3' end of the transcribed portion of the gene. Once nucleotide sequence information from an amplified fragment is obtained, the remainder of the gene (i.e., the 5' end of the gene, when utilizing differential display) can be obtained using, for example, RT-PCR.

A reverse transcription reaction can then be performed on the RNA using an oligonucleotide primer complementary to the mRNA that corresponds to the amplified cloned fragment, for the priming of first strand synthesis. Because the primer is anti-parallel to the mRNA, extension will proceed toward the 5' end of the mRNA. The resulting RNA/DNA hybrid can then be "tailed" with guanines using a standard terminal transferase reaction, the hybrid can be digested with RNAase H, and second strand synthesis can then be primed with a poly-C primer. Using the two primers, the 5' portion of the gene is then amplified using PCR. Sequences obtained can then be isolated and recombined with previously isolated sequences to generate a full-length cDNA of the differentially expressed gene. For a review of cloning strategies and recombinant DNA techniques which can be used, see, e.g., Sambrook et al., 1989, *Molecular Cloning, A Laboratory Manual*, Cold Springs Harbor Press, N.Y.; and Ausubel et al., supra.

II. Examples of the Identification of Differentially Expressed Genes

Described below is the identification of two classes of genes which are differentially expressed in prostate cancer cells.

The first example concerns the identification of 40 genes whose expression is increased in prostate cancer cells in the presence of testosterone. It is known that testosterone is required for the growth and survival of prostate cancer cells. Accordingly, genes whose expression is increased in the presence of testosterone can be used as markers to identify prostate cancers which might be successfully treated by the use of an anti-androgenic drug. In addition, these genes can be used as markers to identify prostate cancers which may have become refractory to anti-androgenic treatment. Because higher expression of these genes is associated with testosterone-exposed prostate cancer cells, they can be used as diagnostic and prognostic markers to identify individuals suffering from or at risk for developing prostate cancer. These genes and the proteins they encode can also be used to identify novel therapeutic agents for treatment of prostate cancer and as diagnostic markers.

The second example concerns the identification of 45 genes whose expression is increased in prostate cancer cells in the presence of bicalutamide, an anti-androgenic compound that is commonly used to treat prostate cancer. Because the increased expression of these genes in prostate cancer cells is associated with a successful treatment for prostate cancer, these genes can be used as markers to identify novel therapeutic compounds and to monitor the course/effectiveness of a therapy, particularly an anti-androgenic therapy.

a) EXAMPLE 1

Identification of Genes Whose Expression is Increased in the Presence of Testosterone LNCaP cells were grown T162 flasks coated with Matrigel in RPMI-1640 medium supplemented with 10% FBS and 50 nM testosterone. Prior to testosterone treatment, the cells were pre-incubated for 24.5 hours in dye-free RPMI-1640 containing 2% charcoal stripped serum.

Five T162 flasks of pretreated cells were treated with testosterone-containing medium (dye-free RPMI-1640, 2% CSS, 100 nM testosterone, 0.09% DMSO). After 25 hours of incubation in testosterone-containing medium, the cells were detached from the flasks with trypsin and pelleted. Five T162 flasks of pretreated cells were used as a control. Untreated cells were collected in the same manner.

Total RNA was prepared from the cell pellets using the RNeasy protocol (Qiagen). Approximately 260 µg of total RNA was obtained from each cell pellet. Next, polyA+ RNA was prepared form approximately 240 µg of each total RNA sample using the Oligotex protocol (Qiagen), approximately 6 µg of polyA+ RNA was obtaining from each 240 µg total RNA sample, and 2 µg of each polyA+ RNA sample was used for the generation of subtraction libraries using the PCR-select protocol (Clontech; Palo Alto, Calif.).

The PCR products representing partial cDNAs of putatively differentially expressed mRNAs were subcloned into pCR2.1 (InVitrogen) and transformed into INValphaF$^1$ cells.

The differentially expressed genes were then identified by screening on a Gene Expression Micro-Array™ (Synteni, Inc.; Fremont, Calif.).

Table 1 is a list of identified genes whose expression is greater in testosterone-treated prostate cancer cells than untreated prostate cancer cells. Generally the genes are listed in ranked order. In some cases only a partial sequence is presented in the corresponding figure. The various methods described herein can employ complete sequences or fragments thereof.

TABLE 1

| Gene | Fold Increase In mRNA | SEQ ID NO. |
| --- | --- | --- |
| Monoamine oxidase | 5.5 | 1 |
| Neprilysin | 2.8 | 2 |
| Cell division control protein 2 homolog (X05360) | * | 3 |
| Cell division protein kinase 6 | 3.1 | 4 |
| 5-hydroxytryptamine 2C receptor | * | 5 |
| Aryl hydrocarbon receptor nuclear translocator | 4.6 | 6 |
| Guanine nucleotide exchange factor MSS4 (U74324) (−76 nucleotide) | 2.7 | 7 |
| DNA mismatch repair protein MSH2 | * | 8 |
| HEK2 protein tyrosine kinase receptor | 2.6 | 9 |
| Ras-like GTP-binding protein RAN | 2.6 | 10 |
| UDP glucuronosyltransferase precursor (UGT2B15) | 2.8 | 11 |
| BM28 mRNA/DNA replication licensing factor (huMCM2) | 2.4 | 12 |
| Yeast guanine nucleotide-binding protein beta subunit-like protein | 2.4 | 13 |
| Thyroid receptor interactor (TRIP7) (L40357) (−92 nucleotide) | 2.4 | 14 |
| Pyruvate kinase (M26252) = human TCB gene encoding cytosolic thyroid hormone-binding protein | 2.3 | 15 |
| EXT1 = putative tumor suppressor/hereditary mult. exostoses candidate gene | 2.4 | 16 |
| Phospholipase A2 (M22430) | 2.7 | 17 |
| UDP-glucuronosyltransferase 2B7 precursor | 3.9 | 18 |
| WILMS' tumor protein (X51630) | * | 19 |
| Apolipoprotein B-100 precursor (XO4506) | * | 20 |
| Forkhead protein FREAC-2 | * | 21 |
| S-adenosylmethionine decarboxylase | 2.3 | 22 |
| Kinesin-related protein | 4.8 | 23 |
| Spectrin alpha chain | 3.5 | 24 |
| KIAA0018 gene (D13643) | 3.3 | 25 |
| Myeloblast KIAA0130 gene (D50920) | 3.3 | 26 |
| Brain-expressed HHCPA78 homolog (S73591) | 3 | 27 |
| Vacuolar ATP synthase subunit AC39; or bovine (P17694) NADH-ubiquinone oxidoreductase 49 kD subunit | 3.1 | 28 |
| Gelsolin precursor | 2.8 | 29 |
| Ankyrin G (ANK-3) (U13616) | 2.7 | 30 |
| High mobility group protein HMG1 (X12597) | 2.6 | 31 |
| S-adenosylmethionine decarboxylase proenzyme (M21154) | 2.5 | 32 |
| p0071 protein (X81889) | 2.4 | 33 |
| F02A9.5 homolog | * | 34 |
| Eukaryotic initiation factor 1A | 2.4 | 35 |
| L-lactate dehydrogenase M chain (X02152, M17516) | 3 | 36 |
| Cytochrome b5 | 3.3 | 37 |
| Fibronectin (S00848, transformation-associated human fragment) | 2.8 | 38 |
| Tubulin beta 1 chain | 2.8 | 39 |
| Histone H2AZ | 2.5 | 40 |
| STS (WI 12919) | 7.7 | 86 |
| ESTs {344156} | 5.9 | 87 |
| STS (WI-8530) | 5 | 88 |
| ESTs {128990} | 5 | 89 |
| ESTs {26259} | 5 | 90 |
| ESTs {48537} | 4.5 | 91 |
| ESTs {221118} | 4.4 | 92 |
| ESTs {195079} | 4.3 | 93 |
| ESTs {242643} | 4.1 | 94 |
| ESTs {41700} | 4 | 95 |
| ESTs {301487} | 3.8 | 96 |
| ESTs {469725} | 3.7 | 97 |

TABLE 1-continued

| Gene | Fold Increase In mRNA | SEQ ID NO. |
| --- | --- | --- |
| Immunoglobulin rearranged H-chain V-region (C-D-J Hg) | 3.6 | 98 |
| ESTs {249347} | 3.5 | 99 |
| ESTs {135326} | 3.4 | 100 |
| ESTs {177150} | 3.1 | 101 |
| ESTs {375900} | 3.1 | 102 |
| ESTs {46287} | 3 | 103 |
| ESTs {264293} | 3 | 104 |
| ESTs {429349} | 3 | 105 |
| ESTs {128055} | 2.8 | 106 |
| ESTs {415795} | 2.8 | 107 |
| ESTs {364618} | 2.7 | 108 |
| ESTs {52371} | 2.6 | 109 |
| ESTs {471083} | 2.6 | 110 |
| ESTs {23605} | 2.5 | 111 |
| ESTs {32161} | 2.5 | 112 |
| ESTs {364477} | 2.5 | 113 |
| 54 kDa progesterone receptor-associated immunophilin FKBP54 | 2.5 | 114 |
| ESTs {488092} | 2.5 | 115 |
| ESTs {151339} | 2.4 | 116 |
| ESTs {174787} | 2.4 | 117 |
| ESTs {230447} | 2.4 | 118 |
| ESTs {131591} | 2.3 | 119 |
| ESTs {141115} | 2.3 | 120 |
| Simian T-cell lymphotropic virus type I DNA for tax/rex region | 2.3 | 121 |
| ESTs {51591} | 2.3 | 122 |
| ESTs {297463} | 2.3 | 123 |
| ESTs {180082} | 2.1 | 124 |
| ESTs {133211} | * | 125 |
| Thymopoietin alpha | * | 126 |
| ESTs {52092} | * | 127 |
| ESTs {238656} | * | 128 |
| ESTs {428502} | * | 129 |
| Zinc finger protein | * | 130 | b) EXAMPLE 2

Identification of Genes Whose Expression is Increased in the Presence of Bicalutamide LNCaP cells were grown in T162 flasks coated with Matrigel in RPMI-1640 medium supplemented with 10% FBS and 50 nM testosterone. Prior to bicalutamide treatment, cells were preincubated for 24.5 hours in dye-free RPMI-1640 containing 2% charcoal stripped serum.

Five T162 flasks of pretreated cells were treated with bicalutamide-containing medium (dye-free RPMI-1640, 2% CSS, 100 nM bicalutamide in DMSO). After 25 hours of incubation in bicalutamide-containing medium, LNCaP cells were detached from the flasks with trypsin and pelleted. Five T162 flasks of pretreated cells were used as a control. Untreated cells were collected in the same manner.

Total RNA was prepared from the cell pellets using the RNeasy protocol (Qiagen). Approximately 260 µg of total RNA was obtained form each cell pellet. Next, polyA+ RNA was prepared form approximately 240 µg of each total RNA sample using the Oligotex protocol (Qiagen), approximately 6 µg of polyA+ RNA was obtaining from each 240 µg total RNA sample, and 2 µg of each polyA+ RNA sample was used for the generation of subtraction libraries using the PCR-select protocol (Clontech; Palo Alto, Calif.).

The PCR products representing partial cDNAs of putatively differentially expressed mRNAs were subcloned into pCR2.1 (InVitrogen) and transformed into INValphaF[1] cells.

The diffentially expressed genes were then identified by screening on a Gene Expression Micro-Array™ (Synteni, Inc.; Fremont, Calif.).

Table 2 is a list of identified genes whose expression is greater in bicalutamide-treated prostate cancer cells than untreated prostate cancer cells. Generally the genes are listed in ranked order. In some cases only a partial sequence is presented in the corresponding figure. The various methods described herein can employ complete sequences or fragments thereof.

TABLE 2

| GENE | FOLD INCREASE IN mRNA | SEQ ID NO. |
| --- | --- | --- |
| Cyclin-dependent kinase inhibitor 1 {268652} | 4.5 | 41 |
| Activating transcription factor 3 (ATF3) {428248} | 11.5 | 42 |
| Defender against cell death 1 {488974} | 2.9 | 43 |
| Transcription factor ITF-2 {380738} | * | 44 |
| CCAAT/Enhancer binding protein BETA {357095} | * | 45 |
| CLCN3 {346749} | 2.4 | 46 |
| Phosphotyrosine independent ligand p62 for the Lck SH2 domain {510278} | 5.8 | 47 |
| Seryl-tRNA synthetase {510431} | 4.3 | 48 |
| D53 (hD53) {510461} | 3.8 | 49 |
| Unknown human protein {512334} | 3.5 | 50 |
| Thioredoxin reductase {510377} | 2.6 | 51 |
| Tryptophanyl-tRNA synthetase {510220} | * | 52 |
| ORF and HepG2 (identical sequence) {510258} | 5.3 | 53 |
| 4F2 cell-surface antigen heavy chain {510504} | 8.1 | 54 |
| Asparagine synthetase {510206} | 2.8 | 55 |
| pM5 {509550} | 2.3 | 56 |
| Archain {488510} | 2.3 | 57 |
| Gravin {488106} | 2.8 | 58 |
| Metallothionein-II (mt-II) {484963} | * | 59 |
| Signal recognition particle receptor alpha subunit {358710} | 2.6 | 60 |
| Phosphoenolpyruvate carboxykinase {363272} | 3.4 | 61 |
| Protein translation factor SUI1 homolog {365542} | 2.7 | 62 |
| NADPH-flavin reductase {365775} | 3.7 | 63 |
| Peptidyl-prolyl CIS-trans isomerase B precursor {376399} | 2.5 | 64 |
| Aspartate aminotransferase {417270} | 3.1 | 65 |
| OS-9 precursor {417136} | 2.7 | 66 |
| KIAA0025 and PIGHEP3 homologous region {418227} | 5.3 | 67 |
| Glucosamine-fructose-6-phosphate aminotransferase {469633} | 3.2 | 68 |
| ADP-ribosylation factor 1 {471384} | 3.1 | 69 |
| Glycyl-tRNA synthetase {471164} | 3.6 | 70 |
| Prion protein (PrP) {470074} | 3.1 | 71 |
| Mitochondrial serine hydroxymethyltransferase {344080} | 2.4 | 72 |
| Alanyl-TRNA synthetase {343998} | 3.8 | 73 |
| bZIP protein NF-IL3A {343273} | * | 74 |
| Interleukin-8 precursor {328692} | * | 75 |
| Translocon-associated protein {324179} | 2.5 | 76 |
| Proto-oncogene tyrosine-protein kinase FYN {323555} | * | 77 |
| Translation initiation factor 5 (eIF5) {299843} | 2.3 | 78 |
| RESTIN {291620} | 2.3 | 79 |
| Transcription elongation factor S-II {257458} | 2.8 | 80 |
| Human clone 137308 {252491} | 2.6 | 81 |
| Glutamate-cysteine ligase regulatory subunit {245939} | 4.1 | 82 |
| Fatty aldehyde dehydrogenase {208950} | 3.1 | 83 |
| MHC class I HLA-Bw58 gene {203448} | 2.3 | 84 |
| Mitochondrial NDA (P)+ dependent malic enzyme {109375} | 2.5 | 85 |
| ESTs {44552} | * | 131 |
| ESTs {381626} | * | 132 |
| ESTs {486242} | * | 133 |
| Tryptophanyl tRNA sythestase (IFNWRS) {489453} | * | 134 |
| AU-rich element RNA-binding protein AUF1 {510536} | * | 135 |
| GADD 153 = Growth arrest and DNA-damage inductor gene {362009} | 11.1 | 136 |
| KIAA0025 gene {30476} | 6.7 | 137 |
| Phosphotyrosine independent ligand p62 for the Lck SH2 domain {471392} | 6.4 | 138 |
| 150 kDa oxygen-regulated protein ORP150 {486858} | 5.9 | 139 |
| 78 KD Glucose regulated protein precursor {366350} | 4 | 140 |
| Smad 1 {345928} | 3.9 | 141 |
| EST28g11 WATM1 {486703} | 3.8 | 142 |
| ESTs {322080} | 3.7 | 143 |
| Seryl-tRNA sythetase {129892} | 3.6 | 144 |
| HU-K4 {470677} | 3.6 | 145 |
| ESTs {126530} | 3.5 | 146 |
| ESTs {429327} | 3.5 | 147 |
| Vascular endothelial growth factor (VEGF (165)) {488697} | 3.2 | 148 |
| ESTs {50914} | 3.1 | 149 |
| ESTs {279847} | 3.1 | 150 |
| ESTs {361548} | 3.1 | 151 |
| ESTs {364730} | 3.1 | 152 |
| ESTs {470212} | 3.1 | 153 |
| ESTs {471210} | 3.1 | 154 |
| ESTs {289300} | 3 | 155 |
| ESTs {427725} | 3 | 156 |
| ESTs {428217} | 2.9 | 157 |
| rfp transforming protein {485268} | 2.8 | 158 |
| ESTs {487420} | 2.8 | 159 |
| 60S RIBOSOMAL PROTEIN L18A {509699} | 2.8 | 160 |
| ESTs {31943} | 2.7 | 161 |
| ESTs {376271} | 2.7 | 162 |
| ESTs {469642} | 2.7 | 163 |
| ESTs {471826} | 2.7 | 164 |
| KIAA0262 {485008} | 2.7 | 165 |
| ESTs {292082} | 2.6 | 166 |
| ESTs {365557} | 2.6 | 167 |
| Immunogloblin light chain (lambda) {119218} | 2.5 | 168 |
| ELP-1 {147979} | 2.5 | 169 |
| TRAMP protein {149355} | 2.5 | 170 |
| ESTs {294078} | 2.5 | 171 |
| ESTs {291005} | 2.5 | 172 |
| ESTs {365907} | 2.5 | 173 |
| ESTs {427801} | 2.5 | 174 |
| ESTs {469515} | 2.5 | 175 |
| Tral mRNA for human homologue of murine tumor rejection antigen gp96 {509486} | 2.5 | 176 |
| Biotin-[propionyl-CoA-carboxylase (ATP-hydrolysing)] {176590} | 2.4 | 177 |
| Tral mRNA for human homologue of murine tumor rejection antigen gp96 {242829} | 2.4 | 178 |
| Cancellous bone osteoblast mRNA for GS3786 {486005} | 2.4 | 179 |
| ESTs {509583} | 2.4 | 180 |
| ESTs {44551} | 2.3 | 181 |
| ESTs {245853} | 2.3 | 182 |
| ESTs {306075} | 2.3 | 183 |
| ESTs {322143} | 2.3 | 184 |
| ESTs {322749} | 2.3 | 185 |
| ESTs {359877} | 2.3 | 186 |
| ESTs {360446} | 2.3 | 187 |
| ESTs {360789} | 2.3 | 188 |
| Protein tyrosine kinase t-Rorl {418257} | 2.3 | 189 |
| ESTs {486712} | 2.3 | 190 |
| ESTs {489106} | 2.3 | 191 |

III. The Use of Differentially Expressed Genes in Selecting and Monitoring Prostate Cancer Therapies The expression level of identified differentially expressed genes may be used to assess patients undergoing clinical evaluation for the treatment of prostate cancer. Thus, the identified genes can be used to select an appropriate therapy for an individual and to monitor an ongoing therapy. They may also be utilized as surrogate markers to monitor clinical human trials of a drug being tested for their efficacy as a prostate cancer treatment. In either case, one or more of the identified differentially expressed genes may be utilized as a marker.

One can determine whether a given patient will benefit from anti-androgenic therapy by examining the expression level of one or more of the differentially expressed genes identified herein as being expressed at a higher level in prostate cancer cells in the presence of testosterone than in the absence of testosterone. If one or more of these genes is more highly expressed in the patient's prostate cancer cells than in normal prostate cells, the prostate cancer cells are more likely to respond to anti-androgenic therapy. As used herein, "anti-androgenic therapy" refers broadly to any therapy which interferes with or blocks the synthesis or action of an androgen. Similarly, "anti-testosterone therapy" refers broadly to any therapy which interferes with or blocks the synthesis or action of testosterone. Such therapies can, for example, block ligand receptor binding (e.g., binding of testosterone to its receptor), receptor signalling (e.g., signal transduction mediated by the binding of testosterone to its receptor), or the activity or expression of a downstream regulated gene.

Accordingly, the invention features a method for determining whether a compound, e.g., an anti-androgenic compound can be used to treat prostate cancer in a patient. The method includes:

a) obtaining a patient biological sample;
b) determining the normalized expression level of one or more genes selected from the group consisting of SEQ ID NOS:1–40, 86–130 in the patient sample;
c) comparing the normalized expression level of the selected one or more genes determined in step b) with the normalized expression level of the selected one or more genes in a non-prostate cancer biological sample; and
d) identifying that a compound can be used to treat prostate cancer in the patient when the normalized expression level of the selected one or more genes in the patient sample is greater than the normalized expression level of the selected one or more genes in the non-prostate cancer sample.

A non-prostate cancer biological sample is a sample of prostate cells, serum, interstitial fluid, blood, or seminal fluid from an individual which is not suffering from prostate cancer or a cell line, e.g., a prostate cell line which is not a prostate cancer cell line.

If the normalized expression of the selected one or more genes in the patient sample is not greater than the normalized expression of the selected one or more genes in the non-prostate cancer cell sample, it is less likely that an anti-androgenic therapy will be successful.

The invention also features a method for determining whether a compound, e.g., an anti-androgenic compound, can be used to treat prostate cancer in a patient, which method includes:

a) obtaining a patient biological sample;
b) determining the normalized expression level of one or more genes elected from the group consisting of SEQ ID NOS:1–40, 86–130 in the patient sample;
c) comparing the normalized expression level of the selected one or more genes determined in step b) with the normalized expression level of the selected one or more genes in a non-prostate cancer sample; and
d) identifying that a compound cannot be used to treat prostate cancer in the patient when the normalized expression level of the selected one or more genes in the patient sample is equal to or less than the normalized expression level of the selected one or more genes in the non-prostate cancer biological sample.

Generally, it is preferable to assess the expression of two, five or more, or even ten or more of the genes that are expressed at a higher level in prostate cancer cells treated with testosterone. Thus, it is preferable to assess the expression of a panel of differentially expressed genes.

In these assays, as well as other assays involving comparison of "normalized" expression levels, normalization refers to correcting the expression level of a differentially expressed gene by comparing its expression to the expression of a gene which is not differentially expressed in response to the selected compound, e.g., a gene that is not differentially expressed in prostate cancer cells in response to testosterone. Suitable genes for nromalization include housekeeping genes, e.g., the actin gene. This normalization allows one to compare the expression level in one sample, e.g., a patient sample, to another sample, e.g., a non-prostate cancer sample.

The expression level can be measured in a number of ways, including: measuring the mRNA encoded by each of the selected one or more genes; measuring the amount of protein encoded by each of the selected one or more genes; and measuring the activity of the protein encoded by each of the selected one or more genes.

Preferably, the expression level of several different selected genes from the group consisting of SEQ ID NOS:1–40, 86–130 are compared. For example, the expression of the gene of SEQ ID NO: 1 is compared in the two samples, and the expression of the gene of SEQ ID NO:2 is compared in the two samples. Preferably the selected genes are five or more genes selected from the group consisting of SEQ ID NOS:1–40, 86–130 or ten or more genes selected from the group consisting of SEQ ID NOS:1–40, 86–130.

The patient biological sample can be derived from, e,g., patient prostate cells, patient serum, patient interstitial fluid, patient blood, or patient seminal fluid. A sample of prostate cancer cells can be obtained by needle biopsy or other method used to biopsy or sample prostate cells.

As discussed above, the identified genes can also be used as markers to assess whether a prostate tumor has become refractory to an ongoing treatment (e.g., anti-androgenic treatment). When a tumor is no longer responding to a treatment the expression profile of the tumor cells is more closely resemble the expression profile of testosterone-treated prostate cancer cells than bicalutamide-treated prostate cancer cells.

Accordingly, the invention features methods for determining whether an anti-androgen treatment should be continued in a prostate cancer patient. One such method includes:

a) obtaining a patient biological sample;
b) determining the normalized expression level of one or more genes selected from the group consisting of SEQ ID NOS:1–40, 86–130 in the patient sample;
c) comparing the normalized expression level of the selected one or more genes determined in step b) with the normalized expression level of the selected one or more genes in a non-prostate cancer biological sample; and
d) discontinuing treatment when the normalized expression level of the selected one or more genes in the patient sample is greater than the normalized expression level of the selected one or more genes in the non-prostate cancer sample.

Another method for determining whether an anti-androgen treatment should be continued in a prostate cancer patient includes:

a) obtaining a patient biological sample;

b) determining the normalized expression level of one or more genes selected from the group consisting of SEQ ID NOS:1–40, 86–130 in the patient sample;

c) comparing the normalized expression level determined in step b) with the normalized expression level of the selected one or more genes in a non-prostate cancer biological sample; and d) continuing treatment when the normalized expression of the selected one or more genes in the patient sample is equal to or less than the normalized expression of the selected one or more genes in the non-prostate cancer sample.

Preferably, the expression level of several different selected genes from the group consisting of SEQ ID NOS: 1–40, 86–130 are compared. For example, the expression of the gene of SEQ ID NO: 1 is compared in the two samples, and the expression of the gene of SEQ ID NO:2 is compared in the two samples. Preferably the selected genes are five or more genes selected from the group consisting of SEQ ID NOS:1–40, 86–130 or ten or more genes selected from the group consisting of SEQ ID NOS:1–40, 86–130.

The patient biological sample can be derived from, e,g., patient prostate cells, patient serum, patient interstitial fluid, patient blood, or patient seminal fluid.

In the context of clinical trials, test patients can be administered compounds suspected of being effective for treatment of prostate cancer. Control patients can be given a placebo. Tumor cells or biopsies can be drawn from each patient after a determined period of treatment. RNA can be isolated and subjected to expression analysis as described above.

Yet another method for determining whether a treatment should be continued in a prostate cancer patient includes:

a) obtaining a patient biological sample, b) determining the normalized expression level of one or more genes selected from the group consisting of SEQ ID NOS: 41–85, 131–191 in the patient sample;

c) comparing the normalized expression level of the selected one or more genes determined in step b) with the normalized expression level of the selected one or more genes in a non-prostate cancer biological sample; and d) discontinuing treatment when the normalized expression level of the selected one or more genes in the patient sample is less than or equal to the normalized expression level of the selected one or more genes in the non-prostate cancer sample.

Yet another method for determining whether a treatment should be continued in a prostate cancer patient includes:

a) obtaining a patient biological sample;

b) determining the normalized expression level of one or more genes selected from the group consisting of SEQ ID NOS:41–85, 131–191 in the patient sample;

c) comparing the normalized expression level determined in step b) with the normalized expression level of the selected one or more genes in a non-prostate cancer biological sample; and d) continuing treatment when the normalized expression of the selected one or more genes in the patient sample is greater than the normalized expression of the selected one or more genes in the non-prostate cancer sample.

Preferably, the expression level of several different selected genes from the group consisting of SEQ ID NOS: 41–85, 131–191 are compared. For example, the expression of the gene of SEQ ID NO: 41 is compared in the two samples, and the expression of the gene of SEQ ID NO:42 is compared in the two samples. Preferably the selected genes are five or more genes selected from the group consisting of SEQ ID NOS:41–85, 131–191 or ten or more genes selected from the group consisting of SEQ ID NOS:41–85, 131–191.

The patient biological sample can be derived from, e,g., patient prostate cells, patient serum, patient interstitial fluid, patient blood, or patient seminal fluid.

In the context of clinical trials, test patients can be administered compounds suspected of being effective for treatment of prostate cancer. Control patients can be given a placebo. Tumor cells or biopsies can be drawn from each patient after a determined period of treatment. RNA can be isolated and subjected to expression analysis as described above.

The identified differentially expressed genes can also be used to determine whether a compound can be used to treat prostate cancer either generally or in a specific patient. In this approach the expression of one or more of the differentially expressed genes identified herein is measured in prostate cancer cells in the presence and absence of the candidate therapeutic compound.

If the gene(s) whose expression is assessed is of the class that is expressed at a higher level in the in the presence bicalutamide than in the absence of bicalutamide (SEQ ID NOS:41–85, 131–191), and it is observed that the gene(s) is more highly expressed in the presence of the candidate compound than in the absence of the candidate compound, then the candidate compound is likely to be a useful therapeutic agent. Thus, the invention features methods for determining whether a compound can be used to treat prostate cancer. The method includes:

a) measuring the expression level of one or more genes selected from the group consisting of SEQ ID NOS:41–85, 131–191 in a prostate cancer cell sample in the presence and absence of the compound; and b) identifying the compound as useful for treating prostate cancer when the expression level of the selected one or more genes in the presence of the compound is greater than the expression level of the selected one or more genes in the absence of the compound.

If the gene(s) whose expression is assessed in the screening assay is of the class that is expressed at a higher level in the in the presence testosterone than in the absence of testosterone (SEQ ID NOS:1–40, 86–130), and it is observed that the gene(s) is not more highly expressed in the presence of the candidate compound than in the absence of the candidate compound, then the candidate compound is likely to be a useful therapeutic. Thus, the invention features a method for determining whether a compound can be used to treat prostate cancer, which method includes:

a) measuring the expression level of one or more genes selected from the group consisting of SEQ ID NOS:1–40, 86–130 in prostate cancer cell sample in the presence and absence of the compound; and b) identifying the compound, as useful for treating prostate cancer when the expression level of the selected one or more genes in the presence of the compound is less than the expression level of the selected one or more genes in the absence of the compound.

Of course, the above-described screening method can entail measuring gene expression in a prostate cancer cell line or in prostate cancer cells isolated from a selected patient. Thus, the method can be used to identify therapeutic compounds which are expected to be generally useful as well and to identify therapeutic compounds which are expected to be beneficial for a particular patient.

It should also be recognized that there can be considerable benefit in assessing the expression of two or more, five or more, or even ten or more identified differentially expressed genes when screening candidate therapeutic agents.

IV. The Use of Differentially Expressed Genes in Diagnosing Prostate Cancer

A variety of methods can be employed for the diagnosis of prostate cancer. Such methods can, for example, utilize reagents such as fingerprint gene nucleotide sequences and antibodies directed against differentially expressed fingerprint gene products. Specifically, such reagents can be used, for example, for the detection of the detection of either over- or under-expression a differentially expressed gene or the presence of a mutation in a differentially expressed gene that is a target gene.

An identified differentially expressed gene which is expressed at a higher level in prostate cancer cells in the presence of testosterone than the absence of testosterone can be used as diagnostic markers. Thus, the invention features a method for determining whether a person has or is at risk of developing prostate cancer, which method includes:

A method for determining whether an individual has or at risk for developing prostate cancer, comprising:
  a) obtaining a biological sample from the individual;
  b) determining the normalized expression level of one or more genes selected from the group consisting of SEQ ID NOS:1–40, 86–130 in the individual sample;
  c) comparing the normalized expression level of the selected one or more genes determined in step b) with the normalized expression level of the selected one or more genes in a non-prostate cancer biological sample; and
  d) indentifying the individual as having or being at risk for developing prostate cancer when the normalized expression level of the selected one or more genes in the individual sample is greater than the normalized expression level of the selected one or more genes in the non-prostate cancer sample.

The methods described herein can be performed, for example, by utilizing pre-packaged diagnostic kits comprising at least one specific fingerprint gene nucleic acid or anti-fingerprint gene antibody reagent described herein, which can be conveniently used, e.g., in clinical settings, to diagnose patients exhibiting symptoms of prostate cancer.

a) Detection of Fingerprint Gene Nucleic Acids

DNA or RNA from the cell type or tissue to be analyzed can easily be isolated using procedures which are well known to those in the art. Diagnostic procedures can also be performed in situ directly upon tissue sections (fixed and/or frozen) of patient tissue obtained from biopsies or resections, such that no nucleic acid purification is necessary. Nucleic acid reagents such as those described above can be used as probes and/or primers for such in situ procedures (see, for example, Nuovo, 1992, *PCR in situ Hybridization: Protocols and Applications,* Raven Press, NY).

Fingerprint gene nucleotide sequences, either RNA or DNA, can, for example, be used in hybridization or amplification assays of biological samples to detect genes and expression patterns associated with prostate cancer. Such assays can include, but are not limited to, Southern or Northern analyses, single stranded conformational polymorphism analyses, in situ hybridization assays, and, polymerase chain reaction analyses. Such analyses can reveal both quantitative aspects of the expression pattern of the fingerprint gene, and qualitative aspects of the fingerprint gene expression and/or gene composition. That is, such techniques can include, for example, point mutations, insertions, deletions, chromosomal rearrangements, and/or activation or inactivation of gene expression.

Preferred diagnostic methods for the detection of fingerprint gene-specific nucleic acid molecules can involve for example, contacting and incubating nucleic acids, derived from the cell type or tissue being analyzed, with one or more labeled nucleic acid reagents under conditions favorable for the specific annealing of these reagents to their complementary sequences within the nucleic acid molecule or interest. Preferably, the lengths of these nucleic acid reagents are at least 15 to 30 nucleotides. After incubation, all non-annealed nucleic acids are removed from the nucleic acid:fingerprint RNA molecule hybrid. The presence of nucleic acids from the target tissue which have hybridized, if any such molecules exist, is then detected. Using such a detection scheme, the nucleic acid from the tissue or cell type of interest can be immobilized, for example, to a solid support such as a membrane, or a plastic surface such as that on a microtiter plate or polystyrene beads. In this case, after incubation, non-annealed, labeled fingerprint nucleic acid reagents are easily removed. Detection of the remaining, annealed, labeled nucleic acid reagents is accomplished using standard techniques well-known to those in the art.

Alternative diagnostic methods for the detection of fingerprint gene specific nucleic acid molecules can involve their amplification, e.g., by PCR (the experimental embodiment set forth in Mullis, 1987, U.S. Pat. No. 4,683,202), ligase chain reaction (Barany, 1991, Proc. Natl. Acad. Sci. USA 88:189–193), self sustained sequence replication (Guatelli et al., 1990, Proc. Natl. Acad. Sci. USA 87:1874–1878), transcriptional amplification system (Kwoh et al., 1989, Proc. Natl. Acad. Sci. USA 86:1173–1177), Q-Beta Replicase (Lizardi et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment of such a detection scheme, a cDNA molecule is obtained from an RNA molecule of interest (e.g., by reverse transcription of the RNA molecule into cDNA). Cell types or tissues from which such RNA can be isolated include any tissue in which wild type fingerprint gene is known to be expressed. A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the fingerprint gene nucleic acid reagents. The preferred lengths of such nucleic acid reagents are at least 19–30 nucleotides. For detection of the amplified product, the nucleic acid amplification can be performed using radioactively or non-radioactively labeled nucleotides. Alternatively, enough amplified product can be made such that the product can be visualized by standard ethidium bromide staining or by utilizing any other suitable nucleic acid staining method.

In addition to methods which focus primarily on the detection of one nucleic acid sequence, fingerprint profiles can also be assessed in such detection schemes. Fingerprint profiles can be generated, for example, by utilizing a differential display procedure, as discussed above, Northern analysis, and/or RT-PCR. Any of the fingerprint gene sequences described above can be used as probes and/or PCR primers for the generation and corroboration of such fingerprint profiles.

b) Detection of Fingerprint Gene Products

Antibodies directed against wild-type or mutant fingerprint gene products can also be used in prostate cancer diagnostics and prognostics. Such diagnostic methods, can be used to detect abnormalities in the level of fingerprint gene protein expression, or abnormalities in the structure and/or tissue, cellular, or subcellular location of fingerprinting gene protein. Structural differences can include, for example, differences in the size, electronegativity, or antigenicity of the mutant fingerprint gene protein relative to the normal fingerprint gene protein.

Protein from the tissue or cell type to be analyzed can easily be isolated using techniques which are well known to those of skill in the art. The protein isolation methods employed herein can, for example, be such as those described in Harlow and Lane (Harlow and Lane, 1988, *Antibodies: A Laboratory Manual*, Cold Spring Harbor Laboratory Press, Cold Spring Harbor, N.Y.), which is incorporated herein by reference in its entirety.

Preferred diagnostic methods for the detection of wild-type or mutant fingerprint gene peptide molecules can involve, for example, immunoassays wherein fingerprint gene peptides are detected by their interaction with an anti-fingerprint gene specific peptide antibody.

For example, antibodies, or fragments of antibodies, useful in the present invention can be used to quantitatively or qualitatively detect the presence of wild-type or mutant fingerprint gene peptides. This can be accomplished, for example, by immunofluorescence techniques employing a fluorescently labeled antibody (see below) coupled with light microscopic, flow cytometric, or fluorimetric detection. Such techniques are especially preferred if the fingerprint gene peptides are expressed on the cell surface.

The antibodies (or fragments thereof) useful in the present invention can, additionally, be employed histologically, as in immunofluorescence or immunoelectron microscopy, for in situ detection of target gene peptides. In situ detection can be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the fingerprint gene peptides, but also their distribution in the examined tissue. Using the present invention, those of ordinary skill will readily perceive that any of a wide variety of histological methods (such as staining procedures) can be modified in order to achieve such in situ detection.

Immunoassays for wild-type or mutant fingerprint gene peptides typically comprise incubating a biological sample, such as a biological fluid, a tissue extract, freshly harvested cells, or cells which have been incubated in tissue culture, in the presence of a detectably labeled antibody capable of identifying fingerprint gene peptides, and detecting the bound antibody by any of a number of techniques well-known in the art.

The biological sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene specific antibody. The solid phase support can then be washed with the buffer a second time to remove unbound antibody. The amount of bound label on solid support can then be detected by conventional means.

Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-wild type or mutant fingerprint gene peptide antibody can be determined according to well-known methods. Those skilled in the art will be able to determine operative and optimal assay conditions for each determination by employing routine experimentation.

One of the ways in which the fingerprint gene peptide-specific antibody can be detectably labeled is by linking the same to an enzyme and use in an enzyme immunoassay (EIA). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect fingerprint gene wild type or mutant peptides through the use of a radioimmunoassay (RIA). The radioactive isotope can be, detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

V. Characterization of Differentially Expressed Genes

Differentially expressed genes can be further characterized by using techniques known to those skilled in the art.

Such characterization can yield information regarding the biological function of the identified genes. An assessment of the biological function of the differentially expressed genes, in addition, will allow for their designation as target and/or fingerprint genes.

Specifically, any of the differentially expressed genes whose further characterization indicates that a modulation of the gene's expression or a modulation of the gene product's activity can reduce symptoms of prostate cancer are designated "target genes." Such target genes and target gene products can be used to identify therapeutics. A differentially expressed genes whose further characterization indicates that it does not influence growth or viability of prostate cancer cells, but whose expression pattern contributes to a gene expression "fingerprint" pattern correlative of, for example, the effectiveness of a drug is designated a "fingerprint gene." Such genes can be used as diagnostic markers and as markers for assessing the effectiveness or potential effectiveness of a therapeutic agent.

A variety of techniques can be utilized to further characterize the identified genes. First, the nucleotide sequence of the identified genes, which can be obtained by utilizing standard techniques well known to those of skill in the art, can be used to further characterize such genes. For example, the sequence of the identified genes can reveal homologies to one or more known sequence motifs which can yield information regarding the biological function of the identified gene product.

Second, an analysis of the tissue and/or cell type distribution of the mRNA produced by the identified genes can be conducted, utilizing standard techniques well known to those of skill in the art. Such techniques can include, for example, Northern analyses, RT-coupled PCR and RNase protection techniques. Such analyses provide information as to whether the identified genes are expressed in tissues expected to contribute to prostate cancer. Such analyses can also provide quantitative information regarding steady state mRNA regulation, yielding data concerning which of the identified genes exhibits a high level of regulation in, preferably, tissues which can be expected to contribute to prostate cancer. Additionally, standard in situ hybridization techniques can be utilized to provide information regarding which cells within a given tissue express the identified gene. Such an analysis can provide information regarding the biological function of an identified gene in instances wherein only a subset of the cells within the tissue is thought to be relevant to prostate cancer.

Third, the sequences of the identified genes can be used, utilizing standard techniques, to place the genes onto genetic maps, e.g., mouse (Copeland and Jenkins 1991, Trends in Genetics 7:113–118) and human genetic maps (Cohen et al., 1993, Nature 366:698–701). Such mapping information can yield information regarding the genes' importance to human disease by, for example, identifying genes which map within genetic regions to which predisposition to prostate cancer also maps.

Fourth, the biological function of the identified genes can be more directly assessed by utilizing relevant in vivo and in vitro systems. In vivo systems can include, but are not limited to, animal systems which naturally exhibit symptoms of prostate cancer or ones which have been engineered to exhibit such symptoms.

The role of identified gene products can be determined by transfecting cDNAs encoding these gene products into appropriate cell lines, such as, for example, a prostate cancer cell line and analyzing the effect of the gene product on cell growth.

In further characterizing the biological function of the identified genes, the expression of these genes can be modulated within the in vivo and/or in vitro systems, i.e., either over-expressed or under-expressed, and the subsequent effect on the system then assayed. Alternatively, the activity of the product of the identified gene can be modulated by either increasing or decreasing the level of activity in the in vivo and/or in vitro system of interest, and assessing the effect of such modulation.

The information obtained through such characterizations can suggest relevant methods for the treatment of prostate cancer. For example, treatment can include a modulation of gene expression and/or gene product activity. Characterization procedures such as those described herein can indicate where such modulation should involve an increase or a decrease in the expression or activity of the gene or gene product of interest.

a) Expression of Proteins Encoded by Differentially Expressed Genes

A variety of host-expression vector systems can be utilized to express the differentially expressed gene coding sequences of the invention. Such host-expression systems represent vehicles by which the coding sequences of interest can be produced and subsequently purified, but also represent cells which can, when transformed or transfected with the appropriate nucleotide coding sequences, exhibit the differentially expressed gene protein in situ. These include but are not limited to microorganisms such as bacteria (e.g., *E. coli* and *B. subtilis*) transformed with recombinant bacteriophage DNA, plasmid DNA or cosmid DNA expression vectors containing differentially expressed gene protein coding sequences; yeast (e.g., Saccharomyces and Pichia) transformed with recombinant yeast expression vectors containing the differentially expressed gene protein coding sequences; insect cell systems infected with recombinant virus expression vectors (e.g., baculovirus) containing the differentially expressed gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing differentially expressed gene protein coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the differentially expressed gene protein being expressed. For example, when a large quantity of such a protein is to be produced, for the generation of antibodies or to screen peptide libraries, for example, vectors which direct the expression of high levels of fusion protein products that are readily purified can be desirable. Such vectors include, but are not limited, to the E. coli expression vector pUR278 (Ruther et al., 1983, EMBO J. 2:1791), in which the differentially expressed-gene protein coding sequence can be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene protein can be released from the GST moiety.

In an insect system, Autographa californica nuclear polyhedrosis virus (AcNPV) is used as a vector to express foreign genes. The virus grows in *Spodoptera frugiperda* cells. The differentially expressed gene coding sequence can be cloned individually into non-essential regions (for example the polyhedrin gene) of the virus and placed under control of an AcNPV promoter (for example, the polyhedrin promoter). Successful insertion of differentially expressed gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., see Smith et al., 1983, J. Viol. 46:584; Smith, U.S. Pat. No. 4,215,051).

In mammalian host cells, a number of viral-based expression systems can be utilized. In cases where an adenovirus is used as an expression vector, the differentially expressed gene coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing differentially expressed gene protein in infected hosts (e.g., see Logan & Shenk, 1984, Proc. Natl. Acad. Sci. USA 81:3655–3659). Specific initiation signals can also be required for efficient translation of inserted differentially expressed gene coding sequences. These signals include the ATG initiation codon and adjacent sequences. In cases where an entire identified gene, including its own initiation codon and adjacent sequences, is inserted into the appropriate expression vector, no additional translational control signals can be needed. However, in cases where only a portion of the identified coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc., (see Bittner et al., 1987, Methods in Enzymol. 153:516–544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, HeLa, COS, MDCK, 293, 3T3, W138, etc.

For long-term, high-yield production of recombinant proteins, stable expression is preferred. For example, cell lines which stably express the differentially expressed gene protein can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the identified gene protein. Such engineered cell lines can be particularly useful in screening and evaluation of compounds that affect the endogenous activity of the differentially expressed gene protein.

A number of selection systems can be used, including, but not limited to, the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes in tk$^-$, hgprt$^-$ or aprt$^-$ cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

An alternative fusion protein system allows for the ready purification of non-denatured fusion proteins expressed in human cell lines (Janknecht et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto ni2+ nitriloacetic acid-agarose columns and histidine-tagged proteins are selectively eluted with imidazole-containing buffers.

When used as a component in assay systems such as that described herein, the differentially expressed gene protein can be labeled, either directly or indirectly, to facilitate detection of a complex formed between the differentially expressed gene protein and a test substance. Any of a variety of suitable labeling systems can be used including but not limited to radioisotopes such as $^{125}$I; enzyme labeling systems that generate a detectable colorimetric signal or light when exposed to substrate; and fluorescent labels.

Where recombinant DNA technology is used to produce the differentially expressed gene protein for such assay systems, it can be advantageous to engineer fusion proteins that can facilitate labeling, solubility, immobilization and/or detection.

Indirect labeling involves the use of a third protein, such as a labeled antibody, which specifically binds to either a differentially expressed gene product. Such antibodies include but are not limited to polyclonal, monoclonal, chimeric, single chain, Fab fragments and fragments produced by a Fab expression library.

b) Antibodies Specific for Differentially Expressed Gene Products

Described below are methods for the production of antibodies capable of specifically recognizing one or more differentially expressed gene products. Such antibodies can include, but are not limited to polyclonal antibodies, monoclonal antibodies (mAbs), humanized or chimeric antibodies, single chain antibodies, Fab fragments, F(ab')$_2$ fragments, fragments produced by a FAb expression library, anti-idiotypic (anti-Id) antibodies, and epitope-binding fragments of any of the above. Such antibodies can be used, for example, in the detection of a fingerprint or target gene product in a biological sample, or, alternatively, as a method for the inhibition of abnormal target gene activity. Thus, such antibodies can be utilized as treatment methods, and/or can be used as pat of diagnostic techniques whereby patients can be tested for abnormal levels of fingerprint or target gene proteins, or for the presence of abnormal forms of the such proteins.

For the production of antibodies to a differentially expressed gene, various host animals can be immunized by injection with a differentially expressed gene protein, or a portion thereof. Such host animals can include but are not limited to rabbits, mice, and rats, to name but a few. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (Bacilli Calmette-Guerin) and *Corynebacterium parvum*.

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, can be immnunized by injection with differentially expressed gene product supplemented with adjuvants as also described above.

Monoclonal antibodies, which are homogeneous populations of antibodies to a particular antigen, can be obtained by any technique which provides for the production of antibody molecules by continuous cell lines in culture. These include, but are not limited to the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the BV-hybridoma technique (Cole et al., 1985, *Monoclonal Antibodies And Cancer Therapy*, Alan R. Liss, Inc., pp. 77–96). Such antibodies can be of any immunoglobulin class including IgG, IgM, IgE, IgA, IgD and any subclass thereof. The hybridoma producing the mAb of this invention can be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454; U.S. Pat. No. 4,816,567) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) and for making humanized monoclonal antibodies (U.S. Pat. No. 5,225,539, which is incorporated herein by reference in its entirety) can be utilized to produce anti-differentially expressed gene product antibodies.

Antibody fragments which recognize specific epitopes can be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries can be constructed (Huse et al., 1989, Science, 246:1275–1281) to allow rapid and easy identification of monoclonal Fab fragments with the desired specificity.

c) In vitro and In vivo Systems for Gene Characterization

Described below are in vitro and in vivo systems which can be used to further characterize differentially Expressed Genes. These system can also be used as part of screening strategies designed to identify compounds which are capable of preventing and/or ameliorating symptoms of prostate cancer. Thus, these systems can be used to identify drugs, pharmaceuticals, therapies and interventions which can be effective in treating prostate cancer and to determine the in vivo efficacy of drugs, pharmaceuticals, therapies and interventions.

1) In Vitro Systems

Cells that contain and express target gene sequences and exhibit cellular phenotypes associated with prostate cancer, can be utilized to identify compounds that exhibit an ability to prevent and/or treat prostate cancer.

Further, the fingerprint pattern of gene expression of cells of interest can be analyzed and compared to the normal fingerprint pattern. Those compounds which cause cells exhibiting cellular phenotypes of prostate cancer to produce a fingerprint pattern more closely resembling a normal fingerprint pattern for the cell of interest can be considered candidates for further testing regarding an ability to ameliorate the symptoms of prostate cancer.

Cells which will be utilized for such assays can, for example, include LNCap cells. In addition, purified primary or secondary tumor cells derived from either transgenic or non-transgenic tumor cells can be used.

Further, cells which can be used for such assays can also include recombinant, transgenic cell lines. While primary cultures derived from the metastasis in transgenic animals can be utilized, the generation of continuous cell lines is preferred. For examples of techniques which can be used to derive a continuous cell line from a transgenic animal, see Small et al., 1985, Mol. Cell Biol. 5:642–648.

Alternatively, cells of a cell type known to be involved in prostate cancer can be transfected with sequences capable of increasing or decreasing the amount of target gene expression within the cell. For examples target gene sequences can be introduced into, and over expressed in, the genome of the cell of interest, or, if endogenous target gene sequences are present, they can either be overexpressed or, alternatively, be disrupted in order to underexpress or inactivate target gene expression.

In order to overexpress a target gene sequence, the coding portion of the target gene sequence can be ligated to a regulatory sequence which is capable of driving gene expression in the cell type of interest. Such regulatory regions will be well known to those of skill in the art.

For under expression of an endogenous target gene sequence, such a sequence can be isolated and engineered such that when reintroduced into the genome of the cell type of interest, the endogenous target gene alleles will be inactivated. Preferably, the engineered target gene sequence is introduced via gene targeting such that the endogenous target sequence is disrupted upon integration of the engineered target gene sequence into the cell's genome.

Transfection of target gene sequence nucleic acid can be accomplished by utilizing standard techniques (see, e.g., Ausubel, supra). Transfected cells should be evaluated for the presence of the recombinant target gene sequences, for expression and accumulation of target gene mRNA, and for the presence of recombinant target gene protein production. In instances wherein a decrease in target gene expression is desired, standard techniques can be used to demonstrate whether a decrease in endogenous target gene expression and/or in target gene product production is achieved.

2) In Vivo Systems

In vivo systems of prostate cancer can be either non-recombinant animals or recombinantly engineered transgenic animals. Such models may be generated, for example, by introducing tumor cells into syngeneic mice using techniques such as implanting prostatic cancer cells into the prostate gland. After an appropriate period of time, the tumors which result from these injections can be counted and analyzed.

For the generation of animal models of prostate cancer, cells derived from, for example, a prostate cancer cell line may be implanted into the prostate of an animal and the resulting tumors may be analyzed and compared to, for example, normal tissue.

The role of identified gene products (i.e., those encoded by target genes) can be determined by transfecting cDNAs encoding such gene products into the appropriate cell line and analyzing its effect on the cells' ability to induce prostate cancer in animal models such as these. The role of the identified gene products may be further analyzed by, for example, culturing cells derived from the tumors which develop in the animal models, introducing these cultured cells into animals, and subsequently measuring the level of identified gene product present in the resulting tumor cells. In this manner, cell line variants are developed which can be useful in analyzing the role of quantitative and/or qualitative differences in the expression of the identified genes on the cells' ability to induce prostate cancer.

Recombinant animal models for prostate cancer can be engineered by utilizing, for example, target gene sequences such as those described herein in conjunction with techniques for producing transgenic animals that are well known to those of skill in the art. For example, target gene sequences can be introduced into, and overexpressed in, the genome of the animal of interest, or, if endogenous target gene sequences are present, they can either be overexpressed or, alternatively, can be disrupted in order to underexpress or inactivate target gene expression.

In order to overexpress a target gene sequence, the coding portion of the target gene sequence can be ligated to a regulatory sequence which is capable of driving gene expression in the animal and cell type of interest. Such regulatory regions will be well known to those of skill in the art.

In order to obtain underexpression of an endogenous target gene sequence, such a sequence can be introduced into the genome of the animal of interest such that the endogenous target gene alleles will be inactivated. Preferably, an engineered sequence comprising at least part of the target gene sequence is utilized and is introduced, via gene targeting, such that the endogenous target sequence is disrupted upon integration of the engineered target gene sequence into the animal's genome.

Animals of any species, including, but not limited to, mice, rats, rabbits, guinea pigs, pigs, micro-pigs, goats, and-non-human primates, e.g., baboons, monkeys, and chimpanzees can be used to generate animal models of prostate cancer.

Any technique known in the art can be used to introduce a target gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten et al., 1985, Proc. Natl. Acad. Sci., USA 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723).

The present invention provides for transgenic animals that carry the transgene in all their cells, as well as animals which carry the transgene in some, but not all their cells, i.e., mosaic animals. The transgene can be integrated, either as a single transgene or in concatamers, e.g., head-to-head tandems or head-to-tail tandems. The transgene can also be selectively introduced into and activated in a particular cell type using known techniques (Lasko et al., 1992, Proc. Natl. Acad. Sci. USA 89:6232–6236). The regulatory sequences required for depend upon the particular cell type of interest, and will be apparent to those of skill in the art.

When it is desired that the target gene transgene be integrated into the chromosomal site of the endogenous target gene, gene targeting is preferred. Briefly, when such a technique is to be utilized, vectors containing some nucleotide sequences homologous to the endogenous target gene of interest are designed for the purpose of integrating, via homologous recombination with chromosomal sequences, into and disrupting the function of, the nucleotide sequence of the endogenous target gene. The transgene can also be selectively introduced into a particular cell type, thus inactivating the endogenous gene of interest in only that cell type, by following, for example, the teaching of Gu et al. (1994, Science 265:103–106). The regulatory sequences required for such a cell-type specific inactivation will depend upon the particular cell type of interest, and will be apparent to those of skill in the art.

Once transgenic animals have been generated, the expression of the recombinant target gene and protein can be assayed utilizing standard techniques. Initial screening can be accomplished by Southern blot analysis or PCR techniques to analyze animal tissues to assay whether integration of the transgene has taken place. The level of mRNA expression of the transgene in the tissues of the transgenic animals can also be assessed using techniques which include, but are not limited to, Northern blot analysis of tissue samples obtained from the animal, in situ hybridization analysis, and RT-coupled PCR. Samples of target gene-expressing tissue, can also be evaluated immunocytochemically using antibodies specific for the transgenic product of interest.

The target gene transgenic animals that express target gene mRNA or target gene transgene peptide (detected immunocytochemically, using antibodies directed against target gene product epitopes) at easily detectable levels should then be further evaluated to identify those animals which display prostate cancer characteristics.

Additionally, specific cell types within the transgenic animals can be analyzed for cellular phenotypes characteristic of prostate cancer. Such cellular phenotypes can include, for example, differential gene expression characteristic of prostate cancer cells. Further, such cellular phenotypes can include as assessment of a particular cell type fingerprint profile and its comparison to known fingerprint profiles of the particular cell type in animals exhibiting prostate cancer. Such transgenic animals serve as suitable model systems for prostate cancer.

Once target gene transgenic founder animals are produced (i.e., those animals which express target gene proteins in cells or tissues of interest, and which, preferably, exhibit prostate cancer characteristics), they can be bred, inbred, outbred, or crossbred to produce colonies of the particular animal. Examples of such breeding strategies include but are not limited to: outbreeding of founder animals with more than one integration site in order to establish separate lines: inbreeding of separate lines in order to produce compound target gene transgenics that express the target gene transgene of interest at higher levels because of the effects of additive expression of each target gene transgene; crossing of heterozygous transgenic animals to produce animals homozygous for a given integration site in order to both augment expression and eliminate the possible need for screening of animals by DNA analysis; crossing of separate homozygous lines to produce compound heterozygous or homozygous lines; breeding animals to different inbred genetic backgrounds so as to examine effects of modifying alleles on expression of the target gene transgene and the development of symptoms of prostate cancer. One such approach is to cross the target gene transgenic founder animals with a wild-type strain to produce an F1 generation that exhibits symptoms of prostate cancer. The F1 generation can then be inbred in order to develop a homozygous line, if it is found that homozygous target gene transgenic animals are viable.

d) Identification of Compounds that Interact with a Target Gene Product

The following assays are designed to identify compounds that bind to target gene products, compounds that bind to other cellular proteins that interact with a target gene product, and compounds that interfere with the interaction of the target gene product with other cellular proteins.

Such compounds can include, but are not limited to, other cellular proteins. Specifically, such compounds can include, but are not limited to, peptides, such as, for example, soluble peptides, including, but not limited to Ig-tailed fusion peptides, comprising extracellular portions of target gene product transmembrane receptors, and members of random peptide libraries (see, e.g., Lam et al., 1991, Nature 354:82–84; Houghten et al., 1991, Nature 354:84–86), made of D-and/or L-configuration amino acids, phosphopeptides (including, but not limited to, members of random or partially degenerate phosphopeptide libraries; see, e.g., Songyang et al., 1993, Cell 72:767–778), antibodies (including, but not limited to, polyclonal, monoclonal, humanized, anti-idiotypic, chimeric or single chain antibodies, and FAb, $F(ab')_2$ and FAb expression libary fragments, and epitope-binding fragments thereof), and small organic or inorganic molecules.

Compounds identified via assays such as those described herein can be useful, for example, in elaborating the biological function of the target gene product, and for ameliorating symptoms of prostate cancer. For example, in instances in which prostate cancer is associated with lower expression of a target gene product, and/or lower target gene product activity, compounds that interact with the target gene product can include ones which increase the activity of the target gene product. Such compounds would bring about an effective increase in the level of target gene activity, thus ameliorating symptoms of prostate cancer. Conversely, in instances in which a mutation within a target gene cause aberrant target gene products to be made which have a deleterious effect that leads to prostate cancer, compounds that bind target gene product can be identified that inhibit the activity of the target gene product.

1) Screening Assays for Compounds and Cellular Proteins that Bind to a Target Gene Product In vitro systems can be designed to identify compounds capable of binding the target gene products of the invention. Compounds identified can be useful, for example, in modulating the activity of wild type and/or mutant target gene products, preferably mutant target gene proteins, can be useful in elaborating the biological function of the target gene product, can be utilized in screens for identifying compounds that disrupt normal target gene interactions, or can in themselves disrupt such interactions.

The principle of the assays used to identify compounds that bind to the target gene product involves preparing a reaction mixture of the target gene protein and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring target gene product or the test substance onto a solid phase and detecting target gene product/test compound complexes anchored on the solid phase at the end of the reaction. In one embodiment of such a method, the target gene product can be anchored onto a solid surface, and the test compound, which is not anchored, can be labeled, either directly or indirectly.

In practice, microtiter plates can conveniently be utilized as the solid phase. The anchored component can be immobilized by non-covalent or covalent attachments. Non-covalent attachment can be accomplished by simply coating the solid surface with a solution of the protein and drying.

Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for target gene or the test compound to anchor any complexes formed in solution, and a labeled antibody specific for the other component of the possible complex to detect anchored complexes.

Any method suitable for detecting protein-protein interactions can be employed for identifying novel target product-cellular or extracellular protein interactions. In such a case, the target gene serves as the known "bait" gene.

2) Assays for Compounds that Interfere with the Binding of a Target Gene Product to a Second Cellular Protein The target gene products of the invention can, in vivo, interact with one or more cellular or extracellular macromolecules, such as proteins. For the purposes of this discussion, such cellular and extracellular macromolecules are referred to herein as "binding partners." Compounds that disrupt such interactions can be useful in regulating the activity of the target gene product, especially mutant target gene products. Such compounds can include, but are not limited to molecules such as antibodies, peptides, and small molecules.

The basic principle of the assay systems used to identify compounds that interfere with the interaction between the target gene product and its cellular or extracellular binding partner or partners involves preparing a reaction mixture containing the target gene product, and the binding partner under conditions and for a time sufficient to allow the two products to interact and bind, thus forming a complex. In order to test a compound for inhibitory activity, the reaction mixture is prepared in the presence and absence of the test compound. The test compound can be initially included in the reaction mixture, or can be added at a time subsequent to the addition of target gene and its cellular or extracellular binding partner. Control reaction mixtures are incubated without the test compound or with a placebo. The formation of any complexes between the target gene product and the cellular or extracellular binding partner is then detected. The formation of a complex in the control reaction, but not in the reaction mixture containing the test compound, indicates that the compound interferes with the interaction of the target gene product and the interactive binding partner. Additionally, complex formation within reaction mixtures containing the test compound and normal target gene product can also be compared to complex formation within reaction mixtures containing the test compound and mutant target gene product. This comparison can be important in those cases wherein it is desirable to identify compounds that disrupt interactions of mutant but not normal target gene products.

The assay for compounds that interfere with the interaction of the target gene products and binding partners can be conducted in a heterogeneous or homogeneous format. Heterogeneous assays involve anchoring either the target gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance; i.e., by adding the test substance to the reaction mixture prior to or simultaneously with the target gene product and interactive cellular or extracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the target gene product or the interactive cellular or extracellular binding partner, is anchored onto a solid surface, while the non-anchored species is labeled, either directly or indirectly. In practice, microtitre plates are conveniently utilized. The anchored species can be immobilized by non-covalent or covalent attachments. Non-covalent attachment can be accomplished simply by coating the solid surface with a solution of the target gene product or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the target gene product and the interactive cellular or extracellular binding partner product is prepared in which either the target gene products or their binding partners are labeled, but the signal generated by the label is quenched due to complex formation (see, e.g., U.S. Pat. No. 4,109,496 which utilizes this approach for immunoassays). The addition of a test substance that competes with and displaces one of the species from the preformed complex will result in the generation of a signal above background. In this way, test substances which disrupt target gene product-cellular or extracellular binding partner interaction can be identified.

In a particular embodiment, the target gene product can be prepared for immobilization using recombinant DNA techniques. For example, the target gene coding region can be fused to a glutathione-S-transferase (GST) gene using a fusion vector such as pGEX-5X-1, in such a manner that its binding activity is maintained in the resulting fusion product. The interactive cellular or extracellular product can be purified and used to raise a monoclonal antibody, using methods routinely practiced in the art. This antibody can be labeled with the radioactive isotope $^{125}$I, for example, by methods routinely practiced in the art. In a heterogeneous assay, e.g., the GST-Target gene fusion product can be anchored to glutathione-agarose beads. The interactive cellular or extracellular binding partner product can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the target gene product and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-target gene fusion product and the interactive cellular or extracellular binding partner product can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

These same techniques can be employed using peptide fragments that correspond to the binding domains of the target gene product and the interactive cellular or extracellular binding partner (in case where the binding partner is a product), in place of one or both of the full length products. Any number of methods routinely practiced in the art can be used to identify and isolate the protein's binding site. These methods include, but are not limited to, mutagenesis of one of the genes encoding one of the products and screening for disruption of binding in a co-immunoprecipitation assay. Compensating mutations in the gene encoding the second species in the complex can be selected. Sequence analysis of the genes encoding the respective products will reveal the mutations that correspond to the region of the product involved in interactive binding. Alternatively, one product can be anchored to a solid surface using methods described above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular or extracellular binding partner product is obtained, short gene segments can be engineered to express peptide fragments of the product, which can then be tested for binding activity and purified or synthesized.

VI. Treatment of Prostate Cancer by Modulation of Differentially Expressed Genes or Gene Products Prostate cancer can be treated by modulating the expression of a target gene or the activity of a target gene product. The modulation can be of a positive or negative nature, depending on the specific situation involved, but each modulatory event yields a net result in which prostate cancer symptoms are ameliorated.

"Negative modulation," refers to a reduction in the level and/or activity of target gene product relative to the level and/or activity of the target gene product in the absence of the modulatory treatment.

"Positive modulation," refers to an increase in the level and/or activity of target gene product relative to the level and/or activity of target gene product in the absence of modulatory treatment.

It is possible that prostate cancer can be caused, at least in part, by an abnormal level of gene product, or by the presence of a gene product exhibiting abnormal activity. As such, the reduction in the level and/or activity of such gene products would bring about the amelioration of prostate cancer symptoms.

Alternatively, it is possible that prostate cancer can be brought about, at least in part, by the absence or reduction of the level of gene expression, or a reduction in the level of a gene product's activity. As such, an increase in the level of gene expression and/or the activity of such gene products would bring about the amelioration of prostate cancer symptoms.

a) Negative Modulatory Techniques

As discussed, above, successful treatment of prostate cancer can be brought about by techniques which serve to inhibit the expression or activity of target gene products.

For example, compounds, e.g., a compound identified using an assays described above, which proves to exhibit negative modulatory activity, can be used in accordance with the invention to prevent and/or ameliorate symptoms of prostate cancer. Such molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, and epitope-binding fragments thereof).

Further, antisense and ribozyme molecules which inhibit expression of the target gene can also be used in accordance with the invention to reduce the level of target gene expression, thus effectively reducing the level of target gene activity. Still further, triple helix molecules can be utilized in reducing the level of target gene activity.

Among the compounds which can exhibit the ability to prevent and/or ameliorate symptoms of prostate cancer are antisense, ribozyme, and triple helix molecules. Such molecules can be designed to reduce or inhibit either wild type, or if appropriate, mutant target gene activity. Techniques for the production and use of such molecules are well known to those of skill in the art.

Anti-sense RNA and DNA molecules act to directly block the translation of mRNA by hybridizing to targeted mRNA and preventing protein translation. With respect to antisense DNA, oligodeoxyribonucleotides derived from the translation initiation site, e.g., between the −10 and +10 regions of the Target gene nucleotide sequence of interest, are preferred.

Ribozymes are enzymatic RNA molecules capable of catalyzing the specific cleavage of RNA. (For a review, see, for example, Rossi, 1994, Current Biology 4:469–471.) The mechanism of ribozyme action involves sequence specific hybridization of the ribozyme molecule to complementary target RNA, followed by a endonucleolytic cleavage. The composition of ribozyme molecules must include one or more sequences complementary to the target gene mRNA and must include the well-known catalytic sequence responsible for mRNA cleavage. For this sequence, see U.S. Pat. No. 5,093,246, which is incorporated by reference herein in its entirety. As such within the scope of the invention are engineered hammerhead motif ribozyme molecules that specifically and efficiently catalyze endonucleolytic cleavage of RNA sequences encoding target gene proteins.

Specific ribozyme cleavage sites within any potential RNA target are initially identified by scanning the molecule of interest for ribozyme cleavage sites which include the following sequences, GUA, GUU, and GUC. Once identified, short RNA sequences of between 15 and 20 ribonucleotides corresponding to the region of the target gene containing the cleavage site can be evaluated for predicted structural features, such as secondary structure, that can render the oligonucleotide sequence unsuitable. The suitability of candidate sequences can also be evaluated by testing their accessibility to hybridization with complementary oligonucleotides, using ribonuclease protection assays.

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences can be pyrimidine-based, which will result in TAT and CGC$^+$ triplets across the three associated strands of the resulting triple helix. The pyrimidine-rich molecules provide base complementarily to a purine-rich region of a single strand of the duplex in a parallel orientation to that strand. In addition, nucleic acid molecules can be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation can be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to reduce or inhibit mutant gene expression, it is possible that the technique utilized can also efficiently reduce or inhibit the transcription (triple helix) and/or translation (antisense, ribozyme) of mRNA produced by normal target gene alleles such that the possibility can arise wherein the concentration of normal target gene product present can be lower than is necessary for a normal phenotype. In such cases, to ensure that substantially normal levels of target gene activity are maintained, nucleic acid molecules that encode and express target gene polypeptides exhibiting normal target gene activity can be introduced into cells via gene therapy method. Alternatively, in instances in which the target gene encodes an extracellular protein, it can be preferable to co-administer normal target gene protein into the cell or tissue in order to maintain the requisite level of cellular or tissue target gene activity.

Anti-sense RNA and DNA, ribozyme and triple helix molecules of the invention can be prepared by any method known in the art for the synthesis of DNA and RNA molecules. These include techniques for chemically synthesizing oligodeoxyribonucleotides and oligoribonucleotides well known in the art such as, for example, solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules can be introduced as a means of increasing intracellular stability and half-life. Possible modifications include but are not limited to the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Antibodies can be generated which are both specific for target gene product and which reduce target gene product activity. Such antibodies may, therefore, by administered in instances whereby negative modulatory techniques are appropriate for the treatment of prostate cancer. Antibodies can be generated using standard techniques against the proteins themselves or against peptides corresponding to portions of the proteins. The antibodies include but are not limited to polyclonal, monoclonal, Fab fragments, single chain antibodies, chimeric antibodies, and the like.

In instances where the target gene protein to which the antibody is directed is intracellular and whole antibodies are used, internalizing antibodies can be preferred. However, lipofectin or liposomes can be used to deliver the antibody or a fragment of the Fab region which binds to the target gene epitope into cells. Where fragments of the antibody are used, the smallest inhibitory fragment which binds to the target protein's binding domain is preferred. For example, peptides having an amino acid sequence corresponding to the domain of the variable region of the antibody that binds to the target gene protein can be used. Such peptides can be synthesized chemically or produced via recombinant DNA technology using methods well known in the art (e.g., see Creighton, 1983, supra; and Sambrook et al., 1989, supra). Alternatively, single chain neutralizing antibodies which bind to intracellular target gene product epitopes can also be administered. Such single chain antibodies can be administered, for example, by expressing nucleotide sequences encoding single-chain antibodies within the target cell population by utilizing, for example, techniques such as those described in Marasco et al. (1993, Proc. Natl. Acad. Sci. USA 90:7889–7893).

b) Positive Modulatory Techniques

As discussed above, successful treatment of prostate cancer symptoms can be brought about by techniques which serve to increase the level of target gene expression or to increase the activity of a target gene product.

For example, compounds, e.g., compounds identified through assays described, which prove to exhibit positive modulatory activity can be used in accordance with the invention to ameliorate prostate cancer symptoms. Such molecules can include, but are not limited to, peptides, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, and epitope-binding fragments thereof).

For example, a target gene protein, at a level sufficient to ameliorate prostate cancer symptoms can be administered to a patient exhibiting such symptoms. One of skill in the art will readily know how to determine the concentration of effective, non-toxic doses of the normal target gene protein.

In instances wherein the compound to be administered is a peptide compound, DNA sequences encoding the peptide compound can, alternatively, be directly administered to a patient exhibiting prostate cancer symptoms, at a concentration sufficient to generate the production of an amount of target gene product adequate to ameliorate prostate cancer symptoms. The DNA molecules can be produced, for example, by well-known recombinant techniques.

In the case of peptide compounds which act extracellularly, the DNA molecules encoding such peptides can be taken up and expressed by any cell type, so long as a sufficient circulating concentration of peptide results for the elicitation of a reduction in prostate cancer symptoms.

In the case of compounds which act intracellularly, the DNA molecules encoding such peptides must be taken up and expressed by cells involved in the prostate cancer at a sufficient level to bring about the reduction of prostate cancer symptoms.

Any technique which serves to selectively administer DNA molecules to a cell involved in prostate cancer is, therefore, preferred for the DNA molecules encoding intracellularly acting peptides.

Further, patients can be treated for symptoms of prostate cancer by gene replacement therapy. One or more copies of a normal target gene or a portion of the gene that directs the production of a normal target gene protein with target gene function can be inserted into cells, using vectors which include, but are not limited, to adenovirus, adeno-associated virus, and retrovirus vectors, in addition to other particles that introduce DNA into cells, such as liposomes. Techniques such as those described above can be utilized for the introduction of normal target gene sequences into human cells.

In instances wherein the target gene encodes an extracellular, secreted gene product, such gene replacement techniques may be accomplished either in vivo or in vitro. For such cases, the cell types expressing the target gene is less important than achieving a sufficient circulating concentration of the extracellular molecules for the amelioration of prostate cancer symptoms to occur. In vitro, target gene sequences can be introduced into autologous cells. Those cells expressing the target gene sequence of interest can then be reintroduced, preferably by intravenous administration, into the patient such that there results an amelioration of prostate cancer symptoms.

In instances wherein the gene replacement involves a gene which encodes a product which acts intracellularly, it is preferred that gene replacement be accomplished in vivo. Further, because the cell type in which the gene replacement must occur is the cell type involved in prostate cancer, such techniques must successfully target such prostate cancer cells.

VII. Therapeutic Treatment

The identified compounds that inhibit target gene expression, synthesis and/or activity can be administered to a patient at therapeutically effective doses to prevent, treat or ameliorate prostate cancer. A therapeutically effective dose refers to that amount of the compound sufficient to result in amelioration of symptoms of prostate cancer.

a) Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected-tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

b) Formulations and Use

Pharmaceutical compositions for use in accordance with the present invention can be formulated in conventional manner using one or more physiologically acceptable carriers or excipients.

Thus, the compounds and their physiologically acceptable salts and solvates can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

Other Embodiments

The present invention is not to be limited in scope by the specific embodiments described which are intended as single illustrations of individual aspects of the invention and functionally equivalent methods and components are within the scope of the invention, in addition to those shown and described herein will become apparent to those skilled in the art from the foregoing description and accompanying drawings. Such modifications are intended to fall within the scope of the appended claims.

What is claimed is:

1. A method for determining whether a compound can be used to treat prostate cancer, comprising:
   a) measuring the expression level of a nucleic acid comprising SEQ ID NO:1 in prostate cancer cell sample in the presence and absence of the compound; and
   b) identifying the compound as useful for treating prostate cancer when the expression level of the nucleic acid in the presence of the compound is less than the expression level of the nucleic acid in the absence of the compound.

2. The method of claim 1 wherein the expression level of the nucleic acid is determined by measuring the mRNA encoded by the nucleic acid.

3. The method of claim 1 wherein the expression level of the nucleic acid is determined by measuring the amount of protein encoded by the nucleic acid.

4. The method of claim 1 wherein the expression level of the nucleic acid is determined by measuring the activity of the protein encoded by the nucleic acid.

* * * * *

SEQUENCE LISTING

<160> NUMBER OF SEQ ID NOS: 191

<210> SEQ ID NO 1
<211> LENGTH: 1931
<212> TYPE: DNA
<213> ORGANISM: Homo sapiens

<400> SEQUENCE: 1

| | | | | | | |
|---|---|---|---|---|---|---|
| gaattcctga | cacgctcctg | ggtcgtaggc | acaggagtgg | gggccaaagc | atggagaatc | 60 |
| aagagaaggc | gagtatcgcg | ggccacatgt | tcgacgtagt | cgtgatcgga | ggtggcattt | 120 |
| caggactatc | tgctgccaaa | ctcttgactg | aatatggcgt | tagtgttttg | gttttagaag | 180 |
| ctcgggacag | ggttggagga | agaacatata | ctataaggaa | tgagcatgtt | gattacgtag | 240 |
| atgttggtgg | agcttatgtg | ggaccaaccc | aaaacagaat | cttacgcttg | tctaaggagc | 300 |
| tgggcataga | gacttacaaa | gtgaatgtca | gtgagcgtct | cgttcaatat | gtcaagggga | 360 |
| aaacatatcc | atttcggggc | gcctttccac | cagtatggaa | tcccattgca | tatttggatt | 420 |
| acaataatct | gtggaggaca | atagataaca | tggggaagga | gattccaact | gatgcaccct | 480 |
| gggaggctca | acatgctgac | aaatgggaca | aaatgaccat | gaaagagctc | attgacaaaa | 540 |
| tctgctggac | aaagactgct | aggcggtttg | cttatctttt | tgtgaatatc | aatgtgacct | 600 |
| ctgagcctca | cgaagtgtct | gccctgtggt | tcttgtggta | tgtgaagcag | tgcgggggca | 660 |
| ccactcggat | attctctgtc | accaatggtg | gccaggaacg | gaagtttgta | ggtggatctg | 720 |

-continued

```
gtcaagtgag cgaacggata atggacctcc tcggagacca agtgaagctg aaccatcctg      780
tcactcacgt tgaccagtca agtgacaaca tcatcataga gacgctgaac catgaacatt      840
atgagtgcaa atacgtaatt aatgcgatcc ctccgacctt gactgccaag attcacttca      900
gaccagagct tccagcagag agaaaccagt taattcagcg tcttccaatg ggagctgtca      960
ttaagtgcat gatgtattac aaggaggcct tctggaagaa gaaggattac tgtggctgca     1020
tgatcattga agatgaagat gctccaattt caataacctt ggatgacacc aagccagatg     1080
ggtcactgcc tgccatcatg ggcttcattc ttgcccggaa agctgatcga cttgctaagc     1140
tacataagga aataaggaag aagaaaatct gtgagctcta tgccaaagtg ctgggatccc     1200
aagaagcttt acatccagtg cattatgaag agaagaactg tgtgaggag  cagtactctg     1260
ggggctgcta cacggcctac ttccctcctg ggatcatgac tcaatatgga agggtgattc     1320
gtcaacccgt gggcaggatt ttctttgcgg gcacagagac tgccacaaag tggagcggct     1380
acatggaagg ggcagttgag gctggagaac gagcagctag ggaggtctta aatggtctcg     1440
ggaaggtgac cgagaaagac atctgggtac aagaacctga atcaaaggac gttccagcgg     1500
tagaaatcac ccacaccttc tgggaaagga acctgccctc tgtttctggc ctgctgaaga     1560
tcattggatt ttccacatca gtaactgccc tggggtttgt gctgtacaaa tacaagctcc     1620
tgccacggtc ttgaagttct gttcttatgc tctctgctca ctggttttca ataccaccaa     1680
gaggaaaata ttgacaagtt taaggctgt gtcattgggc catgtttaag tgtactggat      1740
ttaactacct ttggcttaat tccaatcatt gttaaagtaa aaacaattca agaatcacc      1800
taattaattt cagtaagatc aagctccatc ttatttgtca gtgtagatca actcatgtta     1860
attgatagaa taaagccttg tgatcacttt ctgaaattca caagttaaa  cgtgatgtgc     1920
tcatcagaaa c                                                          1931
```

<210> SEQ ID NO 2
<211> LENGTH: 5508
<212> TYPE: DNA
<213> ORGANISM: Homo sapiens

<400> SEQUENCE: 2

```
gattttaggt gatgggcaag tcagaaagtc agatggatat aactgatatc aacactccaa       60
agccaaagaa gaaacagcga tggactcgac tggagatcag cctctcggtc cttgtcctgc      120
tcctcaccat catagctgtg agaatgatcg cactctatgc aacctacgat gatggtattt      180
gcaagtcatc agactgcata aaatcagctg ctcgactgat ccaaacatg  gatgccacca      240
ctgagccttg tagagacttt ttcaaatatg cttgcggagg ctggttgaaa cgtaatgtca      300
ttcccgagac cagctcccgt tacggcaact ttgacatttt aagagatgaa ctagaagtcg      360
ttttgaaaga tgtccttcaa gaacccaaaa ctgaagatat agtagcagtg cagaaagcaa      420
agcattgta caggtcttgt ataaatgaat ctgctattga tagcagaggt ggagaacctc      480
tactcaaact gttaccagac atatatgggt ggccagtagc aacagaaaac tgggagcaaa      540
atatggtgc ttcttggaca gctgaaaaag ctattgcaca actgaattct aaatatggga      600
aaaaagtcct tattaatttg tttgttggca ctgatgataa gaattctgtg aatcatgtaa      660
ttcatattga ccaacctcga cttggcctcc cttctagaga ttactatgaa tgcactggaa      720
tctataaaga ggcttgtaca gcatatgtgg attttatgat ttctgtggcc agattgattc      780
gtcaggaaga aagattgccc atcgatgaaa accagcttgc tttggaaatg aataaagtta      840
```

-continued

```
tggaattgga aaaagaaatt gccaatgcta cggctaaacc tgaagatcga aatgatccaa    900
tgcttctgta taacaagatg agattggccc agatccaaaa taacttttca ctagagatca    960
atgggaagcc attcagctgg ttgaatttca caaatgaaat catgtcaact gtgaatatta   1020
gtattacaaa tgaggaagat gtggttgttt atgctccaga atatttaacc aaacttaagc   1080
ccattcttac caaatattct gccagagatc ttcaaaattt aatgtcctgg agattcataa   1140
tggatcttgt aagcagcctc agccgaacct acaaggagtc cagaaatgct tccgcaagg    1200
ccctttatgg tacaacctca gaaacagcaa cttggagacg ttgtgcaaac tatgtcaatg   1260
ggaatatgga aaatgctgtg gggaggcttt atgtggaagc agcatttgct ggagagagta   1320
aacatgtggt cgaggatttg attgcacaga tccgagaagt tttttattcag actttagatg  1380
acctcacttg gatggatgcc gagacaaaaa agagagctga agaaaaggcc ttagcaatta   1440
aagaaaggat cggctatcct gatgacattg tttcaaatga taacaaactg aataatgagt   1500
acctcgagtt gaactacaaa aagatgaat acttcgagaa cataattcaa aatttgaaat    1560
tcagccaaag taaacaactg aagaagctcc gagaaaaggt ggacaaagat gagtggataa   1620
gtggagcagc tgtagtcaat gcattttact cttcaggaag aaatcagata gtcttcccag   1680
ccggcattct gcagccccc ttctttagtg cccagcagtc caactcattg aactatgggg    1740
gcatcggcat ggtcatagga cacgaaatca cccatggctt cgatgacaat ggcagaaact   1800
ttaacaaaga tggagacctc gttgactggt ggactcaaca gtctgcaagt aactttaagg   1860
agcaatccca gtgcatggtg tatcagtatg aaacttttc ctgggacctg gcaggtggac    1920
agcaccttaa tggaattaat acactgggag aaaacattgc tgataatgga ggtcttggtc   1980
aagcatacag agcctatcag aattatatta aaaagaatgg cgaagaaaaa ttacttcctg   2040
gacttgacct aaatcacaaa caactatttt tcttgaactt tgcacaggtg tggtgtggaa   2100
cctataggcc agagtatgcg gttaactcca ttaaaacaga tgtgcacagt ccaggcaatt   2160
tcaggattat tgggactttg cagaactctg cagagttttc agaagccttt cactgccgca   2220
agaattcata catgaatcca gaaaagaagt gccgggtttg tgatcttca aaagaagcat    2280
tgcagccctt ggctagactt gccaacacca cagaaatggg gaattctcta atcgaaagaa   2340
aatgggcct agggtcact gtactgactt gagggtgatt aacagagagg gcaccatcac     2400
aatacagata acattaggtt gtcctagaaa gggtgtggag ggaggaaggg ggtctaaggt   2460
ctatcaagtc aatcatttct cactgtgtac ataatgctta atttctaaag ataatattac   2520
tgtttatttc tgtttctcat atggtctacc agtttgctga tgtccctaga aaacaatgca   2580
aaacctttga ggtagaccag gatttctaat caaaagggaa aagaagatgt tgaagaatag   2640
agttaggcac cagaagaaga gtaggtgaca ctatagttta aaacacattg cctaactact   2700
agtttttact tttatttgca acatttacag tccttcaaaa tccttccaaa gaattcttat   2760
acacattggg gccttggagc ttacatagtt ttaaactcat ttttgccata catcagttat   2820
tcattctgtg atcatttatt ttaagcactc ttaaagcaaa aatgaatgt ctaaaattgt     2880
tttttgttgt acctgctttg actgatgctg agattcttca ggcttcctgc aattttctaa   2940
gcaatttctt gctctatctc tcaaaacttg gtattttca gagatttata taaatgtaaa    3000
aataataatt tttatattta attattaact acatttatga gtaactatta ttataggtaa   3060
tcaatgaata ttgaagtttc agcttaaaat aaacagttgt gaaccaagat ctataaagcg   3120
atatacagat gaaaatttga gactatttaa acttataaat catattgatg aaaagattta   3180
agcacaaact ttagggtaaa aattgcgatt ggacagttgt ctagagatat atatacttgt   3240
```

-continued

```
ggttttcaaa ttggactttc aaaattaaat ctgtccctga gagtgtctct gataaaaggg      3300
caaatctgca cctatgtagc tctgcatctc ctgtcttttc aggtttgtca tcagatggaa      3360
atattttgat aataaattga aattgtgaac tcattgctcc ctaagactgt gacaactgtc      3420
taactttaga agtgcatttc tgaatagaaa tgggaggcct ctgatggacc ttctagaatt      3480
ataagtcaca aagagttctg gaaaagaact gtttactgct tgataggaat tcatcttttg      3540
aggcttctgt tcctctcttt tcctgttgta ttgactattt tcgttcatta cttgattaag      3600
attttacaaa agaggagcac ttccaaaatt cttattttc ctaacaaaag atgaaagcag       3660
ggaatttcta tctaaatgat gagtattagt tccctgtctc ttgaaaaatg cccatttgcc      3720
tttaaaaaaa aaagttacag aaatactata acatatgtac ataaattgca taaagcataa      3780
gtatacagtt caataaactt aactttaact gaacaatggc cctgtagcca gcacctgtaa      3840
gaaacagagc agtaccagcg ctctaaaagc acctccttgt cactttatta ctcccagaac      3900
aacaactatc ctgacttcta atatcattca ctagctttgc ctggttttgt cttttatgca      3960
gatagaatca atcagtatgt attcttttgt gcctggcttc tttctctcag ccttacattt      4020
gtgagattcc tctgtattgt gctgattgtg atcttttca ttctcattgc agaataatgt       4080
tctattgtgg gacttattac aatttgttca tcctattgtt gatgggcact tgagaacttt      4140
ccattttggc gctattacaa atagtgcaac tatgaatgta ctgcatgtta ccatcttact      4200
tgagccttta atggacttat ttcttcaaat ccttccaaaa attattataa gcattgaaat      4260
tatagtttca agccaactgt ggatacccct acccttcct cctttatcac aaccaccgtt       4320
acaagtatac ttatatttcc ctaaaataca tttaaaactt acctaagtga catttgtagt      4380
tggagtaata ggagcttcca gctctaataa aacagctgtc tctaacttat tttatttcca      4440
tcatgtcaga gcaggtgaag agccagaagt gaagagtgac tagtcaaat tataaaaagc       4500 cactagactc ttcactgtta gctttttaaa acattaggct cccatcccta tggaggaaca      4560
actctccagt gcctggatcc cctctgtcta caaatataag attttctggg cctaaaggat      4620
agatcaaagt caaaaatagc aatgcctccc tatccctcac acatccagac atcatgaatt      4680
ttacatggta ctcttgttga gttctataga gccttctgat gtctctaaag cactaccgat      4740
tctttggagt tgtcacatca gataagacat atctctaatt ccatccataa atccagttct      4800
actatggctg agttctggtc aaagaaagaa agtttagaag ctgagacaca aagggttggg      4860
agctgatgaa actcacaaat gatggtagga agaagctctc gacaataccc gttggcaagg      4920
agtctgcctc catgctgcag tgttcgagtg gattgtaggt gcaagatgga aaggattgta      4980
ggtgcaagct gtccagagaa aagagtcctt gttccagccc tattctgcca ctcctgacag      5040
ggtgaccttg ggtatttgca atattccttt gggcctctgc ttctctcacc taaaaaaaga      5100
gaattagatt atattggtgg ttctcagcaa gagaaggagt atgtgtccaa tgctgccttc      5160
ccatgaatct gtctcccagt tatgaatcag tgggcaggat aaactgaaaa ctcccatttta     5220 agtgtctgaa tcgagtgaga caaaatttta gtccaaataa caagtaccaa agttttatca      5280
agtttgggtc tgtgctgctg ttactgttaa ccatttaagt ggggcaaaac cttgctaatt      5340
ttctcaaaag catttatcat tcttgttgcc acagctggag ctctcaaact aaaagacatt      5400 tgttatttg gaaagaagaa agactctatt ctcaaagttt cctaatcaga aatttttatc       5460
agtttccagt ctcaaaaata caaaataaaa acaaacgttt ttaatact                   5508
```

<210> SEQ ID NO 3

<211> LENGTH: 1050
<212> TYPE: DNA
<213> ORGANISM: Homo sapiens

<400> SEQUENCE: 3

| | | | | | |
|---|---|---|---|---|---:|
| gggggggggg | ggcacttggc | ttcaaagctg | gctcttggaa | attgagcgga | gacgagcggc | 60 |
| ttgttgtagc | tgccgtgcgg | ccgccgcgga | ataataagcc | gggatctacc | ataccattga | 120 |
| ctaactatgg | aagattatac | caaaatagag | aaaattggag | aaggtaccta | tggagttgtg | 180 |
| tataagggta | gacacaaaac | tacaggtcaa | gtggtagcca | tgaaaaaaat | cagactagaa | 240 |
| agtgaagagg | aagggggttcc | tagtactgca | attcgggaaa | tttctctatt | aaaggaactt | 300 |
| cgtcatccaa | atatagtcag | tcttcaggat | gtgcttatgc | aggattccag | gttatatctc | 360 |
| atctttgagt | ttcttttccat | ggatctgaag | aaatacttgg | attctatccc | tcctggtcag | 420 |
| tacatggatt | cttcacttgt | taagagttat | ttataccaaa | tcctacaggg | gattgtgttt | 480 |
| tgtcactcta | gaagagttct | tcacagagac | ttaaaacctc | aaaatctctt | gattgatgac | 540 |
| aaaggaacaa | ttaaactggc | tgattttggc | cttgccagag | cttttggaat | acctatcaga | 600 |
| gtatatacac | atgaggtagt | aacactctgg | tacagatctc | cagaagtatt | gctggggtca | 660 |
| gctcgttact | caactccagt | tgacatttgg | agtataggca | ccatatttgc | tgaactagca | 720 |
| actaagaaac | cacttttcca | tggggattca | gaaattgatc | aactcttcag | gattttcaga | 780 |
| gctttgggca | ctcccaataa | tgaagtgtgg | ccagaagtgg | aatctttaca | ggactataag | 840 |
| aatacatttc | ccaaatggaa | accaggaagc | ctagcatccc | atgtcaaaaa | cttggatgaa | 900 |
| aatggcttgg | atttgctctc | gaaaatgtta | atctatgatc | cagccaaacg | aatttctggc | 960 |
| aaaatggcac | tgaatcatcc | atattttaat | gatttggaca | atcagattaa | gaagatgtag | 1020 |
| ctttctgaca | aaaagtttcc | atatgttatg | | | | 1050 |

<210> SEQ ID NO 4
<211> LENGTH: 1249
<212> TYPE: DNA
<213> ORGANISM: Homo sapiens

<400> SEQUENCE: 4

| | | | | | |
|---|---|---|---|---|---:|
| gaattccgta | aagctagacc | gatctccggg | gagccccgag | taggcgagcg | gcggccgagc | 60 |
| tagttgagcg | cacccccggg | gcgccccagc | gcgccgcggc | gggcgcgtcc | aggcggcatg | 120 |
| gagaaggacg | gcctgtgccg | cgctgaccag | cagtacgaat | gcgtggcgga | gatcggggag | 180 |
| ggcgcctatg | ggaaggtgtt | caaggcccgc | gacttgaaga | acggaggccg | tttcgtggcg | 240 |
| ttgaagcgcg | tgcgggtgca | gaccggcgag | gagggcatgc | cgctctccac | catccgcgag | 300 |
| gtggcggtgc | tgaggcacct | ggagaccttc | gagcacccca | acgtggtcag | gttgtttgat | 360 |
| gtgtgcacag | tgtcacgaac | agacagagaa | accaaactaa | ctttagtgtt | tgaacatgtc | 420 |
| gatcaagact | tgaccactta | cttggataaa | gttccagagc | ctggagtgcc | cactgaaacc | 480 |
| ataaaggata | tgatgtttca | gcttctccga | ggtctggact | tcttcattc | acccgagta | 540 |
| gtgcatcgcg | atctaaaacc | acagaacatt | ctggtgacca | gcagcggaca | aataaaactc | 600 |
| gctgacttcg | gccttgcccg | catctatagt | ttccagatgg | ctctaacctc | agtggtcgtc | 660 |
| acgctgtggt | acagagcacc | cgaagtcttg | ctccagtcca | gctacgccac | ccccgtggat | 720 |
| ctctggagtg | ttggctgcat | atttgcagaa | atgtttcgta | gaaagcctct | ttttcgtgga | 780 |
| agttcagatg | ttgatcaact | aggaaaaatc | ttggacgtga | ttggactccc | aggagaagaa | 840 |
| gactggccta | gagatgttgc | ccttcccagg | caggcttttc | attcaaaatc | tgcccaacca | 900 |

```
attgagaagt tgtaacaga tatcgatgaa ctaggcaaag acctacttct gaagtgtttg      960
acatttaacc cagccaaaag aatatctgcc tacagtgccc tgtctcaccc atacttccag     1020
gacctggaaa ggtgcaaaga aaacctggat tcccacctgc cgcccagcca gaacacctcg     1080
gagctgaata cagcctgagg cctcagcagc cgccttaagc tgatcctgcg gagaacaccc     1140
ttggtggctt atgggtcccc ctcagcaagc cctacagagc tgtggaggat tgctatctgg     1200
aggccttcca gctgctgtct tctggacagg ctctgcttct ccaaggaaa                 1249

<210> SEQ ID NO 5
<211> LENGTH: 4775
<212> TYPE: DNA
<213> ORGANISM: Homo sapiens

<400> SEQUENCE: 5
acccgcgcga ggtaggcgct ctggtgcttg cggaggacgc ttccttcctc agatgcaccg       60
atcttcccga tactgccttt ggagcggcta gattgctagc cttggctgct ccattggcct      120
gccttgcccc ttacctgccg attgcatatg aactcttctt ctgtctgtac atcgttgtcg      180
tcggagtcgt cgcgatcgtc gtggcgctcg tgtgatggcc ttcgtccgtt tagagtagtg      240
tagttagtta ggggccaacg aagaagaaag aagacgcgat tagtgcagag atgctggagg      300
tggtcagtta ctaagctaga gtaagatagc ggagcgaaaa gagccaaacc tagccggggg      360
gcgcacggtc acccaaagga ggtcgactcg ccggcgcttc ctatcgcgcc gagctccctc      420
cattcctctc cctccgccga ggcgcgaggt tgcggcgcgc agcgcagcgc agctcagcgc      480
accgactgcc gcgggctccg ctgggcgatt gcagccgagt ccgtttctcg tctagctgcc      540
gccgcggcga ccgctgcctg gtcttcctcc cggacgctag tgggttatca gctaacaccc      600
gcgagcatct ataacatagg ccaactgacg ccatccttca aaaacaacta aaggatgata      660
tgatgaacct agcctgttaa tttcgtcttc tcaattttaa actttggttg cttaagactg      720
aagcaatcat ggtgaacctg aggaatgcgg tgcattcatt ccttgtgcac ctaattggcc      780
tattggtttg gcaatgtgat atttctgtga gcccagtagc agctatagta actgacattt      840
tcaatacctc cgatggtgga cgcttcaaat cccagacgg ggtacaaaac tggccagcac       900
tttcaatcgt catcataata atcatgacaa taggtggcaa catccttgtg atcatggcag      960
taagcatgga aaagaaactg cacaatgcca ccaattactt cttaatgtcc ctagccattg     1020
ctgatatgct agtgggacta cttgtcatgc ccctgtctct cctggcaatc ctttatgatt     1080
atgtctggcc actacctaga tatttgtgcc ccgtctggat ttctttagat gttttatttt     1140
caacagcgtc catcatgcac ctctgcgcta tatcgctgga tcggtatgta gcaatacgta     1200
atcctattga gcatagccgt ttcaattcgc ggactaaggc catcatgaag attgctattg     1260
tttgggcaat ttctataggt gtatcagttc ctatccctgt gattggactg agggacgaag     1320
aaaaggtgtt cgtgaacaac acgacgtgcg tgctcaacga cccaaatttc gttcttattg     1380
ggtccttcgt agctttcttc ataccgctga cgattatggt gattacgtat tgcctgacca     1440
tctacgttct gcgccgacaa gctttgatgt tactgcacgg ccacaccgag gaaccgcctg     1500
gactaagtct ggatttcctg aagtgctgca agaggaatac ggccgaggaa gagaactctg     1560
caaaccctaa ccaagaccag aacgcacgcc gaagaaagaa gaaggagaga cgtcctaggg     1620
gcaccatgca ggctatcaac aatgaaagaa aagcttcgaa agtccttggg attgttttct     1680 ttgtgttct gatcatgtgg tgcccatttt tcattaccaa tattctgtct gttctttgtg       1740
```

-continued

```
agaagtcctg taaccaaaag ctcatggaaa agcttctgaa tgtgtttgtt tggattggct    1800
atgtttgttc aggaatcaat cctctggtgt atactctgtt caacaaaatt taccgaaggg    1860
cattctccaa ctatttgcgt tgcaattata aggtagagaa aaagcctcct gtcaggcaga    1920
ttccaagagt tgccgccact gctttgtctg ggagggagct taatgttaac atttatcggc    1980
ataccaatga accggtgatc gagaaagcca gtgacaatga gcccggtata gagatgcaag    2040
ttgagaattt agagttacca gtaaatccct ccagtgtggt tagcgaaagg attagcagtg    2100
tgtgagaaag aacagcacag tcttttccta cggtacaagc tacatatgta ggaaaatttt    2160
cttctttaat ttttctgttg gtcttaacta atgtaaatat tgctgtctga aaaagtgttt    2220
ttacatatag ctttgcaacc ttgtacttta caatcatgcc tacattagtg agatttaggg    2280
ttctatattt actgtttata ataggtggag actaacttat tttgattgtt tgatgaataa    2340
aatgtttatt tttgctctcc ctcccttctt tccttcctttt tttcctttct tccttccttt    2400
ctctctttct tttgtgcata tggcaacgtt catgttcatc tcaggtggca tttgcaggtg    2460
accagaatga ggcacatgac agtggttata tttcaaccac acctaaatta acaaattcag    2520
tggacatttg ttctgggtta acagtaaata tacactttac attcttgctc tgctcatcta    2580
cacatataaa cacagtaaga taggttctgc tttctgatac atctgtcagt gagtcagagg    2640
cagaacctag tcttgttgtt catataggg caaaaatttg acattgtcag aatgttgtgt    2700
tggtatttac tgcaatgtct gtccctaaac atagtggtat tttaacatag cagctggtta    2760
accgggacta cagaagtgga aggataatga gatgtaatac accaaatagc ttttcacttc    2820
ttaaggacag tgttcaaatt ctgattatta caacaagcaa actgaaatta gtgttttcat    2880
tctggtcctt agtaaattcc taattctatg attaaactgg gaaatgagat cccagagtta    2940
tttcccaacc caggattcaa catcaattgg gttttgatct cagcatcctg gaaatttgtg    3000
tgcttcacac aaagtgaaat tagtattttg agccttatta aaatattttc ttaattatgg    3060
tacctctgtc tataggactt aatttagcag tccattttg agtaaaactt gtattggaag    3120
tatagatggt agaaactttg gaagttttac ttgattaagg actacagaat tgggccctta    3180
gaatgtgaaa aaaaaagta attaaaaaga cacttttacc gaactcggga ttacagaaac    3240
acggagtttc catttggatt ttaaacaaaa tttatgtcat tttcagatcc ttccaaactc    3300
tctagtgcag gaaaaggctg cagctaattt gtgaaagtgg caagctcttc attgcactgc    3360
agttatttac cagaagttta aatctttgtt aaaatatagt gttgtgttac aataagtgtt    3420
ggccatcatt tcattcgtgg gcctgctgct ctctaagaat tcagtagcat tttaatagtt    3480
tctaaaccat gaaaagtttt caagcattgc taaagtcagg ccattcagtc tatgctgtgt    3540
gcagagtata caagtgtttc tagtaacagt atttccatac gtgcccattt cacacaactg    3600
tggataaatt ttggaagaat tcatgatgct agttcttacg cttgacagtt acttacacac    3660
ctgagaatgt gcctctcagt atcttaaaat tggttaatga aaaatctgaa tttctaaaac    3720
ccttggtctg tgttctcaac acacagtata gataaatcca atagtctgcc acaagggcag    3780
tggaagagct gctgtatttg aggaaactca tacagtctct atttgatttg caacactggc    3840
caaacatcag tcatttgctt gagcatgccc aaatattaca tgaaagtcaa gtctacctgc    3900
cttgcctgtt aggtctgttg aagtgcatgt taaaataatt atatgaagca gaatgagatg    3960
atttaattct taccgaaatg aaaatggctg aagaaacaca gcatgcattt agcatgagtt    4020
ctgcacatac agatggtgtc ctgcatgtat gccatgtatg ttgcatgaat ccatcgattt    4080
gtattaatgt agggcagaat agctgataga agaaggactg aagaaaatcc ttcagcaatc    4140
```

-continued

```
cttaaaaaga ccatgcattc agatctgaag tagtgtgagt gttagaaaaa actggaaaca      4200
tctgatttct gaactatcag ggcaagctca tagcacatgt tttacaaaga aacaaaatat      4260
aaatcacaga tttccaaaag tactagcaat aagttgaatg ataatagctc acagcacatt      4320
tgttaatgat tcttgtgtca tcaagtagta gtacttaata gtacccaacc tggtaattat      4380
cctcaagttg tgtgctattc gtaagttctg tgcagtttgg tatgaaacaa atatactcat      4440
ttggatataa atcttaccct tcaatgttaa atctacaaac ttttataaat gttttaaaga      4500
agtccatgtg ataattgtaa aggtgatgaa tttaccatca aacaaatcat tttgatgtat      4560
tattatatat gtatatctgt gtaagacacg tgcaacagac tgccttatat tattttctgt      4620
aattcttctc ctttgtcaaa tggtattttt tgtgaatggt tgcaaagtgt tgtcttattc      4680
ctaattcctg tatgttatcc actacaggtt ttatgagact tcctattaat ttattaaatt      4740
tattaaatgt tgaaaaaaaa aaaaaaaaaa aaaaa                                 4775

<210> SEQ ID NO 6
<211> LENGTH: 2616
<212> TYPE: DNA
<213> ORGANISM: Homo sapiens

<400> SEQUENCE: 6
atggcggctc ctcccactgg ggggggggtg gcgcggcggc ggtggcatct gcggccatgg        60
cggcgactac tgccaacccc gaaatgacat cagatgtacc atcactgggt ccagccattg       120
cctctggaaa ctctggacct ggaattcaag gtggaggagc cattgtccag agggctatta       180
agcggcgacc agggctggat tttgatgatg atggagaagg gaacagtaaa tttttgaggt       240
gtgatgatga tcagatgtct aacgataagg agcggtttgc caggtcggat gatgagcaga       300
gctctgcgga taaagagaga cttgccaggg aaaatcacag tgaaattgaa cggcggcgac       360
ggaacaagat gacagcctac atcacagaac tgtcagatat ggtacccacc tgtagtgccc       420
tggctcgaaa accagacaag ctaaccatct tacgcatggc agtttctcac atgaagtcct       480
tgcggggaac tggcaacaca tccactgatg ctcctataa gccgtctttc ctcactgatc       540
aggaactgaa acatttgatc ttggaggcag cagatggctt tctgtttatt gtctcatgtg       600
agacaggcag ggtggtgtat gtgtctgact ccgtgactcc tgttttgaac cagccacagt       660
ctgaatggtt tggcagcaca ctctatgatc aggtgcaccc agatgatgtg gataaacttc       720
gtgagcagct ttccacttca gaaaatgccc tgacagggcg tatcctggat ctaaagactg       780
gaacagtgaa aaaggaaggt cagcagtctt ccatgagaat gtgtatgggc tcaaggagat       840
cgtttatttg ccgaatgagg tgtggcagta gctctgtgga cccagtttct gtgaataggc       900
tgagctttgt gaggaacaga tgcaggaatg gacttggctc tgtaaaggat ggggaacctc       960
acttcgtggt ggtccactgc acaggctaca tcaaggcctg gccccagca ggtgtttccc      1020 tcccagatga tgacccagag gctggccagg gaagcaagtt ttgcctagtg gccattggca      1080
gattgcaggt aactagttct cccaactgta cagacatgag taatgtttgt caaccaacag      1140
agttcatctc ccgacacaac attgagggta tcttcacttt tgtggatcac gctgtgtgg       1200 ctactgttgg ctaccagcca caggaactct taggaaagaa tattgtagaa ttctgtcatc      1260
ctgaagacca gcagcttcta agagacagct ccaacaggt agtgaaatta aaaggccaag       1320
tgctgtctgt catgttccgg ttccggtcta agaaccaaga atggctctgg atgagaacca      1380
gctcctttac tttccagaac ccttactcag atgaaattga gtacatcatc tgtaccaaca      1440
```

-continued

| | |
|---|---|
| ccaatgtgaa gaactctagc caagaaccac ggcctacact ctccaacaca atccagaggc | 1500 |
| cacaactagg tcccacagct aatttacccc tggagatggg ctcaggacag ctggcaccca | 1560 |
| ggcagcagca acagcaaaca gaattggaca tggtaccagg aagagatgga ctggccagct | 1620 |
| acaatcattc ccaggtggtt cagcctgtga caaccacagg accagaacac agcaagcccc | 1680 |
| ttgagaagtc agatggttta tttgcccagg atagagatcc aagattttca gaaatctatc | 1740 |
| acaacatcaa tgcggatcag agtaaaggca tctcctccag cactgtccct gccacccaac | 1800 |
| agctattctc ccagggcaac acattccctc ctaccccccg gccggcagag aatttcagga | 1860 |
| atagtggcct agcccctcct gtaaccattg tccagccatc agcttctgca ggacagatgt | 1920 |
| tggcccagat ttcccgccac tccaacccca cccaaggagc aacccaact tggaccccta | 1980 |
| ctacccgctc aggcttttct gcccagcagg tggctaccca ggctactgct aagactcgta | 2040 |
| cttcccagtt tggtgtgggc agctttcaga ctccatcctc cttcagctcc atgtccctcc | 2100 |
| ctggtgcccc aactgcatcg cctggtgctg ctgcctaccc tagtctcacc aatcgtggat | 2160 |
| ctaactttgc tcctgagact ggacagactg caggacaatt ccagacacgg acagcagagg | 2220 |
| gtgtgggtgt ctggccacag tggcagggcc agcagcctca tcatcgttca agttctagtg | 2280 |
| agcaacatgt tcaacaaccg ccagcacagc aacctggcca gcctgaggtc ttccaggaga | 2340 |
| tgctgtccat gctgggagat cagagcaaca gctacaacaa tgaagaattc cctgatctaa | 2400 |
| ctatgttcc cccttttca gaatagaact attggggtga ggataagggg tgggggagaa | 2460 |
| aaaatcactg tttgtttta aaagcaaat ctttctgtaa acagaataaa agttcctctc | 2520 |
| ccttcccttc cctcaccct gacatgtacc cctttccct tctggctgtt cccctgctct | 2580 |
| gttgcctcct aagtaacat ttataaaaaa aaaaaa | 2616 |

<210> SEQ ID NO 7
<211> LENGTH: 2392
<212> TYPE: DNA
<213> ORGANISM: Homo sapiens

<400> SEQUENCE: 7

| | |
|---|---|
| gcgatggaac cagcggagca gccgagcgag ttagtgtcag ccgagggccg aaaccggaag | 60 |
| gcggtgctgt gccagcgttg cggctcccgg gtgctgcagc cagggaccgc tctcttctct | 120 |
| cgccgacagc ttttccttcc ctccatgaga aagaagccag ctctgtctga cggcagcaat | 180 |
| cctgacggcg atccctcca ggaacactgg ctggttgagg acatgttcat ttttgagaat | 240 |
| gtgggcttca ccaaggacgt gggcaacatc aagtttctgg tctgcgcaga ctgtgaaatt | 300 |
| ggaccaattg gctggcattg cctagatgac aagaacagtt tctatgtggc cttggaacga | 360 |
| gtttcccatg agtaactgag gggagggta ctcagctcca tctccaaaga taaacctact | 420 |
| ccccacaaga actggccttt aatgtggtat aactgttccg ctgccttctt gtctgtgcca | 480 |
| atataaatac tgagtaccag catgtccatt tgaacatgca gagggttaat cctgcttcct | 540 |
| aaagcctcaa gtacatgcct cctgcttagt tcactttgta tcacatttcc taagctcccc | 600 |
| tttcccccag ttttgggaca ctgtgcttac ctccaaaaat ctcatctctt ccctggcatt | 660 |
| ctccctaggc tctgttttgc ccaggggctc ccgcttttc ttgctctaga agagcagtat | 720 |
| tcaaccttt agctatgatg acacataaca aaagatgctt atgtactaat agttgaaatc | 780 |
| tgccttttc tcattcaaga aggcatacaa atatctgaga gtgactttgt tgtatggcta | 840 |
| cccttgtgat ctacagtaat ttattctttc taaaagtaaa gcattttcaa aactcagtat | 900 |
| ttaaaccact aaccagaaac attactttgg atgcatctct aataccatgt ttgagcacct | 960 |

```
ctgctctagg ttgagaatga cattttattg tgaagatggg tgtggtccct cttcccttga    1020
aatcttgtag tttctttta tattagctcc tcactgctac agcctagaag gtgagaagca    1080
gattttaacc ccatctggca gccattcaag gaaaacccag ccctggctgt ttactcaggc    1140
tctcttagaa tgagagtgga gggtgtagga tatgagggtt aggcctttgc cacattatac    1200
aaaagtttat aatttgccac atctggacaa gtaactttct tcttttgttc ataggcaaga    1260
cttctttaat ggatagtatc atttactgaa cctactgggc atggtcctca tggagttttg    1320
gttcaactgg aatctctgtg ccaacccagg atacaaactt ccatccagat gcatggatac    1380
aaatttccat agctccgggg ctgctctaac agtttgatat cagcagacgt gtttaagcct    1440
tcaacttgat ttccaattat tccatcattt ctattctgaa atgactcact gtcgtagaag    1500
gaagtttatt ataaaccaa ggtttcaggt atcctcctgt caccacctct actattcagg    1560
aggcctaaaa ttgaaataag tactaaacag aaaccttacc atctgaagtc ccttccattg    1620
ttttctagtt gcttcctcat tcctttaccc ccaaactttc taagggctcc ccgactgcag    1680
tgcaaggtgg ccttgggcac agttttgcaa ccaacctact cccctggaaa gatggcttcc    1740
ttctccaatt agcctgaatg agctttagta agcaattgag agaactgtgt ttttccgaca    1800
aacggtcaca tgtccatcgt tatggcatgt gcagaaaaac agagttatcc acacaagtca    1860
ggagcaaaac ccaagtagat gcctctaggg gcacatggcc cctcacatca caagccagaa    1920
cctaagctaa gcatttttta aattgagttt gagactagcc tgggcaacat agtgagaccc    1980
catctctatt taaaaatga acaaaattac ctgggcatag tggtgtatac ctgtagtccc    2040
tgctacttgg gaggctcagg tgggaggatc acttgagccc caaagatggt ggctgcagta    2100
agccaagatc acaccactgg cactccagcc tgggcaacag agtgagaccc tgtctcaaac    2160
aaacaacaac agtaacaaca aaaaaatata tagcgacttg aataggaaac catagtattt    2220
cattgtttta atttgcattt attttatttc tagtgaaact tttatatacg tatcggtcat    2280
ttctatttcc ttttttgaga actgccaaat gttgccctag tagccaaaaa tatcaggttg    2340
ctattctgcc ttttcagttt gatctgaaag aaataaaggc atttaagcaa tg           2392
```

<210> SEQ ID NO 8
<211> LENGTH: 2947
<212> TYPE: DNA
<213> ORGANISM: Homo sapiens

<400> SEQUENCE: 8

```
ggcgggaaac agcttagtgg gtgtgggtc gcgcattttc ttcaaccagg aggtgaggag      60
gtttcgacat ggcggtgcag ccgaaggaga cgctgcagtt ggagagcgcg gccgaggtcg    120
gcttcgtgcg cttctttcag ggcatgccgg agaagccgac caccacagtg cgccttttcg    180
accggggcga cttctatacg gcgcacggcg aggacgcgcg gctggccgcc gggaggtgt     240 tcaagaccca gggggtgatc aagtacatgg ggccggcagg agcaaagaat ctgcagagtg    300
ttgtgcttag taaatgaat tttgaatctt ttgtaaaaga tcttcttctg gttcgtcagt    360
atagagttga agtttataag aatagagctg gaaataaggc atccaaggag aatgattggt    420
atttggcata taaggcttct cctggcaatc tctctcagtt tgaagacatt ctctttggta    480
acaatgatat gtcagcttcc attggtgttg tgggtgttaa aatgtccgca gttgatggcc    540
agagacaggt tggagttggg tatgtggatt ccatacagag gaaactagga ctgtgtgaat    600
tccctgataa tgatcagttc tccaatcttg aggctctcct catccagatt ggaccaaagg    660
```

-continued

| | |
|---|---|
| aatgtgtttt acccggagga gagactgctg gagacatggg gaaactgaga cagataattc | 720 |
| aaagaggagg aattctgatc acagaaagaa aaaaagctga cttttccaca aaagacattt | 780 |
| atcaggacct caaccggttg ttgaaaggca aaaagggaga gcagatgaat agtgctgtat | 840 |
| tgccagaaat ggagaatcag gttgcagttt catcactgtc tgcggtaatc aagtttttag | 900 |
| aactcttatc agatgattcc aactttggac agtttgaact gactacttt gacttcagcc | 960 |
| agtatatgaa attggatatt gcagcagtca gagcccttaa cctttttcag ggttctgttg | 1020 |
| aagataccac tggctctcag tctctggctg ccttgctgaa taagtgtaaa acccctcaag | 1080 |
| gacaaagact tgttaaccag tggattaagc agcctctcat ggataagaac agaatagagg | 1140 |
| agagattgaa tttagtggaa gcttttgtag aagatgcaga attgaggcag actttacaag | 1200 |
| aagatttact tcgtcgattc ccagatctta accgacttgc caagaagttt caaagacaag | 1260 |
| cagcaaactt acaagattgt taccgactct atcagggtat aaatcaacta cctaatgtta | 1320 |
| tacaggctct ggaaaaacat gaaggaaaac accagaaatt attgttggca gtttttgtga | 1380 |
| ctcctcttac tgatcttcgt tctgacttct ccaagtttca ggaaatgata gaaacaactt | 1440 |
| tagatatgga tcaggtggaa aaccatgaat tccttgtaaa accttcattt gatcctaatc | 1500 |
| tcagtgaatt aagagaaata atgaatgact tggaaaagaa gatgcagtca acattaataa | 1560 |
| gtgcagccag agatcttggc ttggaccctg gcaaacagat taaactggat tccagtgcac | 1620 |
| agtttggata ttactttcgt gtaacctgta aggaagaaaa agtccttcgt aacaataaaa | 1680 |
| actttagtac tgtagatatc cagaagaatg gtgttaaatt taccaacagc aaattgactt | 1740 |
| ctttaaatga agagtatacc aaaaataaaa cagaatatga agaagcccag gatgccattg | 1800 |
| ttaaagaaat tgtcaatatt tcttcaggct atgtagaacc aatgcagaca ctcaatgatg | 1860 |
| tgttagctca gctagatgct gttgtcagct ttgctcacgt gtcaaatgga gcacctgttc | 1920 |
| catatgtacg accagccatt ttggagaaag gacaaggaag aattatatta aaagcatcca | 1980 |
| ggcatgcttg tgttgaagtt caagatgaaa ttgcatttat tcctaatgac gtatactttg | 2040 |
| aaaaagataa acagatgttc cacatcatta ctggccccaa tatgggaggt aaatcaacat | 2100 |
| atattcgaca aactggggtg atagtactca tggcccaaat tgggtgtttt gtgccatgtg | 2160 |
| agtcagcaga agtgtccatt gtggactgca tcttagcccg agtaggggct ggtgacagtc | 2220 |
| aattgaaagg agtctccacg ttcatggctg aaatgttgga aactgcttct atcctcaggt | 2280 |
| ctgcaaccaa agattcatta ataatcatag atgaattggg aagaggaact tctacctacg | 2340 |
| atggatttgg gttagcatgg gctatatcag aatacattgc aacaaagatt ggtgcttttt | 2400 |
| gcatgtttgc aacccatttt catgaactta ctgccttggc caatcagata ccaactgtta | 2460 |
| ataatctaca tgtcacagca ctcaccactg aagagacctt aactatgctt tatcaggtga | 2520 |
| agaaaggtgt ctgtgatcaa agttttggga ttcatgttgc agagcttgct aatttcccta | 2580 |
| agcatgtaat agagtgtgct aaacagaaag ccctggaact tgaggagttt cagtatattg | 2640 |
| gagaatcgca aggatatgat atcatggaac cagcagcaaa gaagtgctat ctggaaagag | 2700 |
| agcaaggtga aaaattatt caggagttcc tgtccaaggt gaaacaaatg ccctttactg | 2760 |
| aaatgtcaga agaaaacatc acaataaagt taaacagct aaaagctgaa gtaatagcaa | 2820 |
| agaataatag ctttgtaaat gaaatcattt cacgaataaa agttactacg tgaaaaatcc | 2880 |
| cagtaatgga atgaaggtaa tattgataag ctattgtctg taatagtttt atattgtttt | 2940 |
| atattaa | 2947 |

-continued

<210> SEQ ID NO 9
<211> LENGTH: 3805
<212> TYPE: DNA
<213> ORGANISM: Homo sapiens

<400> SEQUENCE: 9

| | | | | | |
|---|---|---|---|---|---|
| ggctcggctc | ctagagctgc | cacggccatg | ccagagccc | gccgccgcc | gccgccgtcg | 60 |
| ccgccgccgg | ggcttctgcc | gctgctccct | ccgctgctgc | tgctgccgct | gctgctgctg | 120 |
| cccgccggct | gccgggcgct | ggaagagacc | ctcatggaca | caaaatggt | aacatctgag | 180 |
| ttggcgtgga | catctcatcc | agaaagtggg | tgggaagagg | tgagtggcta | cgatgaggcc | 240 |
| atgaatccca | tccgcacata | ccaggtgtgt | aatgtgcgcg | agtcaagcca | gaacaactgg | 300 |
| cttcgcacgg | ggttcatctg | gcggcgggat | gtgcagcggg | tctacgtgga | gctcaagttc | 360 |
| actgtgcgtg | actgcaacag | catccccaac | atccccggct | cctgcaagga | gaccttcaac | 420 |
| ctcttctact | acgaggctga | cagcgatgtg | gcctcagcct | cctccccctt | ctggatggag | 480 |
| aaccctacg | tgaaagtgga | caccattgca | cccgatgaga | gcttctcgcg | gctggatgcc | 540 |
| ggccgtgtca | acaccaaggt | gcgcagcttt | ggcccacttt | ccaaggctgg | cttctacctg | 600 |
| gccttccagg | accagggcgc | ctgcatgtcg | ctcatctccg | tgcgcgcctt | ctacaagaag | 660 |
| tgtgcatcca | ccaccgcagg | cttcgcactc | ttccccgaga | ccctcactgg | ggcggagccc | 720 |
| acctcgctgg | tcattgctcc | tggcacctgc | atccctaacg | ccgtggaggt | gtcggtgcca | 780 |
| ctcaagctct | actgcaacgg | cgatgggag | tggatggtgc | ctgtgggtgc | ctgcacctgt | 840 |
| gccaccggcc | atgagccagc | tgccaaggag | tcccagtgcc | gcccctgtcc | ccctgggagc | 900 |
| tacaaggcga | gcagggaga | ggggccctgc | ctcccatgtc | ccccaacag | ccgtaccacc | 960 |
| tccccagccg | ccagcatctg | cacctgccac | aataacttct | accgtgcaga | ctcggactct | 1020 |
| gcggacagtg | cctgtaccac | cgtgccatct | ccaccccgag | gtgtgatctc | caatgtgaat | 1080 |
| gaaacctcac | tgatcctcga | gtggagtgag | ccccgggacc | tgggtgtccg | ggatgacctc | 1140 |
| ctgtacaatg | tcatctgcaa | gaagtgccat | ggggctggag | gggcctcagc | ctgctcacgc | 1200 |
| tgtgatgaca | acgtggagtt | tgtgcctcgg | cagctggcc | tgtcggagcc | ccgggtccac | 1260 |
| accagccatc | tgctggccca | cacgcgctac | acctttgagg | tgcaggcggt | caacggtgtc | 1320 |
| tcgggcaaga | gccctctgcc | gcctcgttat | gcggccgtga | atatcaccac | aaaccaggct | 1380 |
| gccccgtctg | aagtgcccac | actacgcctg | cacagcagct | caggcagcag | cctcacccta | 1440 |
| tcctgggcac | cccagagcg | gcccaacgga | gtcatcctgg | actacgagat | gaagtacttt | 1500 |
| gagaagagcg | agggcatcgc | ctccacagtg | accagccaga | tgaactccgt | gcagctggac | 1560 |
| gggcttcggc | ctgacgcccg | ctatgtggtc | caggtccgtg | cccgcacagt | agctggctat | 1620 |
| gggcagtaca | gccgccctgc | cgagtttgag | accacaagtg | agagaggctc | tgggcccag | 1680 |
| cagctccagg | agcagcttcc | cctcatcgtg | ggctccgcta | cagctgggct | tgtcttcgtg | 1740 |
| gtggctgtcg | tggtcatcgc | tatcgtctgc | ctcaggaagc | agcgacacgg | ctctgattcg | 1800 |
| gagtacacgg | agaagctgca | gcagtacatt | gctcctggaa | tgaaggttta | tattgaccct | 1860 |
| tttacctacg | aggaccctaa | tgaggctgtt | cgggagtttg | ccaaggagat | cgacgtgtcc | 1920 |
| tgcgtcaaga | tcgaggaggt | gatcggagct | ggggaatttg | ggaagtgtg | ccgtggtcga | 1980 |
| ctgaaacagc | ctggccgccg | agaggtgttt | gtggccatca | agacgctgaa | ggtgggctac | 2040 |
| accgagaggc | agcggcggga | cttcctaagc | gaggcctcca | tcatgggtca | gtttgatcac | 2100 |
| cccaatataa | tccggctcga | gggcgtggtc | accaaaagtc | ggccagttat | gatcctcact | 2160 |

-continued

```
gagttcatgg aaaactgcgc cctggactcc ttcctccggc tcaacgatgg gcagttcacg    2220
gtcatccagc tggtgggcat gttgcggggc attgctgccg gcatgaagta cctgtccgag    2280
atgaactatg tgcaccgcga cctggctgct cgcaacatcc ttgtcaacag caacctggtc    2340
tgcaaagtct cagactttgg cctctcccgc ttcctggagg atgacccctc cgatcctacc    2400
tacaccagtt ccctgggcgg gaagatcccc atccgctgga ctgccccaga ggccatagcc    2460
tatcggaagt tcacttctgc tagtgatgtc tggagctacg gaattgtcat gtgggaggtc    2520
atgagctatg gagagcgacc ctactgggac atgagcaacc aggatgtcat caatgccgtg    2580
gagcaggatt accggctgcc accacccatg gactgtccca cagcactgca ccagctcatg    2640
ctggactgct gggtgcggga ccggaacctc aggcccaaat tctcccagat tgtcaatacc    2700
ctggacaagc tcatccgcaa tgctgccagc ctcaaggtca ttgccagcgc tcagtctggc    2760
atgtcacagc cctcctgga ccgcacggtc ccagattaca caaccttcac gacagttggt    2820
gattggctgg atgccatcaa gatggggcgg tacaaggaga gcttcgtcag tgcggggttt    2880
gcatcttttg acctggtggc ccagatgacg gcagaagacc tgctccgtat tgggtcacc    2940 ctggccggcc accagaagaa gatcctgagc agtatccagg acatgcggct gcagatgaac    3000
cagacgctgc ctgtgcaggt ctgacaccgg ctcccacggg gacctgagg accgtgcagg    3060 gatgccaagc agccggctgg actttcggac tcttggactt ttggatgcct ggccttaggc    3120
tgtggcccag aagctggaag tttgggaaag gcccaagctg ggacttctcc aggcctgtgt    3180
tccctcccca ggaagtgcgc cccaaacctc ttcatattga agatgattaa ggagaggggg    3240
tgatgacccc tccccaagcc cctcagggcc cagaccttcc tgctctccag caggggatcc    3300
ccacaacctc acacttgtct gttcttcagt gctggaggtc ctggcagggt caggctgggg    3360
taagccgggg ttccacaggg cccagccctg gcagggtctg gccccccag gtaggcggag    3420 agcagtccct ccctcaggaa ctggaggagg ggactccagg aatggggaaa tgtgacacca    3480
ccatcctgaa gccagcttgc acctccagtt tgcacaggga tttgtcctgg gggctgaggg    3540
ccctgtcccc acccccgccc ttggtgctgt cataaaaggg caggcagggg caggctgagg    3600
agttgcccgt tgccccccag agactgactc tcagagccag agatgggatg tgtgagtgtg    3660
tgtgtgtgtg tgtgcgcgcg cgcgcgcgtg tgtgtgtgca cgcactggcc tgcacagaga    3720
gcatgggtga gcgtgtaaaa gcttggccct gtgccctaca gtggggacag ctgggccgac    3780
agcagaataa aggcaataag atgaa                                         3805
```

<210> SEQ ID NO 10
<211> LENGTH: 541
<212> TYPE: DNA
<213> ORGANISM: Homo sapiens
<220> FEATURE:
<221> NAME/KEY: misc_feature
<222> LOCATION: (1)...(541)
<223> OTHER INFORMATION: n = A,T,C or G

<400> SEQUENCE: 10

```
tttttttttt ttaggatatt tgnaaataca actttattnc tgnattgcta aacgcaaaag     60
gnaatgggna atgacagtaa caaacaagtt ttcaccactg naatattgtg atgtgactgc    120
agacagtctt atatatgnaa actcaaggga atcaactgcg ttccaaaaca gctaaatatg    180
caggtccaaa caatgaagtt attttttaaa ctgccacatt cactccgaag ncccactcat    240
ctccttcagg catcccacag atgaaggcac atgttccgct tagctagata ataatgaggt    300
gggcacacac gctgcaccgc tgacatcaca ggacagctgc ctataaaact agacttctga    360
```

-continued

```
cgctgggctc cagcttcatt ctcacaggtc atcatcctca tccgggagag cagttgtctg    420
agcaacctct aagtcgtgct catactgtgc tgccaaagct gggtccatga caactttggt    480
ggggcgagan agggcatggc aacaaattca agttgggttc aatgagttct gcaagcagag    540
g                                                                    541
```

<210> SEQ ID NO 11
<211> LENGTH: 1860
<212> TYPE: DNA
<213> ORGANISM: Homo sapiens

<400> SEQUENCE: 11

```
cgtgaacggt cgttgcagag attgcgggcg gctgagacgc cgcctgcctg gcacctagga     60
gcgcagcgga gccccgacac cgccgccgcc gccatggagt ccgagaccga acccgagccc    120
gtcacgctcc tggtgaagag ccccaaccag cgccaccgcg acttggagct gagtggcgac    180
cgcggctgga gtgtgggcca cctcaaggcc cacctgagcc gcgtctaccc cgagcgtccg    240
cgtccagagg accagaggtt aatttattct gggaagctgt tgttggatca ccaatgtctc    300
agggacttgc ttccaaagca ggaaaaacgg catgttttgc atctggtgtg caatgtgaag    360
agtccttcaa aaatgccaga atcaacgcc aaggtggctg aatccacaga ggagcctgct    420
ggttctaatc ggggacagta tcctgaggat tcctcaagtg atggtttaag gcaaagggaa    480
gttcttcgga accttcttcc ccctggatgg gaaaacatct caaggcctga agctgcccag    540
caggcattcc aaggcctggg tcctggtttc tccggttaca caccctatgg gtggcttcag    600
ctttcctggt tccagcagat atatgcacga cagtactaca tgcaatattt agcagccact    660
gctgcatcag ggcttttgt tccaccacca agtgcacaag agatacctgt ggtctctgca    720
cctgctccag cccctattca caaccagttt ccagctgaaa accagcctgc caatcagaat    780
gctgctcctc aagtggttgt taatcctgga gccaatcaaa atttgcggat gaatgcacaa    840
ggtggcccta ttgtggaaga agatgatgaa ataaatcgag attggttgga ttggacctat    900
tcagcagcta cattttctgt ttttctcagt atcctctact tctactcctc cctgagcaga    960
ttcctcatgg tcatgggggc caccgttgtt atgtacctgc atcacgttgg gtggtttcca   1020
tttagaccga ggccggttca gaacttccca aatgatggtc ctcctcctga cgttgtaaat   1080
caggacccca acaataactt acaggaaggc actgatcctg aaactgaaga ccccaaccac   1140
ctccctccag acagggatgt actagatggc gagcagacca gccctccctt tatgagcaca   1200
gcatggcttg tcttcaagac tttctttgcc tctcttcttc cagaaggccc cccagccatc   1260
gcaaactgat ggtgtttgtg ctgtagctgt tggaggcttt gacaggaatg gactggatca   1320
cctgactcca gctagattgc ctctcctgga catggcaatg atgagttttt aaaaaacagt   1380
gtggatgatg atatgctttt gtgagcaagc aaaagcagaa acgtgaagcc gtgatacaaa   1440
ttggtgaaca aaaatgccc aaggcttctc atgtgtttat tctgaagagc tttaatatat   1500
actctatgta gtttaataag cactgtacgt agaaggcctt aggtgttgca tgtctatgct   1560
tgaggaactt ttccaaatgt gtgtgtctgc atgtgtgttt gtacatagaa gtcatagatg   1620
cagaagtggt tctgctggta agatttgatt cctgttggaa tgtttaaatt acactaagtg   1680
tactacttta tataatcaat gaaattgcta gacatgtttt agcaggactt tctaggaaa    1740 gacttatgta taattgcttt ttaaaatgca gtgcttact ttaaactaag gggaactttg    1800
cggaggtgaa aacctttgct gggttttctg ttcaataaag ttttactatg aatgaccctg   1860
```

<210> SEQ ID NO 12
<211> LENGTH: 3379
<212> TYPE: DNA
<213> ORGANISM: Homo sapiens

<400> SEQUENCE: 12

| | | | | | |
|---|---|---|---|---|---|
| aattccgcgg | aatcatcgga | atccttcacc | atggcatcca | gcccggccca | gcgtcggcga | 60 |
| ggcaatgatc | ctctcacctc | cagccctggc | cgaagctccc | ggcgtactga | tgccctcacc | 120 |
| tccagccctg | gccgtgacct | tccaccattt | gaggatgagt | ccgaggggct | cctaggcaca | 180 |
| gaggggcccc | tggaggaaga | agaggatgga | gaggagctca | ttggagatgg | catggaaagg | 240 |
| gactaccgcg | ccatcccaga | gctggacgcc | tatgaggccg | agggactggc | tctggatgat | 300 |
| gaggacgtag | aggagctgac | ggccagtcga | agggaggcag | cagacgggcc | atgcggcacg | 360 |
| gtgaccggga | gctggccggg | gctgggcgca | tgcgccgtgg | gctcctgtat | gacagcgatg | 420 |
| aggaggacga | ggagcgccct | gcccgcaagc | gccgccagtg | gagccggcac | ggaggacggc | 480 |
| gaggaggacg | agcagatgat | tgagagcatc | gagaacctgg | aggatctcaa | aggccactct | 540 |
| gtgcgcgagt | gggtgagcat | ggcgggcccc | cggctggaga | tccaccaccg | cttcaagaac | 600 |
| ttcctgcgca | ctcacgtcga | cagccacggc | cacaacgtct | tcaaggagcg | catcagcgac | 660 |
| atgtgcaaag | agaaccgtga | gagcctggtg | gtgaactatg | aggacttggc | agccagggag | 720 |
| cacgtgctgg | cctacttcct | gcctgaggca | ccggcggagc | tgctgcagat | ctttgatgag | 780 |
| gctgccctgg | aggtggtact | ggccatgtac | cccaagtacg | accgcatcac | caaccacatc | 840 |
| catgtccgca | tctcccacct | gcctctggtg | gaggagctgc | gctcgctgag | gcagctgcat | 900 |
| ctgaaccagc | tgatccgcac | cagtggggtg | gtgaccagct | gcactggcgt | cctgcccccag | 960 |
| ctcagcatgg | tcaagtacaa | ctgcaacaag | tgcaatttcg | tcctgggtcc | tttctgccag | 1020 |
| tcccagaacc | aggaggtgaa | accaggctcc | tgtcctgagt | gccagtcggc | cggcccctttt | 1080 |
| gaggtcaaca | tggaggagac | catctatcag | aactaccagc | gtatccgaat | ccaggagagt | 1140 |
| ccaggcaaag | tggcggctcg | gcggctgccc | cgctccaagg | acgccattct | cctcgcagat | 1200 |
| ctggtggaca | gctgcaacgc | aggagacgag | atagagctga | ctggcatcta | tcacaacaac | 1260 |
| tatgatggct | ccctcaacac | tgccaatggc | ttccctgtct | tgccactgt | catcctagcc | 1320 |
| aaccacgtgg | ccaagaagga | caacaaggtt | gctgtagggg | aactgaccga | tgaagatgtg | 1380 |
| aagatgatca | ctagcctctc | caaggatcag | cagatcggag | agaagatctt | tgccagcatt | 1440 |
| gctccttcca | tctatggtca | tgaagacatc | aagagaggcc | ctgctctggc | cctgttcgga | 1500 |
| ggggagccca | aaacccagg | tggcaagcac | aaggtacgtg | gtgatatcaa | cgtgctcttg | 1560 |
| tgcggagacc | ctggcacagc | gaagtcgcag | tttctcaagt | atattgagaa | agtgtccagc | 1620 |
| cgagccatct | tcaccactgg | ccagggggcg | tcggctgtgg | ccgtcacggc | gtatgtccag | 1680 |
| cggcaccctg | tcagcaggga | gtggaccttg | gaggctgggg | ccctggttct | ggctgaccga | 1740 |
| ggagtgtgtc | tcattgatga | atttgacaag | atgaatgacc | aggacagaac | cagcatccat | 1800 |
| gaggccatgg | agcaacagag | catctccatc | tcgaaggctg | gcatcgtcac | ctccctgcag | 1860 |
| gctcgctgca | cggtcattgc | tgccgccaac | cccataggag | ggcgctacga | cccctcgctg | 1920 |
| actttctctg | agaacgtgga | cctcacagag | cccatcatct | cacgctttga | catcctgtgt | 1980 |
| gtggtgaggg | acaccgtgga | cccagtccag | gacgagatgc | tggcccgctt | cgtggtgggc | 2040 |
| agccacgtca | gacaccaccc | cagcaacaag | gaggaggagg | ggctggccaa | tggcagcgct | 2100 |
| gctgagcccg | ccatgcccaa | cacgtatggc | gtggagcccc | tgcccccagga | ggtcctgaag | 2160 |

```
aagtacatca tctacgccaa ggagagggtc cacccgaagc tcaaccagat ggaccaggac    2220
aaggtggcca agatgtacag tgacctgagg aaagaatcta tggcgacagg cagcatcccc    2280
attacggtgc ggcacatcga gtccatgagt catggcggag gcccacgcgc gcatccatct    2340
gcgggactat gtgatcgaag acgacgtcaa catggccatc cgcgtgatgc tggagagctt    2400
catagacaca cagaagttca gcgtcatcgc agcatgcgca agacttttgc ccgctacctt    2460
tcattccggc gtgacaacaa tgagctgttg ctcttcatac tgaagcagtt agtggcagag    2520
caggtgacat atcagcgcaa ccgctttggg gcccagcagg acactattga ggtccctgag    2580
aaggacttgg tggataaggc tcgtcagatc aacatccaca acctctctgc attttatgac    2640
agtgagctct tcaggatgaa caagttcagc cacgacctga aaaggaaaat gatcctgcag    2700
cagttctgag gccctatgcc atccataagg attccttggg attctggttt ggggtggtca    2760
gtgccctctg tgctttatgg acacaaaacc agagcacttg atgaactcgg ggtactaggg    2820
tcagggctta tagcaggatg tctggctgca cctggcatga ctgtttgttt ctccaagcct    2880
gctttgtgct tctcacctt  gggtgggatg ccttgccagt gtgtcttact tggttgctga    2940
acatcttgcc acctccgagt gctttgtctc cactcagtac cttggatcag agctgctgag    3000
ttcaggatgc ctgcgtgtgg tttaggtgtt agccttctta catggatgtc aggagagctg    3060
ctgccctctt ggcgtgagtt gcgtattcag gctgcttttg ctcgctttgg ccagagagct    3120
ggttgaagat gttttgtaatc gttttcagtc tcctgcaggt ttctgtgccc ctgtggtgga    3180
agaggcacga cagtgccagc gcagcgttct gggctcctca gtcgcagggg tgggatgtga    3240
gtcatgcgga ttatccactc gccacagtta tcagctgcca ttgctccctg tctgtttccc    3300
cactctctta tttgtgcatt cggtttggtt tctgtagttt aattttttaa taaagttgaa    3360
taaaatataa aaaaaaaa                                                  3379

<210> SEQ ID NO 13
<211> LENGTH: 767
<212> TYPE: DNA
<213> ORGANISM: Homo sapiens
<220> FEATURE:
<221> NAME/KEY: misc_feature
<222> LOCATION: (1)...(767)
<223> OTHER INFORMATION: n = A,T,C or G

<400> SEQUENCE: 13
agatgaagta gagtgctctg acaaggacga gcccgacctc gatgggatg tgtccagcga      60 ctgccccacc atccgcgtcc cactgacatc cctcaagagc caccagggcg tggtcatcgc    120
ctccgactgg ctggttgggg ggaagcaggc tgtgactgcc tcctgggacc ggacggcaaa    180
cctgtacgac gtggagacgt ccgagctcgt tcactctctg acagggcacg accaggagtt    240
gacgcactgc tgcacacacc ccacccagcg gctcgtggtg acctcctccc gtgacacgac    300
tttccgcctc tgggattttca gggaccctc catccactct tatggaacat ggacatttta    360
atgaatttca tattgcaatg aagacagtca acacttagag acaattatat cgatacaata    420
aaaactgatt ccatggaaca cttataaatg catacatttt cctccaaaga aatatgtttt    480
tcacagactt aagtaacaaa tgatttacat aggattcttc agattccaaa atatgtacag    540 agttttgtc tctacagaaa ctgatgagca gtggttgaaa aagagttgct ttgcccaaca     600
gcatggctct tatgaaattc ctgtatcata tacagttttc agtaaccaca cattttcccg    660
tctatcatta aatggaattc tgggacacat ccagcatacc nggaccaaac tggttcccac    720
```
tttnccaaac actggtttca gacgagattc acgtggtngg tttgaac         767

<210> SEQ ID NO 14
<211> LENGTH: 500
<212> TYPE: DNA
<213> ORGANISM: Homo sapiens

<400> SEQUENCE: 14
tgccgctgca gcagcgcagt tccagtccgt tgctttactt tttgcttcac cgacatagtc    60
attatgccga agagaaagtc tccagagaat acagagggca agatggatc caaagtaact    120 aaacaggagc ccacaagacg gtctgccaga ttgtcagcga aacctgctcc accaaaacct   180
gaacccaaac caagaaaaac atctgctaag aaagaacctg agcaaagat tagcagaggt    240 gctaagggga agaaggagga aaagcaggaa gctggaaagg aaggtactgc accatctgaa   300
aatggtgaaa ctaaagctga agaggcacag aaaactgaat ctgtagataa cgagggagaa   360
tgaattgtca tgaaaaattg gggttgattt tatgtatctc ttgggacaac ttttaaaagc   420 tattttttacc aagtattttg taaatgctaa tttttttagga ctctactagt tggcatacga  480
aaatatataa ggatggacat                                                500

<210> SEQ ID NO 15
<211> LENGTH: 2287
<212> TYPE: DNA
<213> ORGANISM: Homo sapiens

<400> SEQUENCE: 15
ggctgaggca gtggctcctt gcacagcagc tgcacgcgcc gtggctccgg atcttcttcg    60
tctttgcagc gtagcccgag tcggtcagcg ccagaggacc tcagcagcca tgtcgaagcc   120
ccatagtgaa gccgggactg ccttcattca gacccagcag ctgcacgcag ccatggctga   180
cacattcctg gagcacatgt gccgcctgga cattgattca ccaccatca cagcccggaa    240 cactggcatc atctgtacca ttggcccagc ttcccgatca gtggagacgt tgaaggagat   300
gattaagtct ggaatgaatg tggctcgtct gaacttctct catggaactc atgagtacca   360
tgcggagacc atcaagaatg tgcgcacagc cacggaaagc tttgcttctg accccatcct   420
ctaccggccc gttgctgtgg ctctagacac taaaggacct gagatccgaa ctgggctcat    480
caagggcagc ggcactgcag aggtggagct gaagaaggga gccactctca aaatcacgct   540
ggataacgcc tacatggaaa agtgtgacga aacatcctg tggctggact acaagaacat    600
ctgcaaggtg gtggaagtgg gcagcaagat ctacgtggat gatgggctta tttctctcca   660
ggtgaagcag aaaggtgccg acttcctggt gacgagggtg gaaaatggtg gctccttggg  720
cagcaagaag ggtgtgaacc ttcctggggc tgctgtggac ttgcctgctg tgtcggagaa   780
ggacatccag gatctgaagt ttgggtcga gcaggatgtt gatatggtgt ttgcgtcatt    840
catccgcaag gcatctgatg tccatgaagt taggaaggtc ctgggagaga agggaaagaa   900
catcaagatt atcagcaaaa tcgagaatca tgagggggtt cggaggtttg atgaaatcct   960
ggaggccagt gatgggatca tggtggctcg tggtgatcta ggcattgaga ttcctgcaga   1020
gaaggtcttc cttgctcaga agatgatgat tggacggtgc aaccgagctg ggaagcctgt    1080
catctgtgct actcagatgc tggagagcat gatcaagaag ccccgcccca ctcgggctga   1140
aggcagtgat gtggccaatg cagtcctgga tggagccgac tgcatcatgc tgtctggaga   1200
aacagccaaa gggactatc ctctggaggc tgtgcgcatg cagaacctga ttgcccgtga    1260
ggcagaggct gccatctacc acttgcaatt atttgaggaa ctccgccgcc tggcgcccat   1320

-continued

```
taccagcgac cccacagaag ccaccgccgt gggtgccgtg gaggcctcct tcaagtgctg    1380
cagtggggcc ataatcgtcc tcaccaagtc tggcaggtct gctcaccagg tggccagata    1440
ccgcccacgt gcccccatca ttgctgtgac ccggaatccc cagacagctc gtcaggccca    1500
cctgtaccgt ggcatcttcc ctgtgctgtg caaggaccca gtccaggagg cctgggctga    1560
ggacgtggac ctccgggtga actttgccat gaatgttggc aaggcccgag gcttcttcaa    1620
gaagggagat gtggtcattg tgctgaccgg atggcgccct ggctccggct tcaccaacac    1680
catgcgtgtt gttcctgtgc cgtgatggac cccagagccc ctcctccagc cctgtccca    1740 cccccttccc ccagcccatc cattaggcca gcaacgcttg tagaactcac tctgggctgt    1800
aacgtggcac tggtaggttg ggacaccagg gaagaagatc aacgcctcac tgaaacatgg    1860
ctgtgtttgc agcctgctct agtgggacag cccagagcct ggctgcccca tcatgtggcc    1920
ccacccaatc aagggaagaa ggaggaatgc tggactggag gccctggag ccagatggca    1980 agagggtgac agcttccttt cctgtgtgta ctctgtccag ttcctttaga aaaaatggat    2040
gcccagagga ctcccaaccc tggcttgggg tcaagaaaca gccagcaaga gttaggggcc    2100
ttagggcact gggctgttgt tccattgaag ccgactctgg ccctggccct tacttgcttc    2160
tctagctctc taggcctctc cagtttgcac ctgtccccac cctccactca gctgtcctgc    2220
agcaaacact ccaccctcca ccttccattt tcccccacta ctgcagcacc tccaggcctg    2280
ttgccgc                                                              2287

<210> SEQ ID NO 16
<211> LENGTH: 3183
<212> TYPE: DNA
<213> ORGANISM: Homo sapiens

<400> SEQUENCE: 16
cctccaggcc ccgccgcgcg tcccggggc cggccccgcg agcgcaggag taaacaccgc      60
cggagtcttg gagccgctgc agaagggaat aaagagagat gcagggattt gtgaggttac     120
ggcgccccag ctgcaagatg cactagccgg ctgaacccgg gatcggctga cttgttggaa     180
ccggagtgct ctgcacggag agtggtggat gagttgaagt tgccttcccg gggctcattt     240
tccacgctgc cgagaggaat ccgagaggca aggcaatcac ttcgtcttgc cattgattgg     300
gtatcgggag cttttttttt ctcccctctc tctttctttt cctccgtctt gttgcatgca     360
agaaaattac agtccgctgc tcgcccgccc tgggtgcgag atattcagcc ccgctctctc     420
ccgtgcattg tgcaacccaa agatgaaaga ccgaagggga gaaagttaaa gaaatcgccc     480
acatgcgctg gatcagtcca cggcttgggg aaaggcatcc agagaaggtg ggagcggaga     540
gtttgaagtc tttacaggcg ggaagatggc ggactggagc tgaaagtgtt gattgggaaa     600
cttgggtgat tcttgtgttt atttacaatc tccttgaccc aggcaggaca catgcaggcc     660
aaaaaacgct atttcatcct gctctcagct ggctcttgtc tcgccctttt gttttatttc     720
ggaggcttgc agtttagggc atcgaggagc cacagccgga gagaagaaca cagcggtagg     780
aatggcttgc accaccccag tccggatcat ttctggcccc gcttcccgga gcctctgcgc     840
cccttcgttc cttgggatca attggaaaac gaggattcca gcgtgcacat ttccccccgg     900
cagaagcgag atgccaactc cagcatctac aaaggcaaga agtgccgcat ggagtcctgc     960
ttcgatttca cccttttgcaa gaaaaacggc ttcaaagtct acgtataccc acagcaaaaa    1020
ggggagaaaa tcgccgaaag ttaccaaaac attctagcgg ccatcgaggg ctccaggttc    1080
```

-continued

```
tacacctcgg accccagcca ggcgtgcctc tttgtcctga gtctggatac tttagacaga    1140
gaccagttgt cacctcagta tgtgcacaat ttgagatcca aagtgcagag tctccacttg    1200
tggaacaatg gtaggaatca tttaattttt aatttatatt ccggcacttg gcctgactac    1260
accgaggacg tggggtttga catcggccag gcgatgctgg ccaaagccag catcagtact    1320
gaaaacttcc gacccaactt tgatgtttct attcccctct tttctaagga tcatcccagg    1380
acaggagggg agaggggtt tttgaagttc aacaccatcc ctcctctcag gaagtacatg    1440
ctggtattca agggaagag gtacctgaca gggataggat cagacaccag gaatgcctta    1500
tatcacgtcc ataacgggga ggacgttgtg ctcctcacca cctgcaagca tggcaaagac    1560
tggcaaaagc acaaggattc tcgctgtgac agagacaaca ccgagtatga gaagtatgat    1620
tatcgggaaa tgctgcacaa tgccactttc tgtctggttc ctcgtggtcg caggcttggg    1680
tccttcagat tcctggaggc tttgcaggct gcctgcgtcc ctgtgatgct cagcaatgga    1740
tgggagttgc cattctctga agtgattaat tggaaccaag ctgccgtcat aggcgatgag    1800
agattgttat tacagattcc ttctacaatc aggtctattc atcaggataa aatcctagca    1860
cttagacagc agacacaatt cttgtgggag gcttattttt cttcagttga aagattgta    1920 ttaactacac tagagattat tcaggacaga atattcaagc acatatcacg taacagttta    1980
atatggaaca aacatcctgg aggattgttc gtactaccac agtattcatc ttatctggga    2040
gattttcctt actactatgc taatttaggt ttaaagcccc cctccaaatt cactgcagtc    2100
atccatgcgg tgaccccct ggtctctcag tcccagccag tgttgaagct tctcgtggct    2160
gcagccaagt cccagtactg tgcccagatc atagttctat ggaattgtga caagccccta    2220
ccagccaaac accgctggcc tgccactgct gtgcctgtcg tcgtcattga aggagagagc    2280
aaggttatga gcagccgttt tctgccctac gacaacatca tcacagacgc cgtgctcagc    2340
cttgacgagg acacggtgct ttcaacaaca gaggtggatt tcgccttcac agtgtggcag    2400
agcttccctg agaggattgt ggggtacccc gcgcgcagcc acttctggga taactctaag    2460
gagcggtggg gatacacatc aaagtggacg aacgactact ccatggtgtt gacaggagct    2520
gctatttacc acaaatatta tcactaccta tactcccatt acctgccagc cagcctgaag    2580
aacatggtgg accaattggc caattgtgag gacattctca tgaacttcct ggtgtctgct    2640
gtgacaaaat tgcctccaat caaagtgacc cagaagaagc agtataagga cacaatgatg    2700
ggacagactt ctcgggcttc ccgttgggct gaccctgacc actttgccca gcacagagc    2760 tgcatgaata cgtttgccag ctggtttggc tacatgccgc tgatccactc tcagatgagg    2820
ctcgaccccg tcctctttaa agaccaggtc tctattttga ggaagaaata ccgagacatt    2880
gagcgacttt gaggaatccg gctgagtggg ggagggaag caagaaggga tgggggtcaa    2940
gctgctctct cttcccagtg cagatccact catcagcaga gccagattgt gccaactatc    3000
caaaaactta gatgagcaga atgacaaaaa aaaaaaggc caatgagaac tcaactcctg    3060
gctcctggga ctgcaccaga ctgctccaaa ctcacctcac tggcttctgt gtcccaagac    3120
taggttggta cagtttaatt atggaacatt aaataattat ttttgaaaaa aaaaaaaaa    3180 aaa                                                                   3183
```

<210> SEQ ID NO 17
<211> LENGTH: 1016
<212> TYPE: DNA
<213> ORGANISM: Homo sapiens

<400> SEQUENCE: 17

```
atggatacca atgttccgac tggagacggg gagcccgcga gacccgggtc tccagggtct    60
gcccaaggaa gttgctcatg ggagcagacc cctagagcag gatttgaggc caggccaaag   120 agaacccag agatgaaagg cctcctccca ctggcttggt tcctggcttg tagtgtgcct   180
gctgtgcaag gaggcttgct ggacctaaaa tcaatgatcg agaaggtgac agggaagaac   240
gccctgacaa actacggctt ctacggctgt tactgcggct ggggcggccg aggaaccccc   300
aaggatggca ccgattggtg ctgttgggcg catgaccact gctatgggcg gctggaggag   360
aagggctgca acattcgcac acagtcctac aaatacagat tcgcgtgggg cgtggtcacc   420
tgcgagcccg ggcccttctg ccatgtgaac ctctgtgcct gtgaccggaa gctcgtctac   480
tgcctcaaga gaaacctacg gagctacaac ccacagtacc aatactttcc caacatcctc   540
tgctcctagg cctccccagc gagctcctcc cagaccaaga cttttgttct gttttttctac   600 aacacagagt actgactctg cctggttcct gagagaggcc cctaagtcac agacctcagt   660
ctttctcgaa gcttggcgga ccccaggg c cacactgtac cctccagcga gtcccaggag   720
agtgactctg gtcataggac ttggtagggt cccagggtcc ctaggcctcc acttctgagg   780
gcagcccctc tggtgccaag agctctcctc caactcaggg ttggctgtgt ctcttttctt   840
ctctgaagac agcgtcctgg ctccagttgg aacactttcc tgagatgcac ttacttctca   900
gcttctgcga tcagattatc atcaccacca ccctccagag aattttacgc aagaagagcc   960
aaattgactc tctaaatctg gtgtatgggt attaaataaa attcattctc aaggct       1016
```

<210> SEQ ID NO 18
<211> LENGTH: 483
<212> TYPE: DNA
<213> ORGANISM: Homo sapiens
<220> FEATURE:
<221> NAME/KEY: misc_feature
<222> LOCATION: (1)...(483)
<223> OTHER INFORMATION: n = A,T,C or G

<400> SEQUENCE: 18

```
nntttttttt tgttttttaaa aagaattgtt tatttaccga acctgggggca tattagatac    60 aaccaatttt aaatttacat cttttaaatc agttttgaag tgtttcacac acacaaaaaa   120
cttggcatgc aacagttgtc ctaaggtgaa agtcacctca ttaataaact gttgcaagtg   180
ttctcaccca aggtggaagt atggtttatc ctgaacatga aaacctgtaa caaatttaaa   240
ttaattatat aaaactcgtt acttgtagtt ttgcccttgc aaagatccaa aaaaaaaaaa   300
aaaaagcaca gtaactaat atgtatcagt cacaacataa tcctggatca tncccatacc   360
aaaaccggat gctcttttaa ttttaaaccc atcatcagag aacaagagaa agtaatttca   420
ttttacacaa aacaagattn acatgtgcca aaaagaaat accccaaaag aaacaaaaac   480
caa                                                                 483
```

<210> SEQ ID NO 19
<211> LENGTH: 3020
<212> TYPE: DNA
<213> ORGANISM: Homo sapiens

<400> SEQUENCE: 19

```
gttcaaggca gcgcccacac ccgggggctc tccgcaaccc gaccgcctgt ccgctccccc    60
acttcccgcc ctccctccca cctactcatt cacccaccca cccacccaga gccgggacgg   120
cagcccaggc gcccgggccc cgccgtctcc tcgccgcgat cctggacttc ctcttgctgc   180
```

-continued

```
aggacccggc ttccacgtgt gtcccggagc cggcgtctca gcacacgctc cgctccgggc    240
ctgggtgcct acagcagcca gagcagcagg gagtccggga cccggcggc atctgggcca     300 agttaggcgc cgccgaggcc agcgctgaac gtctccaggg ccggaggagc cgcggggcgt    360
ccgggtctga gcctcagcaa atgggctccg acgtgcggga cctgaacgcg ctgctgcccg    420
ccgtcccctc cctgggtggc ggcggcggct gtgccctgcc tgtgagcggc gcggcgcagt    480
gggcgccggt gctggacttt cgcccccgg gcgcttcggc ttacgggtcg ttgggcggcc     540
ccgcgccgcc accggctccg ccgccacccc gccgccgcc gcctcactcc ttcatcaaac     600
aggagccgag ctgggcggc gcggagccgc acgaggagca gtgcctgagc gccttcactg     660 tccactttc cggccagttc actggcacag ccggagcctg tcgctacggg cccttcggtc     720
ctcctccgcc cagccaggcg tcatccggcc aggccaggat gtttcctaac gcgccctacc    780
tgcccagctg cctcgagagc cagcccgcta ttcgcaatca gggttacagc acggtcacct    840
tcgacgggac gcccagctac ggtcacacgc cctcgcacca tgcggcgcag ttccccaacc    900
actcattcaa gcatgaggat ccatgggcc agcagggctc gctgggtgag cagcagtact    960
cggtgccgcc cccggtctat ggctgccaca ccccaccga cagctgcacc ggcagccagg   1020
ctttgctgct gaggacgccc tacagcagtg acaatttata ccaaatgaca tcccagcttg   1080
aatgcatgac ctggaatcag atgaacttag gagccacctt aaagggagtt gctgctggga   1140
gctccagctc agtgaaatgg acagaagggc agagcaacca cagcacaggg tacgagagcg   1200
ataaccacac aacgcccatc ctctgcgag cccaatacag aatacacacg cacggtgtct    1260
tcagaggcat tcaggatgtg cgacgtgtgc ctggagtagc cccgactctt gtacggtcgg   1320
catctgagac cagtgagaaa cgccccttca tgtgtgctta cccaggctgc aataagagat   1380
attttaagct gtcccactta cagatgcaca gcaggaagca cactggtgag aaaccatacc   1440
agtgtgactt caaggactgt gaacgaaggt tttctcgttc agaccagctc aaaagacacc   1500
aaaggagaca tacaggtgtg aaaccattcc agtgtaaaac ttgtcagcga agttctcccc   1560
ggtccgacca cctgaagacc cacaccagga ctcatacagg taaaacaagt gaaaagccct   1620
tcagctgtcg gtggccaagt tgtcagaaaa gtttgcccg gtcagatgaa ttagtccgcc   1680 atcacaaacat gcatcagaga acatgacca aactccagct ggcgctttga ggggtctccc   1740
tcggggaccg ttcagtgtcc caggcagcac agtgtgtgaa ctgctttcaa gtctgactct   1800
ccactcctcc tcactaaaaa ggaaacttca gttgatcttc ttcatccaac ttccaagaca   1860
agataccggt gcttctggaa actaccaggt gtgcctggaa gagttggtct ctgccctgcc   1920
tacttttagt tgactcacag gccctggaga agcagctaac aatgtctggt tagttaaaag   1980
cccattgcca tttggtctgg attttctact gtaagaagag ccatagctga tcatgtcccc   2040
ctgacccttc ccttctttt ttatgctcgt tttcgctggg gatggaatta ttgtaccatt    2100
ttctatcatg gaatatttat aggccagggc atgtgtatgt gtctgctaat gtaaactttg   2160
tcatggtttc catttactaa cagcaacagc aagaaataaa tcagagagca aggcatcggg   2220
ggtgaatctt gtctaacatt cccgaggtca gccaggctgc taacctggaa agcaggatgt   2280
agttctgcca ggcaactttt aaagctcatg catttcaagc agctgaagaa agaatcagaa   2340
ctaaccagta cctctgtata gaaatctaaa agaatttac cattcagtta attcaatgtg    2400
aacactggca cactgctctt aagaaactat gaagatctga gattttttg tgtatgtttt    2460 tgactctttt gagtggtaat catatgtgtc tttatagatg tacatacctc cttgcacaaa   2520
tggaggggaa ttcattttca tcactgggac tgtccttagt gtataaaaac catgctggta   2580
```

```
tatggcttca agttgtaaaa atgaaagtga ctttaaaaga aaatagggga tggtccagga    2640
tctccactga taagactgtt tttaagtaac ttaaggacct ttgggtctac aagtatatgt    2700
gaaaaaaatg agacttactg ggtgaggaaa tccattgttt aaagatggtc gtgtgtgtgt    2760
gtgtgtgtgt gtgtgtgttg tgttgtgttt tgtttttaa gggagggaat ttattattta     2820
ccgttgcttg aaattactgt gtaaatatat gtctgataat gatttgctct ttgacaacta    2880
aaattaggac tgtataagta ctagatgcat cactgggtgt tgatcttaca agatattgat    2940
gataacactt aaaattgtaa cctgcatttt tcactttgct ctcaattaaa gtctattcaa    3000
aaggaaaaaa aaaaaaaaa                                                 3020

<210> SEQ ID NO 20
<211> LENGTH: 13993
<212> TYPE: DNA
<213> ORGANISM: Homo sapiens

<400> SEQUENCE: 20
atggacccgc cgaggcccgc gctgctggcg ctgctggcgc tgcctgcgct gctgctgctg    60
ctgctggcgg gcgccagggc cgaagaggaa atgctggaaa atgtcagcct ggtctgtcca    120
aaagatgcga cccgattcaa gcacctccgg aagtacacat acaactatga ggctgagagt    180
tccagtggag tccctgggac tgctgattca agaagtgcca ccaggatcaa ctgcaaggtt    240
gagctggagg ttccccagct ctgcagcttc atcctgaaga ccagccagtg caccctgaaa    300
gaggtgtatg cttcaaccc tgagggcaaa gccttgctga gaaaaccaa gaactctgag    360 gagtttgctg cagccatgtc caggtatgag ctcaagctgg ccattccaga agggaagcag    420
gtttttcctt acccggagaa agatgaacct acttacatcc tgaacatcaa gagggggcatc    480 atttctgccc tcctggttcc cccagagaca gaagaagcca agcaagtgtt gtttctggat    540
accgtgtatg gaaactgctc cactcacttt accgtcaaga cgaggaaggg caatgtggca    600
acagaaatat ccactgaaag agacctgggg cagtgtgatc gcttcaagcc catccgcaca    660
ggcatcagcc cacttgctct catcaaaggc atgacccgcc ccttgtcaac tctgatcagc    720
agcagccagt cctgtcagta cactggac gctaagagga agcatgtggc agaagccatc    780
tgcaaggagc aacacctctt cctgcctttc tcctacaaga taagtatgg gatggtagca    840 caagtgacac agacttgaa acttgaagac acaccaaaga tcaacagccg cttcttggt    900 gaaggtacta gaagatggg cctcgcattt gagagcacca atccacatc acctccaaag    960 caggccgaag ctgttttgaa gactctccag gaactgaaaa aactaaccat ctctgagcaa    1020
aatatccaga gagctaatct cttcaataag ctggttactg agctgagagg cctcagtgat    1080
gaagcagtca catctctctt gccacagctg attgaggtgt ccagccccat cactttacaa    1140
gccttggttc agtgtggaca gcctcagtgc tccactcaca tcctccagtg gctgaaacgt    1200
gtgcatgcca ccccttct gatagatgtg gtcacctacc tggtggccct gatccccgag    1260
ccctcagcac agcagctgcg agagatcttc aacatgcgca gggatcagcg cagccgagcc    1320
accttgtatg cgctgagcca cgcggtcaac aactatcata gacaaaccc tacagggacc    1380 caggagctgc tggacattgc taattacctg atggaacaga ttcaagatga ctgcactggg    1440
gatgaagatt acacctattt gattctgcgg gtcattggaa atatgggcca aaccatggag    1500
cagttaactc cagaactcaa gtcttcaatc ctgaaatgtg tccaaagtac aaagccatca    1560
ctgatgatcc agaaagctgc catccaggct ctgcggaaaa tggagcctaa agacaaggac    1620
```

-continued

```
caggaggttc ttcttcagac tttccttgat gatgcttctc cgggagataa gcgactggct    1680
gcctatctta tgttgatgag gagtccttca caggcagata ttaacaaaat tgtccaaatt    1740
ctaccatggg aacagaatga gcaagtgaag aactttgtgg cttcccatat tgccaatatc    1800
ttgaactcag aagaattgga tatccaagat ctgaaaaagt tagtgaaaga agctctgaaa    1860
gaatctcaac ttccaactgt catggacttc agaaaattct ctcggaacta tcaactctac    1920
aaatctgttt ctcttccatc acttgaccca gcctcagcca aaatagaagg gaatcttata    1980
tttgatccaa ataactacct tcctaaagaa agcatgctga aaactaccct cactgccttt    2040
ggatttgctt cagctgacct catcgagatt ggcttggaag gaaaaggctt tgagccaaca    2100
ttggaggctc cttttgggaa gcaaggattt tcccagaca gtgtcaacaa agctttgtac     2160
tgggttaatg gtcaagttcc tgatggtgtc tctaaggtct tagtggacca ctttggctat    2220
accaaagatg ataaacatga gcaggatatg gtaaatggaa taatgctcag tgttgagaag    2280
ctgattaaag atttgaaatc caagaagtc ccggaagcca gagcctacct ccgcatcttg     2340
ggagaggagc ttggttttgc cagtctccat gacctccgac tcctgggaaa gctgcttctg    2400
atgggtgccc gcactctgca ggggatcccc cagatgattg gagaggtcat caggaagggc    2460
tcaaagaatg acttttttct tcactacatc ttcatggaga atgcctttga actccccact    2520
ggagctggat tacagttgca aatatcttca tctggagtca ttgctcccgg agccaaggct    2580
ggagtaaaac tggaagtagc caacatgcag gctgaactgg tggcaaaacc ctccgtgtct    2640
gtggagtttg tgacaaatat gggcatcatc attccggact tcgctaggag tggggtccag    2700
atgaacacca acttcttcca cgagtcgggt ctggaggctc atgttgccct aaaagctggg    2760
aagctgaagt ttatcattcc ttccccaaag agaccagtca agctgctcag tggaggcaac    2820
acattacatt tggtctctac caccaaaacg gaggtcatcc cacctctcat tgagaacagg    2880
cagtcctggt cagtttgcaa gcaagtcttt cctggcctga attactgcac tcaggcgct    2940 tactccaacg ccagctccac agactccgcc tcctactatc cgctgaccgg ggacaccaga    3000
ttagagctgg aactgaggcc tacaggagag attgagcagt attctgtcag cgcaacctat    3060
gagctccaga gagaggacag agccttggtg gatacccctga gtttgtaac tcaagcagaa    3120 ggcgcgaagc agactgaggc taccatgaca ttcaaatata tcggcagag tatgaccttg    3180 tccagtgaag tccaaattcc ggattttgat gttgacctcg aacaatcct cagagttaat    3240 gatgaatcta ctgagggcaa aacgtcttac agactcaccc tggacattca gaacaagaaa    3300
attactgagg tcgccctcat gggccaccta agttgtgaca caaaggaaga agaaaaaatc    3360
aagggtgtta tttccatacc ccgtttgcaa gcagaagcca gaagtgagat cctcgcccac    3420
tggtcgcctg ccaaactgct tctccaaatg gactcatctg ctacagctta tggctccaca    3480
gtttccaaga gggtggcatg gcattatgat aagagaaga ttgaatttga atggaacaca    3540
ggcaccaatg tagataccaa aaaatgact tccaatttcc ctgtggatct ctccgattat    3600
cctaagagct tgcatatgta tgctaataga ctcctggatc acagagtccc tcaaacagac    3660
atgactttcc ggcacgtggg ttccaaatta atagttgcaa tgagctcatg gcttcagaag    3720
gcatctggga gtcttcctta tacccagact ttgcaagacc acctcaatag cctgaaggag    3780
ttcaacctcc agaacatggg attgccagac tcccacatcc cagaaaacct cttcttaaaa    3840
agcgatggcc gcgtcaaata taccttgaac aagaacagtt tgaaaattga gattcctttg    3900
ccttttggtg gcaaatcctc cagagatcta aagatgttag agactgttag gacaccagcc    3960
ctccacttca gtctgtggg attccatctg ccatctcgag agttccaagt ccctactttt    4020
```

```
accattccca agttgtatca actgcaagtg cctctcctgg gtgttctaga cctctccacg    4080
aatgtctaca gcaacttgta caactggtcc gcctcctaca gtggtggcaa caccagcaca    4140
gaccatttca gccttcgggc tcgttaccac atgaaggctg actctgtggt tgacctgctt    4200
tcctacaatg tgcaaggatc tggagaaaca acatatgacc acaagaatac gttcacacta    4260
tcatgtgatg ggtctctacg ccacaaattt ctagattcga atatcaaatt cagtcatgta    4320
gaaaaacttg gaaacaaccc agtctcaaaa ggtttactaa tattcgatgc atctagttcc    4380
tggggaccac agatgtctgc ttcagttcat ttggactcca aaaagaaaca gcatttgttt    4440
gtcaaagaag tcaagattga tgggcagttc agagtctctt cgttctatgc taaaggcaca    4500
tatggcctgt cttgtcagag ggatcctaac actggccggc tcaatggaga gtccaacctg    4560
aggtttaact cctcctacct ccaaggcacc aaccagataa caggaagata tgaagatgga    4620
accctctccc tcacctccac ctctgatctg caaagtggca tcattaaaaa tactgcttcc    4680
ctaaagtatg agaactacga gctgacttta aaatctgaca ccaatgggaa gtataagaac    4740
tttgccactt ctaacaagat ggatatgacc ttctctaagc aaaatgcact gctgcgttct    4800
gaatatcagg ctgattacga gtcattgagg ttcttcagcc tgctttctgg atcactaaat    4860
tcccatggtc ttgagttaaa tgctgacatc ttaggcactg acaaaattaa tagtggtgct    4920
cacaaggcga cactaaggat tggccaagat ggaatatcta ccagtgcaac gaccaacttg    4980
aagtgtagtc tcctggtgct ggagaatgag ctgaatgcag agcttggcct ctctggggca    5040
tctatgaaat taacaacaaa tggccgcttc agggaacaca atgcaaaatt cagtctggat    5100
gggaaagccg ccctcacaga gctatcactg ggaagtgctt atcaggccat gattctgggt    5160
gtcgacagca aaaacatttt caacttcaag gtcagtcaag aaggacttaa gctctcaaat    5220
gacatgatgg gctcatatgc tgaaatgaaa tttgaccaca caaacagtct gaacattgca    5280
ggcttatcac tggacttctc ttcaaaactt gacaacattt acagctctga caagttttat    5340
aagcaaactg ttaatttaca gctacagccc tattctctgg taactacttt aaacagtgac    5400
ctgaaataca atgctctgga tctcaccaac aatgggaaac tacggctaga cccctgaag    5460 ctgcatgtgg ctggtaacct aaaaggagcc taccaaaata tgaaataaa acacatctat    5520 gccatctctt ctgctgcctt atcagcaagc tataaagcag acactgttgc taaggttcag    5580
ggtgtggagt ttagccatgg gctcaacaca gacatcgctg ggctggcttc agccattgac    5640
atgagcacaa actataattc agactcactg catttcagca atgtcttccg ttctgtaatg    5700
gccccgttta ccatgaccat cgatgcacat acaaatggca atgggaaact cgctctctgg    5760
ggagaacata ctgggcagct gtatagcaaa ttcctgttga aagcagaacc tctggcattt    5820
actttctctc atgattacaa aggctccaca agtcatcatc tcgtgtctag gaaaagcatc    5880
agtgcagctc ttgaacacaa agtcagtgcc ctgcttactc cagctgagca gacaggcacc    5940
tggaaactca agacccaatt taacaacaat gaatacagcc aggacttgga tgcttacaac    6000
actaaagata aaattggcgt ggagcttact ggacgaactc tggctgacct aactctacta    6060
gactccccaa ttaaagtgcc acttttactc agtgagccca tcaatatcaa tgatgcttta    6120
gagatgagag atgccgttga gaagcccaa gaatttacaa ttgttgcttt tgtaaagtat    6180
gataaaaacc aagatgttca ctccattaac ctcccatttt ttgagacctt gcaagaatat    6240
tttgagagga atcgacaaac cattatagtt gtactgaaaa acgtacagag aaacctgaag    6300
cacatcaata ttgatcaatt tgtaagaaaa tacagagcag ccctgggaaa actcccacag    6360
```

```
caagctaatg attatctgaa ttcattcaat tgggagagac aagtttcaca tgccaaggag    6420
aaactgactg ctctcacaaa aaagtataga attacagaaa atgatataca aattgcatta    6480
gatgatgcca aaatcaactt taatgaaaaa ctatctcaac tgcagacata tatgatacaa    6540
tttgatcagt atattaaaga tagttatgat ttacatgatt tgaaaatagc tattgctaat    6600
attattgatg aaatcattga aaattaaaa agtcttgatg agcactatca tacccgtgta     6660
aatttagtaa aaacaatcca tgatctacat ttgtttattg aaaatattga ttttaacaaa    6720
agtggaagta gtactgcatc ctggattcaa aatgtggata ctaagtacca aatcagaatc    6780
cagatacaag aaaaactgca gcagcttaag agacacatac agaatataga catccagcac    6840
ctagctggaa agttaaaaca acacattgag gctattgatg ttagagtgct tttagatcaa    6900
ttgggaacta caatttcatt tgaaagaata atgatgttc ttgagcatgt caaacacttt     6960
gttataaatc ttattgggga ttttgaagta gctgagaaaa tcaatgcctt cagagccaaa    7020
gtccatgagt taatcgagag gtatgaagta gaccaacaaa tccaggtttt aatggataaa    7080
ttagtagagt tggcccacca atacaagttg aaggagacta ttcagaagct aagcaatgtc    7140
ctacaacaag ttaagataaa agattacttt gagaaattgg ttggatttat tgatgatgct    7200
gtcaagaagc ttaatgaatt atcttttaaa acattcattg aagatgttaa caaattcctt    7260
gacatgttga taaagaaatt aaagtcattt gattaccacc agtttgtaga tgaaaccaat    7320
gacaaaatcc gtgaggtgac tcagagactc aatggtgaaa ttcaggctct ggaactacca    7380
caaaaagctg aagcattaaa actgttttta gaggaaacca aggccacagt tgcagtgtat    7440
ctggaaagcc tacaggacac caaaataacc ttaatcatca attggttaca ggaggcttta    7500
agttcagcat ctttggctca catgaaggcc aaattccgag agactctaga agatacacga    7560
gaccgaatgt atcaaatgga cattcagcag gaacttcaac gatacctgtc tctggtaggc    7620
caggtttata gcacacttgt cacctacatt tctgattggt ggactcttgc tgctaagaac    7680
cttactgact tgcagagca atattctatc caagattggg ctaaacgtat gaaagcattg    7740
gtagagcaag ggttcactgt tcctgaaatc aagaccatcc ttgggaccat gcctgccttt    7800
gaagtcagtc ttcaggctct tcagaaagct accttccaga cacctgattt tatagtcccc    7860
ctaacagatt tgaggattcc atcagttcag ataaacttca aagacttaaa aaatataaaa    7920
atcccatcca ggttttccac accagaattt accatcctta cacctcca cattcctcc       7980 tttcaattg actttgtaga aatgaaagta aagatcatca gaaccattga ccagatgctg    8040
aacagtgagc tgcagtggcc cgttccagat atatatctca gggatctgaa ggtggaggac    8100
attcctctag cgagaatcac cctgccagac ttccgtttac cagaaatcgc aattccagaa    8160
ttcataatcc caactctcaa ccttaatgat tttcaagttc ctgaccttca cataccagaa    8220
ttccagcttc cccacatctc acacacaatt gaagtaccta cttttggcaa gctatacagt    8280
attctgaaaa tccaatctcc tctttttcaca ttagatgcaa atgctgacat agggaatgga    8340
accacctcag caaacgaagc aggtatcgca gcttccatca ctgccaaagg agagtccaaa    8400
ttagaagttc tcaattttga ttttcaagca aatgcacaac tctcaaaccc taagattaat    8460
ccgctggctc tgaaggagtc agtgaagttc tccagcaagt acctgagaac ggagcatggg    8520
agtgaaatgc tgttttttgg aaatgctatt gagggaaaat caaacacagt ggcaagttta    8580
cacacagaaa aaaatacact ggagcttagt aatggagtga ttgtcaagat aaacaatcag    8640
cttaccctgg atagcaacac taaatacttc acaaaattga acatccccaa actggacttc    8700
tctagtcagg ctgacctgcg caacgagatc aagacactgt tgaaagctgg ccacatagca    8760
```

-continued

```
tggacttctt ctggaaaagg gtcatggaaa tgggcctcgc ccagattctc agatgaggga    8820
acacatgaat cacaaattag tttcaccata gaaggacccc tcacttcctt tggactgtcc    8880
aataagatca atagcaaaca cctaagagta aaccaaaact tggtttatga atctggctcc    8940
ctcaactttt ctaaacttga aattcaatca caagtcgatt cccagcatgt gggccacagt    9000
gttctaactg ctaaaggcat ggcactgttt ggagaaggga aggcagagtt tactgggagg    9060
catgatgctc atttaaatgg aaaggttatt ggaactttga aaaattctct tttcttttca    9120
gcccagccat ttgagatcac ggcatccaca aacaatgaag ggaatttgaa agttcgtttt    9180
ccattaaggt taacagggaa gatagacttc ctgaataact atgcactgtt tctgagtccc    9240
agtgcccagc aagcaagttg gcaagtaagt gctaggttca atcagtataa gtacaaccaa    9300
aatttctctg ctggaaacaa cgagaacatt atggaggccc atgtaggaat aaatggagaa    9360
gcaaatctgg atttcttaaa cattccttta acaattcctg aaatgcgtct accttacaca    9420
ataatcacaa ctcctccact gaaagatttc tctctatggg aaaaaacagg cttgaaggaa    9480
ttcttgaaaa cgacaaagca atcatttgat ttaagtgtaa aagctcagta taagaaaaac    9540
aaacacaggc attccatcac aaatcctttg gctgtgcttt gtgagtttat cagtcagagc    9600
atcaaatcct ttgacaggca ttttgaaaaa aacagaaaca atgcattaga ttttgtcacc    9660
aaatcctata atgaaacaaa aattaagttt gataagtaca aagctgaaaa atctcacgac    9720
gagctcccca ggacctttca aattcctgga tacactgttc cagttgtcaa tgttgaagtg    9780
tctccattca ccatagagat gtcggcattc ggctatgtgt cccaaaagc agtcagcatg    9840 cctagtttct ccatcatagg ttctgacgtc cgtgtgcctt catacacatt aatcctgcca    9900
tcattagagc tgccagtcct tcatgtccct agaaatctca agctttctct tccagatttc    9960
aaggaattgt gtaccataag ccatattttt attcctgcca tgggcaatat tacctatgat   10020 ttctcccttta aatcaagtgt catcacactg aataccaatg ctgaactttt taaccagtca   10080
gatattgttg ctcatctcct ttcttcatct tcatctgtca ttgatgcact gcagtacaaa   10140
ttagagggca ccacaagatt gacaagaaaa aggggattga agttagccac agctctgtct   10200
ctgagcaaca aatttgtgga gggtagtcat aacagtactg tgagcttaac cacgaaaaat   10260
atggaagtgt cagtggcaaa aaccacaaaa ccggaaattc caattttgag aatgaatttc   10320
aagcaagaac ttaatggaaa taccaagtca aaacctactg tctcttcctc catggaattt   10380
aagtatgatt tcaattcttc aatgctgtac tctaccgcta aaggagcagt tgaccacaag   10440
cttagcttgg aaagcctcac ctcttacttt tccattgagt catctaccaa aggagatgtc   10500
aagggttcgg ttctttctcg ggaatattca ggaactattg ctagtgaggc caacacttac   10560
ttgaattcca agagcacacg gtcttcagtg aagctgcagg gcacttccaa aattgatgat   10620
atctggaacc ttgaagtaaa agaaaatttt gctggagaag ccacactcca acgcatatat   10680
tccctctggg agcacagtac gaaaaaccac ttacagctag agggcctctt tttcaccaac   10740
ggagaacata caagcaaagc cacccctggaa ctctctccat ggcaaatgtc agctcttgtt   10800
caggtccatg caagtcagcc cagttccttc catgatttcc ctgaccttgg ccaggaagtg   10860
gccctgaatg ctaacactaa gaaccagaag atcagatgga aaaatgaagt ccggattcat   10920 tctggtgtctt tccagagcca ggtcgagctt tccaatgacc aagaaaaggc acaccttgac   10980
attgcaggat cctttagaagg acacctaagg ttcctcaaaa atatcatcct accagtctat   11040
gacaagagct tatgggattt cctaaagctg gatgtcacca ccagcattgg taggagacag   11100
```

-continued

```
catcttcgtg tttcaactgc ctttgtgtac accaaaaacc ccaatggcta ttcattctcc    11160
atccctgtaa aagttttggc tgataaattc attattcctg ggctgaaact aaatgatcta    11220
aattcagttc ttgtcatgcc tacgttccat gtcccattta cagatcttca ggttccatcg    11280
tgcaaacttg acttcagaga aatacaaatc tataagaagc tgagaacttc atcatttgcc    11340
ctcaccctac caacactccc cgaggtaaaa ttccctgaag ttgatgtgtt aacaaaatat    11400
tctcaaccag aagactcctt gattcccttt tttgagataa ccgtgcctga atctcagtta    11460
actgtgtccc agttcacgct tccaaaaagt gtttcagatg cattgctgc tttggatcta     11520 aatgcagtag ccaacaagat cgcagacttt gagttgccca ccatcatcgt gcctgagcag    11580
accattgaga ttccctccat taagttctct gtacctgctg gaattgtcat tccttccttt    11640
caagcactga ctgcacgctt tgaggtagac tctcccgtgt ataatgccac ttggagtgcc    11700
agtttgaaaa acaaagcaga ttatgttgaa acagtcctgg attccacatg cagctcaacc    11760
gtacagttcc tagaatatga actaaatgtt ttgggaacac acaaaatcga agatggtacg    11820
ttagcctcta agactaaagg aacacttgca caccgtgact tcagtgcaga atatgaagaa    11880
gatggcaaat atgaaggact tcaggaatgg aaggaaaag cgcacctcaa tatcaaaagc     11940
ccagcgttca ccgatctcca tctgcgctac cagaaagaca agaaaggcat ctccacctca    12000
gcagcctccc cagccgtagg caccgtgggc atggatatgg atgaagatga cgacttttct    12060 aaaatggaact tctactacag ccctcagtcc tctccagata aaaaactcac catattcaaa    12120
actgagttga gggtccggga atctgatgag gaaactcaga tcaaagttaa ttgggaagaa    12180
gaggcagctt ctggcttgct aacctctctg aaagacaacg tgcccaaggc cacaggggtc    12240
ctttatgatt atgtcaacaa gtaccactgg gaacacacag ggctcaccct gagagaagtg    12300
tcttcaaagc tgagaagaaa tctgcagaac aatgctgagt gggtttatca agggccatt     12360 aggcaaattg atgatatcga cgtgaggttc cagaaagcag ccagtggcac cactgggacc    12420
taccaagagt ggaaggacaa ggcccagaat ctgtaccagg aactgttgac tcaggaaggc    12480
caagccagtt ccagggact caaggataac gtgtttgatg gcttggtacg agttactcaa     12540
aaattccata tgaaagtcaa gaagctgatt gactcactca ttgattttct gaacttcccc    12600
agattccagt ttccggggaa acctgggata tacactaggg aggaactttg cactatgttc    12660
atgagggagg tagggacggt actgtcccag gtatattcga aagtccataa tggttcagaa    12720
atactgtttt cctatttcca agacctagtg attcacttc ctttcgagtt aaggaaacat      12780
aaactaatag atgtaatctc gatgtatagg gaactgttga agatttatc aaaagaagcc     12840 caagaggtat ttaaagccat tcagtctctc aagaccacag aggtgctacg taatcttcag    12900
gaccttttac aattcatttt ccaactaata gaagataaca ttaaacagct gaaagagatg    12960
aaatttactt atcttattaa ttatatccaa gatgagatca cacaatctt caatgattat      13020 atcccatatg tttttaaatt gttgaaagaa aacctatgcc ttaatcttca agttcaat       13080 gaatttattc aaaacgagct tcaggaagct tctcaagagt tacagcagat ccatcaatac    13140
attatggccc ttcgtgaaga atattttgat ccaagtatag ttggctggac agtgaaatat    13200
tatgaacttg aagaaagat agtcagtctg atcaagaacc tgttagttgc tcttaaggac     13260
ttccattctg aatatattgt cagtgcctct aactttactt cccaactctc aagtcaagtt    13320
gagcaatttc tgcacagaaa tattcaggaa tatcttagca tccttaccga tccagatgga    13380
aaagggaaag agaagattgc agagctttct gccactgctc aggaaataat taaaagccag    13440
gccattgcga cgaagaaaat aatttctgat taccaccagc agtttagata taaactgcaa    13500
```

-continued

| | |
|---|---|
| gatttttcag accaactctc tgattactat gaaaaattta ttgctgaatc caaaagattg | 13560 |
| attgacctgt ccattcaaaa ctaccacaca tttctgatat acatcacgga gttactgaaa | 13620 |
| aagctgcaat caaccacagt catgaacccc tacatgaagc ttgctccagg agaacttact | 13680 |
| atcatcctct aatttttta aaagaaatct tcatttattc ttcttttcca attgaacttt | 13740 |
| cacatagcac agaaaaaatt caaactgcct atattgataa aaccatacag tgagccagcc | 13800 |
| ttgcagtagg cagtagacta taagcagaag cacatatgaa ctggacctgc accaaagctg | 13860 |
| gcaccagggc tcggaaggtc tctgaactca gaaggatggc attttttgca agttaaagaa | 13920 |
| aatcaggatc tgagttattt tgctaaactt gggggaggag gaacaaataa atggagtctt | 13980 |
| tattgtgtat cat | 13993 |

<210> SEQ ID NO 21
<211> LENGTH: 1965
<212> TYPE: DNA
<213> ORGANISM: Homo sapiens

<400> SEQUENCE: 21

| | |
|---|---|
| caattccggg ccgccccgga gaccacctcc tcctcctcgt cgtcgtcctc cgcctcctgc | 60 |
| gcctcgtcct cgtcctcctc caattcggcc agcgccccct cggctgcctg caagagcgcg | 120 |
| ggcggcggcg gcgcgggcgc cgggagcggg ggcgccaaga aggcgagctc ggggctgcgg | 180 |
| cggcccgaga agccgcccta ctcgtacatc gcgctcatcg tcatggccat ccagagctcg | 240 |
| cccagcaagc gcctgacgct cagcgagatc taccagttcc tgcaggcgcg cttccccttc | 300 |
| ttccgcggcg cctaccaggg ctggaagaac tcggtgcgcc acaatctctc gctcaacgag | 360 |
| tgcttcatca agctgcctaa gggcctcggg cggcccggca agggccacta ctggaccatc | 420 |
| gacccggcca gcgagttcat gttcgaggag ggctcgttcc gccgccggcc gcgcggcttc | 480 |
| aggcggaagt gccaggcgct caagcccatg taccaccgcg tggtgagcgg cttgggcttc | 540 |
| ggggcgtcgc tgctgcccca gggcttcgac ttccaggcgc cccgtcggc gccgctcggc | 600 |
| tgccacagcc agggcggcta cggcggcctc gacatgatgc ccgcgggcta cgacgccggc | 660 |
| gcgggcgccc ccagccacgc gcaccctcac caccaccacc accaccacgt cccgcacatg | 720 |
| tcgcccaacc cgggttccac ctacatggcc agctgcccgg tgcccgcggg acccgggggc | 780 |
| gtcggtgcgg ccggggcgg cggcggcggc gactacgggc cggacagcag cagcagcccg | 840 |
| gtaccctcgt ccccggccat ggcgagcgcc atcgaatgcc actcgcccta cacgagccct | 900 |
| gcggcgcact ggagctcgcc tggcgcctcg ccttacctca agcagccgcc tgccctgacg | 960 |
| cccagcagca cccccgccgc ctcggcaggc ctgcactcca gcatgtcctc ctactcgctg | 1020 |
| gagcagagct acttgcacca gaacgctcgc gaggacctct cagtgggact gcccgttac | 1080 |
| cagcatcact ctactccagt gtgtgacaga aagatttcg tcctcaactt caatgggatt | 1140 |
| tcttctttcc atccctcagc tagcgggtcg tattatcacc atcaccacca gagcgtctgt | 1200 |
| caggatatta agccctgcgt catgtgaacg gaaagaggcc aagcgatggc cgctctctcc | 1260 |
| tctcccctcc tcagaggggg cagatagaaa ctgggacgga ttcaagtcac atgcacgcgg | 1320 |
| atagcagtaa gccacacacc tgccacttag ccagaatgcc caggatcgcg ttggtcactg | 1380 |
| ttatttgcct actgctggaa gaaggacaac cgctggcaag gtagcgttcc ccaatctgaa | 1440 |
| tacctgcagg ctcccacatg agggagaggg cagactcagg tgggaagatg tgccatgcgt | 1500 |
| aaggcatcaa cgtgtatctg tgggatcttc gttgccttca gtaatcaggg tgtgaaaaaa | 1560 |

-continued

| | | |
|---|---|---|
| gcagacaagt tgtgtgtgtg tgtgtgtgtc taagaaaact tgtgtgcttt tcaaaaaggc | 1620 |
| agtgctaagc acaagatttc aagaaagcct cttcttgttg cctagctgag tgggagagtc | 1680 |
| attttcccca gacactacat ttggatacag gtgccaaaga acattattaa ggaattattt | 1740 |
| agaaacaatg tgtctagttt aagaaagtgg ttttcagtat tgtgacaata caacgttttt | 1800 |
| acaaggttgt tttctaccac catattttaa agatatttt atgaccgtgt atactcacac | 1860 |
| tttgcttgta ttttaaaagg aggatatatt tgcacttatg tatactttta cagtttgcca | 1920 |
| aaatatttg ttgtaaaatt tttttcaat aaaatgtata taaca | 1965 |

<210> SEQ ID NO 22
<211> LENGTH: 1805
<212> TYPE: DNA
<213> ORGANISM: Homo sapiens

<400> SEQUENCE: 22

| | | |
|---|---|---|
| aagagactga actgtatctg cctctatttc caaaagactc acgttcaact ttcgctcaca | 60 |
| caaagccggg aaaattttat tagtcctttt tttaaaaaaa gttaatataa aattatagca | 120 |
| aaaaaaaaaa ggaacctgaa ctttagtaac acagctggaa caatcgcagc ggcggcggca | 180 |
| gcggcgggag aagaggttta atttagttga ttttctgtgg ttgttggttg ttcgctagtc | 240 |
| tcacggtgat ggaagctgca cattttttcg aagggaccga gaagctgctg gaggtttggt | 300 |
| tctcccggca gcagcccgac gcaaaccaag gatctgggga tcttcgcact atcccaagat | 360 |
| ctgagtggga catactttg aaggatgtgc aatgttcaat cataagtgtg acaaaaactg | 420 |
| acaagcagga agcttatgta ctcagtgaga gtagcatgtt tgtctccaag agacgtttca | 480 |
| ttttgaagac atgtggtacc accctcttgc tgaaagcact ggttccctg ttgaagcttg | 540 |
| ctagggatta cagtgggttt gactcaattc aaagcttctt ttattctcgt aagaatttca | 600 |
| tgaagccttc tcaccaaggg tacccacacc ggaatttcca ggaagaaata gagtttctta | 660 |
| atgcaatttt cccaaatgga gcaggatatt gtatgggacg tatgaattct gactgttggt | 720 |
| acttatatac tctggatttc ccagagagtc gggtaatcag tcagccagat caaaccttgg | 780 |
| aaattctgat gagtgagctt gacccagcag ttatggacca gttctacatg aaagatggtg | 840 |
| ttactgcaaa ggatgtcact cgtgagagtg gaattcgtga cctgatacca ggttctgtca | 900 |
| tgatgccac aatgttcaat ccttgtgggt attcgatgaa tggaatgaaa tcggatggaa | 960 |
| cttattggac tattcacatc actccagaac cagaattttc ttatgttagc tttgaaacaa | 1020 |
| acttaagtca gacctcctat gatgacctga tcaggaaagt tgtagaagtc ttcaagccag | 1080 |
| gaaaatttgt gaccaccttg tttgttaatc agagttctaa atgtcgcaca gtgcttgctt | 1140 |
| cgccccagaa gattgaaggt tttaagcgtc ttgattgcca gagtgctatg ttcaatgatt | 1200 |
| acaattttgt ttttaccagt tttgctaaga agcagcaaca acagcagagt tgattaagaa | 1260 |
| aaatgaagaa aaaacgcaaa aagagaacac atgtagaagg tggtggatgc tttctagatg | 1320 |
| tcgatgctgg gggcagtgct ttccataacc accactgtgt agttgcagaa agccctagat | 1380 |
| gtaatgatag tgtaatcatt ttgaattgta tgcattatta tatcaaggag ttagatatct | 1440 |
| tgcatgaatg ctctcttctg tgtttaggta ttctctgcca ctcttgctgt gaaattgaag | 1500 |
| tggatgtaga aaaaaccttt tactatatga aacttacaa cacttgtgaa agcaactcaa | 1560 |
| tttggtttat gcacagtgta atatttctcc aagtatcatc caaaattccc cacagacaag | 1620 |
| gctttcgtcc tcattaggtg ttggcctcag cctaaccctc taggactgtt ctattaaatt | 1680 |
| gctgccagaa ttttacatcc agttacctcc actttctaga acatattctt tactaatgtt | 1740 |

-continued

```
attgaaacca atttctactt catactgatg tttttggaaa cagcaattaa agttttctt     1800 ccatg                                                                1805

<210> SEQ ID NO 23
<211> LENGTH: 3741
<212> TYPE: DNA
<213> ORGANISM: Homo sapiens

<400> SEQUENCE: 23
gaattccgtc atggcgtcgc agccaaattc gtctgcgaag aagaaagagg agaaggggaa      60
gaacatccag gtggtggtga gatgcagacc atttaatttg gcagagcgga aagctagcgc     120
ccattcaata gtagaatgtg atcctgtacg aaaagaagtt agtgtacgaa ctggaggatt     180
ggctgacaag agctcaagga aaacatacac ttttgatatg gtgtttggag catctactaa     240
acagattgat gtttaccgaa gtgttgtttg tccaattctg gatgaagtta ttatgggcta     300
taattgcact atctttgcgt atggccaaac tggcactgga aaaacttttta caatggaagg     360 tgaaaggtca cctaatgaag agtataccctg ggaagaggat cccttggctg gtataattcc     420
acgtaccctt catcaaattt ttgagaaact tactgataat ggtactgaat tttcagtcaa     480
agtgtctctg ttggagatct ataatgaaga gcttttttgat cttcttaatc catcatctga     540
tgtttctgag agactacaga tgtttgatga tccccgtaac aagagaggag tgataattaa     600
aggtttagaa gaaattacag tacacaacaa ggatgaagtc tatcaaattt tagaaaaggg     660
ggcagcaaaa aggacaactg cagctactct gatgaatgca tactctagtc gttcccactc     720
agttttctct gttacaatac atatgaaaga aactacgatt gatggagaag agcttgttaa     780
aatcggaaag ttgaacttgg ttgatcttgc aggaagtgaa aacattggcc gttctggagc     840
tgttgataag agagctcggg aagctggaaa tataaatcaa tccctgttga ctttgggaag     900
ggtcattact gcccttgtag aaagaacacc tcatgttcct tatcgagaat ctaaactaac     960
tagaatcctc caggattctc ttggagggcg tacaagaaca tctataattg caacaatttc    1020
tcctgcatct ctcaatcttg aggaaactct gagtacattg gaatatgctc atagagcaaa    1080
gaacatattg aataagcctg aagtgaatca gaaactcacc aaaaaagctc ttattaagga    1140
gtatacggag gagatagaac gtttaaaacg agatcttgct gcagcccgtg agaaaaatgg    1200
agtgtatatt tctgaagaaa attttagagt catgagtgga aaattaactg ttcaagaaga    1260
gcagattgta gaattgattg aaaaaattgg tgctgttgag gaggagctga ataggttac    1320 agagttgttt atggataata aaaatgaact tgaccagtgt aaatctgacc tgcaaaataa    1380
aacacaagaa cttgaaacca ctcaaaaaca tttgcaagaa actaaattac aacttgttaa    1440
agaagaatat atcacatcag ctttggaaag tactgaggag aaacttcatg atgctgccag    1500
caagctgctt aacacagttg aagaaactac aaaagatgta tctggtctcc attccaaact    1560
ggatcgtaag aaggcagttg accaacacaa tgcagaagct caggatattt ttggcaaaaa    1620
cctgaatagt ctgtttaata atatggaaga attaattaag gatggcagct caaagcaaaa    1680
ggccatgcta gaagtacata agaccttatt tggtaatctg ctgtcttcca gtgtctctgc    1740
attagatacc attactacag tagcacttgg atctctcaca tctattccag aaaatgtgtc    1800
tactcatgtt tctcagattt ttaatatgat actaaaagaa caatcattag cagcagaaag    1860
taaaactgta ctacaggaat tgattaatgt actcaagact gatcttctaa gttcactgga    1920 aatgattta tcccccaactg tggtgtctat actgaaaatc aatagtcaac taaagcatat    1980
```

-continued

| | |
|---|---|
| tttcaagact tcattgacag tggccgataa gatagaagat caaaaaaaaa ggaactcaga | 2040 |
| tggctttctc agtatactgt gtaacaatct acatgaacta caagaaaata ccatttgttc | 2100 |
| cttggttgag tcacaaaagc aatgtggaaa cctaactgaa gacctgaaga caataaagca | 2160 |
| gacccattcc caggaacttt gcaagttaat gaatctttgg acagagagat tctgtgcttt | 2220 |
| ggaggaaaag tgtgaaaata tacagaaacc acttagtagt gtccaggaaa atatacagca | 2280 |
| gaaatctaag gatatagtca acaaaatgac ttttcacagt caaaaatttt gtgctgattc | 2340 |
| tgatggcttc tcacaggaac tcagaaattt taaccaagaa ggtacaaaat tggttgaaga | 2400 |
| atctgtgaaa cactctgata aactcaatgg caacctggaa aaaatatctc aagagactga | 2460 |
| acagagatgt gaatctctga acacaagaac agtttatttt tctgaacagt gggtatcttc | 2520 |
| cttaaatgaa agggaacagg aacttcacaa cttattggag gttgtaagcc aatgttgtga | 2580 |
| ggcttcaagt tcagacatca ctgagaaatc agatggacgt aaggcagctc atgagaaaca | 2640 |
| gcataacatt tttcttgatc agatgactat tgatgaagat aaattgatag cacaaaatct | 2700 |
| agaacttaat gaaaccataa aaattggttt gactaagctt aattgctttc tggaacagga | 2760 |
| tctgaaactg gatatcccaa caggtacgac accacagagg aaaagttatt tatacccatc | 2820 |
| aacactggta agaactgaac cacgtgaaca tctccttgat cagctgaaaa ggaaacagcc | 2880 |
| tgagctgtta atgatgctaa actgttcaga aaacaacaaa gaagagacaa ttccggatgt | 2940 |
| ggatgtagaa gaggcagttc tggggcagta tactgaagaa cctctaagtc aagagccatc | 3000 |
| tgtagatgct ggtgtggatt gttcatcaat tggcgggggtt ccattttttcc agcataaaaa | 3060 |
| atcacatgga aaagacaaag aaaacagagg cattaacaca ctggagaggt ctaaagtgga | 3120 |
| agaaactaca gagcacttgg ttacaaagag cagattacct ctgcgagccc agatcaacct | 3180 |
| ttaattcact tgggggttgg caattttatt tttaaagaaa aacttaaaaa taaaacctga | 3240 |
| aaccccagaa cttgagcctt tgtgtatagat tttaaagaa tatatatatc agccgggcgc | 3300 |
| gtggctctag ctgtaatccc agctaacttt ggaggctgag gcgggtggat tgcttgagcc | 3360 |
| caggagtttg agaccagcct ggccaacgtg cgctaaaacc ttcgtctctg ttaaaaatta | 3420 |
| gccgggcgtg gtgggcacac tcctgtaatc ccagctactg gggaggctga ggcacgagaa | 3480 |
| tcacttgaac ccagaagcgg ggttgcagtg agccaaaggt acaccactac actccagcct | 3540 |
| gggcaacaga gcaagactcg gtctcaaaaa taaaatttaa aaaagatata aggcagtact | 3600 |
| gtaaattcag ttgaattttg atatctaccc atttttctgt catccctata gttcactttg | 3660 |
| tattaaattg ggtttcattt gggatttgca atgtaaatac gtatttctag ttttcatata | 3720 |
| aagtagttct tttaggaatt c | 3741 |

<210> SEQ ID NO 24
<211> LENGTH: 7672
<212> TYPE: DNA
<213> ORGANISM: Homo sapiens

<400> SEQUENCE: 24

| | |
|---|---|
| gaggctcctc ggtccttcag cacccctcgg cccgacgcac ccacgcccct cacccccga | 60 |
| gagccgaaaa tggacccaag tggggtcaaa gtgctggaaa cagcagagga catccaggag | 120 |
| aggcggcagc aggtcctaga ccgataccac cgcttcaagg aactctcaac ccttaggcgt | 180 |
| cagaagctgg aagattccta tcgattccag ttctttcaaa gagatgctga agagctggag | 240 |
| aaatggatac aggaaaaact tcagattgca tctgatgaga attataaaga cccaaccaac | 300 |
| ttgcagggaa agcttcagaa gcatcaagca tttgaagctg aagtgcaggc caactcagga | 360 |

-continued

```
gccattgtta agctggatga aactggaaac ctgatgatct cagaagggca ttttgcatct    420
gaaaccatac ggacccgttt gatggagctg caccgccagt gggaattact tttggagaag    480
atgcgagaaa aaggaatcaa actgctgcag gcccagaagt tggtgcagta cttacgagaa    540
tgtgaggacg tgatggactg gatcaatgac aaggaagcaa ttgttacttc tgaagagctg    600
ggccaggatc tggagcatgt agaggtttta cagaagaaat ttgaagagtt tcaaacagat    660
atggctgctc atgaagaaag agttaatgaa gtgaaccagt ttgctgccaa actcatacag    720
gagcagcacc ctgaggagga actgatcaag actaagcagg atgaagtcaa tgcagcctgg    780
cagcggctga agggcctggc tctgcagagg caggggaagc tctttggggc agcagaagtt    840
cagcgcttta cagggatgt ggatgagact atcagttgga ttaaggaaaa ggagcagtta    900
atggcctctg atgattttgg ccgagacctg gcaagtgttc aggctctgct tcggaagcac    960
gagggtctgg agagagatct tgctgctcta aagacaagtc aaagccct gtgtgctgag    1020 gctgaccgcc tgcaacagtc ccaccctctg agtgcaacac agattcaagt gaagcgagag    1080
gaactgatta caaactggga gcagatccgc accttggcgg cagagagaca tgcacggctc    1140
aatgattcat acaggcttca acgcttcctt gctgacttcc gtgacctcac cagctgggtg    1200
actgagatga aagccctcat caatgcagat gagcttgcca gtgatgtggc tggggctgaa    1260
gccctgctag atagacacca agagcacaag ggtgaaattg atgcccatga agacagcttc    1320
aaatctgcag atgaatctgg acaggactg cttgctgctg tcactatgc ctcagatgaa    1380 gtgagggaga agctgaccgt ccttttccgag agagagcgg cgctgctgga gctgtgggag    1440
ctgcgcaggc agcagtacga gcagtgcatg gacctgcagc tcttctaccg ggacactgag    1500
caggtggaca actggatgag caagcaggag gcgttcctgt gaatgaaga cttgggagat    1560 tccttggata gtgtggaagc gcttcttaag aagcacgaag actttgagaa atcccttagt    1620
gcccaggagg aaaagattac agcattagat gaatttgcaa ccaagctaat tcagaacaac    1680
cactatgcaa tggaagatgt ggccactcgc gagatgctc tgttgagccg ccgcaatgcc    1740
cttcacgaga gagccatgcg tcgccgggcc cagctagccg attctttcca tctgcagcag    1800
tttttccgtg attctgatga gctcaagagt tgggtcaatg agaagatgaa aactgccaca    1860
gatgaagctt ataaagatcc atccaaccta caaggaaaag tacagaagca tcaggctttt    1920
gaggctgagc tctcagcaaa ccagagccga attgatgcct tggagaaagc tggccaaaag    1980
ctgattgatg tcaaccacta tgccaaggat gaagtggcag ctcgtatgaa tgaggtgatc    2040
agtttgtgga gaaactgct agaggccact gaactgaaag gaataaagct tcgtgaagcc    2100
aaccagcaac agcaatttaa tcgcaatgtt gaggatattg aattgtggct atatgaagta    2160
gaaggtcact tggcttcgga tgattacggc aaagatctta ccaatgtgca gaacctccag    2220
aagaaacatg ccctgctaga ggcagatgtg gctgctcacc aggaccgaat tgatggcatc    2280
accattcagg cccgccagtt ccaagatgct ggccattttg atgcagaaaa catcaagaag    2340
aaacaggaag ccctcgtggc tcgctatgag gcactcaagg agcccatggt tgcccggaag    2400
cagaagctgg ccgattctct gcggttgcag cagctcttcc gggatgttga ggatgaggag    2460 acgtggatt gagagaaga gcccattgcc gcatctacca acagaggtaa ggatttaatt    2520
ggggtccaga atctgctaaa gaaacatcaa gccttacaag cagaaattgc tggacatgaa    2580
ccacgcatca aagcagttac acagaagggg aatgccatgg tggaggaagg ccattttgct    2640
gcagaggatg tgaaggccaa gcttcacgag ctgaaccaaa agtgggaggc actgaaagcc    2700
```

-continued

```
aaagcttccc agcgtcggca ggacctggag gactctctgc aggcccagca gtactttgct    2760
gatgctaacg aggctgaatc ctggatgcgg gagaaggaac ccattgtggg cagcactgac    2820
tatggcaagc acgaagactc tgctgaggct ctactgaaga acacgaagc tttgatgtca     2880
gatctcagtg cctacggcag cagcatccag gctttgcgag aacaagcaca gtcctgccgg    2940
caacaagtgg cccccacgga tgatgagact gggaaggagc tggtcttggc tctctacgac    3000
tatcaggaga gagtccccg agaggtcacc atgaagaagg gagatatcct taccttactc     3060
aacagcacca caaggattg gtggaaagtg gaagtgaacg atcgtcaggg ttttgtgccg      3120
gctgcgtacg tgaagaaatt ggaccccgcc cagtcagcct cccgggagaa tctcctggag    3180
gagcaaggca gcatagcact gcggcaggag cagattgaca atcagacacg cataactaag    3240
gaggccggca gtgtatctct gcgtatgaag caggtggaag aactatatca ttctctgctg    3300
gaactgggtg agaagcgtaa aggcatgttg gagaagagtt gcaagaagtt tatgttgttc    3360
cgtgaagcga atgaactaca gcaatggatc aatgagaagg aagccgctct gacaagtgag    3420
gaggtcggag cagacttgga gcaggttgag gtgctccaga gaagtttga tgacttccag     3480
aaggacctga aggccaatga gtcacggttg aaggacatta caaggtagc tgaagacctg     3540
gagtctgaag gtcttatggc agaggaggtg caggctgtgc aacaacagga agtgtatggc    3600
atgatgccca gggatgaaac tgattccaag acagcctccc cgtggaagtc tgctcgtctg    3660
atggttcaca ccgtgccac ctttaattcc atcaaggagc tgaatgagcg ctggcggtcc      3720
ctacagcagc tggccgagga acggagccag ctcttgggca gcgcccatga agtacagagg    3780
ttccacagag atgctgatga aaccaaagaa tggattgaag agaagaatca agctctaaac    3840
acagacaatt atgacatga tctcgccagt gtccaggccc tgcaacgcaa gcatgagggc     3900
ttcgagaggg accttgcggc tctcggtgac aaggtaaact cccttggtga acagcagag     3960
cgcctgatcc agtcccatcc cgagtcagca gaagacctgc aggaaaagtg cacagagtta    4020
aaccaggcct ggagcagcct ggggaaacgt gcagatcagc gcaaggcaaa gttgggtgac    4080
tcccacgacc tgcagcgctt ccttagcgat ttccggaccc tcatgtcttg gatcaatgga    4140
atacgggggt tggtgtcctc agatgagcta gccaaggatg tcaccggagc tgaggcattg    4200
ctggagcgac accaggaaca ccggacagaa atcgatgcca gggctggcac tttccaggca   4260
tttgagcagt ttggacagca gctgttggct cacggacact atgccagccc tgagatcaag    4320
cagaaacttg atattcttga ccaggagcgt gcagacctgg agaaggcctg ggttcagcgc    4380
aggatgatgc tggatcagtg ccttgaactg cagctgttcc atcgggactg tgagcaagct    4440
gagaactgga tggctgcccg ggaggccttc ttgaataccg aagacaaagg agactcactg    4500
gacagcgtag aggctctgat caaaaaacat gaagactttg acaaagcgat taacgtccag    4560
gaagagaaga ttgctgctct gcaggccttt gccgaccagc tcatcgctgc cggccattat    4620
gccaagggag acatttctag ccggcgcaat gaggtcttgg acaggtggcg acgtctgaaa    4680
gcccagatga ttgagaaaag gtcaaagcta ggagaatctc aaaccctcca acagttcagc    4740
cgggatgtgg atgagattga ggcttggatc agtgaaaaat gcaaacagc gagtgatgag     4800
tcgtacaagg atcccaccaa catccagctt ccaagctgc tgagcaagca ccagaagcac     4860
caggcttttg aagcagagct gcatgccaac gctgaccgga tccgtggggt tatcgacatg    4920
ggcaactccc tcattgaacg tggagcctgt gccggcagtg aggatgctgt caaggcccgc    4980
ctggctgcct tagctgacca gtggcagttc ttggtgcaaa agtcagcgga aaagagccag    5040
aaactgaaag aagccaacaa gcagcagaac ttcaacacag ggatcaagga ctttgacttc    5100
```

```
tggctgtctg aggtggaggc cctgctggca tccgaagatt atggcaaaga cctggcttct    5160
gtgaacaacc tgctgaaaaa gcatcaactg ctggaagcag atatatctgc ccatgaggat    5220
cgcctgaagg acctgaacag ccaggcagac agcctgatga ccagcagtgc cttcgacacc    5280
tcccaagtaa aggacaagag ggacaccatc aacgggcgct tccagaagat caagagcatg    5340
gcggcctccc ggcgagccaa gctgaatgaa tcccatcgcc tgcaccagtt cttccgggac    5400
atggatgacg aggagtcctg gatcaaggag aagaagctgc tggtgggctc agaggactac    5460
ggccgggacc taactggcgt gcagaacctg aggaagaagc acaagcggct ggaagcagaa    5520
ctggctgcgc atgagccggc tattcagggt gtcctggaca ctggcaagaa gctgtccgat    5580
gacaacacca tcgggaaaga ggagatccag cagcggctgg cgcagtttgt ggagcactgg    5640
aaagagctga agcagctggc agctgcccgg ggtcagcggc tggaagagtc cttggaatat    5700
cagcagtttg tagccaatgt ggaagaggaa gaagcctgga tcaatgagaa aatgaccctg    5760
gtggccagcg aagattatgg cgacactctt gccgccatcc agggcttact gaagaaacat    5820
gaagcttttg agacagactt caccgtccac aaggatcgcg tgaatgatgt ctgcaccaat    5880
ggacaagacc tcattaagaa gaacaatcac catgaggaga acatctcttc aaagatgaag    5940
ggcctgaacg ggaaagtgtc agacctggag aaagctgcag cccagagaaa ggcgaacgtg    6000
gatgagaact cggccttcct tcagttcaac tggaaggcgg acgtggtgga gtcctggatc    6060
ggtgaaaagg agaacagctt gaagacagat gattatggcc gagacctgtc ttctgtgcag    6120
acgctcctca ccaaacagga aacttttgac gctgggctgc aggccttcca gcaggaaggc    6180
attgccaaca tcactgccct caaagatcag cttctcgccg ccaaacacgt tcagtccaag    6240
gccatcgagg cccggcacgc ctccctcatg aagaggtgga gccagcttct ggccaactca    6300
gccgcccgca agaagaagct tctggaggct cagagtcact tccgcaaggt ggaggacctc    6360
ttcctgacct tcgccaaaaa ggcttctgcc ttcaacagct ggtttgaaaa tgcagaggag    6420
gacttaacag accccgtgcg ctgcaactcc ttggaagaaa tcaaagcttt gcgcgaggcc    6480
cacgacgcct tccgctcctc cctcagctct gcccaggctg acttcaacca gctggccgag    6540
ctggaccgcc agatcaagag cttccgcgta gcctccaacc cctacacctg gtttaccatg    6600
gaggccctgg aggagacctg gaggaaccta cagaaaatca tcaaggagag ggagctggag    6660
ctgcagaagg aacagcggcg gcaggaggag aacgacaagc tgcgccagga gttttgccccag    6720 cacgccaacg ccttccacca gtggatccaa gagaccagga catacctcct cgatgggtcc    6780
tgtatggtgg aagagtcggg gaccctcgaa tcccagcttg aagctaccaa acgcaagcac    6840
caggaaatcc gagccatgag aagtcagctc aaaaagatcg aggacctggg ggccgccatg    6900
gaggaggccc tcatcctgga caacaagtac acggagcaca gcaccgtggg cctcgcccag    6960
cagtgggacc agctggacca gctggcatg cgcatgcagc acaacctgga gcagcagatc    7020
caggccagga acacaacagg tgtgactgag gaggccctca agaattcag catgatgttt    7080 aaacactttg acaggacaa gtctggcagg ctgaaccatc aggagttcaa atcttgcctg    7140
cgctccctgg gctatgacct gcccatggtg gaggaagggg aacctgaccc tgagttcgag    7200
gcaatcctgg acacggtgga tccgaacaga gatggccatg tctccttgca agaatacatg    7260
gctttcatga tcagccgcga aactgagaac gtcaagtcca gcgaggagat tgagagcgcc    7320
ttccgggccc tcagctcaga gggaaagcct tacgtgacca aggaggagct ctaccagaac    7380
ctgacccggg aacaagccga ctactgcgtc tcccacatga agccctacgt ggacggcaag    7440
```

```
ggccgcgagc tcccaccgc gttcgactac gtggagttca cccgctcgct tttcgtgaac    7500
tgagccactc cctgggtcac ccaccccctcg ctgcttgccc tgcgtcgcct tgctgcatgt    7560
ccgctcctct gtgtgctctc actttccact gtaaccttaa gcctgcttag cttggaataa    7620
gacttaggag aaaatggtgc ttcactaacc cgcttccggt ccagtcacaa tc            7672
```

<210> SEQ ID NO 25
<211> LENGTH: 1121
<212> TYPE: DNA
<213> ORGANISM: Homo sapiens

<400> SEQUENCE: 25

```
ggaattccct atagagccgg gtgagagagc gagcgcccgt cggcgggtgt cgagggcggg     60
ttgcctcgcg ctgacccttc ccgccctcct tctcgtcaca caccaggtcc ccgcggaagc    120
cgcggtgtcg gcgccatggc ggagctgacg gctcttgaga gtctcatcga gatgggcttc    180
cccaggggac gcgcggagaa ggctctggcc ctcacaggga accagggcat cgaggctgcg    240
atggactggc tgatggagca cgaagacgac cccgatgtgg acgagccttt agagactccc    300
cttggacata tcctgggacg ggagcccact tcctcagagc aaggcggcct tgaaggatct    360
gcttctgctg ccggagaagg caaacccgct ttgagtgaag aggaaagaca ggaacaaact    420
aagaggatgt tggagctggt ggcccagaag cagcgggagc gtgaagaaag agaggaacgg    480
gaggcattgg aacgggaacg gcagcgcagg agacaagggc aagagttgtc agcagcacga    540
cagcggctac aggaagatga gatgcgccgg gctgctgctg aggagaggcg gagggaaaat    600
gccgaggagt tagcagccag acaaagagtt agagaaaaga tcgagaggga caaagcagag    660
agagccaaga agtatggtgg cagtgtgggc tctcagccac ccccagtggc accagagcca    720
ggtcctgttc cctcttctcc cagccaggag cctcccacca gcgggagta tgaccagtgt    780 cgcatacagg tcaggctgcc agatgggacc tcactgaccc agacgttccg ggcccgggaa    840
cagctggcag ctgtgaggct ctatgtggag ctccaccgtg gggaggaact aggtgggggc    900
caggaccctg tgcaattgct cagtggcttc cccagacggg ccttctcaga agctgacatg    960
gagcggcctc tgcaggagct gggactcgtg ccttctgctg ttctcattgt ggccaagaaa   1020
tgtcccagct gagggccttt gtcccattgt ccctctgtga ccccttcatc tttgataaag   1080
cactgacatc tccttcctaa taaatagacc ctgagttctg t                        1121
```

<210> SEQ ID NO 26
<211> LENGTH: 3468
<212> TYPE: DNA
<213> ORGANISM: Homo sapiens

<400> SEQUENCE: 26

```
aatggcgatg cctaccacct agaactggat tgtgcgctgg ccgccaccgc tgccacctgc     60
tcagagtgaa ataatgaagg tggtcaacct gaagcaagcc attttgcaag cctggaagga    120
gcgctggagt tactaccaat gggcaatcaa catgaagaaa ttctttccta aaggagccac    180
ctgggatatt ctcaacctgg cagatgcgtt actagagcag gccatgattg gaccatcccc    240
caatcctctc atcttgtcct acctgaagta tgccattagt tcccagatgg tgtcctactc    300
ttctgtcctc acagccatca gtaagtttga tgacttttct cgggacctgt gtgtccaggc    360
attgctggac atcatggaca tgttttgtga ccgtctgagc tgtcacggca aagcagagga    420
atgcatcgga ctgtgccgag cccttcttag cgccctccac tggctgctgc gctgcacggc    480
agcctctgca gagcggctgc gggaggggct ggaggccggc actccagccg ctggggagaa    540
```

-continued

```
gcagcttgcc atgtgccttc agcgcctgga gaaaaccctc agcagcacca agaaccgggc     600
cctgctgcac atcgccaaac tagaggaggc ctcttcttgg actgccatcg agcattctct     660
cttgaaactt ggagagatcc tgaccaatct cagcaacccg cagctccgga gtcaggccga     720
gcagtgtggc accctcatta ggagcatccc cacgatgctg tctgtgcatg cggagcagat     780
gcacaagacc ggcttcccca ctgtccacgc cgtgatcctc ctcgagggca ccatgaacct     840
gacaggcgag acgcagtccc tggtggagca gctgacgatg gtgaagcgca tgcagcatat     900
ccccacccca cttttgtcc tggagatctg gaaagcttgc ttcgtggggc tcattgagtc     960
tcccgagggt acggaggagc tcaagtggac agctttcact ttcctcaaga ttccacaggt    1020
tttggtgaag ttgaagaagt actctcatgg agacaaggac ttcactgagg atgtcaactg    1080
tgcttttgag ttcctgctga agctcacccc cttgttggac aaagctgacc agcgctgcaa    1140
ctgtgactgt acaaacttcc tgctccaaga atgtggcaag caggggcttc tgtctgaggc    1200
cagcgtcaac aaccttatgg ctaagcgcaa agcggaccga gagcacgcac cccagcagaa    1260
atcgggagag aatgccaaca tccagcccaa catccagctg atcctccggg cggagcccac    1320
tgtcacaaac atcctcaaga cgatggatgc agaccactct aagtcaccgg agggactgct    1380
gggagtcctg ggccacatgc tgtccgggaa gagtctggac ttgctgctgg ctgccgccgc    1440
cgccactgga aagctgaaat ccttcgcccg gaaattcatc aatttgaatg aattcacaac    1500
ctatggcagc gaagaaagca ccaaaccggc ctccgtccgg gccctgctgt ttgacatctc    1560
cttcctcatg ctgtgccatg tgcccagac ctatggttca gaggtgattc tgtccgagtc    1620
gcgcacagga gctgaggtgc ccttcttcga gacctggatg cagacctgca tgcctgagga    1680
gggcaagatc ctgaaccctg accacccctg cttccgcccc gactccacca agtggagtc    1740 cctggtggcc ctgctcaaca actcctcgga gatgaagcta gtgcagatga gtggcatga    1800 ggcctgtctc agcatctcag ccgccatctt ggaaatcctc aatgcctggg agaatgggt    1860 cctggccttc gagtccatcc agaaaatcac tgataacatc aaagggaagg tatgcagtct    1920
ggcggtgtgt gctgtggctt ggcttgtggc ccacgtccgg atgctggggc tggatgagcg    1980
tgagaagtcg ctgcagatga tccgccagct ggcagggcca ctgtttagtg agaacaccct    2040
gcagttctac aatgagaggg tggtgatcat gaactcgatc ctggagcgca tgtgtgccga    2100
cgtgctgcag cagacagcca cgcagatcaa gtttccctcc accggggtgg acacaatgcc    2160
ctactggaac ctgctgcccc ccaagcggcc catcaaagag gtgctgacgg acatttttgc    2220
caaggtgctg gagaagggct gggtggacag ccgctccatc cacatctttg acaccctgct    2280
gcacatgggc ggcgtctact ggttctgcaa caacctgatt aaggagctgc tgaaggagac    2340
gcggaaggag cacacgctgc gggcagtgga gctgctctac tccatcttct gcctggacat    2400
gcagcaagtg accctggtcc tgctgggcca catcctacct ggcctgctca ctgactcctc    2460
caagtggcac agcctcatgg accccccggg cactgctctt gccaagctgg ccgtgtggtg    2520
tgccctcagt tcctactcct cccacaaggg acaggcgtcc accgccaga agaagagaca    2580 ccgcgaagac attgaggatt atatcagcct cttccccctg gacgatgtgc agccttcgaa    2640
gttgatgcga ctgctgagct ctaatgagga cgatgccaac atcctttcga gcccacaga    2700 ccgatccatg agcagctccc tctcagcctc tcagctccac acggtcaaca tgcgggaccc    2760
tctgaaccga gtcctggcca acctgttcct gctcatctcc tccatcctgg ggtctcgcac    2820
cgctggcccc cacacccagt tcgtgcagtg gttcatggag gagtgtgtgg actgcctgga    2880
```

-continued

| | |
|---|---|
| gcagggtggc cgtggcagcg tcctgcagtt catgcccttc accaccgtgt cggaactggt | 2940 |
| gaaggtgtca gccatgtcca gccccaaggt ggttctggcc atcacggacc tcagcctgcc | 3000 |
| cctgggccgc caggtggctg ctaaagccat tgctgcactc tgagggcgtt ggcatggccg | 3060 |
| cagtgggggc tggggactgg cgcagcccca ggcgcctcca agggaagcag tgaggaaaga | 3120 |
| tgaggcatcg tgcctcacat ccgctccaca tggtgcaaga gcctctagcg gcttccagtt | 3180 |
| ccccgctcct gactcctgac ctccaggatg tctcccggtt tcttctttca aaatttcctc | 3240 |
| tccatctgct ggcacctgag gagagtgagc agcctggacc acaagcccag tggtcacccc | 3300 |
| tgtgtgcgcc cgcccagcc caggagtagt cttacctctg aggaactttc tagatgcaaa | 3360 |
| gtgtgtatgt gtgtgtgtgt gtgtgtgtgt gtgtttgtgt gtattttgta atatgtgagg | 3420 |
| gaaatctacc ttcgttcatg tataaataaa gctcctcgtg gctcccctt | 3468 |

<210> SEQ ID NO 27
<211> LENGTH: 2704
<212> TYPE: DNA
<213> ORGANISM: Homo sapiens

<400> SEQUENCE: 27

| | |
|---|---|
| gcttagtgta accagcggcg tatattttt aggcgccttt tcgaaaacct agtagttaat | 60 |
| attcatttgt ttaaatctta ttttattttt aagctcaaac tgcttaagaa taccttaatt | 120 |
| ccttaaagtg aaataatttt ttgcaaaggg gtttcctcga tttggagctt ttttttttctt | 180 |
| ccaccgtcat ttctaactct taaaaccaac tcagttccat catggtgatg ttcaagaaga | 240 |
| tcaagtcttt tgaggtggtc tttaacgacc ctgaaaaggt gtacggcagt ggcgagaggg | 300 |
| tggctggccg ggtgatagtg gaggtgtgtg aagttactcg tgtcaaagcc gttaggatcc | 360 |
| tggcttgcgg agtggctaaa gtgctttgga tgcagggatc ccagcagtgc aaacagactt | 420 |
| cggagtacct gcgctatgaa gacacgcttc ttctggaaga ccagccaaca ggtgagaatg | 480 |
| agatggtgat catgagacct ggaaacaaat atgagtacaa gttcggcttt gagcttcctc | 540 |
| aggggcctct gggaacatcc ttcaaaggaa aatatgggtg tgtagactac tgggtgaagg | 600 |
| ctttttcttga ccgcccgagc cagccaactc aagagacaaa gaaaaacttt gaagtagtgg | 660 |
| atctggtgga tgtcaatacc cctgatttaa tggcacctgt gtctgctaaa aagaaaaga | 720 |
| aagtttcctg catgttcatt cctgatgggc gggtgtctgt ctctgctcga attgacagaa | 780 |
| aaggattctg tgaaggtgat gagatttcca tccatgctga ctttgagaat acatgttccc | 840 |
| gaattgtggt ccccaaagct gccattgtgg cccgccacac ttaccttgcc aatggccaga | 900 |
| ccaaggtgct gactcagaag ttgtcatcag tcagaggcaa tcatattatc tcagggacat | 960 |
| gcgcatcatg gcgtggcaag agccttcggg ttcagaagat caggccttct atcctgggct | 1020 |
| gcaacatcct tcgagttgaa tattccttac tgatctatgt tagcgttcct ggatccaaga | 1080 |
| aggtcatcct tgacctgccc ctggtaattg gcagcagatc aggtctaagc agcagaacat | 1140 |
| ccagcatggc cagccgaacc agctctgaga tgagttgggt agatctgaac atccctgata | 1200 |
| ccccagaagc tcctccctgc tatatggatg tcattcctga agatcaccga ttggagagcc | 1260 |
| caacaactcc tctgctagat gacatggatg gctctcaaga cagccctatc tttatgtatg | 1320 |
| cccctgagtt caagttcatg ccaccaccga cttatactga ggtggatccc tgcatcctca | 1380 |
| acaacaatgt gcagtgagca tgtggaagaa aagaagcagc tttacctact tgtttctttt | 1440 |
| tgtctctctt cctggacact cactttttca gagactcaac agtctcgtca atggagtgtg | 1500 |
| ggtccacctt agcctctgac ttcctaatgt aggaggtggt cagcaggcaa tctcctgggc | 1560 |

```
cttaaaggat gcggactcat cctcagccag cgcccatgtt gtgatacagg ggtgtttgtt    1620
ggatgggttt aaaataact agaaaaactc aggcccatcc attttctcag atctccttga    1680
aaattgaggc cttttcgata gtttcgggtc aggtaaaaat ggcctcctgg cgtaagcttt    1740
tcaaggtttt ttggaggctt tttgtaaatt gtgataggaa ctttggacct tgaacttacg    1800
tatcatgtgg agaagagcca atttaacaaa ctaggaagat gaaaagggaa attgtggcca    1860
aaactttggg aaaaggaggt tcttaaaatc agtgtttccc ctttgtgcac ttgtagaaaa    1920
aaaagaaaaa ccttctagag ctgatttgat ggacaatgga gagagctttc cctgtgatta    1980
taaaaaagga agctagctgc tctacggtca tctttgctta gagtatactt taacctggct    2040
tttaaagcag tagtaactgc cccaccaaag gtcttaaaag ccattttggg agcctattgc    2100
actgtgttct cctactgcaa atattttcat atgggaggat ggttttctct tcatgtaagt    2160
ccttggaatt gattctaagg tgatgttctt agcactttaa ttcctgtcaa attttttgtt    2220
ctccccttct gccatcttaa atgtaagctg aaactggtct actgtgtctc tagggttaag    2280
ccaaaagaca aaaaaattt tactactttt gagattgccc caatgtacag aattatataa    2340
ttctaacgct taaatcatgt gaaaggggttg ctgctgtcag ccttgcccac tgtgacttca    2400
aacccaagga ggaactcttg atcaagatgc ccaaccctgt gatcagaacc tccaaatact    2460
gccatgagaa actagagggc aggtgttcat aaaagccctt tgaaccccct tcctgccctg    2520
tgttaggaga tagggatatt ggcccctcac tgcagctgcc agcacttggt cagtcactct    2580
cagccatagc actttgttca ctgtcctgtg tcagagcact gagctccacc cttttctgag    2640
agttattaca gccagaaagt gtgggctgaa gatggttggt ttcatgtggg ggtattatgt    2700
accc                                                                 2704
```

<210> SEQ ID NO 28
<211> LENGTH: 413
<212> TYPE: DNA
<213> ORGANISM: Homo sapiens
<220> FEATURE:
<221> NAME/KEY: misc_feature
<222> LOCATION: (1)...(413)
<223> OTHER INFORMATION: n = A,T,C or G

<400> SEQUENCE: 28

```
acaggcacac tgcaccagcg ttcaatagct gaacttgtgc ccaagtgcca tccgctagca      60
gctttgagca gatggaggct gtgaacatcg cacagacacc tgcagagctc tacaatgcca     120
ttctggtgga cacaccctg gcggttttt tccaggactg catctcagag caggaccttg     180
atgagatgaa catcgagata atccgaaata cgctttacaa ggcctacttg gaagtccttc     240
tacaagttct gtactctgtt gggtgggacc acagctgatg ccatgtgtcc tatcctagag     300
tttgaagcag accgccgcgc tttcatcatc accatcaact ctttccggca cagagctgtc     360
caaggaggac cgtgccaagc tcttcccgca ctgtggccgg ctctanccctg agg           413
```

<210> SEQ ID NO 29
<211> LENGTH: 2602
<212> TYPE: DNA
<213> ORGANISM: Homo sapiens

<400> SEQUENCE: 29

```
gccgtgtcgc caccatggct ccgcaccgcc ccgcgccgc gctgctttgc gcgctgtccc      60
tggcgctgtg cgcgctgtcg ctgcccgtcc gcgcggccac tgcgtcgcgg ggggcgtccc     120
```

-continued

```
aggcggggc gccccagggg cgggtgcccg aggcgcggcc caacagcatg gtggtggaac    180
acccgagtt cctcaaggca gggaaggagc ctggcctgca gatctggcgt gtggagaagt    240
tcgatctggt gcccgtgccc accaacctt atggagactt cttcacgggc gacgcctacg    300
tcatcctgaa gacagtgcag ctgaggaacg gaaatctgca gtatgacctc cactactggc    360
tgggcaatga gtgcagccag gatgagagcg gggcggccgc catctttacc gtgcagctgg    420
atgactacct gaacggccgg gccgtgcagc accgtgaggt ccagggcttc gagtcggcca    480
ccttcctagg ctacttcaag tctggcctga agtacaagaa aggaggtgtg gcatcaggat    540
tcaagcacgt ggtacccaac gaggtggtgg tgcagagact cttccaggtc aaagggcggc    600
gtgtggtccg tgccaccgag gtacctgtgt cctgggagag cttcaacaat ggcgactgct    660
tcatcctgga cctgggcaac aacatccacc agtggtgtgg ttccaacagc aatcggtatg    720
aaagactgaa ggccacacag gtgtccaagg catccggga caacgagcgg agtggccggg    780
cccgagtgca cgtgtctgag gagggcactg agcccgaggc gatgctccag gtgctgggcc    840
ccagccggc tctgcctgca ggtaccgagg acaccgccaa ggaggatgcg gccaaccgca    900
agctggccaa gctctacaag gtctccaatg gtgcaggac catgtccgtc tccctcgtgg    960
ctgatgagaa ccccttcgcc caggggccc tgaagtcaga ggactgcttc atcctggacc    1020
acggcaaaga tgggaaaatc tttgtctgga aaggcaagca ggcaaacacg gaggagagga    1080
aggctgccct caaaacagcc tctgacttca tcaccaagat ggactacccc aagcagactc    1140
aggtctcggt ccttcctgag ggcggtgaga ccccactgtt caagcagttc ttcaagaact    1200
ggcgggaccc agaccagaca gatggcctgg gcttgtccta cctttccagc catatcgcca    1260
acgtggagcg ggtgcccttc gacgccgcca ccctgcacac ctccactgcc atggccgccc    1320
agcacggcat ggatgacgat ggcacaggcc agaaacagat ctggagaatc gaaggttcca    1380
acaaggtgcc cgtggaccct gccacatatg gacagttcta tggaggcgac agctacatca    1440
ttctgtacaa ctaccgccat ggtggccgcc aggggcagat aatctataac tggcagggtg    1500
cccagtctac caggatgag gtcgctgcat ctgccatcct gactgctcag ctggatgagg    1560
agctgggagg tacccctgtc cagagccgtg tggtccaagg caaggagccc gcccacctca    1620
tgagcctgtt tggtgggaag cccatgatca tctacaaggg cggcacctcc cgcgagggcg    1680
ggcagacagc ccctgccagc acccgcctct tccaggtccg cgccaacagc gctggagcca    1740
cccgggctgt tgaggtattg cctaaggctg gtgcactgaa ctccaacgat gcctttgttc    1800
tgaaaacccc ctcagccgcc tacctgtggg tgggtacagg agccagcgag gcagagaaga    1860
cggggccca ggagctgctc aggggtgctgc gggcccaacc tgtgcaggtg gcagaaggca    1920
gcgagccaga tggcttctgg gaggccctgg gcgggaaggc tgcctaccgc acatccccac    1980
ggctgaagga caagaagatg gatgcccatc ctcctcgcct ctttgcctgc tccaacaaga    2040
ttggacgttt tgtgatcgaa gaggttcctg gtgagctcat gcaggaagac ctggcaacgg    2100
atgacgtcat gcttctggac acctgggacc aggtctttgt ctgggttgga aaggattctc    2160
aagaagaaga aaagacagaa gccttgactt ctgctaagcg gtacatcgag acggacccag    2220
ccaatcggga tcggcggacg cccatcaccg tggtgaagca aggctttgag cctccctcct    2280
tgtgggctg gttccttggc tgggatgatg attactggtc tgtggacccc ttggacaggg    2340
ccatggctga gctggctgcc tgaggagggg cagggcccac ccatgtcacc ggtcagtgcc    2400
tttggaact gtccttccct caaagaggcc ttagagcgag cagagcagct ctgctatgag    2460
tgtgtgtgtg tgtgtgtgtt gtttcttttt tttttttta cagtatccaa aaatagccct    2520
```

-continued

| gcaaaaattc agagtccttg caaaattgtc taaaatgtca gtgtttggga aattaaatcc | 2580 |
| aataaaaaca ttttgaagtg tg | 2602 |

<210> SEQ ID NO 30
<211> LENGTH: 14770
<212> TYPE: DNA
<213> ORGANISM: Homo sapiens

<400> SEQUENCE: 30

| gggacaccat catttgggtt tttaaaagct tcagcttctc cagcatcttt gcattgtgaa | 60 |
| tatcttcctg cttctagtca aagctttctc tctagtgatt ggaatgctgc tgtaagccta | 120 |
| ttagaggtgc ctgaggatat cacctttac aaggaagccg tgtgtgcttg agaggatctt | 180 |
| tttaaatgca ttatggctca tgcagcctca caattaaaga aaaacaggga tttagaaatc | 240 |
| aatgctgaag aagagcctga gaaaaaaagg aaacaccgca aacggtcccg ggatcggaag | 300 |
| aaaaagtctg atgccaatgc aagttactta agagcagctc gagctggaca ccttgaaaag | 360 |
| gccctcgact acataaaaaa tggagttgac atcaacattt gcaatcagaa tgggttgaac | 420 |
| gctctccacc ttgcttccaa agaaggccat gtagaggttg tttctgagct gctgcagaga | 480 |
| gaagccaatg tggatgcagc tacaaagaaa ggaaacacag cattgcacat cgcatctttg | 540 |
| gctgggcaag cagaggtggt aaaagtcttg gttacaaatg gagccaatgt caatgcacaa | 600 |
| tctcagaatg gtttcacgcc attgtatatg gcagcccagg aaaatcacct ggaagttgtc | 660 |
| aagtttcttc ttgacaatgg tgcaagccag agcctagcca cagaggatgg cttcacacca | 720 |
| ttggcagtgg ctttgcaaca aggtcacgac caagtcgttt cgctcctgct agagaatgac | 780 |
| accaaaggaa aagtgcgtct cccagctctt catatcgcgg cccgcaaaga cgacacaaaa | 840 |
| gccgccgccc tgctgctgca gaatgacaac aatgcagatg tggaatcaaa gagtggcttc | 900 |
| actccgctcc acatagctgc tcactatgga aatatcaatg tagccacgtt gctgttaaac | 960 |
| cgagcggctg ctgtggattt caccgcaagg aatgacatca ctccttaca tgttgcatca | 1020 |
| aaaagaggaa atgcaaatat ggtaaaacta ttgctcgatc gaggagctaa aatcgatgcc | 1080 |
| aaaaccaggg atggtctgac accactgcac tgtggagcaa ggagtggcca cgagcaggtg | 1140 |
| gtagaaatgt tgcttgatcg agctgccccc attctttcaa aaaccaagaa tggattatct | 1200 |
| ccattgcaca tggccacaca agggatcat ttaaactgcg tccagcttct cctccagcat | 1260 |
| aatgtacccg tggatgatgt caccaatgac tacctgactg ccctacacgt ggctgcccac | 1320 |
| tgtggccatt acaaagttgc caaggttctc ttggataaga agctaaccc caatgccaaa | 1380 |
| gccctgaatg gctttaccccc tcttcatatc gcctgcaaga gaatcgaat taaagtaatg | 1440 |
| gaactccttc tgaaacacgg tgcatccatc caagctgtaa ccgagtcggg ccttacccca | 1500 |
| atccatgttc tgcccttcat ggggcatgta aatattgtat cacaactaat gcatcatgga | 1560 |
| gcctcaccaa acaccaccaa tgtgagagga gaaacagcac tgcacatggc agctcgctcc | 1620 |
| ggccaagctg aagttgtgcg gtatctggta caagacggag ctcaggtaga agctaaagct | 1680 |
| aaggatgacc aaacaccact ccacatttca gcccgactgg ggaaagcaga catagtacaa | 1740 |
| cagctgttgc agcaagggc atctccaaat gcagccacaa cttctgggta caccccactt | 1800 |
| cacctttccg cccgagaggg gcatgaggat gtggccgcgt tccttttgga tcatggagcg | 1860 |
| tctttatcta taacaacaaa gaaaggattt actcctcttc atgtggcagc aaaatatgga | 1920 |
| aagcttgaag tcgccaatct cctgctacag aaaagtcatc ctccagatgc tgctgggaag | 1980 |

```
agcgggctaa caccactgca tgtagctgca cattacgata atcagaaagt ggcccttctg   2040
cttttggacc aaggagcctc acctcacgca gccgcaaaga atggttatac gccactgcac   2100
atcgctgcca aaaagaacca gatggacata gcgacaactc tgctggaata tggtgctgat   2160
gccaacgcag ttacccggca aggaattgct tccgtccatc tcgcagctca ggaagggcac   2220
gtggacatgg tgtcgctgct cctcggtaga atgcgaatg tgaacctgag caataagagc    2280
ggcctgaccc cactccattt ggctgctcaa gaagatcgag tgaatgtggc agaagtcctc   2340
gtaaaccaag gggctcatgt ggacgcccag acaaagatgg gatacacacc actgcatgtg   2400
ggctgccact atggaaatat caagattgtt aatttcctgc tccagcattc tgcaaaagtt   2460
aatgccaaaa caaagaatgg gtatacgcca ttacatcaag cagcacagca ggggcatacg   2520
catataataa atgtcttact tcagaacaac gcctccccca atgaactcac tgtgaatggg   2580
aatactgccc ttggcattgc ccggcgcctc ggctacatct cagtagtgga caccctgaag   2640
atagtgaccg aagaaaccat gaccacaact actgtcacag agaagcacaa aatgaatgtt   2700
ccagaaacga tgaatgaagt tcttgatatg tctgatgatg aagttcgtaa agccaatgcc   2760
cctgaaatgc tcagtgatgg cgaatatatc tcagatgttg aagaaggtga agatgcaatg   2820
accggggaca cagacaaata tcttgggcca caggaccta aggaattggg tgatgattcc    2880
ctgcctgcag agggttacat gggctttagt ctcggagcgc gttctgccag cctccgctcc   2940
ttcagttcgg ataggtctta caccttgaac agaagctcct atgcacggga cagcatgatg   3000
attgaagaac tccttgtgcc atccaaagag cagcatctaa cattcacaag ggaatttgat   3060
tcagattctc ttagacatta cagctgggct gcagacacct tagacaatgt caatcttgtt   3120
tcaagcccca ttcattctgg gtttctggtt agctttatgg tggacgcgag aggggctcc    3180 atgagaggaa gccgtcatca cgggatgaga atcatcattc ctccacgcaa gtgtacggcc   3240
cccactcgaa tcacctgccg tttggtaaag agacataaac tggccaaccc accccacat    3300 ggtgaaagga gagggattag cagtaggctg gtagaaatgg gtcctgcagg ggcacaattt   3360
ttaggccctg tcatagtgga aatccctcac tttgggtcca tgagaggaaa agagagagaa   3420
ctcattgttc ttcgaagtga aaatggtgaa acttggaagg agcatcagtt tgacagcaaa   3480
aatgaagatt taaccgagtt acttaatggc atggatgaag aacttgatag cccagaagag   3540
ttagggaaaa agcgtatctg caggattatc acgaaagatt tcccccagta ttttgcagtg   3600
gtttcccgga ttaagcagga aagcaaccag attggtcctg aaggtggaat tctgagcagc   3660
accacagtgc cccttgttca agcatctttc ccagagggtg ccctaactaa agaattcga    3720 gtgggcctcc aggcccagcc tgttccagat gaaattgtga aaaagatcct tggaaacaaa   3780 gcaacttta gcccaattgt cactgtggaa ccaagaagac ggaaattcca taaaccaatc    3840
acaatgacca ttccggtgcc cccgccctca ggagaaggtg tatccaatgg atacaaaggg   3900
gacactacac ccaatctgcg tcttctctgt agcattacag ggggcacttc gcctgctcag   3960
tgggaagaca tcacaggaac aactcctttg acgtttataa aagattgtgt ctcctttaca   4020
accaatgttt cagccagatt ttggcttgca gactgccatc aagttttaga aactgtgggg   4080
ttagccacgc aactgtacag agaattgata tgtgttccat atatggccaa gtttgttgtt   4140
tttgccaaaa tgaatgatcc cgtagaatct tccttgcgat gtttctgcat gacagatgac   4200
aaagtggaca aaactttaga gcaacaagag aattttgagg aagtcgcaag aagcaaagat   4260
attgaggttc tggaaggaaa acctatttat gttgattgtt atggaaattt ggccccactt   4320
accaaaggag gacagcaact tgttttaac ttttattctt tcaaagaaaa tagactgcca    4380
```

```
ttttccatca agattagaga caccagccaa gagccctgtg gtcgtctgtc ttttctgaaa    4440
gaacgaaaga caacaaaagg actgcctcaa acagcggttt gcaacttaaa tatcactctg    4500
ccagcacata aaaggagac agagtcagat caagatgatg agattgagaa aacagataga     4560
cgacagagct tcgcatcctt agctttacgt aagcgctaca gctacttgac tgagcctgga    4620
atgattgaac ggagtacagg agcaacaaga tccctcccca ccacttactc atacaagcca    4680 ttctttcta caagaccata ccagtcctgg acaacagctc cgattacagt gcctgggcca     4740
gccaagtcag gcttcacttc cttatcaagt tcttcctcta atacgccatc agcttctccg    4800
ttaaaatcaa tatggtctgt ttcgacacct tctccaatca aatccacatt aggcgcgtca    4860
actacatctt cagttaaatc cattagtgac gtggcatctc caattagatc cttacggaca    4920
atgtcttcgc cgataaaaac tgtggtgtca caatctccat acaatatcca ggtttcctct    4980
ggtaccctgg ctagagctcc agcagtcacg gaagctacgc ccttaaaagg gctggcatcc    5040
aattctacgt tttcctctcg aacctctcca gtgactacag cagggtctct tttggagagg    5100
tcatcaatta ctatgacacc ccctgcctcc cccaaatcaa acattaatat gtattcctca    5160
agtttgccat ttaagtcaat tattacatca gcagcaccgc taatatcttc acctttaaag    5220
tcagtggtgt ctccagttaa atcacgagtt gatgtcattt catcagccaa aattacaatg    5280
gcatcttctc tctcatcacc tgtgaagcag atgcctggac atgcagaggt agcattagtc    5340
aatggatcta tttcccctct aaaatatgca tcatcctcaa ctttaattaa tggatgcaaa    5400
gccactgcca cgttacagga aaaaatttct tctgctacaa actctgtgag ctctgtggtc    5460
agtgcagcca ctgacacagt tgagaaagtg ttttctacca cgactgcaat gccattttcc    5520
ccactcaggt catatgtttc tgcagcacca tcagcttttc agtctctaag aactccttcc    5580
gcaagtgcac tctatacatc ccttgggtcg tcaatatctg caactacctc atctgtaact    5640
tcatcaatta taacagtgcc agtatactct gtagtcaatg ttttgccaga accagcatta    5700
aagaaacttc cagactctaa ttcatttaca aaatcagcag cagccttgct gtcacccatt    5760
aaaacattga ctacggagac acatcctcag cctcacttca gtcgaacttc atctccagtt    5820
aagtcatctt tgttccttgc accctctgcc cttaagttgt ctacaccatc ttctttatct    5880
tccagtcagg agatactaaa agatgtagct gaaatgaaag aggacctaat gcggatgacc    5940
gcaatactac agacagatgt gcctgaggag aagccattcc aacctgaact cccaaaggaa    6000
gggagaatag atgatgaaga acctttcaaa attgtagaga aagtaaagga agacttagtg    6060
aaagttagtg aaatccttaa aaaggatgta tgtgtagata ataaaggatc acccaaatca    6120
ccaaagagtg acaaaggaca ctctcctgaa gatgactgga tagaatttag ttcggaagaa    6180
atccgggaag ccagacaaca agctgctgcg agccagtctc catctctgcc agagagagtg    6240
caagtaaaag caaaagccgc ctccgaaaag gattataact tgaccaaagt tattgattac    6300
ctaacaaatg atattgggag tagttcactg acaaacttaa aatacaagtt tgaggatgca    6360
aagaaggatg gtgagggagg acagaaaaga gttttaaaac cagcaattgc tttgcaggaa    6420
cacaaactca aaatgcctcc agcctccatg aggacttcca cctctgagaa agaattgtgt    6480
aaaatggctg attccttttt tggaacagat actattttag agtctcctga tgacttttct    6540
caacacgacc aagataaaag tcccttgtct gacagtggct ttgaaacaag aagtgaaaag    6600
acaccttcag ccccacaaag cgctgaaacg actggtccta aaccacttttt tcatgaagtt    6660 cccatccctc ctgttattac agaaacaaga actgaagtgg ttcatgttat caggagctat    6720
```

```
gatccctcag ctggggatgt tccccagacc caaccagagg agcctgtgtc acctaaacct    6780
tcacctactt ttatggaatt ggaaccaaag cccaccacct ctagtattaa agaaaaggtt    6840
aaagcatttc aaatgaaagc cagtagtgaa gaagatgacc acaatcgggt tttaagcaaa    6900
ggcatgcgtg ttaaagaaga gactcacata accacaacca ccagaatggt ttatcattct    6960
ccaccaggcg gtgaaggtgc atctgaagaa attgaagaaa ccatgtcagt ccatgacatc    7020
atgaaggcct ttcagtccgg gcgggatcct tccaaagaac tggcaggtct gttttgaacat   7080
aagtcggcag tgtctccaga tgttcacaag tctgctgctg aaacctcagc ccagcatgca    7140
gagaaggaca accaaatgaa acccaaactg agcgtataa tagaagtcca catcgaaaaa     7200
ggtaaccaag ctgagcccac tgaagtcatt attagagaaa ccaaaaagca tccagaaaaa    7260
gaaatgtatg tatatcagaa agacttatcc cggggagata ttaacctaaa agattttctg    7320
ccagaaaaac acgatgcttt tccttgttca gaggaacagg gtcagcaaga agaagaagaa    7380
cttactgctg aagagtcatt gccttcttat ctggagtctt ccagagtaaa cactcctgtg    7440
tcccaagaag aagatagccg ccctagttct gctcaactca tatctgatga ctcttataaa    7500
acattgaagc ttttgagtca acactcaata gaataccatg acgatgagtt gtcagaacta    7560
agagggagt cttacaggtt tgctgagaaa atgcttctgt cagaaaagct agatgtgtct    7620
cattctgata ctgaggaatc ggttacagac catgcaggac ccctagctc agagttacag     7680
gggtctgata gcggtccag agaaaaaata gccactgccc ccaaaaaaga aattctctcc     7740
aaaatctata agatgtttc tgaaaatggt gtaggtaaag tgtctaaaga tgagcatttt     7800
gataaagtga cagtgttgca ctattctggc aatgttagta gtccaaaaca tgccatgtgg    7860
atgcgcttta ctgaggacag attagacaga ggtagagaga agttgatata tgaagatagg    7920
gtggacagga ctgtgaagga ggctgaagaa aaactgactg aagtgtcaca gttttttcgt    7980
gacaaaactg aaaagctaaa tgatgaactg cagtccccag agaaaaggc acgcctaaa     8040
aatggcaaag aatattcttc tcaaagccct accagtagca gccctgagaa agtgctactg    8100
acagaactgc tggcatccaa tgatgagtgg gttaaggcaa gacagcatgg ccctgatgga   8160
caaggcttcc ccaaggccga ggagaaggca cccagtctgc ccagcagccc agagaagatg   8220
gttctctccc aacagactga ggacagcaag tccacagtgg aagccaaagg aagtatttca   8280
cagagcaaag caccagatgg gccccagtct ggattccagc tcaaacaatc taaactcagt   8340
tccattagat taaaatttga acaaggcaca cacgcaaaaa gtaaggacat gtctcaagaa   8400
gacagaaagt cagatggcca gtccagaatc ccagttaaaa aaatacagga gagcaagcta   8460
cccgtctacc aagttttttgc tagagaaaaa cagcagaagg ccatagacct cccagatgaa   8520
agtgtatctg tgcaaaaaga ttttatggta ttaaaaacca agatgagca tgcccaaagc    8580
aacgaaattg ttgtaaatga ttctggctct gataatgtga aaaaacagag aactgaaatg   8640
tcaagtaaag caatgcctga ctctttttct gagcagcagg ctaaagactt ggcatgtcat   8700
ataacctcag atttagcaac taggggacca tgggacaaaa aggtctttag aacatgggag   8760
agttcgggag ccactaacaa taagtctcag aaagaaaac tttcgcatgt acttgttcat    8820
gatgtaagag agaatcacat tggtcaccct gagagtaaaa gtgttgatca aaagaatgaa   8880
tttatgtctg tgactgagag agaacgcaaa ttgttaacaa acggctctct ctcagaaatt   8940
aaagaaatga ctgtaaaatc tccctccaaa aaagtcttat ataggaata tgttgtgaaa    9000
gaaggggacc atccaggcgg attgcttgat cagccttcca ggaggagcga gagctcagca   9060
gtgtcacaca ttcccgtcag agttgctgat gagaggagaa tgctgtcttc taatattccc   9120
```

```
gatggttttt gtgaacagtc ggcatttcca aaacatgaac tatcacaaaa attgtcccag    9180
tcaagcatga gtaaagagac agttgagaca cagcacttta attctataga agatgaaaaa    9240
gttacctatt cagaaatcag caaagtttcc aaacaccaga gttatgtagg tttatgccca    9300
cctctcgagg aaaccgaaac ctcccccacc aaatctcctg attctttaga gtttagccca    9360
ggaaaggaat ctccctctag tgatgtattc gaccacagtc ccattgatgg attggaaaaa    9420
ctcgcaccac tagcccagac agagggaggg aaagagataa aaactttacc cgtttatgtc    9480
agttttgtac aagtggggaa gcaatatgaa aaggagatac aacaaggagg tgtaaaaaaa    9540
atcataagtc aggaatgtaa gacagtacaa gaaccagggg ggacctttta tacaactaga    9600
cagcaaaagc aacctccttc tccccaaggt agtccagaag atgatactct agagcaagta    9660
tcctttctag acagctctgg gaaaagccct ttaaccccag aaacacccag ttcagaggaa    9720
gtgagttatg aatttacatc taagacacct gactcgctca tagcttatat accaggcaaa    9780
cccagcccaa ttcccgaggt ttctgaggag tcagaggagg aggaacaggc caagtcaacc    9840
tcccttaagc agactacagt ggaggaaaca gcagttgagc gtgaaatgcc taatgacgtg    9900
agcaaagact ctaaccaaag acccaaaaat aacagagttg cctatattga atttccccct    9960
cctccaccac tggatgcgga ccagattgag tcagataaga agcatcatta tctcccagaa    10020
aaagaggttg acatgattga agtcaatctg caagatgagc atgacaagta ccagctggct    10080
gaacctgtca ttagagtgca gccaccttca ccagttcctc ccggggcaga cgtcagtgat    10140
tcaagcgatg acgaatctat ttatcagcca gtcccagtta aaaaatatac cttcaaatta    10200
aaggaagtgg acgatgaaca aaaagaaaaa cccaaagctt ctgctgaaaa ggcttccaac    10260
cagaaagaac tggaaagtaa tggatctgga aaagataatg aatttggcct tggccttgat    10320
tcacctcaga atgaaattgc ccagaatggg aacaacgacc agtccatcac agagtgttcc    10380
attgccacca cagcagagtt ttctcatgac acggatgcca cagagatcga ctctctggat    10440
ggctatgacc tgcaagatga agatgatggc ttgacagaga gtgattctaa actcccaatt    10500
caagccatgg aaattaagaa agatatctgg aacacagagg gcattctgaa gccagctgac    10560
cgctctttta gccaaagtaa acttgaagtt atcgaggagg agggaaaggt gggaccagat    10620
gaggacaagc caccttctaa aagttcttca tctgaaaaga ctcctgataa gactgatcag    10680
aagtcagggg cccagttctt cacactggaa ggcagacatc ctgacagatc agtgtttcct    10740
gatacttact tcagttacaa agtagatgaa gaatttgcca ctccttttaa aacagtagct    10800
accaaaggtc tagattttga cccttggtct aataaccgag gggatgatga agtttttgac    10860
agtaaatcac gggaagatga aactaagcca tttgggctgg cggtagaaga ccgctctcca    10920
gcaacaaccc ctgatacaac gccagccaga acgccaactg atgaaagtac cccaactagt    10980
gagcctaacc ccttcccatt tcatgaagga aaaatgtttg agatgactcg cagtggtgca    11040
attgacatga gcaagaggga ttttgttgaa gagaggctcc aattttttcca gattggtgag    11100 catacttctg aagggaagtc aggggaccag ggggaagggg ataaaagtat ggtcactgcc    11160
acaccacagc cacagtcagg ggacaccact gtagaaacca atctagagag aaatgtagag    11220
acacctacag tggaacctaa ccccagcatc ccgaccagcg agagtgtcag ggaaggcaca    11280
tccagtagtg gctccctgga gaaatcagca gcagccacta acacctctaa agttgacccc    11340
aagttgcgca cgcctataaa aatgggaatt tctgcatcca ccatgaccat gaagaaagaa    11400
ggccctggag aaataacaga taagatagaa gcggtgatga ccagttgtca gggattagaa    11460
```

```
aatgaaacta taacaatgat ttcaaataca gccaatagcc agatgggcgt taggccccat  11520
gaaaaacatg attttcaaaa agataacttt aataacaaca acaatttgga ttcttccact  11580
atacagacag ataacattat gagtaatata gttctgacag aacattctgc acccacttgt  11640
accacagaga aagataaccc agtgaaagtc tcatcaggaa aaagacagg ggtactacaa   11700 ggacactgtg taagagataa gcagaaagtt cttggagaac agcaaaaaac aaaggaattg  11760
atagggatta ggcaaaaatc caaacttccc ataaaggcca cttcaccaaa agatacctct  11820
ccaccgaacc atatgtcaaa cactaaagca agtaaaatga agcaggttag tcaatccgag  11880
aaaaccaaag cccttactac ttcttcatgt gtagatgtaa agtccagaat tccagtgaaa  11940
aacacaccca gggataacat aattgcagtt agaaaagcat gtgccacaca aaagcaaggg  12000
cagccagaga aaggcaaggc caaacagctt ccatccaagt tgccagtaaa ggtaagatcc  12060
acctgtgtca ctaccaccac caccactgcc accaccacca ccactaccac cactaccacc  12120
accaccagct gcacagttaa agttaggaaa agtcagctca aggaagtatg taaacattcc  12180
attgaatatt ttaagggaat tagtggtgag accttaaagc ttgtggaccg cctctctgaa  12240
gaagaaaaaa agatgcagtc cgagttgtcc gatgaggaag aaagtacctc aagaaacacg  12300
tcgttgtccg agacttcccg gggtggccag ccttcggtta caacgaagtc tgctagagat  12360
aagaaaacag aggcagcacc tttaaaatca aagagtgaaa aggccggcag tgagaaaagg  12420
agcagtagaa ggactggtcc acagagtcca tgtgaacgga cagatatcag gatggcaata  12480
gtagccgatc acctgggact tagttggaca gaactggcaa gggaactgaa tttttcagtg  12540
gatgaaatca atcaaatacg tgtggaaaat ccaaattctt taatttctca gagcttcatg  12600
ttattaaaaa aatgggttac cagagacgga aaaaatgcca caactgatgc cttaacttcg  12660
gtcttgacaa aaattaatcg aatagatata gtgacactgc tagaaggacc aatatttgat  12720
tatggaaata tttcaggcac cagaagtttt gcagatgaga acaatgtttt ccatgaccct  12780
gttgatggtt ggcagaatga gacatcaagt ggaaacctag agtcctgcgc tcaagctcga  12840
agagtaactg gtgggttact agatcgactg gatgacagcc ctgaccagtg tagagattcc  12900
attacctcat atctcaaagg agaagctggc aaatttgaag caaatggaag ccatacagaa  12960
atcactccag aagcaaagac aaaatcttac tttccagaat cccaaaatga tgtaggaaaa  13020
cagagtacca aggaaactct gaaaccaaaa atacatggat ctggtcatgt tgaagaacca  13080
gcatcaccac tagcagcata tcagaaatct ctagaagaaa ccagcaagct tataatagaa  13140
gagactaaac cctgtgtgcc tgtcagtatg aaaaagatga gtaggacttc tccagcagat  13200
ggcaagccaa ggcttagcct ccatgaagaa gaggggtcca gtgggtctga gcaaaagcag  13260
ggagaaggtt ttaaggtgaa aacgaagaaa gaaatccggc atgtggaaaa gaagagccac  13320
tcgtaacagc gaacggtcag tcaaggatca taagttttta ctgccagtat tgagaaattc  13380
gtggaagaaa tgtcagcagg aagtaaaaat tcaccgagaa gtgtgtgtgt gttcgctgct  13440
tccacacatt aatggcatga tttttttat gcaaaaagaa aagaaaagaa accacccac   13500 atttttaattt agcatgagcc aatttacaga gcatggaaat cactttcatt tccggattgg  13560
cgcgtgtgca attagcaatg cagtgtatat acaagaagcc atgctgttaa cagtttatct  13620
caagtaattt ggtgtcattt acaaaaggaa gaaattcttg ccatcagaag ggacagaagg  13680
agatggaatg atcaaatcac agagaaacac taaaattact aaatctacaa cagctcgcct  13740
tatttttctt ggacccaaac tgtcagggta taaacactat ttgtttcttt tttaaaacat  13800
cgatagtttt gctgtaaata ataacactgt ataaattcta acagaaaaat agaataaaat  13860
```

| | |
|---|---|
| gttgataagg cactgcctct tagaacacaa acagaatatt gcaaatgcat ttaacaaata | 13920 |
| ggggtctcaa gtgacttcac cctagaagag gagggaggga ttctgggtgg gggtgactct | 13980 |
| tcactgattc ttgtatatta gcaattataa tgtttgtata tgcaaaactg ctagcttgat | 14040 |
| tttaaaaaaa aacaaatctt taaaatctgc tgcaaattta ataattccc aaaatgagga | 14100 |
| attctgtagt tctgtgaaaa attttttttct tcagaatact aatattttga tgcatgtgta | 14160 |
| tcaccttatt ttgattaaat cttttccaat tttgcaaaca ctacagtata ctgcaacaca | 14220 |
| aaagatttta tctgtaaaca caaagccctt catctaatat ttgttgctat tgccaatttt | 14280 |
| tcaatgaaat gacctaaaaa caacaaaaaa aaataaccta tacggtagtt gctttagggg | 14340 |
| gtgggggat gctatctgtt agtgcttaaa aggggtaaa tgcttgccgc tttagaggtg | 14400 |
| gatggtgctc ataaaaggcc ccagtcgggg gtatttaaaa aggactgaac agaaatcctt | 14460 |
| agctagtaga atggcagcac gctgtaaaat tattactgta ttgtgtactg gctataagat | 14520 |
| gtagacacct ttcagtaagc caatcatttg taaccattct agcagtgtca tattaggtta | 14580 |
| ataaggctgc tgtgttttaa agggcatttt tatttgggtt ttggtgaaat tcttttaattt | 14640 |
| gttgattata ttcacataaa atcagcattc attgacacat agctctaatg acatatgtat | 14700 |
| gaaaaaccat acactggatg acctagtcga ttatttaagc ataaaataaa ttgtgttaaa | 14760 |
| ctcttcacct | 14770 |

<210> SEQ ID NO 31
<211> LENGTH: 1194
<212> TYPE: DNA
<213> ORGANISM: Homo sapiens

<400> SEQUENCE: 31

| | |
|---|---|
| ttaattcggc ggccgcggat ccgagccgga cgggcactgg gcgactctgt gcttcgctga | 60 |
| ggaaaaataa ctaaacatgg gcaaaggaga tcctaagaag ccgagacgga aaatgtcatc | 120 |
| atatgcattt tttgtgcaaa cttgtcggga ggagcataag aagaagcacc cagatgcttc | 180 |
| agtcaacttc tcagagtttt ctaagaagtg ctcagagagg tggaagacca tgtctgctaa | 240 |
| agagaaagga aaatttgaag atatggcaaa agcggacaag gcccgttatg aaagagaaat | 300 |
| gaaaacctat atccctccca aagggagac aaaaaagaag ttcaaggatc ccaatgcacc | 360 |
| caagaggcct ccttcggcct tcttcctctt ctgctctgag tatcgcccaa aaatcaaagg | 420 |
| agaacatcct ggcctgtcca ttggtgatgt tgcgaagaaa ctgggagaga tgtggaataa | 480 |
| cactgctgca gatgacaagc agccttatga aagaaggct gaaaagctga aggaaaaata | 540 |
| cgaaaaggat attgctgcat atcgagctaa aggaaagcct gatgcagcaa aaaagggagt | 600 |
| tgtcaaggct gaaaaagca agaaaaagaa ggaagaggag aaggtgaggg aagatgaaga | 660 |
| ggatgaggag gaggaggaag atgaagaaga tgaagatgaa gaagaagatg atgatgatga | 720 |
| ataagttggt tctagcgcag tttttttttt cttgtctata aagcatttaa ccccctgta | 780 |
| cacaactcac tcctttaaa gaaaaaatt gaaatgtaag gctgtgtaag atttgttttt | 840 |
| aaactgtaca gtgtcttttt ttgtatagtt aacacactac cgaatgtgtc tttagatagc | 900 |
| cctgtcctgg tggtatcttc aatagccact aaccctgcct ggtacagtat ggggttgta | 960 |
| aattggcatg gaaatttaaa gcaggttctt gtttgggcac agcacaaatt agttatatat | 1020 |
| ggggatggta gtttttcat cttcagttgt ctctgatgca gctatacgaa ataattgttg | 1080 |
| ttctgttaac tgaataccac tctgtaattg caaaaaaaaa aaaaagttg cagctgtttt | 1140 |

```
gttgacattc tgaatgcttc taagtaaata caattttttt tattaaaaaa aaaa         1194
```

<210> SEQ ID NO 32
<211> LENGTH: 1805
<212> TYPE: DNA
<213> ORGANISM: Homo sapiens

<400> SEQUENCE: 32

```
aagagactga actgtatctg cctctatttc caaaagactc acgttcaact ttcgctcaca     60
caaagccggg aaaattttat tagtcctttt tttaaaaaaa gttaatataa aattatagca    120
aaaaaaaaaa ggaacctgaa ctttagtaac acagctggaa caatcgcagc ggcggcggca    180
gcggcgggag aagaggttta atttagttga ttttctgtgg ttgttggttg ttcgctagtc    240
tcacggtgat ggaagctgca cattttttcg aagggaccga gaagctgctg gaggtttggt    300
tctcccggca gcagcccgac gcaaaccaag gatctgggga tcttcgcact atcccaagat    360
ctgagtggga catactttg aaggatgtgc aatgttcaat cataagtgtg acaaaaactg     420
acaagcagga agcttatgta ctcagtgaga gtagcatgtt tgtctccaag agacgtttca    480
ttttgaagac atgtggtacc accctcttgc tgaaagcact ggttcccctg ttgaagcttg    540
ctagggatta cagtgggttt gactcaattc aaagcttctt ttattctcgt aagaatttca    600
tgaagccttc tcaccaaggg tacccacacc ggaatttcca ggaagaaata gagtttctta    660
atgcattttt cccaaatgga gcaggatatt gtatgggacg tatgaattct gactgttggt    720
acttatatac tctggatttc ccagagagtc gggtaatcag tcagccagat caaaccttgg    780
aaattctgat gagtgagctt gacccagcag ttatggacca gttctacatg aaagatggtg    840
ttactgcaaa ggatgtcact cgtgagagtg gaattcgtga cctgatacca ggttctgtca    900
ttgatgccac aatgttcaat ccttgtgggt attcgatgaa tggaatgaaa tcggatggaa    960
cttattggac tattccacatc actccagaac cagaattttc ttatgttagc tttgaaacaa   1020
acttaagtca gacctcctat gatgacctga tcaggaaagt tgtagaagtc ttcaagccag   1080
gaaaatttgt gaccaccttg tttgttaatc agagttctaa atgtcgcaca gtgcttgctt   1140
cgccccagaa gattgaaggt tttaagcgtc ttgattgcca gagtgctatg ttcaatgatt   1200
acaattttgt ttttaccagt tttgctaaga agcagcaaca acagcagagt tgattaagaa   1260
aaatgaagaa aaaacgcaaa aagagaacac atgtagaagg tggtggatgc tttctagatg   1320
tcgatgctgg gggcagtgct ttccataacc accactgtgt agttgcagaa agccctagat   1380
gtaatgatag tgtaatcatt ttgaattgta tgcattatta tatcaaggag ttagatatct   1440
tgcatgaatg ctctcttctg tgtttaggta ttctctgcca ctcttgctgt gaaattgaag   1500
tggatgtaga aaaaaccttt tactatatga aactttacaa cacttgtgaa agcaactcaa   1560
tttggtttat gcacagtgta atatttctcc aagtatcatc caaaattccc cacagacaag   1620
gctttcgtcc tcattaggtg ttggcctcag cctaaccctc taggactgtt ctattaaatt   1680
gctgccagaa ttttacatcc agttacctcc actttctaga acatattctt tactaatgtt   1740
attgaaacca atttctactt catactgatg tttttggaaa cagcaattaa agttttctt    1800
ccatg                                                                1805
```

<210> SEQ ID NO 33
<211> LENGTH: 3907
<212> TYPE: DNA
<213> ORGANISM: Homo sapiens

<400> SEQUENCE: 33

-continued

```
ctactgttgt ttttgagggg cgggcagccg cgccgccgcg gcactttttt aattttttcg      60
ggtgccgcag cagcgacccc tcggcgccga tgtccctgat ccctggagcg acgacggccg     120
ctgcctaagc tgggaagagg aatgccagct cctgagcagg cctcattggt ggaggagggg     180
caaccacaga cccgccagga agctgcctcc actggcccag gcatggaacc cgagaccaca     240
gccaccacta ttctagcatc cgtgaaggag caggagcttc agtttcagcg actcacccga     300
gaactggaag tggaaaggca gattgttgcc agtcagctag aaagatgtag gcttggagca     360
gaatcaccaa gcatcgccag caccagctca actgagaagt catttccttg gagatcaaca     420
gacgtgccaa atactggtgt aagcaaacct agagtttctg acgctgtcca gcccaacaac     480
tatctcatca ggacagagcc agaacaagga accctctatt caccgaaaca gacatctctc     540
catgaaagtg agggatcatt gggtaactca agaagttcaa cacaaatgaa ttcttattcc     600
gacagtggat accaggaagc agggagtttc cacaacagcc agaacgtgag caaggcagac     660
aacagacagc agcattcatt cataggatca actaacaacc atgtggtgag gaattcaaga     720
gctgaaggac aaacactggt tcagccatca gtagccaatc gggccatgag aagagttagt     780
tcagttccat ctagagcaca gtctccttct tatgttatca gcacaggcgt gtctccttca     840
agggggtctc tgagaacttc tctgggtagt ggatttggct ctccgtcagt gaccgacccc     900
cgacctctga accccagtgc atattcctcc accacattac ctgctgcacg ggcagcctct     960
ccgtactcac agagacccgc ctccccaaca gctatacggc ggattgggtc agtcacctcc    1020
cggcagacct ccaatcccaa cggaccaacc cctcaatacc aaaccaccgc cagagtgggg    1080
tccccactga ccctgacgga tgcacagact cgagtagctt ccccatccca aggccaggtg    1140
gggtcgtcgt cccccaaacg ctcagggatg accgccgtac cacagcatct gggaccttca    1200
ctgcaaagga ctgttcatga catggagcaa ttcggacagc agcagtatga catttatgag    1260
aggatggttc cacccaggcc agacagcctg acaggcttac ggagttccta tgctagtcag    1320
catagtcagc ttgggcaaga ccttcgttct gccgtgtctc ccgacttgca cattactcct    1380
atatatgagg ggaggaccta ttacagccca gtgtaccgca gcccaaacca tggaactgtg    1440
gagctccaag gatcgcagac ggcgttgtat cgcacaggtg tatcaggtat tggaaatcta    1500
caaaggacat ccagccaacg aagtacgctt acataccaaa gaaataatta tgctctgaac    1560
acaacagcta cctacgcgga gccctacagg cctatacaat accgagtgca agagtgcaat    1620
tataacaggc ttcagcatgc agtgccggct gatgatggca ccacaagatc cccatcaata    1680
gacagcattc agaaggaccc cagggagttt gcctggcgtg atcctgagtt gcctgaggtc    1740
attcacatgc ttgagcacca gttcccatct gttcaggcaa atgcagcggc ctacctgcag    1800
cacctgtgct ttggtgacaa caaagtgaag atggaggtgt gtaggttagg gggaatcaag    1860
catctggttg accttctgga ccacagagtt ttggaagttc agaagaatgc ttgtggtgcc    1920
cttcgaaacc tcgtttttgg caagtctaca gatgaaaata aaatagcaat gaagaatgtt    1980
ggtgggatac ctgccttgtt gcgactgttg agaaaatcta ttgatgcaga gtaagggag     2040
cttgttacag gagttctttg gaatttatcc tcatgtgatg ctgtaaaaat gacaatcatt    2100
cgagatgctc tctcaacctt aacaaacact gtgattgttc cacattctgg atggaataac    2160
tcttcttttg atgatgatca taaaattaaa tttcagactt cactagttct gcgtaacacg    2220
acaggttgcc taaggaacct cacgtccgcg ggggaagaag ctcggaagca aatgcggtcc    2280
tgcgaggggc tggtagactc actgttgtat gtgatccaca cgtgtgtgaa cacatccgat    2340
```

-continued

```
tacgacagca agacggtgga gaactgcgtg tgcaccctga ggaacctgtc ctatcggctg        2400
gagctggagg tgccccaggc ccggttactg ggactgaacg aattggatga cttactagga        2460
aaagagtctc ccagcaaaga ctctgagcca agttgctggg ggaagaagaa gaaaagaaa        2520 aagaggactc cgcaagaaga tcaatgggat ggagttggtc ctatcccagg actgtcgaag        2580
tcccccaaag gggttgagat gctgtggcac ccatcggtgg taaaaccata tctgactctt        2640
ctagcagaaa gttccaaccc agccaccttg gaaggctctg cagggtctct ccagaacctc        2700
tctgctagca actggaagtt tgcagcatat atccggggcg gccgtccgaa agaaaaggg         2760 ctccccatcc ttgtggagct tctgagaatg gataacgata gagttgtttc ttccggtgca        2820
acagccttga ggaatatggc actagatgtt cgcaacaagg agctcatagg caaatacgcc        2880
atgcgagacc tggtcaaccg gctccccggc ggcaatggcc ccagtgtctt gtctgatgag        2940
accatggcag ccatctgctg tgctctgcac gaggtcacca gcaaaaacat ggagaacgca        3000
aaagccctgg ccgactcagg aggcatagag aagctggtga acataaccaa aggcaggggc        3060
gacagatcat ctctgaaagt ggtgaaggca gcagcccagg tcttgaatac attatggcaa        3120
tatcgggacc tccggagcat ttataaaaag gatgggtgga atcagaacca tttattaca         3180 cctgtgtcga cattggagcg agaccgattc aaatcacatc cttccttgtc taccaccaac        3240
caacagatgt cacccatcat tcagtcagtc ggcagcacct cttcctcacc agcactgtta        3300
ggaatcagag accctcgctc tgaatacgat aggacccagc cacctatgca gtattacaat        3360
agccaagggg atgccacaca taaaggcctg taccctggct ccagcaaacc ttcaccaatt        3420
tacatcagtt cctattcctc accagcaaga gaacaaaata gacggctaca gcatcaacag        3480
ctgtattata gtcaagatga ctccaacaga agaactttg atgcatacag attgtatttg         3540
cagtctcctc atagctatga agatccttat tttgatgacc gagttcactt tccagcttct        3600
actgattact caacacagta tggactgaaa tcgaccacaa attatgtaga cttttattcc        3660
actaaacgac cttcttatag agcagaacag tacccagggt ccccagactc atgggtgtac        3720
gatcaagatg cccaacagag gaactctttc tttctaacct tgttcagatt gaggtgaaaa        3780
gtccatcttg ctgatttcat gattgaaatg tgaaagtgaa gtggaaggaa tgaatgaagt        3840
gtgttttttt ttccttttg aggaattatc agggaattc gatatcaagc ttatcgatac         3900
cgtcgac                                                                   3907
```

<210> SEQ ID NO 34
<211> LENGTH: 568
<212> TYPE: DNA
<213> ORGANISM: Homo sapiens
<220> FEATURE:
<221> NAME/KEY: misc_feature
<222> LOCATION: (1)...(568)
<223> OTHER INFORMATION: n = A,T,C or G

<400> SEQUENCE: 34

```
cagtgaaaat acaactttat attaatcatc tcaataatac agattacaga actgagttta         60
cagattacag aacttttcat actttgtggg tcagaaagga taaccgtaaa ttactgtctc        120
cgctttatgg gtggtaaaac tgagccacag agaaatttct ctaagaaaat ttaaaggaa         180 ttgatgttca ttaaataaat atcctcactg atttttttaa ggtagaaaag tacaatgcac        240
agtgttaaaa aaattactgt aacagcctca tgttcgagaa gtctaaaatt ttaaggctac        300
tacatgtgtt aattttcagt acatgtccaa cagaaaacat cctttattcc agttacatcc        360
tgaagatacc gaagtcagtc ttctctattg gtgcgttgag ggctgcacta aaactggaga        420
```

```
cccaagacca gtctggtgtc tgctgggatc aatgatccca tcatcccata ccctgcgct    480 gggaatagta aggggttccc tcctcttcca acntcctaat ggatggggcc cttttaaagc    540
cgcttcatca gcactggggn actgcttt                                       568
```

<210> SEQ ID NO 35
<211> LENGTH: 362
<212> TYPE: DNA
<213> ORGANISM: Homo sapiens

<400> SEQUENCE: 35

```
gtcggctctt agagtagtaa ccgccagaaa ggagtcggaa gaggtctcac gaggctgtca     60
tcaccgccat gcccaagaat aaaggtaaag gaggtaaaaa caggcgcagg ggtaaaaatg    120
agaatgaatc tgaaaaaaga gagttggtgt ttaaagagga tggacaagag tatgctcagg    180
taatcaaaat gttgggaaat ggacgattgg aagcattgtg ttttgatggt gtaaagaggt    240
tatgccatat cagagggaaa ttgagaaaaa aggtttggat aaatacatca gacattatat    300
tggttggtct acgggactat caggataaca agctgatgt aattttttaaa gtacattgca    360 ga                                                                   362
```

<210> SEQ ID NO 36
<211> LENGTH: 1661
<212> TYPE: DNA
<213> ORGANISM: Homo sapiens

<400> SEQUENCE: 36

```
tgctgcagcc gctgccgccg attccggatc tcattgccac gcgcccccga cgaccgcccg     60
acgtgcattc ccgattcctt ttggttccaa gtccaatatg gcaactctaa aggatcagct    120
gatttataat cttctaaagg aagaacagac cccccagaat aagattacag ttgttggggt    180
tggtgctgtt ggcatggcct gtgccatcag tatcttaatg aaggacttgg cagatgaact    240
tgctcttgtt gatgtcatcg aagacaaatt gaagggagag atgatggatc tccaacatgg    300
cagccttttc cttagaacac caaagattgt ctctggcaaa gactataatg taactgcaaa    360
ctccaagctg gtcattatca cggctggggc acgtcagcaa gagggagaaa gccgtcttaa    420
tttggtccag cgtaacgtga acatatttaa attcatcatt cctaatgttg taaaatacag    480
cccgaactgc aagttgctta ttgtttcaaa tccagtggat atcttgacct acgtggcttg    540
gaagataagt ggttttccca aaaccgtgt tattggaagt ggttgcaatc tggattcagc    600
ccgattccgt tacctgatgg gggaaaggct gggagttcac ccattaagct gtcatggtg    660 ggtccttggg gaacatggag attccagtgt gcctgtatgg agtggaatga atgttgctgg    720
tgtctctctg aagactctgc acccagattt agggactgat aaagataagg aacagtggaa    780
agaggttcac aagcaggtgg ttgagagtgc ttatgaggtg atcaaactca aaggctacac    840
atcctgggct attggactct ctgtagcaga tttggcagag agtataatga agaatcttag    900
gcgggtgcac ccagtttcca ccatgattaa gggtctttac ggaataaagg atgatgtctt    960
ccttagtgtt ccttgcattt tgggacagaa tggaatctca gaccttgtga aggtgactct   1020
gacttctgag gaagaggccc gtttgaagaa gagtgcagat acactttggg ggatccaaaa   1080
ggagctgcaa ttttaaagtc ttctgatgtc atatcatttc actgtctagg ctacaacagg   1140
attctaggtg gaggttgtgc atgttgtcct ttttatctga tctgtgatta agcagtaat   1200 atttttaagat ggactgggaa aaacatcaac tcctgaagtt agaaataaga atggtttgta   1260
```

-continued

| | | |
|---|---|---|
| aaatccacag ctatatcctg atgctggatg gtattaatct tgtgtagtct tcaactggtt | 1320 | |
| agtgtgaaat agttctgcca cctctgacgc accactgcca atgctgtacg tactgcattt | 1380 | |
| gccccttgag ccaggtggat gtttaccgtg tgttatataa cttcctggct ccttcactga | 1440 | |
| acatgcctag tccaacattt tttcccagtg agtcacatcc tgggatccag tgtataaatc | 1500 | |
| caatatcatg tcttgtgcat aattcttcca aaggatctta ttttgtgaac tatatcagta | 1560 | |
| gtgtacatta ccatataatg taaaaagatc tacatacaaa caatgcaacc aactatccaa | 1620 | |
| gtgttatacc aactaaaacc cccaataaac cttgaacagt g | 1661 | |

<210> SEQ ID NO 37
<211> LENGTH: 743
<212> TYPE: DNA
<213> ORGANISM: Homo sapiens

<400> SEQUENCE: 37

| | | |
|---|---|---|
| cagccagctc gacggggctg tgtgtgctgg gcctggctcg cggcgaaccg agatggcaga | 60 | |
| gcagtcggac gaggccgtga agtactacac cctagaggag attcagaagc acaaccacag | 120 | |
| caagagcacc tggctgatcc tgcaccacaa ggtgtacgat ttgaccaaat ttctggaaga | 180 | |
| gcatcctggt ggggaagaag ttttaaggga acaagctgga ggtgacgcta ctgagaactt | 240 | |
| tgaggatgtc gggcactcta cagatgccag ggaaatgtcc aaaacattca tcattgggga | 300 | |
| gctccatcca gatgacagac caaagttaaa caagcctccg gaaactctta tcactactat | 360 | |
| tgattctagt tccagttggt ggaccaactg gtgatccct gccatctctg cagtggccgt | 420 | |
| cgccttgatg tatcgcctat acatggcaga ggactgaaca cctcctcaga agtcagcgca | 480 | |
| ggccgagcct gctttggaca cgggagaaaa gaagccattg ctaactactt caactgacag | 540 | |
| aaaccttcac ttgaaaacaa tgattttaat atatctcttt cttttcttc cgacattaga | 600 | |
| aacaaaacaa aaagaactgt cctttctgcg ctcaaatttt tcgagtgtgc ctttttattc | 660 | |
| atctacttta ttttgatgtt tccttaatgt gtaatttact tattataagc atgatctttt | 720 | |
| aaaaatatat ttggctttta aag | 743 | |

<210> SEQ ID NO 38
<211> LENGTH: 7679
<212> TYPE: DNA
<213> ORGANISM: Homo sapiens

<400> SEQUENCE: 38

| | | |
|---|---|---|
| gaagagcaag aggcaggctc agcaaatggt tcagccccag tccccggtgg ctgtcagtca | 60 | |
| aagcaagccc ggttgttatg acaatggaaa acactatcag ataaatcaac agtgggagcg | 120 | |
| gacctaccta ggtaatgtgt tggtttgtac ttgttatgga ggaagccgag gttttaactg | 180 | |
| cgaaagtaaa cctgaagctg aagagacttg ctttgacaag tacactggga acacttaccg | 240 | |
| agtgggtgac acttatgagc gtcctaaaga ctccatgatc tgggactgta cctgcatcgg | 300 | |
| ggctgggcga gggagaataa gctgtaccat cgcaaaccgc tgccatgaag ggggtcagtc | 360 | |
| ctacaagatt ggtgacacct ggaggagacc acatgagact ggtggttaca tgttagagtg | 420 | |
| tgtgtgtctt ggtaatggaa aaggagaatg gacctgcaag cccatagctg agaagtgttt | 480 | |
| tgatcatgct gctgggactt cctatgtggt cggagaaacg tgggagaagc cctaccaagg | 540 | |
| ctggatgatg gtagattgta cttgcctggg agaaggcagc ggacgcatca cttgcacttc | 600 | |
| tagaaataga tgcaacgatc aggacacaag gacatcccta agaattggag acacctggag | 660 | |
| caagaaggat aatcgaggaa acctgctcca gtgcatctgc acaggcaacg gccgaggaga | 720 | |

```
gtggaagtgt gagaggcaca cctctgtgca gaccacatcg agcggatctg gccccttcac    780
cgatgttcgt gcagctgttt accaaccgca gcctcacccc cagcctcctc cctatggcca    840
ctgtgtcaca gacagtggtg tggtctactc tgtggggatg cagtggttga agacacaagg    900
aaataagcaa atgctttgca cgtgcctggg caacggagtc agctgccaag agacagctgt    960
aacccagact tacggtggca acttaaatgg agagccatgt gtcttaccat tcacctacaa   1020
tggcaggacg ttctactcct gcaccacgga agggcgacag gacggacatc tttggtgcag   1080
cacaacttcg aattatgagc aggaccagaa atactctttc tgcacagacc acactgtttt   1140
ggttcagact caaggaggaa attccaatgg tgccttgtgc cacttcccct cctatacaa    1200 caaccacaat tacactgatt gcacttctga gggcagaaga gacaacatga agtggtgtgg   1260
gaccacacag aactatgatg ccgaccagaa gtttgggttc tgccccatgg ctgcccacga   1320
ggaaatctgc acaaccaatg aagggtcat gtaccgcatt ggagatcagt gggataagca    1380
gcatgacatg ggtcacatga tgaggtgcac gtgtgttggg aatggtcgtg gggaatggac   1440
atgcattgcc tactcgcaac ttcgagatca gtgcattgtt gatgacatca cttacaatgt   1500
gaacgacaca ttccacaagc gtcatgaaga ggggcacatg ctgaactgta catgcttcgg   1560
tcagggtcgg ggcaggtgga agtgtgatcc cgtcgaccaa tgccaggatt cagagactgg   1620
gacgttttat caaattggag attcatggga gaagtatgtg catggtgtca gataccagtg   1680
ctactgctat ggccgtggca ttggggagtg gcattgccaa cctttacaga cctatccaag   1740
ctcaagtggt cctgtcgaag tatttatcac tgagactccg agtcagccca actcccaccc   1800
catccagtgg aatgcaccac agccatctca catttccaag tacattctca ggtggagacc   1860
taaaaattct gtaggccgtt ggaaggaagc taccatacca ggccacttaa actcctacac   1920
catcaaaggc ctgaagcctg gtgtggtata cgagggccag ctcatcagca tccagcagta   1980
cggccaccaa gaagtgactc gctttgactt caccaccacc agcaccagca cacctgtgac   2040
cagcaacacc gtgacaggag agacgactcc cttttctcct cttgtggcca cttctgaatc   2100
tgtgaccgaa atcacagcca gtagctttgt ggtctcctgg gtctcagctt ccgacaccgt   2160
gtcgggattc cgggtggaat atgagctgag tgaggaggga gatgagccac agtacctgga   2220
tcttccaagc acagccactt ctgtgaacat ccctgacctg cttcctggcc gaaaatacat   2280
tgtaaatgtc tatcagatat ctgaggatgg ggagcagagt ttgatcctgt ctacttcaca   2340
aacaacagcg cctgatgccc ctcctgaccc gactgtggac caagttgatg acacctcaat   2400
tgttgttcgc tggagcagac cccaggctcc catcacaggg tacagaatag tctattcgcc   2460
atcagtagaa ggtagcagca cagaactcaa ccttcctgaa actgcaaact ccgtcaccct   2520
cagtgacttg caacctggtg ttcagtataa catcactatc tatgctgtgg aagaaaatca   2580
agaaagtaca cctgttgtca ttcaacaaga aaccactggc accccacgct cagatacagt   2640
gccctctccc agggacctgc agtttgtgga agtgacagac gtgaaggtca ccatcatgtg   2700
gacaccgcct gagagtgcag tgaccggcta ccgtgtggat gtgatccccg tcaacctgcc   2760
tggcgagcac gggcagaggc tgcccatcag caggaacacc tttgcagaag tcaccgggct   2820
gtcccctggg gtcacctatt acttcaaagt ctttgcagtg agccatggga gggagagcaa   2880
gcctctgact gctcaacaga accaaaact ggatgctccc actaacctcc agtttgtcaa    2940
tgaaactgat tctactgtcc tggtgagatg gactccacct cgggcccaga taacaggata   3000
ccgactgacc gtgggcctta cccgaagagg ccagcccagg cagtacaatg tgggtccctc   3060
```

```
tgtctccaag tacccctga ggaatctgca gcctgcatct gagtacaccg tatccctcgt   3120
ggccataaag ggcaaccaag agagccccaa agccactgga gtctttacca cactgcagcc   3180
tgggagctct attccacctt acaacaccga ggtgactgag accaccatcg tgatcacatg   3240
gacgcctgct ccaagaattg gttttaagct gggtgtacga ccaagccagg gaggagaggc   3300
accacgagaa gtgacttcag actcaggaag catcgttgtg tccggcttga ctccaggagt   3360
agaatacgtc tacaccatcc aagtcctgag agatggacag gaaagagatg cgccaattgt   3420
aaacaaagtg gtgacaccat tgtctccacc aacaaacttg catctggagg caaaccctga   3480
cactggagtg ctcacagtct cctgggagag gagcaccacc ccagacatta ctggttatag   3540
aattaccaca accccctacaa acggccagca gggaaattct ttggaagaag tggtccatgc   3600
tgatcagagc tcctgcactt ttgataacct gagtcccggc ctggagtaca atgtcagtgt   3660
ttacactgtc aaggatgaca aggaaagtgt ccctatctct gataccatca tcccagctgt   3720
tcctcctccc actgacctgc gattcaccaa cattggtcca gacaccatgc gtgtcacctg   3780
ggctccaccc ccatccattg atttaaccaa cttcctggtg cgttactcac ctgtgaaaaa   3840
tgaggaagat gttgcagagt tgtcaatttc tccttcagac aatgcagtgg tcttaacaaa   3900
tctcctgcct ggtacagaat atgtagtgag tgtctccagt gtctacgaac aacatgagag   3960
cacacctctt agaggaagac agaaaacagg tcttgattcc ccaactggca ttgactttc   4020 tgatattact gccaactctt ttactgtgca ctggattgct cctcgagcca ccatcactgg   4080
ctacaggatc cgccatcatc ccgagcactt cagtgggaga cctcgagaag atcgggtgcc   4140
ccactctcgg aattccatca ccctcaccaa cctcactcca ggcacagagt atgtggtcag   4200
catcgttgct cttaatggca gagaggaaag tcccttattg attggccaac aatcaacagt   4260
ttctgatgtt ccgagggacc tggaagttgt tgctgcgacc cccaccagcc tactgatcag   4320
ctgggatgct cctgctgtca cagtgagata ttacaggatc acttacgag aaacaggagg   4380 aaatagccct gtccaggagt tcactgtgcc tgggagcaag tctacagcta ccatcagcgg   4440
ccttaaacct ggagttgatt ataccatcac tgtgtatgct gtcactggcc gtggagacag   4500
ccccgcaagc agcaagccaa tttccattaa ttaccgaaca gaaattgaca accatccca   4560 gatgcaagtg accgatgttc aggacaacag cattagtgtc aagtggctgc cttcaagttc   4620
ccctgttact ggttacagag taaccaccac tcccaaaaat ggaccaggac aacaaaaac   4680 taaaactgca ggtccagatc aaacagaaat gactattgaa ggcttgcagc ccacagtgga   4740
gtatgtggtt agtgtctatg ctcagaatcc aagcggagag agtcagcctc tggttcagac   4800
tgcagtaacc aacattgatc gccctaaagg actggcattc actgatgtgg atgtcgattc   4860
catcaaaatt gcttgggaaa gcccacaggg gcaagtttcc aggtacaggg tgacctactc   4920
gagccctgag gatggaatcc atgagctatt ccctgcacct gatggtgaag aagacactgc   4980
agagctgcaa ggcctcagac cgggttctga gtacacagtc agtgtggttg ccttgcacga   5040
tgatatggag agccagcccc tgattggaac ccagtccaca gctattcctg caccaactga   5100
cctgaagttc actcaggtca cacccacaag cctgagcgcc cagtggacac cacccaatgt   5160
tcagctcact ggatatcgag tgcgggtgac ccccaaggag aagaccggac caatgaaaga   5220
aatcaacctt gctcctgaca gctcatccgt ggttgtatca ggacttatgg tggccaccaa   5280
atatgaagtg agtgtctatg ctcttaagga cactttgaca agcagaccag ctcagggtgt   5340
tgtcaccact ctggagaatg tcagcccacc aagaagggc cgtgtgacag atgctactga   5400
gaccaccatc accattagct ggagaaccaa gactgagacg atcactggct ccaagttga   5460
```

```
tgccgttcca gccaatggcc agactccaat ccagagaacc atcaagccag atgtcagaag    5520
ctacaccatc acaggtttac aaccaggcac tgactacaag atctacctgt acaccttgaa    5580
tgacaatgct cggagctccc ctgtggtcat cgacgcctcc actgccattg atgcaccatc    5640
caacctgcgt ttcctggcca ccacacccaa ttccttgctg gtatcatggc agccgccacg    5700
tgccaggatt accggctaca tcatcaagta tgagaagcct gggtctcctc cagagaagt    5760 ggtccctcgg ccccgccctg gtgtcacaga ggctactatt actggcctgg aaccgggaac    5820
cgaatataca atttatgtca ttgccctgaa gaataatcag aagagcgagc ccctgattgg    5880
aaggaaaaag acagacgagc ttccccaact ggtaacccctt ccacacccca atcttcatgg    5940
accagagatc ttggatgttc cttccacagt tcaaaagacc cctttcgtca cccaccctgg    6000
gtatgacact ggaaatggta ttcagcttcc tggcacttct ggtcagcaac ccagtgttgg    6060
gcaacaaatg atctttgagg aacatggttt taggcggacc acaccgccca caacggccac    6120
ccccataagg cataggccaa gaccatacccc gccgaatgta ggacaagaag ctctctctca    6180
gacaaccatc tcatgggccc cattccagga cacttctgag tacatcattt catgtcatcc    6240
tgttggcact gatgaagaac ccttacagtt cagggttcct ggaacttcta ccagtgccac    6300
tctgacaggc ctcaccagag gtgccaccta caacatcata gtggaggcac tgaaagacca    6360
gcagaggcat aaggttcggg aagaggttgt taccgtgggc aactctgtca cgaaggctt    6420 gaaccaacct acggatgact cgtgctttga ccccctacaca gtttcccatt atgccgttgg    6480
agatgagtgg gaacgaatgt ctgaatcagg cttaaactg ttgtgccagt gcttaggctt    6540
tggaagtggt catttcagat gtgattcatc tagatggtgc catgacaatg gtgtgaacta    6600
caagattgga gagaagtggg accgtcaggg agaaaatggc cagatgatga gctgcacatg    6660
tcttgggaac ggaaaaggag aattcaagtg tgaccctcat gaggcaacgt gttacgatga    6720
tgggaagaca taccacgtag gagaacagtg gcagaaggaa tatctcggtg ccatttgctc    6780
ctgcacatgc tttggaggcc agcggggctg gcgctgtgac aactgccgca gacctggggg    6840
tgaacccagt cccgaaggca ctactggcca gtcctacaac cagtattctc agagatacca    6900
tcagagaaca aacactaatg ttaattgccc aattgagtgc ttcatgcctt tagatgtaca    6960
ggctgacaga gaagattccc gagagtaaat catctttcca atccagagga caagcatgt    7020 ctctctgcca agatccatct aaactggagt gatgttagca gacccagctt agagttcttc    7080
tttctttctt aagccctttg ctctggagga agttctccag cttcagctca actcacagct    7140
tctccaagca tcaccctggg agtttcctga gggttttctc ataaatgagg gctgcacatt    7200
gcctgttctg cttcgaagta ttcaataccg ctcagtattt taaatgaagt gattctaaga    7260
tttggtttgg gatcaatagg aaagcatatg cagccaacca agatgcaaat gttttgaaat    7320
gatatgacca aaatttttaag taggaaagtc acccaaacac ttctgctttc acttaagtgt    7380
ctggcccgca atactgtagg aacaagcatg atcttgttac tgtgatattt taaatatcca    7440
cagtactcac tttttccaaa tgatcctagt aattgcctag aaatatcttt ctcttacctg    7500
ttatttatca atttttccca gtatttttat acggaaaaaa ttgtattgaa aacacttaga    7560
tgcagttgat aagaggaatt tggtataatt atggtgggtg attatttttt atactgtatg    7620
tgccaaagct ttactactgt ggaaagacaa ctgttttaat aaaagattta cattccaca    7679
```

<210> SEQ ID NO 39
<211> LENGTH: 1441
<212> TYPE: DNA
<213> ORGANISM: Homo sapiens

<400> SEQUENCE: 39

```
caggctggtc aatgtggcaa ccagatcggt gccaagttct gggaggtgat cagtgatgaa      60
catggcatcg accccaccgg cacctaccac ggggacagcg acctgcagct ggaccgcatc     120
tctgtgtact acaatgaagc cacagtggcc aaatatgttc ctcgtgccat cctggtggat     180
ctagaacctg ggaccatgga ctctgttcgc tcaggtcctt ttggccagat ctttagacca     240
gacaactttg tatttggtca gtctggggca ggtaacaact gggccaaagg ccactacaca     300
gagggcgccg agctggttga ttctgtcctg gatgtggtac ggaaggaggc agagagctgt     360
gactgcctgc agggcttcca gctgacccac tcactgggcg ggggcacagg ctctggaatg     420
ggcactctcc ttatcagcaa gatccgagaa gaatacccctg atcgcatcat gaataccttc     480
agtgtggtgc cttcacccaa agtgtctgac accgtggtcg agccctacaa tgccaccctc     540
tccgtccatc agttggtaga gaatactgat gagacctatt gcattgacaa cgaggccctc     600
tatgatatct gcttccgcac tctgaggctg accacaccaa cctacgggga tctgaaccac     660
cttgtctcag gcaccatgga gtgtgtcacc acctgcctcc gtttccctgg ccagctcaat     720
gctgacctcc gcaagttggc agtcaacatg gtccccttcc cacgtctcca tttctttatg     780
cctggctttg cccctctcac cagccgtgga agccagcagt atcgagctct cacagtgccg     840
gacctcaccc agcaggtctt cgatgccaag aacatgatgg ctgcctgtga ccccgccac      900
ggccgatacc tcaccgtggc tgctgtcttc cgtggtcgga tgtccatgaa ggaggtcgat     960
gagcagatgc ttaacgtgca gaacaagaac agcagctact ttgtggaatg gatccccaac    1020
aatgtcaaga cagccgtctg tgacatccca cctcgtggcc tcaagatggc agtcaccttc    1080
attggcaata gcacagccat ccaggagctc ttcaagcgca tctcggagca gttcactgcc    1140
atgttccgcc ggaaggcctt cctccactgg tacacaggcg agggcatgga cgagatggag    1200
ttcaccgagg ctgagagcaa catgaacgac ctcgtctctg agtatcagca gtaccaggat    1260
gccaccgcag aagaggagga ggatttcggt gaggaggccg aagaggaggc ctaaggagag    1320
ccccatcac ctcaggcttc tcagttccct tagccgtctt actcaactgc cccctttcct    1380
ctccctcaga atttgtgttt gctgcctcta tcttgttttt tgttttttct tctgggggg      1440
g                                                                    1441
```

<210> SEQ ID NO 40
<211> LENGTH: 873
<212> TYPE: DNA
<213> ORGANISM: Homo sapiens

<400> SEQUENCE: 40

```
cagtttgaat cgcggtgcga ccgaaggagt aggtgctggg atcgtcaccg tggcaccgat      60
tagccttttc tctgccttgc ttgcttgagc ttcagcggaa ttcgaaatgg ctggcggtaa     120
ggctggaaag gactccggaa aggccaagac aaaggcggtt tcccgctcgc agagagccgg     180
cttgcagttc ccagtgggcc gtattcatcg acacctaaaa tctaggacga ccagtcatgg     240
acgtgtgggc gcgactgccg ctgtgtacag cgcagccatc ctggagtacc tcaccgcaga     300
ggtacttgaa ctggcaggaa atgcatcaaa agacttaaag gtaaagcgta ttaccccctcg     360
tcacttgcaa cttgctattc gtggagatga agaattggat tctctcatca aggctacaat     420
tgctggtggt ggtgtcattc cacacatcca caatctctg attgggaaga aggacaaca     480
gaagactgtc taaaggatgc ctggattcct tgttatctca ggactctaaa tactctaaca    540
```

```
gctgtccagt gttggtgatt ccagtggact gtatctctgt gaaaaacaca attttgcctt     600
tttgtaattc tatttgagca agttggaagt ttaattagct ttccaaccaa ccaaatttct     660
gcattcgagt cttaaccata tttaagtgtt actgtggctt caaagaagct attgattctg     720
aagtagtggg ttttgattga gttgactgtt tttaaaaaac tgtttggatt ttaattgtga     780
tgcagaagtt atagtaacaa acatttggtt ttgttcagac cttatttcca ctctggtgga     840
taagttcaat aaaggtcata tcccaaacta aaa                                  873

<210> SEQ ID NO 41
<211> LENGTH: 2098
<212> TYPE: DNA
<213> ORGANISM: Homo sapiens

<400> SEQUENCE: 41
cctgccgaag tcagttcctt gtggagccgg agctgggcgc ggattcgccg aggcaccgag      60
gcactcagag gaggcgccat gtcagaaccg gctggggatg tccgtcagaa cccatgcggc     120
agcaaggcct gccgccgcct cttcggccca gtggacagcg agcagctgag ccgcgactgt     180
gatgcgctaa tggcgggctg catccaggag gcccgtgagc gatggaactt cgactttgtc     240
accgagacac cactggaggg tgacttcgcc tgggagcgtg tgcggggcct tggcctgccc     300
aagctctacc ttcccacggg gccccggcga ggccgggatg agttgggagg aggcaggcgg     360
cctggcacct cacctgctct gctgcagggg acagcagagg aagaccatgt ggacctgtca     420
ctgtcttgta cccttgtgcc tcgctcaggg gagcaggctg aagggtcccc aggtggacct     480
ggagactctc agggtcgaaa acggcggcag accagcatga cagatttcta ccactccaaa     540
cgccggctga tcttctccaa gaggaagccc taatccgccc acaggaagcc tgcagtcctg     600
gaagcgcgag ggcctcaaag gcccgctcta catcttctgc cttagtctca gtttgtgtgt     660
cttaattatt atttgtgttt taatttaaac acctcctcat gtacataccc tggccgcccc     720
ctgcccccca gcctctggca ttagaattat ttaaacaaaa actaggcggt tgaatgagag     780
gttcctaaga gtgctgggca tttttatttt atgaaatact atttaaagcc tcctcatccc     840
gtgttctcct tttcctctct cccggaggtt gggtgggccg gcttcatgcc agctacttcc     900
tcctccccac ttgtccgctg ggtggtaccc tctggagggg tgtggctcct tcccatcgct     960
gtcacaggcg gttatgaaat tcaccccctt tcctggacac tcagacctga attcttttc    1020 atttgagaag taaacagatg gcactttgaa ggggcctcac cgagtggggg catcatcaaa    1080
aactttggag tcccctcacc tcctctaagg ttgggcaggg tgaccctgaa gtgagcacag    1140
cctagggctg agctggggac ctggtaccct cctggctctt gataccccc tctgtcttgt    1200 gaaggcaggg ggaaggtggg gtcctggagc agaccacccc gcctgccctc atggcccctc    1260
tgacctgcac tggggagccc gtctcagtgt tgagccttt ccctctttgg ctcccctgta    1320
ccttttgagg agccccagct acccttcttc tccagctggg ctctgcaatt cccctctgct    1380
gctgtccctc ccccttgtcc tttcccttca gtacccctctc agctccaggt ggctctgagg    1440
tgcctgtccc accccccaccc ccagctcaat ggactggaag gggaagggac acacaagaag    1500
aagggcaccc tagttctacc tcaggcagct caagcagcga ccgcccctc ctctagctgt    1560 gggggtgagg gtcccatgtg gtggcacagg ccccccttgag tggggttatc tctgtgttag    1620 ggtatatga tggggagta gatctttcta ggagggagac actggcccct caaatcgtcc    1680
agcgaccttc ctcatccacc ccatccctcc ccagttcatt gcactttgat tagcagcgga    1740
acaaggagtc agacatttta agatggtggc agtagaggct atggacaggg catgccacgt    1800
```

-continued

```
gggctcatat ggggctggga gtagttgtct ttcctggcac taacgttgag cccctggagg      1860
cactgaagtg cttagtgtac ttggagtatt ggggtctgac cccaaacacc ttccagctcc      1920
tgtaacatac tggcctggac tgttttctct cggctcccca tgtgtcctgg ttcccgtttc      1980
tccacctaga ctgtaaacct ctcgagggca gggaccacac cctgtactgt tctgtgtctt      2040
tcacagctcc tcccacaatg ctgatataca gcaggtgctc aataaacgat tcttagtg        2098
```

<210> SEQ ID NO 42
<211> LENGTH: 1914
<212> TYPE: DNA
<213> ORGANISM: Homo sapiens

<400> SEQUENCE: 42

```
gcagccaggc gcgcactgca cagctctctt ctctcgccgc cgcccgagcg cacccttcag        60
cccgcgcgcc ggccgtgagt cctcggtgct cgcccgccgg ccagacaaac agcccgcccg       120
accccgtccc gaccctggcc gccccgagcg gagcctggag caaaatgatg cttcaacacc       180
caggccaggt ctctgcctcg gaagtgagtg cttctgccat cgtcccctgc ctgtcccctc       240
ctgggtcact ggtgtttgag gattttgcta acctgacgcc ctttgtcaag gaagagctga       300
ggtttgccat ccagaacaag cacctctgcc accggatgtc ctctgcgctg gaatcagtca       360
ctgtcagcga cagacccctc ggggtgtcca tcacaaaagc cgaggtagcc cctgaagaag       420
atgaaaggaa aaagaggcga cgagaaagaa ataagattgc agctgcaaag tgccgaaaca       480
agaagaagga gaagacggag tgcctgcaga aagagtcgga gaagctggaa agtgtgaatg       540
ctgaactgaa ggctcagatt gaggagctca agaacgagaa gcagcatttg atatacatgc       600
tcaaccttca tcggcccacg tgtattgtcc gggctcagaa tgggaggact ccagaagatg       660
agagaaacct ctttatccaa cagataaaag aaggaacatt gcagagctaa gcagtcgtgg       720 tatggggcg actggggagt cctcattgaa tcctcatttt atacccaaaa ccctgaagcc       780
attggagagc tgtcttcctg tgtacctcta gaatcccagc agcagagaac catcaaggcg       840
ggagggcctg cagtgattca gcaggccctt cccattctgc cccagagtgg gtcttggacc       900
agggcaagtg catctttgcc tcaactccag gatttaggcc ttaacacact ggccattctt       960
atgttccaga tggcccccag ctggtgtcct gcccgccttt catctggatt ctacaaaaaa      1020
ccaggatgcc caccgttaga ttcaggcagc agtgtctgta cctcgggtgg gagggatggg      1080
gccatctcct tcaccgtggc taccattgtc actcgtaggg gatgtggagt gagaacagca      1140
tttagtgaag ttgtgcaacg gccagggttg tgctttctag caaatatgct gttatgtcca      1200
gaaattgtgt gtgcaagaaa actaggcaat gtactcttcc gatgtttgtg tcacacaaca      1260
ctgatgtgac tttatatgc tttttctcag atctggtttc taagagtttt gggggcggg       1320 gctgtcacca cgtgcagtat ctcaagatat tcaggtggcc agaagagctt gtcagcaaga      1380
ggaggaacag aattctccca gcgttaacac aaaatccatg ggcagcatga tggcaggtcc      1440
tctgttgcaa actcagttcc aaagtcacag gaagaaagca gaaagttcaa cttccaaagg      1500
gttaggactc tccactcaat gtcttaggtc aggagttgtg tctaggctgg aagagccaaa      1560
gaaatattcc attttccttt ccttgtggtt gaaaccacag tcagtggaga gatgtttgga      1620
acacagtcag tggagctggt ggtaccaggt ttagcattat tggatgtcaa aagcatttt       1680 tttgtcatgt agctgttta agaaatctgg cccagggtgt ttgcagctgt gagaagtcac       1740
tcacactggc cacaaggacg ctggctactg tctattaaaa ttctgatgtt tctgtgaaat      1800
```

-continued

| tctcagagtg | tttaattgta | ctcaatggta | tcattacaat | tttctgtaag | agaaaatatt | 1860 |
| acttatttat | cctagtattc | ctaacctgtc | agaataataa | atattgtggt | aaaa | 1914 |

<210> SEQ ID NO 43
<211> LENGTH: 699
<212> TYPE: DNA
<213> ORGANISM: Homo sapiens

<400> SEQUENCE: 43

| catccggtgt | ggtcgacggg | tcctccaaga | gtttggggcg | cggaccggag | taccttgcgt | 60 |
| gcagttatgt | cggcgtcggt | agtgtctgtc | atttcgcggt | tcttagaaga | gtacttgagc | 120 |
| tccactccgc | agcgtctgaa | gttgctggac | gcgtacctgc | tgtatatact | gctgaccggg | 180 |
| gcgctgcagt | tcggttactg | tctcctcgtg | gggaccttcc | ccttcaactc | ttttctctcg | 240 |
| ggcttcatct | cttgtgtggg | gagtttcatc | ctagcggttt | gcctgagaat | acagatcaac | 300 |
| ccacagaaca | aagcggattt | ccaaggcatc | tccccagagc | gagcctttgc | tgattttctc | 360 |
| tttgccagca | ccatcctgca | ccttgttgtc | atgaactttg | ttggctgaat | cattctcatt | 420 |
| tacttaattg | aggagtagga | gactaaaaga | atgttcactc | tttgaatttc | ctggataaga | 480 |
| gttctggaga | tggcagctta | ttggacacat | ggattttctt | cagatttgac | acttactgct | 540 |
| agctctgctt | tttatgacag | gagaaaagcc | cagagttcac | tgtgtgtcag | aacaactttc | 600 |
| taacaaacat | ttattaatcc | agcctctgcc | tttcattaaa | tgtaaccttt | tgctttccaa | 660 |
| attaaagaac | tccatgccac | tcctcaaaaa | aaaaaaaaa | | | 699 |

<210> SEQ ID NO 44
<211> LENGTH: 2049
<212> TYPE: DNA
<213> ORGANISM: Homo sapiens

<400> SEQUENCE: 44

| gaattcgggg | gggtagaaga | cagaagtagc | tcagggtcct | ggggaatgg | aggacatcca | 60 |
| agcccgtcca | ggaactatgg | agatgggact | ccctatgacc | acatgaccag | cagggacctt | 120 |
| gggtcacatg | acaatctctc | tccaccttt | gtcaattcca | gaatacaaag | taaaacagaa | 180 |
| agggctcat | actcatctta | tgggagagaa | tcaaacttac | agggttgcca | ccagcagagt | 240 |
| ctccttggag | gtgacatgga | tatgggcaac | ccaggaaccc | tttcgcccac | caaacctggt | 300 |
| tcccagtact | atcagtattc | tagcaataat | ccccgaagga | ggcctcttca | cagtagtgcc | 360 |
| atggaggtac | agacaaagaa | agttcgaaaa | gttcctccag | gtttgccatc | ttcagtctat | 420 |
| gctccatcag | caagcactgc | cgactacaat | agggactcgc | caggctatcc | ttcctccaaa | 480 |
| ccagcaacca | gcactttccc | tagctccttc | ttcatgcaag | atggccatca | cagcagtgac | 540 |
| ccttggagct | cctccagtgg | gatgaatcag | cctggctatg | caggaatgtt | gggcaactct | 600 |
| tctcatattc | cacagtccag | cagctactgt | agcctgcatc | cacatgaacg | tttgagctat | 660 |
| ccatcacact | cctcagcaga | catcaattcc | agtcttcctc | cgatgtccac | tttccatcgt | 720 |
| agtggtacaa | accattacag | cacctcttcc | tgtacgcctc | ctgccaacgg | gacagacagt | 780 |
| ataatggcaa | atagaggaag | cggggcagcc | ggcagctccc | agactggaga | tgctctgggg | 840 |
| aaagcacttg | cttcgatcta | ttcttcagat | cacactaaca | acagcttttc | atcaaaccct | 900 |
| tcaactcctg | ttggctctcc | tccatctctc | tcagcaggca | cagctgtttg | gtctagaaat | 960 |
| ggaggacagg | cctcatcgtc | tcctaattat | gaaggaccct | tacactcttt | gcaaagccga | 1020 |
| attgaagatc | gtttagaaag | actggatgat | gctattcatg | ttctccggaa | ccatgcagtg | 1080 |

```
ggcccatcca cagctatgcc tggtggtcat ggggacatgc atggaatcat tggaccttct    1140
cataatggag ccatgggtgg tctgggctca gggtatggaa ccggccttct ttcagccaac    1200
agacattcac tcatggtggg gacccatcgt gaagatggcg tggccctgag aggcagccat    1260
tctcttctgc caaaccaggt tccggttcca cagcttcctg tccagtctgc gacttcccct    1320
gacctgaacc caccccagga cccttacaga ggcatgccac caggactaca ggggcagagt    1380
gtctcctctg gcagctctga gatcaaatcc gatgacgagg gtgatgagaa cctgcaagac    1440
acgaaatctt cggaggacaa gaaattagat gacgacaaga aggatatcaa atcaattact    1500
agcaataatg acgatgagga cctgacacca gagcagaagg cagagcgtga aaggagcgg    1560 aggatggcca acaatgcccg agagcgtctg cgggtccgtg acatcaacga ggctttcaaa    1620
gagctcggcc gcatggtgca gctccacctc aagagtgaca agccccagac caagctcctg    1680
atcctccacc aggcggtggc cgtcatcctc agtctggagc agcaagtccg agaaaggaat    1740
ctgaatccga aagctgcgtg tctgaaaaga agggaggaag agaaggtgtc ctcggagcct    1800
ccccctctct ccttggccgg cccacaccct ggaatgggag acgcatcgaa tcacatggga    1860
cagatgtaaa agggtccaag ttgccacatt gcttcattaa acaagagac cacttcctta    1920 acagctgtat tatcttaaac ccacataaac acttctcctt aaccccatt tttgtaatat    1980 aagacaagtc tgagtagtta tgaatcgcag acgcaagagg tttcagcatt cccaattatc    2040
aaaaaacag                                                           2049

<210> SEQ ID NO 45
<211> LENGTH: 316
<212> TYPE: DNA
<213> ORGANISM: Homo sapiens
<220> FEATURE:
<221> NAME/KEY: misc_feature
<222> LOCATION: (1)...(316)
<223> OTHER INFORMATION: n = A,T,C or G

<400> SEQUENCE: 45
tctatgtgta cagatgaatg ataaactctc tgcttctccc tctgcccctc tccaggcgcc     60
ggcgggcgcg ccngtcttcg aagttgatgc aatcggttta acatggctg aacgcgtgtg    120 tacacgggac tgacgcaacc cacgtgtaac tgtcagccgg gccctgagta atcgcttaaa    180
gatgttccta cgggcttgtt gctgttgatg ttttgttttg ttttgttttt tggtcttttt    240
ttgtatnata aaaataatc tatttctatg agaaaagacg gcgtctgtat atnttgggaa    300
tcttttccgt ttcaag                                                   316

<210> SEQ ID NO 46
<211> LENGTH: 3953
<212> TYPE: DNA
<213> ORGANISM: Homo sapiens

<400> SEQUENCE: 46
ggggtcacgg gcgaactaga acactgggaa agggctgca ggttccggac cggaccggcc      60
ctgacccgga ataatgagca aggagggtgt ggtgggttga aagccatcct actttactcc    120
cgagttagag catggattca gttttagtct taaggggggaa gtgagattgg agattttttat  180 ttttaatttt gggcagaagc aggttgactc tagggatctc cagagcgaga ggatttaact    240
tcatgttgct cccgtgtttg aaggaggaca ataaaagtcc caccgggcaa aattttcgta    300
acctctgcgg tagaaaacgt caggtatctt ttaaatcgcg atagttttcg ctgtgtcagg    360
```

-continued

```
ctttcttcgg tggagctccg agggtagcta ggttctaggt ttgaaacaga tgcagaatcc    420
aaaggcagcg caaaaaacag ccaccgattt tgctatgtct ctgagctgcg agataatcag    480
acagctaaat ggagtctgag cagctgttcc atagaggcta ctatagaaac agctacaaca    540
gtataacaag tgcaagtagt gatgaggaac ttttagatgg agcaggtgtt attatggact    600
ttcaaacatc tgaagatgac aatttattag atggtgacac tgcagttgga actcattata    660
caatgacaaa tggaggcagc attaacagtt ctacacattt actggatctt ttggatgaac    720
caattccagg tgttggtaca tatgatgatt ccatactat tgattgggtg cgagaaaaat     780
gtaaagacag agaaggcat agacggatca acagcaaaaa gaaagaatca gcatgggaaa     840
tgacaaaaag tttgtatgat gcgtggtcag atggctagt agtaacacta acaggattgg      900
catcagggc actggccgga ttaatagaca ttgctgccga ttggatgact gacctaaagg      960
agggcatttg ccttagtgcg ttgtggtaca accacgaaca gtgctgttgg ggatctaatg    1020
aaacaacatt tgaagagagg gataaatgtc cacagtggaa aacatgggca gaattaatca    1080
taggtcaagc agagggtcct ggttcttata tcatgaacta cataatgtac atcttctggg    1140
ccttgagttt tgcctttctt gcagtttccc tggtaaaggt atttgctcca tatgcctgtg    1200
gctctggaat tccagagatt aaaactattt taagtggatt catcatcaga ggttacttgg    1260
gaaaatggac tttaatgatt aaaaccatca cattagtcct ggctgtggca tcaggtttga    1320
gtttaggaaa agaaggtccc ctggtacatg ttgcctgttg ctgcggaaat atctttttcct   1380
acctcttttcc aaagtatagc acaaacgaag ctaaaaaaag ggaggtgcta tcagctgcct   1440
cagctgcagg ggtttctgta gcttttggtg caccaattgg aggagttctt tttagcctgg   1500
aagaggttag ctattatttt cctctcaaaa ctttatggag atcatttttt gctgctttag   1560
tggctgcatt tgttttgagg tccatcaatc catttggtaa cagccgtctg gtccttttttt   1620
atgtggagta tcatacacca tggtaccttt ttgaactgtt tccttttatt cttctagggg   1680
tatttggagg gctttgggga gccttttttca ttagggcaaa tattgcctgg tgtcgtcgac   1740
gcaagtccac gaaatttgga aagtatcccg ttctggaagt cattattgtt gcagccatta   1800
ctgctgtgat agccttccct aatccataca ctaggctaaa caccagtgaa ctgatcaaag   1860
agcttttttac agactgtggt cccctggaat cctcttctct ttgtgactac agaaatgaca   1920
tgaatgccag taaaattgtc gatgacattc ctgatcgtcc agcaggcatt ggagtatatt   1980
cagctatatg gcagttatgc ctggcactca tatttaaaat cataatgaca gtattcactt   2040
ttggcatcaa ggttccatca ggcttgttca tccccagcat ggccattgga gcgatcgcag   2100
gaaggattgt ggggattgcg gtggagcagc ttgcctacta tcaccacgac tggtttatct   2160
ttaaggagtg gtgtgaggtc ggggctgatt gcattacacc tggcctttat gccatggttg   2220
gtgctgctgc atgcttaggt ggtgtgacaa gaatgactgt ctccctggtg gttattgttt   2280
ttgagcttac tggaggcttg aatatattg ttcccccttat ggctgcagtc atgaccagta    2340
aatgggttgg agatgccttt ggcagggaag gcatttatga agcacacatc cgattaaatg   2400
gatacccttt cttggatgca aaagaagaat tcgaattcac tcataccacc ctggctgctg   2460
acgttatgag acctcgaagg aatgatcctc cttagctgt cctgacacag gacaatatga     2520
cagtggatga tatagaaaac atgattaatg aaaccagcta caatggattt cctgtcataa   2580
tgtcaaagaga atctcagaga ttagtgggat tgccctcag aagagacctg acaattgcaa   2640
tagaaagtgc caggaaaaaa caagaaggta tcgttggcag ttctcgggtg tgttttgcac   2700
agcacacccc atctcttcca gcagaaagtc ctcggccatt gaagcttcga agcattcttg   2760
```

```
acatgagccc ttttacagtg acagaccaca ccccaatgga gattgtggtg gatattttcc    2820
gaaagctggg actgaggcag tgccttgtaa ctcacaatgg gcgcctcctt ggcattataa    2880
caaaaaaaga tatcctccgg catatggccc agacggcaaa ccaagacccc gcttcaataa    2940
tgttcaactg aatctcacag atgaggagag agaagaaacg gaagaggaag tttatttgtt    3000
gaatagcaca actcttttaac ctgagggagt catctacttt ttttccctcc tttacaaaaa   3060
aagaaaggaa atataaaagc cgggttttttg caacatggtt tgcaaataat gctggtggaa   3120
tggaggagtt gtttggggag ggaaggaga gagaaggaaa ggagtgaggt atttcccgtc    3180
taacagaaag cagcgtatca actcctattg ttctgcactg gatgcattca gctgaggatg    3240
tgcctgatag tgcaggcttg cgcctcaaca gagatgacac cagagtcctc gagcacctgg    3300
cctgtttgct cacatgcaag acacatacag ccctattcta gaggatactt gaatggacct    3360
ctataaacgc aaggttcttg cctttttttta atcaaaactg ttctgtttaa ttcatgaatt    3420
gtatagttaa gcattacctt tctacattcc agaagagcct ttatttctct ctctctctct    3480
ctctctctct ctctctctac tgagctgtaa caaagcctct ttaaatcggt gtatcctttt    3540
gaagcagtcc tttctcatat tgagatgtac tgtgatttta ctgaggtttc atcacaagaa    3600
gggagtgttt cttgtgccat taaccatgta gtttgtacca tcactaaatg cttggaacag    3660
tacacatgca ccacaacaaa ggctcatcaa acaggtaaag tctcgaagga agcgagaacg    3720
aaatctctca ttgtgtgccg tgtggctcaa accgaaaac aatgaagctt ggttttaaag     3780
gataaagttt tctttttttgt tttcctctca gactttatgg ataatgtgac cgggtcttat    3840
gcaaattttc tatttctaaa actactacta tgatatacaa gtgctgttga gcataattaa    3900
ataaaatgct gctgctttga cagtaaagag aaggaagtat tctgaaaaaa aac           3953
```

<210> SEQ ID NO 47
<211> LENGTH: 2074
<212> TYPE: DNA
<213> ORGANISM: Homo sapiens

<400> SEQUENCE: 47

```
gaattcggca cgaggcgcgg cggctgcgac cgggacggcc cattttccgc cagctcgccg    60
ctcgctatgg cgtcgctcac cgtgaaggcc taccttctgg gcaaggagga cgcggcgcgc    120
gagattcgcc gcttcagctt ctgctgcagc cccgagcctg aggcggaagc cgaggctgcg    180
gcgggtccgg gaccctgcga gcggctgctg agccgggtgg ccgccctgtt ccccgcgctg    240
cggcctggcg gcttccaggc gcactaccgc gatgaggacg gggacttggt tgccttttcc    300
agtgacgagg aattgacaat ggccatgtcc tacgtgaagg atgacatctt ccgaatctac    360
attaaagaga aaaagagtg ccggcgggac caccgcccac cgtgtgctca ggaggcgccc    420
cgcaacatgg tgcaccccaa tgtgatctgc gatggctgca atgggcctgt ggtaggaacc    480
cgctacaagt gcagcgtctg cccagactac gacttgtgta gcgtctgcga gggaaagggc    540
ttgcaccggg gcacaccaa gctcgcattc cccagcccct cgggcacct gtctgagggc    600
ttctcgcaca gccgctggct ccggaaggtg aaacacggac acttcgggtg gccaggatgg    660
gaaatgggtc caccaggaaa ctggagccca cgtcctcctc gtgcagggga ggcccgccct    720
ggccccacgg cagaatcagc ttctggtcca tcggaggatc cgagtgtgaa tttcctgaag    780
aacgttgggg agagtgtggc agctgccctt agcctctgg gcattgaagt tgatatcgat    840
gtggagcacg gagggaaaag aagccgcctg accccgtct ctccagagag ttccagcaca    900
```

```
gaggagaaga gcagctcaca gccaagcagc tgctgctctg accccagcaa gccgggtggg      960
aatgttgagg gcgccacgca gtctctggcg gagcagatga ggaagatcgc cttggagtcc     1020 gagggcgcc ctgaggaaca gatggagtcg gataactgtt caggaggaga tgatgactgg     1080
acccatctgt cttcaaaaga agtggacccg tctacaggtg aactccagtc cctacagatg     1140
ccagaatccg aagggccaag ctctctggac ccctcccagg agggacccac agggctgaag     1200
gaagctgcct tgtacccaca tctcccgcca gaggctgacc cgcggctgat tgagtccctc     1260
tcccagatgc tgtccatggg cttctctgat gaaggcggct ggctcaccag gctcctgcag     1320
accaagaact atgacatcgg agcggctctg gacaccatcc agtattcaaa gcatccccg     1380 ccgttgtgac cacttttgcc cacctcttct gcgtgcccct cttctgtctc atagttgtgt     1440
taagcttgcg tagaattgca ggtctctgta cgggccagtt tctctgcctt cttccaggat     1500 cagggggttag ggtgcaagaa gccatttagg gcagcaaaac aagtgacatg aagggagggt     1560
ccctgtgtgt gtgtgtgctg atgtttcctg ggtgccctgg ctccttgcag cagggctggg     1620
cctgcgagac ccaaggctca ctgcagcgcg ctcctgaccc ctccctgcag gggctacgtt     1680
agcagcccag cacatagctt gcctaatggc tttcactttc tcttttgttt taaatgactc     1740
ataggtccct gacatttagt tgattatttt ctgctacaga cctggtacac tctgattta     1800 gataaagtaa gcctaggtgt tgtcagcagg caggctgggg aggccagtgt tgtgggcttc     1860
ctgctgggac tgagaaggct cacgaagggc atccgcaatg ttggtttcac tgagagctgc     1920
ctcctggtct cttcaccact gtagttctct catttccaaa ccatcagctg ctttaaaat     1980 aagatctctt tgtagccatc ctgttaaatt tgtaaacaat ctaattaaat ggcatcagca     2040
ctttaaccaa taaaaaaaaa aaaaaaaaaa aaaa                                2074

<210> SEQ ID NO 48
<211> LENGTH: 1846
<212> TYPE: DNA
<213> ORGANISM: Homo sapiens

<400> SEQUENCE: 48
gcagtgcggc ggtcacaggc tgagtgctgc ggcgcgatcc ttgcttccct gagcgttggc      60 ccggaggaa agaagatggt gctggatctg gatttgtttc gggtggataa aggaggggac     120
ccagccctca tccgagagac gcaggagaag cgcttcaagg acccgggact agtggaccag     180
ctggtgaagg cagacagcga gtggcgacga tgtagatttc gggcagacaa cttgagcaag     240
ctgaagaacc tatgcagcaa gacaatcgga gagaaatga agaaaaaaga gccagtggga     300
gatgatgagt ctgtcccaga gaatgtgctg agtttcgatg accttactgc agacgcttta     360
gctaacctga aagtctcaca aatcaaaaaa gtccgactcc tcattgatga agccatcctg     420
aagtgtgacg cggagcggat aaagttggaa gcagagcggt ttgagaacct ccgagagatt     480
gggaaccttc tgcacccttc tgtacccatc agtaacgatg aggatgtgga caacaaagta     540
gagaggattt ggggcgattg tacagtcagg aagaagtact ctcatgtgga cctggtggtg     600
atggtagatg gctttgaagg cgaaaagggg gccgtggtgg ctgggagtcg agggtacttc     660 ttgaagggg tcctggtgtt cctggaacag gctctcatcc agtatgccct tcgcaccttg     720
ggaagtcggg gctacattcc catttatacc cccttttca tgaggaagga ggtcatgcag     780
gaggtggcac agctcagcca gtttgatgaa gaactttata aggtgattgg caaaggcagt     840
gaaaagtctg atgacaactc ctatgatgag aagtacctga ttgccacctc agagcagccc     900
attgctgccc tgcaccggga tgagtggctc cggccggagg acctgcccat caagtatgct     960
```

```
ggcctgtcta cctgcttccg tcaggaggtg ggctcccatg gccgtgacac ccgtggcatc    1020
ttccgagtcc atcagtttga gaagattgaa cagtttgtgt actcatcacc ccatgacaac    1080
aagtcatggg agatgtttga agagatgatt accaccgcag aggagttcta ccagtccctg    1140
gggattcctt accacattgt gaatattgtc tcaggttctt tgaatcatgc tgccagtaag    1200
aagcttgacc tggaggcctg gtttccgggc tcaggagcct ccgtgagtt ggtctcctgt    1260 tctaattgca cggattacca ggctcgccgg cttcgaatcc gatatgggca aaccaagaag    1320
atgatggaca aggtggagtt tgtccatatg ctcaatgcta ccatgtgcgc cactacccgt    1380
accatctgcg ccatcctgga gaactaccag acagagaagg gcatcactgt gcctgagaaa    1440
ttgaaggagt tcatgccgcc aggactgcaa gaactgatcc cctttgtgaa gcctgcgccc    1500
attgagcagg agccatcaaa gaagcagaag aagcaacatg agggcagcaa aagaaagca    1560 gcagcaagag acgtcaccct agaaaacagg ctgcagaaca tggaggtcac cgatgcttga    1620
acattcctgc ctccctattt gccaggcttt catttctgtc tgctgagatc tcagagcctg    1680
cccaacagca gggaagccaa gcacccattc atccccctgc ccccatctga ctgcgtagct    1740 gagagggaa cagtgccatg taccacacag atgttcctgt ctcctcgcat gggcataggg    1800
acccatcatt gatgactgat gaaaccatgt aataaagcat ctctgg             1846

<210> SEQ ID NO 49
<211> LENGTH: 1325
<212> TYPE: DNA
<213> ORGANISM: Homo sapiens

<400> SEQUENCE: 49
cagaagcggc tagtggcggc tgcctgcgtc cccaacccc tccgcgcagc gctcgcgaca      60
cgcgtgccag gagtgggagc gagcggcggg gccagctgcg ttctgagcct gggcgcagct    120
gccatctgct ctgggaagca ccagggtgtc cccgccgccc tcagctcgaa gtcagccacc    180
atggaggcgc aggcacaagg tttgttggag actgaaccgt tgcaaggaac agacgaagat    240
gcagtagcca gtgctgactt ctctagcatg ctctctgagg aggaaaagga agagtaaaa    300 gcagagttag ttcagctaga agacgaaatt acaacactac gacaagtttt gtcagcgaaa    360
gaaaggcatc tagttgagat aaaacaaaaa ctcggcatga acctgatgaa tgaattaaaa    420
cagaacttca gcaaaagctg gcatgacatg cagactacca ctgcctacaa gaaaacacat    480
gaaaccctga gtcacgcagg gcaaaaggca actgcagctt tcagcaacgt tggaacggcc    540
atcagcaaga agttcggaga catgagttac tccattcgcc attccataag tatgcctgct    600
atgaggaatt ctcctacttt caaatcattt gaggagaggg ttgagacaac tgtcacaagc    660
ctcaagacga agtaggcgg tacgaaccct aatggaggca gttttgagga ggtcctcagc    720
tccacggccc atgccagtgc ccagagcttg gcaggaggct cccggcggac caaggaggag    780
gagctgcagt gctaagtcca gccagcgtgc agctgcatcc agaaaccggc cactacccag    840
cccatctctg cctgtgctta tccagataag aagaccaaaa tcccgctggg aaaaacccag    900
gccttgacat tgttattcaa atggcccctc cagaaagttt aatgatttcc atttgtattt    960
gtgttgatga tggaccactt gaccatcaca tttcagtatt catagatgac tgtcacattt    1020
taaaatgttc ccacttgagc aggtacacaa ctggtcataa ttcctgtctg tgtaattcga    1080
tgtatatttt tccaaacatg tagctattgt ttgctttgat ttttgcttgg cctccttat    1140 gatgtgcatg tccttgaagg ctgaatgaac agtcccttc agttcagcag atcaacagga    1200
```

-continued

| | |
|---|---|
| tggagctctt catgactgtc tccagcaata ggatgattta ctataaattt catccaacta | 1260 |
| cttgtgatct ctctcaccta catcaattat gtatgttaat ttcagcaatt aaaagaattg | 1320 |
| atttt | 1325 |

<210> SEQ ID NO 50
<211> LENGTH: 1216
<212> TYPE: DNA
<213> ORGANISM: Homo sapiens

<400> SEQUENCE: 50

| | |
|---|---|
| ccacgagtga gccttgaacg cctggacctg gacctcacag ctgacagcca gccacccgtc | 60 |
| ttcaaggtct tcccaggcag taccactgag gactacaacc ttattgttat tgaacgtggc | 120 |
| gctgccgctg cagctaccgg ccagccaggg actgcgcctg caggaacccc tggtgcccca | 180 |
| cccctggctg gcatggccat tgtcaaggag gaggagacgg aggctgccat tggagcccct | 240 |
| cctactgcca ctgagggccc tgagaccaaa cctgtgctta tggctcttgc ggagggtcct | 300 |
| ggtgctgagg gtccccgcct ggcctcacct agtggcagca ccagctcagg ctggaggtg | 360 |
| gtggctcctg agggtacctc agcccaggt ggtggcccgg gaaccctgga tgacagtgcc | 420 |
| accatttgcc gtgtctgcca gaagccaggc gatctggtta tgtgcaacca gtgtgagttt | 480 |
| tgtttccacc tggactgtca cctgccgcc ctgcaggatg taccagggga ggagtggagc | 540 |
| tgctcactct gccatgtgct ccctgacctg aaggaggagg atggcagcct cagcctggat | 600 |
| ggtgcagaca gcactggcgt ggtggccaag ctctcaccag ccaaccagcg gaaatgtgag | 660 |
| cgtgtactgc tggccctatt ctgtcacgaa ccctgccgcc ccctgcatca gctggctacc | 720 |
| gactccacct tctccctgga ccagcccggt ggcaccctgg atctgaccct gatccgtgcc | 780 |
| cgcctccagg agaagttgtc acctccctac agctccccac aggagtttgc ccaggatgtg | 840 |
| ggccgcatgt tcaagcaatt caacaagtta actgaggaca aggcagacgt gcagtccatc | 900 |
| atcggcctgc agcgcttctt cgagacgcgc atgaacgagg ccttcggtga caccaagttc | 960 |
| tctgctgtgt tggtggagcc cccgccgatg agcctgcctg gtgctggcct gagttcccag | 1020 |
| gagctgtctg gtggccctgg tgatggcccc tgaggctgga gccccatgg ccagcccagc | 1080 |
| ctggctctgt tctctgtcct gtcacccat ccccactccc ctggtggcct gactcccact | 1140 |
| ccctggtggc cccatccccc agttcctcac gatatggttt ttacttctgt ggatttaata | 1200 |
| aaaacttcac cagtta | 1216 |

<210> SEQ ID NO 51
<211> LENGTH: 3826
<212> TYPE: DNA
<213> ORGANISM: Homo sapiens

<400> SEQUENCE: 51

| | |
|---|---|
| gaattcgggt ggagtcctga aggagggcct gatgtcttca tcattctcaa attcttgtaa | 60 |
| gctctgcgtc gggtgaaacc agacaaagcc gcgagcccag ggatgggagc acgcggggga | 120 |
| cggcctgccg gcggggacga cagcattgcg cctgggtgca gcagtgtgcg tctcggggaa | 180 |
| gggaagatat tttaaggcgt gtctgagcag acggggaggc ttttccaaac ccaggcagct | 240 |
| tcgtggcgtg tgcggtttcg acccggtcac acaaagcttc agcatgtcat gtgaggacgg | 300 |
| tcgggccctg aaaggaacgc tctcggaatt ggccgcggaa accgatctgc ccgttgtgtt | 360 |
| tgtgaaacag agaaagatag gcggccatgg tccaaccttg aaggcttatc aggagggcag | 420 |
| acttcaaaag ctactaaaaa tgaacggccc tgaagatctt cccaagtcct atgactatga | 480 |

```
ccttatcatc attggaggtg gctcaggagg tctggcagct gctaaggagg cagcccaata    540
tggcaagaag gtgatggtcc tggactttgt cactcccacc cctcttggaa ctagatgggg    600
tcttggagga acatgtgtga atgtggttg catacctaaa aaactgatgc atcaagcagc     660
tttgttagga caagccctgc aagactctcg aaattatgga tggaaagtcg aggagacagt    720
taagcatgat tgggacagaa tgatagaagc tgtacagaat cacattggct ctttgaattg    780
gggctaccga gtagctctgc gggagaaaaa agtcgtctat gagaatgctt atgggcaatt    840
tattggtcct cacaggatta aggcaacaaa taataaaggc aaagaaaaaa tttattcagc    900
agagagtttt ctcattgcca ctggtgaaag accacgttac ttgggcatcc ctggtgacaa    960
agaatactgc atcagcagtg atgatctttt ctccttgcct tactgcccgg gtaagaccct    1020
ggttgttgga gcatcctatg tcgctttgga gtgcgctgga tttcttgctg gtattggttt    1080
aggcgtcact gttatggtta ggtccattct tcttagagga tttgaccagg acatggccaa    1140
caaaattggt gaacacatgg aagaacatgg catcaagttt ataagacagt tcgtaccaat    1200
taaagttgaa caaattgaag cagggacacc aggccgactc agagtagtag ctcagtccac    1260
caatagtgag gaaatcattg aaggagaata taatacggtg atgctggcaa taggaagaga    1320
tgcttgcaca agaaaaattg cttagaaaac cgtagggggtg aagataaatg aaaagactgg    1380
aaaaatacct gtcacagatg aagaacagac caatgtgcct tacatctatg ccattggcga    1440
tatattggag gataaggtgg agctcacccc agttgcaatc caggcaggaa gattgctggc    1500
tcagaggctc tatgcaggtt ccactgtcaa gtgtgactat gaaaatgttc caaccactgt    1560
atttactcct ttggaatatg gtgcttgtgg cctttctgag gagaaagctg tggagaagtt    1620 tgggaagaa aatattgagg tttaccatag ttacttttgg ccattggaat ggacgattcc     1680
gtcaagagat aacaacaaat gttatgcaaa aataatctgt aatactaaag acaatgaacg    1740
tgttgtgggc tttcacgtac tgggtccaaa tgctggagaa gttacacaag ctttgcagc    1800 tgcgctcaaa tgtggactga ccaaaaagca gctggacagc acaattggaa tccaccctgt    1860
ctgtgcagag gtattcacaa cattgtctgt gaccaagcgc tctggggcaa gcatcctcca    1920
ggctggctgc tgaggttaag ccccagtgtg gatgctgttg ccaagactgc aaaccactgg    1980
ctcgtttccg tgcccaaatc caaggcgaag ttttctagag ggttcttggg ctcttggcac    2040
ctgcgtgtcc tgtgcttacc accgcccaag gccccctggg atctcttgga taggagttgg    2100
tgaatagaag gcaggcagca tcacactggg gtcactgaca gacttgaagc tgacatttgg    2160
cagggcatcg aagggatgca tccatgaagt caccagtctc aagcccatgt ggtaggcggt    2220
gatggaacaa ctgtcaaatc agttttagca tgacctttcc ttgtggattt tcttattctc    2280
gttgtcaagt tttctagggt tgaattttt tcttttttct ccatggtgtt aatgatatta     2340
gagatgaaaa acgttagcag ttgatttttg tccaaaagca agtcatggct agagtatcca    2400
tgcaaggtgt cttgttgcat ggaagggata gtttggctcc cttggaggct atgtaggctt    2460
gtcccgggaa agagaactgt cctgcagctg aaatggactg ttctttactg acctgctcag    2520
cagtttcttc tctcatatat tcccaaaaca agtacatctg cgatcaactc tagccaaatt    2580 tgccctgtg tgctacatga tggatgatta ttattttaag gtctgtttag gaagggaaat     2640
ggctacttgg ccagccattg cctggcattt ggtagtatag tatgattctc accattattt    2700
gtcatggagg cagacataca ccagaaatgg gggagaaaca gtacatatct ttctgtcttt    2760
agtttattgt gtgctggtct aagcaagctg agatcatttg caatggaaaa cacgtaactt    2820
```

-continued

```
gtttaaaagt ttttctggta gctttagctt tatgctaaaa aaaataatga cattgggtat      2880
ctatttcttt ctaagacata cattagtagg aaaataagtc ttttcatgct tatgatttag      2940
ctgttttgtg gtaattgctt tttaaaggaa gttattaata tcataagtta ttattaatat      3000
tttgaacaca ggtggatgtg aaggattttc atttaaaaac caagtggttt tgactttttc      3060
tgttgaatga acaactgtgc cttgtggaat ttttgcagaa gtgtttatgc tttgttagca      3120
tttcaacttg cattattata aagaggtatt aatgcctcag ttatgtgttt gtcaatgtac      3180
tggctgagga ttctatctca gctgtctttt ctaactgtgt aggttgagtt ttgaacacgt      3240
gcttgtggac atcagcctcc tgccagcagt tcttgaagct tcttttttcat tcctgctact     3300 ctacctgtat ttctcagttg cagcactgag tggtcaaaat acatttctgg gccacctcag      3360
ggaacccatg catctgcctg gcatttaggc agcagagccc ctgaccgtcc cccacaggct      3420
ctgcctcacg tcctcatctc atttggctgt gtaaagaaat gggaaagggg aaaggagag      3480 agcaattgag gcagttgacc atattcagtt ttatttattt attttttaatt tgttttttc     3540 tccaagtcca ccagtctctg aaattagaac agtaggcggt atgagataat caggcctaat     3600
catgttgtga ttctcttttc ttagtggagt ggaatgttct atccccacaa gaaggattat     3660
atcttataga cttgtcttgt tcagattctg tatttaccca ttttattgaa acatatacta     3720
agttccatgt attttgtta caaatcttct gaaaaaaaac aaaacaatgt gaaacattaa       3780
aattaaaagg cattaataat aaaaaaaaaa aaaaaaccc gaattc                      3826
```

<210> SEQ ID NO 52
<211> LENGTH: 1959
<212> TYPE: DNA
<213> ORGANISM: Homo sapiens

<400> SEQUENCE: 52

```
cgaaaaaaga ggggaagagt attaaagacc atttctggct gggcagggca ctctcagcag        60
ctcaactgcc cagcgtgacc agtggccacc tctgcagtgt cttccacaac ctggtcttga       120
ctcgtctgct gaacaaatcc tctgacctca ggccggctgt gaacgtagtt cctgagagat       180
agcaaacatg cccaacagtg agcccgcatc tctgctggag ctgttcaaca gcatcgccac       240 acaagggggag ctcgtaaggt ccctcaaagc gggaaatgcg tcaaaggatg aaattgattc      300
tgcagtaaag atgttggtgt cattaaaaat gagctacaaa gctgccgcgg gggaggatta      360
caaggctgac tgtcctccag ggaacccagc acctaccagt aatcatgcc cagatgccac       420 agaagctgaa gaggattttg tggacccatg gacagtacag acaagcagtg caaaaggcat     480
agactacgat aagctcattg ttcggtttgg aagtagtaaa attgacaaag agctaataaa      540
ccgaatagag agagccaccg gccaaagacc acaccacttc ctgcgcagag gcatcttctt     600
ctcacacaga gatatgaatc aggttcttga tgcctatgaa aataagaagc cattttatct      660
gtacacgggc cggggcccct cttctgaagc aatgcatgta ggtcacctca ttccatttat     720
tttcacaaag tggctccagg atgtatttaa cgtgcccttg gtcatccaga tgacggatga      780
cgagaagtat ctgtggaagg acctgaccct ggaccaggcc tatggcgatg ctgttgagaa      840
tgccaaggac atcatcgcct gtggctttga catcaacaag actttcatat tctctgacct      900
ggactacatg gggatgagct caggtttcta caaaaatgtg gtgaagattc aaaagcatgt      960
taccttcaac caagtgaaag gcattttcgg cttcactgac agcgactgca ttgggaagat     1020
cagttttcct gccatccagg ctgctccctc cttcagcaac tcattcccac agatcttccg    1080
agacaggacg gatatccagt gccttatccc atgtgccatt gaccaggatc cttactttag    1140
```

```
aatgacaagg gacgtcgccc ccaggatcgg ctatcctaaa ccagccctgt tgcactccac    1200
cttcttccca gccctgcagg gcgcccagac caaaatgagt gccagcgacc caaactcctc    1260
catcttcctc accgacacgg ccaagcagat caaaaccaag gtcaataagc atgcgttttc    1320
tggagggaga gacaccatcg aggagcacag gcagtttggg ggcaactgtg atgtggacgt    1380
gtctttcatg tacctgacct tcttcctcga ggacgacgac aagctcgagc agatcaggaa    1440
ggattacacc agcggagcca tgctcaccgg tgagctcaag aaggcactca tagaggttct    1500
gcagcccttg atcgcagagc accaggcccg gcgcaaggag gtcacggatg agatagtgaa    1560
agagttcatg actccccgga agctgtcctt cgactttcag tagcactcgt tttacatatg    1620
cttataaaag aagtgatgta tcagtaatgt atcaataatc ccagcccagt caaagcaccg    1680
ccacctgtag gcttctgtct catggtaatt actgggcctg gcctctgtaa gcctgtgtat    1740
gttatcaata ctgtttcttc ctgtgagttc cattatttct atctcttatg ggcaaagcat    1800
tgtgggtaat tggtgctggc taacattgca tggtcggata gagaagtcca gctgtgagtc    1860
tctccccaaa gcagccccac agtggagcct tcggctggaa gtccatgggc caccctgttc    1920
ttgtccatgg aggacttccg agggttccaa gtatactct                           1959

<210> SEQ ID NO 53
<211> LENGTH: 1826
<212> TYPE: DNA
<213> ORGANISM: Homo sapiens

<400> SEQUENCE: 53
cacgtcggct gctgggaaga tctggattct cgtttcaggt caccatcaga aaagctaagt      60
ttgctgtata gtgaggatca ggagatctga tcctgattgc agaaccttcc ctgattacag     120
aatcttggat gatttcacaa aagttcatct tcattgcaga tacctgcctt tctttctagg     180
ttgtatctcc cacttcaccc ttctagacca tcccagaaga tctataagat ttcatctggg     240
aaatcactag gagttcttgg aagggaaaga aggaagattg ttggttggaa taaaaacagg     300
gttgaatgag ttccagaaag cagggttctc aacctcgtgg acagcaatct gcagaagaag     360
agaacttcaa aaaccaact agaagcaaca tgcagagaag taaaatgaga ggggcctcct     420
caggaaagaa gacagctggt ccacagcaga aaaatcttga accagctctc ccaggaagat     480 gggggtggtcg ctctgcagag accccccctt caggatccgt gaggaagacc agaaagaaca     540
agcagaagac tcctggaaac ggagatggtg gcagtaccag cgaagcacct cagccccctc     600
ggaagaaaag ggcccgggca gaccccactg ttgaaagtga ggaggcgttt aagaatagaa     660
tggaggttaa agtgaagatt cctgaagaat taaaaccatg gcttgttgag gactgggact     720
tagttaccag gcagaagcag ctgtttcaac tccctgccaa gaaaaatgta gatgcaattc     780
tggaggagta tgcaaattgc aagaaatcgc agggaaatgt tgataataag gaatatgcgg     840
ttaatgaagt tgtggcagga ataaaagaat atttcaatgt gatgttgggc actcagctgc     900
tctacaaatt tgagaggccc cagtatgctg aaatcctctt ggctcaccct gatgctccaa     960
tgtcccaggt ttatggagca ccacacctac tgagattatt tgtaagaatt ggagcaatgt    1020
tggcctatac gccccttgat gagaaaagcc ttgcattatt gttgggctat ttgcatgatt    1080
tcctaaaata tctggcaaag aattctgcat ctctctttac tgccagtgat tacaaagtgg    1140
cttctgctga gtaccaccgc aaagcccgtg gagcgtctac agacagctca ccattttgt     1200 cctgtatctg taaacacttt ttgttcttag tcttttttctt gtaaaattga tgttctttaa    1260
```

```
aatcgttaat gtataacagg gcttatgttt cagtttgttt tccgttctgt tttaaacaga    1320
aaataaaagg agtgtaagct ccttttctca tttcaaagtt gctaccagtg tatgcagtaa    1380
ttagaacaaa gaagaaacat tcagtagaac attttattgc ctagttgaca acattgcttg    1440
aatgctggtg gttcctatcc ctttgacact acacaatttt ctaatatgtg ttaatgctat    1500
gtgacaaaac gccctgattc ctagtgccaa aggttcaact taatgtatat acctgaaaac    1560
ccatgcattt gtgctctttt ttttttttatg gtgcttgaag taaaacagcc catcctctgc    1620
aagtccatct atgttgttct taggcattct atctttgctc aaattgttga aggatggtga    1680
tttgtttcat ggttttttgta tttgagtcta atgcacgttc taacatgata gaggcaatgc    1740
attattgtgt agccacggtt ttctggaaaa gttgatattt taggaattgt atttcagatc    1800
ttaaataaaa tttgtttcta aatttc    1826

<210> SEQ ID NO 54
<211> LENGTH: 1822
<212> TYPE: DNA
<213> ORGANISM: Homo sapiens

<400> SEQUENCE: 54
ttgagccacc atctgaccgc aagctgcgtc gtgtcgccgg ttctgcaggc accatgagcc      60
aggacaccga ggtggatatg aaggaggtgg agctgaatga gttagagccc gagaagcagc     120
cgatgaacgc ggcgtctggg gcggccatgt ccctggcggg agccgagaag aatggtctgg     180
tgaagatcaa ggtggcggaa gacgaggcgg aggcggcagc gccggctaag ttcacgggcc     240
tgtccaagga ggagctgctg aaggtggcag gcagccccgg ctgggtacgc acccgctggg     300
cactgctgct gctcttctgg ctcggctggc tcggcatgct tgctggtgcc gtggtcataa     360
tcgtgcgagc gccgcgttgt cgcgagctac cggcgcagaa gtggtggcac acgggcgccc     420
tctaccgcat cggcgacctt caggccttcc agggccacgg cgcgggcaac ctggcgggtc     480
tgaaggggcg tctcgattac ctgagctctc tgaaggtgaa gggccttgtg ctgggtccaa     540
ttcacaagaa ccagaaggat gatgtcgctc agactgactt gctgcagatc gaccccaatt     600
ttggctccaa ggaagatttt gacagtctct tgcaatcggc taaaaaaaag agcatccgtg     660
tcattctgga ccttactccc aactaccggg gtgagaactc gtggttctcc actcaggttg     720
acactgtggc caccaaggtg aaggatgctc tggagttttg gctgcaagct ggcgtggatg     780
ggttccaggt tcgggacata gagaatctga aggatgcatc ctcattcttg gctgagtggc     840
aaaatatcac caagggcttc agtgaagaca ggctcttgat tgcggggact aactcctccg     900
accttcagca gatcctgagc ctactcgaat ccaacaaaga cttgctgttg actagctcat     960
acctgtctga ttctggttct actggggagc atacaaaatc cctagtcaca cagtatttga    1020
atgccactgg caatcgctgg tgcagctgga gtttgtctca ggcaaggctc ctgacttcct    1080
tcttgccggc tcaacttctc cgactctacc agctgatgct cttcaccctg ccagggaccc    1140
ctgttttcag ctacggggat gagattggct ggatgcagc tgcccttcct ggacagccta    1200
tggaggctcc agtcatgctg tgggatgagt ccagcttccc tgacatccca ggggctgtaa    1260
gtgccaacat gactgtgaag ggccagagtg aagaccctgg ctccctcctt tccttgttcc    1320
ggcggctgag tgaccagcgg agtaaggagc gctccctact gcatgggggac ttccacgcgt    1380 tctccgctgg gcctggactc ttctcctata tccgccactg ggaccagaat gagcgttttc    1440
tggtagtgct taactttggg gatgtgggcc tctcggctgg actgcaggcc tccgacctgc    1500
ctgccagcgc cagcctgcca gccaaggctg acctcctgct cagcacccag ccaggccgtg    1560
```

```
aggagggctc ccctcttgag ctggaacgcc tgaaactgga gcctcacgaa gggctgctgc    1620
tccgcttccc ctacgcggcc tgacttcagc ctgacatgga cccactaccc ttctcctttc    1680
cttcccaggc cctttggctt ctgattttc  tcttttttaa aaacaaacaa acaaactgtt    1740
gcagattatg agtgaacccc caaatagggt gttttctgcc ttcaaataaa agtcacccct    1800
gcatggtgaa gtcttccctc tg                                             1822

<210> SEQ ID NO 55
<211> LENGTH: 1992
<212> TYPE: DNA
<213> ORGANISM: Homo sapiens

<400> SEQUENCE: 55
aaacttcccg cacgcgttac aggagccagg tcggtataag cgccacgcct cgccgcccgt      60
caagctgtcc acatccctgg cctcagcccg ccacatcacc ctgacctgct tacgcccaga     120
ttttcttcaa tcacatctga ataaatcact tgaagaaagc ttatagcttc attgcaccat     180
gtgtggcatt tgggcgctgt ttggcagtga tgattgcctt tctgttcagt gtctgagtgc     240
tatgaagatt gcacacagag gtccagatgc attccgtttt gagaatgtca atggatacac     300
caactgctgc tttggatttc accggttggc ggtagttgac ccgctgtttg gaatgcagcc     360
aattcgagtg aagaaatatc cgtatttgtg gctctgttac aatggtgaaa tctacaacca     420
taagaagatg caacagcatt tgaatttga  ataccagacc aaagtggatg gtgagataat     480
ccttcatctt tatgacaaag gaggaattga gcaaacaatt tgtatgttgg atggtgtgtt     540
tgcatttgtt ttactggata ctgccaataa gaaagtgttc ctgggtagag atacatatgg     600
agtcagacct ttgtttaaag caatgacaga agatggattt ttggctgtat gttcagaagc     660
taaaggtctt gttacattga agcactccgc gactcccttt ttaaaagtgg agccttttct     720
tcctggacac tatgaagttt tggatttaaa gccaaatggc aaagttgcat ccgtggaaat     780
ggttaaatat catcactgtc gggatgtacc cctgcacgcc ctctatgaca atgtggagaa     840
actctttcca ggttttgaga tagaaactgt gaagaacaac ctcaggatcc ttttaataa      900 tgctgtaaag aaacgtttga tgacagacag aaggattggc tgcctttta  caggggctt      960 ggactccagc ttggttgctg ccactctgtt gaagcagctg aaagaagccc aagtacagta    1020
tcctctccag acatttgcaa ttggcatgga agacagcccc gatttactgg ctgctagaaa    1080
ggtggcagat catattggaa gtgaacatta tgaagtcctt tttaactctg aggaaggcat    1140
tcaggctctg gatgaagtca tattttcctt ggaaacttat gacattacaa cagttcgtgc    1200
ttcagtaggt atgtatttaa tttccaagta tattcggaag aacacagata gcgtggtgat    1260
cttctctgga gaaggatcag atgaacttac gcagggttac atatattttc acaaggctcc    1320
ttctcctgaa aaagccgagg aggagagtga gaggcttctg agggaactct atttgtttga    1380
tgttctccgc gcagatcgaa ctactgctgc ccatggtctt gaactgagag tcccatttct    1440
agatcatcga tttttttcct attacttgtc tctgccacca gaaatgagaa ttccaaagaa    1500
tgggatagaa aaacatctcc tgagagagac gtttgaggat tccaatctga tacccaaaga    1560
gattctctgg cgaccaaaag aagccttcag tgatggaata acttcagtta agaattcctg    1620
gtttaagatt ttacaggaat acgttgaaca tcaggttgat gatgcaatga tggcaaatgc    1680
agcccagaaa tttcccttca atactcctaa aaccaaagaa ggatattact accgtcaagt    1740
ctttgaacgc cattacccag gccgggctga ctggctgagc cattactgga tgcccaagtg    1800
```

-continued

```
gatcaatgcc actgacccett ctgcccgcac gctgacccac tacaagtcag ctgtcaaagc    1860
ttaggtggtc tttatgctgt aatgtgaaag caaatatttc ttcgtgttgg atgggactg      1920 tgggtagata ggggaacaat gagagtcaac tcaggctaac ttgggtttga aaaaaataaa     1980
attcctaaat tt                                                         1992
```

<210> SEQ ID NO 56
<211> LENGTH: 4086
<212> TYPE: DNA
<213> ORGANISM: Homo sapiens

<400> SEQUENCE: 56

```
cgcgacctcg tggtgggctg cggtggcttc gtcaagtcgg acgtggagat caactactct      60
ctcatcgaga taaagctgta caccaagcat gggactttga ataccagac agactgtgcc      120 cctaataatg gttactttat gatcccttgg tatgataagg gggatttcat tctgaagatt      180
gagcctcccc tagggtggag ttttgagccg acgaccgtgg agctccatgt ggatggagtc      240
agtgacatct gcacaaaggg tgggacatc aactttgtct tcactgggtt ctctgtgaat      300
ggcaaggtcc tcagcaaagg gcagcccctg gtcctgcgg gagttcaggt gtctctgaga      360
aacactggga ccgaagcaaa gatccagtcc acagttacac agcctggcgg aaagtttgca      420
ttttttaaag ttctgcctgg agattatgaa atcctcgcaa ctcatccaac ctgggcgttg      480
aaagaggcaa gcaccacagt gagtgtaacc aactccaatg ccaatgcggc cagtcccctc      540
atagttgctg gctacaatgt gtctggctct gtccgaagtg atggggagcc catgaaaggc      600
gtgaagtttc ttctcttttc ttctttagta actaaagagg atgtcctggg ctgcaatgtc      660
tcaccagtgc ctgggttcca gcccaagac gagagtctgg tgtatttgtg ctacacggtc      720
tccagagaag atggctcgtt ctctttctat tccttgccaa gtgggggcta cactgtgatt      780
ccgttctatc gagggagag gattacccttt gatgtggcgc cttccagact tgacttcaca      840
gtggagcatg acagcttgaa atcgagccc gtgttccacg tcatgggatt ctccgtcacc      900 gggaggtct tgaacggacc cgaaggagat ggtgttccag aagcagtagt caccctgaat      960
aaccaaatca agttaaaac aaaagctgat ggctcattcc gccttgagaa cataaccaca     1020
gggacataca ccatccatgc tcagaaagag cacctctact ttgaaacggt caccatcaaa     1080
attgcaccga acacacctca gctggctgac attattgcaa caggttcag tgtctgtggt     1140 cagatatcaa tcattcgctt ccccgacacc gtcaagcaga tgaataaata caagttgtc     1200 ctgtcatctc aagacaagga caagtctttg gtcaccgtgg agacagatgc tcatggatca     1260
ttttgtttta aagcaaaacc agggacttac aaagtgcagg tgatggttcc tgaggcagaa     1320
accagagcag ggctgacgtt gaaaccccag acatttcctc ttactgtgac caacaggccc     1380
atgatggatg tggcctttgt acagttcttg gcatcagttt ctgggaaagt ctcttgcttg     1440
aacacctgtg gtgacttgct ggtgactcta cagtccctga gccgccaggg tgagaagcgg     1500
agcctccagc tctccggcaa ggtcaacgcc atgactttca cctttgacaa cgtgctcccet    1560 ggaaaataca aaataagcat catgcatgag gattggtgct ggaagaacaa gagcctggag     1620
gtggaagtgc tggaggatga catgtctgca gttgagttca ggcagacggg ctacatgctg     1680
agatgttccc tgtctcacgc catcactctg gaatttatc aggatggaaa tgggcgtgag     1740
aatgtgggga tttatagcct cttcaaagga gtcaaccgat tctgcctgtc caagcctggt     1800
gtgtacaaag tgaccccctcg ctcctgccac cggtttgagc aagcgttcta tatctatgac     1860
acgtcttcac ctagtatctt tacattgaca gccattcgcc accatgtcct tggaactatc     1920
```

```
accaccgaca aaatgatgga tgtcactgtg actatcaagt cttccatcga cagtgaaccc   1980
gccttggtct taggccctct gaagtctgtg caggagctgc ggagggagca gcagctggct   2040
gagatcgagg cccgcaggca ggagagggag aaaaacggca atgaggaagg cgaagaaaga   2100
atgaccaagc ctcccgtgca ggagatggta gatgagttac aaggcccctt ctcgtatgat   2160
ttctcttact gggcgcggtc tggagagaaa atcactgtta caccgtcatc taaagagctg   2220
ctcttttatc ccccttcaat ggaagccgtt gtcagtggag aaagctgccc agggaagctg   2280
atcgagatcc atgggaaggc aggcctgttt ttagaaggcc agatccaccc cgagttggaa   2340
ggagtcgaga ttgtcatcag tgaaaagggg gcaagttcac cgctgatcac agtctttact   2400
gatgacaaag gtgcctacag tgttggcccc ctgcacagtg acctggagta cacggtgacc   2460
tcacagaagg agggctatgt tctgactgcg gtggaaggaa ccatcggaga cttcaaggcc   2520
tatgccctgg caggcgtaag ctttgagata aagctgaggg atgaccagcc cctcccggga   2580
gtcctcttat ccctgagcgg tggcctgttt cgttccaacc tcttgaccca ggacaacggc   2640
attctgacat tctcaaacct gagccctggc cagtattact tcaaacccat gatgaaggag   2700
ttccggtttg agccatcctc acagatgatc gaggtgcagg aaggccagaa cctgaagatc   2760
accatcacgg gtaccgaac cgcttacagt tgctatggca cagtgtcttc cttaaacgga   2820
gagcccgaac aaggggttgc catggaagcg gtgggccaga acgactgcag catttacgga   2880
gaagacaccg tgcagacga gagggcaag ttcagattac gtggattgct gccgggatgt   2940
gtgtaccacg ttcagctcaa ggcagaaggc aacgaccaca ttgagcgggc gctcccccac   3000
cataggggtga ttgaggttgg gaataatgac atcgatgatg taaacatcat agttttccgg   3060
cagattaatc aatttgattt aagtggaaat gtgatcactt cctctgaata ccttcctaca   3120
ttatgggtca agctttacaa aagcgaaaac ctcgacaatc caatccagac agtttcccctt   3180
ggccagtccc tgttcttcca tttcccccca ctgctcagag acggcgagaa ctatgttgtg   3240
cttctggact ccacactccc cagatccag tatgactaca tcttgcctca agtttctttc   3300
accgcagtgg gctaccataa acacaccacc ttgattttta atcccacgag gaagctgcct   3360
gaacaggaca tcgcacaagg atcctacatt gccctgccat tgacgctgct ggttctgctg   3420
gccggttaca accatgacaa gctcattcct ttgctgctgc agttgacaag ccggctacag   3480
ggagtccgcg cgctcggcca ggcagcctct gacaatagcg gcccagaaga tgcaaagaga   3540
caagccaaga aacagaagac aaggcggact tgaggaggaa ggggacagtt gcagtctcac   3600
ttgggacagg ccagccag gggtccggcc actaccccgcc cgtgggataa aagccaaaag   3660
catgcgtcag ctaacttcag cctgtgctgc tgggcccgca ccccatgtcc cttgtcactg   3720
tgacatcctg cacccatcct cacccctccg tagagcccct cgtgcaatgc aatgaatgga   3780
ccctcctgtc actctgctga acagaattta ttttctgagt caaatataat ttattattat   3840
tttcgtcaaa gaagtattta agctgtgctg tggtgtgaga atgtcattct tgatcttcag   3900
ccttcgtttg caaggagagt tccagttgac gtggtgtttg gttccatggc ggggtaccct   3960
ggggattcat ctgtttttctt cacttcccctt tgcatctgag atcctgttgg aaaccacagc   4020
aacctgtatt cattattagg aaataaaaat cgaaaaaaag gttcattctt ttgtgttgta   4080
gtttttg                                                             4086
```

<210> SEQ ID NO 57
<211> LENGTH: 3701
<212> TYPE: DNA

<213> ORGANISM: Homo sapiens

<400> SEQUENCE: 57

| | | | | | |
|---|---|---|---|---|---|
| cggaaatcat | cctagtaata | aagtgaaatc | agacccacaa | cgaatgaatg | aacagccacg | 60 |
| tcagcttttc | caaagctcat | gaacactgga | aaacaacata | cgtttgttga | aacagagagt | 120 |
| gtaagatatg | tctaccagcc | tatggagaaa | ctgtatatgg | tactgatcac | taccaaaaac | 180 |
| agcaacattt | tagaagattt | ggagaccct a | aggctcttct | caagagtgat | ccctgaatat | 240 |
| tgccgagcct | tagaagagaa | tgaaatatct | gagcactgtt | ttgatttgat | ttttgctttt | 300 |
| gatgaaattg | tcgcactggg | ataccgggag | aatgttaact | tggcacagat | cagaaccttc | 360 |
| acagaaatgg | attctcatga | ggagaaggtg | ttcagagccg | tcagagagac | tcaagaacgt | 420 |
| gaagctaagg | ctgagatgcg | tcgtaaagca | aaggaattac | aacaggcccg | aagagatgca | 480 |
| gagagacagg | gcaaaaaagc | accaggattt | ggcggatttg | gcagctctgc | agtatctgga | 540 |
| ggcagcacag | ctgccatgat | cacagagacc | atcattgaaa | ctgataaacc | aaaagtggca | 600 |
| cctgcaccag | ccaggccttc | aggccccagc | aaggctttaa | aacttggagc | caaaggaaag | 660 |
| gaagtagata | actttgtgga | caaattaaaa | tctgaaggtg | aaaccatcat | gtcctctagt | 720 |
| atgggcaagc | gtacttctga | agcaaccaaa | atgcatgctc | cacccattaa | tatggaaagt | 780 |
| gtacatatga | agattgaaga | aaagataaca | ttaacctgtg | gacgagacgg | aggattacag | 840 |
| aatatggagt | tgcatggcat | gatcatgctt | aggatctcag | atgacaacta | tggccgaatt | 900 |
| cgtcttcatg | tggaaatga | agataagaaa | ggggtgcagc | tacagaccca | tccaaatgtg | 960 |
| gataaaaaac | ttttcactgc | agagtctcta | attggcctga | agaatccaga | gaagtcattt | 1020 |
| ccagtcaaca | gtgacgtagg | ggtgctaaag | tggagactac | aaaccacaga | ggaatctttt | 1080 |
| attccactga | caattaattg | ctggccctcg | gagagtggaa | atggctgtga | tgtcaacata | 1140 |
| gaatatgagc | tacaagaaga | taatttagaa | ctgaatgatg | tggttatcac | catcccactc | 1200 |
| ccgtctggtg | tcggcgcgcc | tgttatcggt | gagatcgatg | gggagtatcg | acatgacagt | 1260 |
| cgacgaaata | ccctggagtg | gtgcctgcct | gtgattgatg | ccaaaaataa | gagtggcagc | 1320 |
| ctggagttta | gcattgctgg | gcagcccaat | gacttcttcc | ctgttcaagt | ttcctttgtc | 1380 |
| tccaagaaaa | attactgtaa | catacaggtt | accaaagtga | cccaggtaga | tggaaacagc | 1440 |
| cccgtcaggt | tttccacaga | gaccactttc | ctagtggata | agtatgaaat | tctgtaatac | 1500 |
| caagaagagg | gagctgaaaa | ggaaaatttt | cagattaata | agaagacgc | caatgatggc | 1560 |
| tgaagagttt | ttcccagatt | tacaagccac | tggagacccc | ttttttctga | tacaatgcac | 1620 |
| gattctctgc | gcgcaaggac | cctcgactca | ccccccatgtt | tcagtgtcac | agagacattc | 1680 |
| tttgataagg | aaatggcaca | aacataaagg | gaaaggctgc | taattttctt | tggcagattg | 1740 |
| tattggccag | caggaaagca | agctctccag | agaatgcccc | cagttaaata | cctcctctac | 1800 |
| ctttacctaa | gttgctcctt | tattttt att | ttattattat | tattattatt | attattttt | 1860 |
| gagatggagt | ctcactttgt | aacccaggct | ggaatgcaat | ggcatgatct | cagctcactg | 1920 |
| caacctccgc | ctcctgggtt | caagcaagtc | tcctgcctca | gcctccgagt | agctgggact | 1980 |
| acaggtgcac | gccaccacgc | ctggctaatt | ttttgtattt | tagtagagac | ggggtttcac | 2040 |
| cgtgttgccc | aggctggtcg | cgaactcctg | agctcaggca | atccgcccac | ctcagcctcc | 2100 |
| caaagtgttg | ggattacagg | catgagccac | catgcccagc | tgctccttta | ttttaatccc | 2160 |
| taaatataat | ccctaaatat | agttatattt | catacttagt | ttgttttaa | aaagttttct | 2220 |
| ctgtagaaaa | ttttaatcat | tcatacccctt | tacctttagg | ttttctttc | tatacattca | 2280 |

```
gtcaggcact gggatcatct gtttacaggc attatattta tttggcactc ctggaacaag    2340
tatatctaac ccattcttga tttttggact attcaggtga actatttgag gggtatgggg    2400
tctagaagtt aaaagatacg catgtcttct rttcttttcc cgtatcaatt cattccttca    2460
tctctttgcc aagttgtttt cctttcaggg cctgtccttc cagtttagaa cagtaccatg    2520
aatcccactt gtgtcaatat taaagatagc tgagaagcac ctttcaaatg gcacagtccc    2580
tcttcaagat gtctaaaaga atggttatgt ctgtccagtt agggatttca catccacatg    2640
taatcatgtc tgctgctgtt gctacccaaa ttttcatttc tccacatttt gggtacttaa    2700
gctaaaacgt aatggccaca gtctgtaatc cattcacatt cctcagtttc accacctccc    2760
tcttccagac tgcactctct gtcatcagtc ccctcctttc taacagaaat ggggttatga    2820
ttttgaaggc tgtgggttca gggagtcttt gccaatcctg ttggccctaa actatcaagg    2880
aggctccatt tcaccatttg atttttttgca tttcaggagg caactgattg tttcgatatg    2940
tacatattac tcacgtatac cccatttcct tccagtcagc ccaacatttt ccaccagtct    3000
gtccccatct ctgaaatcct tccttctctt tccccctaag tcttttgagt gtcatcatgt    3060
actggtggtt tctcggttcc atctcatcca tttccttttc aatggagact acagcgtcag    3120
ccagctcagc cttggctttt aactcaatat tccagtccat aggggtggtt aaaagttgct    3180
gcaaggctgc aggcactggc agtgggaaga ggcagacgac tagatgactt ctgcactttt    3240
agctggttga aaagtaccac tcccactctg aacatctggc cgtccctgca aagagtgtac    3300
tgtgcttgaa gcagagcact cacacataaa tggctgtgtg tggaattgct tgccaaagaa    3360
gtttctagcc tttcccttc ccctaactgc atcaggaag aattcttatc tctagcttgg      3420
tttccacatg aggtttttct gagaagggct tgggacaaga agtctgtcat gttagttaag    3480
caggcaagaa atcctactaa tccagttttg tttgaaagtt gtttgtccgt atgatttttt    3540
aaaagtcaag tttaatttca aaaacctttt tttttctgag attacttttg gggtaatatt    3600
taaaatgaga gacattttgt aaccctgtaa aatacatagg gaatataaca ttccagtgta    3660
tacaaagaag gcaaattcca aaaaaaaaaa aaaaaaaaa a                         3701

<210> SEQ ID NO 58
<211> LENGTH: 6608
<212> TYPE: DNA
<213> ORGANISM: Homo sapiens

<400> SEQUENCE: 58 ccttcttttta aggagtttgc cgcgagcgcg tctccttcat tcgcaggctg ggcgcgttcg      60
cagtcggctg gcggcgaagg aaggcgctct cgggacctca cgggcgcgcg tcttttggct    120 cttgccctg tccctgcggc ttggggaaag cgtaacccgg cggctaggcg cgggagaagt     180
gcggaggagc catgggcgcc gggagctcca ccgagcagcg cagcccggag cagccgcccg    240 agggagctc cacgccggct gagcccgagc ccagcggcgg cggcccctcg gccgaggcgg     300
cgccagacac caccgcggac cccgccatcg ctgcctcgga ccccgccacc aagtcctac     360 agaagaatgg tcagctgtcc accatcaatg gcgtagctga gcaagatgag ctcagcctcc    420
aggagggtga cctaaatggc cagaaaggag ccctgaacgg tcaaggagcc ctaaacagcc    480
aggaggaaga agaagtcatt gtcacggagg ttggacagag agactctgaa gatgtgagcg    540
aaagagactc cgataaagag atggctacta agtcagcggt tgttcacgac atcacagatg    600
atgggcagga ggagaaccga aatatcgaac agattccttc ttcagaaagc aatttagaag    660
```

-continued

```
agctaacaca acccactgag tcccaggcta atgatattgg atttaagaag gtgtttaagt    720
ttgttggctt taaattcact gtgaaaaagg ataagacaga gaagcctgac actgtccagc    780
tactcactgt gaagaaagat gaaggggagg gagcagcagg ggctggcgac caccaggacc    840
ccagccttgg ggctggagaa gcagcatcca agaaagcga acccaaacaa tctacagaga     900
aacccgaaga gaccctgaag cgtgagcaaa gccacgcaga aatttctccc ccagccgaat    960
ctggccaagc agtggaggaa tgcaaagagg aaggagaaga gaaacaagaa aaagaaccta   1020
gcaagtctgc agaatctccg actagtcccg tgaccagtga acaggatca accttcaaaa    1080
aattcttcac tcaaggttgg gccggctggc gcaaaaagac cagtttcagg aagccgaagg   1140
aggatgaagt ggaagcttca gagaagaaaa aggaacaaga gccagaaaaa gtagacacag   1200
aagaagacgg aaaggcagag gttgcctccg agaaactgac cgcctccgag caagcccacc   1260
cacaggagcc ggcagaaagt gcccacgagc cccggttatc agctgaatat gagaaagttg   1320
agctgccctc agaggagcaa gtcagtggct cgcagggacc ttctgaagag aaacctgctc   1380
cgttggcgac agaagtgttt gatgagaaaa tagaagtcca ccaagaagag gttgtggccg   1440
aagtccacgt cagcaccgtg gaggagagaa ccgaagagca gaaaacggag gtggaagaaa   1500
cagcagggtc tgtgccagct gaagaattgg ttggaatgga tgcagaacct caggaagccg   1560
aacctgccaa ggagctggtg aagctcaaag aaacgtgtgt ttccggagag gaccctacac   1620
agggagctga cctcagtcct gatgagaagg tgctgtccaa acccccgaa ggcgttgtga    1680
gtgaggtgga aatgctgtca tcacaggaga gaatgaaggt gcagggaagt ccactaaaga   1740
agctttttac cagcactggc ttaaaaaagc tttctggaaa gaaacagaaa gggaaaagag   1800
gaggaggaga cgaggaatca ggggagcaca ctcaggttcc agccgattct ccggacagcc   1860
aggaggagca aaagggcgag agctctgcct catcccctga ggagcccgag gagatcacgt   1920
gtctggaaaa gggcttagcc gaggtgcagc aggatgggga agctgaagaa ggagctactt   1980
ccgatggaga gaaaaaaaga gaaggtgtca ctccctgggc atcattcaaa aagatggtga   2040
cgcccaagaa gcgtgttaga cggccttcgg aaagtgataa agaagatgag ctggacaagg   2100
tcaagagcgc taccttgtct tccaccgaga gcacagcctc tgaaatgcaa gaagaaatga   2160
aagggagcgt ggaagagcca aagccggaag aaccaaagcg caaggtggat acctcagtat   2220
cttgggaagc tttaatttgt gtgggatcat ccaagaaaag agcaaggaga aggtcctctt   2280
ctgatgagga aggggaccca aaagcaatgg gaggagacca ccagaaagct gatgaggccg   2340
gaaaagacaa agagacgggg acagacggga tccttgctgg ttcccaagaa catgatccag   2400
ggcagggaag ttcctccccg gagcaagctg gaagccctac cgaaggggag ggcgtttcca   2460
cctgggagtc atttaaaagg ttagtcacgc caagaaaaaa atcaaagtcc aagctggaag   2520
agaaaagcga agactccata gctgggtctg tgtagaacaa ttccactcca gacactgaac   2580
ccggtaaaga agaatcctgg gtctcaatca agaagtttat tcctggacga aggaagaaaa   2640
ggccagatgg gaaacaagaa caagcccctg ttgaagacgc agggccaaca ggggccaacg   2700
aagatgactc tgatgtcccg gccgtggtcc ctctgtctga gtatgatgct gtagaaaggg   2760
agaaaatgga ggcacagcaa gcccaaaaag gcgcagagca gcccgagcag aaggcagcca   2820
ctgaggtgtc caaggagctc agcgagagtc aggttcatat gatggcagca gctgtcgctg   2880
acgggacgag ggcagctacc attattgaag aaaggtctcc ttcttggata tctgcttcag   2940
tgacagaacc tcttgaacaa gtagaagctg aagccgcact gttaactgag gaggtattgg   3000
aaagagaagt aattgcagaa gaagaacccc ccacggttac tgaacctctg ccagagaaca   3060
```

```
gagaggcccg ggcgacacg gtcgttagtg aggcggaatt gaccccgaa gctgtgacag      3120 ctgcagaaac tgcagggcca ttgggttccg aagaaggaac cgaagcatct gctgctgaag      3180
agaccacaga aatggtgtca gcagtctccc agttaaccga ctccccagac accacagagg      3240
aggccactcc ggtgcaggag gtggaaggtg gcgtacctga catagaagag caagagaggc      3300
ggactcaaga ggtcctccag gcagtggcag aaaaagtgaa agaggaatcc cagctgcctg      3360
gcaccggtgg gccagaagat gtgcttcagc ctgtgcagag agcagaggca gaaagaccag      3420
aagagcaggc tgaagcgtcg ggtctgaaga agagacgga tgtagtgttg aaagtagatg      3480
ctcaggaggc aaaaactgag cctttttacac aagggaaggt ggtggggcag accaccccag      3540 aaaagctttga aaaagctcct caagtcacag agagcataga gtccagtgag cttgtaacca      3600
cttgtcaagc cgaaacctta gctggggtaa aatcacagga gatggtgatg aacaggcta      3660 tcccccctga ctcggtggaa acccctacag acagtgagac tgatggaagc accccgtag      3720 ccgactttga cgcaccaggc acaacccaga aagacgagat tgtggaaatc catgaggaga      3780
atgaggtcgc atctggtacc cagtcagggg gcacagaagc agaggcagtt cctgcacaga      3840
aagagaggcc tccagcacct tccagtttg tgttccagga agaaactaaa gaacaatcaa      3900
agatggaaga cactctagag catacagata agaggtgtc agtggaaact gtatccattc      3960
tgtcaaagac tgagggggact caagaggctg accagtatgc tgatgagaaa accaaagacg      4020 taccatttt cgaaggactt gaggggtcta tagacacagg cataacagtc agtcgggaaa      4080
aggtcactga agttgcccttt aaaggtgaag ggacagaaga agctgaatgt aaaaaggatg      4140
atgctcttga actgcagagt cacgctaagt ctcctccatc ccccgtggag agagagatgg      4200
tagttcaagt cgaaagggag aaaacagaag cagagccaac ccatgtgaat aagagaagc      4260 ttgagcacga aacagctgtt accgtatctg aagaggtcag taagcagctc ctccagacag      4320
tgaatgtgcc catcatagat ggggcaaagg aagtcagcag tttggaagga agccctcctc      4380
cctgcctagg tcaagaggag gcagtatgca ccaaaattca agttcagagc tctgaggcat      4440
cattcactct aacagcggct gcagaggagg aaaaggtctt aggagaaact gccaacattt      4500
tagaaacagg tgaaacgttg gagcctgcag gtgcacattt agttctggaa gagaaatcct      4560
ctgaaaaaaa tgaagacttt gccgctcatc caggggaaga tgctgtgccc acagggcccg      4620
actgtcaggc aaaatcgaca ccagtgatag tatctgctac taccaagaaa ggcttaagtt      4680
ccgacctgga aggagagaaa accacatcac tgaagtggga gtcagatgaa gtcgatgagc      4740
aggttgcttg ccaggaggtc aaagtgagtg tagcaattga ggatttagag cctgaaaatg      4800
ggattttgga acttgagacc aaaagcagta aacttgtcca aacatcatc cagacagccg      4860 ttgaccagtt tgtacgtaca gaagaaacag ccaccgaaat gttgacgtct gagttacaga      4920
cacaagctca cgtgataaaa gctgacagcc aggacgctgg acaggaaacg gagaaagaag      4980
gagaggaacc tcaggcctct gcacaggatg aaacaccaat tacttcagcc aaagaggagt      5040
cagagtcaac cgcagtggga caagcacatt ctgatatttc caaagacatg agtgaagcct      5100
cagaaaagac catgactgtt gaggtagaag gttccactgt aaatgatcag cagctggaag      5160
aggtcgtcct cccatctgag gaagagggag gtggagctgg aacaaagtct gtgccagaag      5220
atgatggtca tgccttgtta gcagaaagaa tagagaagtc actagttgaa ccgaaagaag      5280
atgaaaaagg tgatgatgtt gatgaccctg aaaaccagaa ctcagccctg gctgatactg      5340
atgcctcagg aggcttaacc aaagagtccc cagatacaaa tggaccaaaa caaaaagaga      5400
```

-continued

| | |
|---|---|
| aggaggatgc ccaggaagta gaattgcagg aaggaaaagt gcacagtgaa tcagataaag | 5460 |
| cgatcacacc ccaagcacag gaggagttac agaaacaaga gagagaatct gcaaagtcag | 5520 |
| aacttacaga atcttaaaac atcatgcagt taaactcatt gtctgtttgg aagaccagaa | 5580 |
| tgtgaagaca agtagtagaa gaaaatgaat gctgctgctg agactgaaga ccagtatttc | 5640 |
| agaactttga gaattggaga gcaggcacat caactgatct catttctaga gagcccctga | 5700 |
| caatcctgag gcttcatcag gagctagagc catttaacat ttcctctttc caagaccaac | 5760 |
| ctacaatttt cccttgataa ccatataaat tctgatttaa ggtcctaaat tcttaacctg | 5820 |
| gaactggagt tggcaatacc tagttctgct tctgaaactg gagtatcatt ctttacatat | 5880 |
| ttatatgtat gttttaagta gtcctcctgt atctattgta tattttttc ttaatgttta | 5940 |
| aggaaatgtg caggatacta catgctttt gtatcacaca gtatatgatg gggcatgtgc | 6000 |
| catagtgcag gcttggggag ctttaagcct cagttatata acccacaaaa aacagagcct | 6060 |
| cctagatgta acattcctga tcaaggtaca attctttaaa attcactaat gattgaggtc | 6120 |
| catatttagt ggtactctga aattggtcac tttcctatta cacggagtgt gccaaaacta | 6180 |
| aaaagcattt tgaaacatac agaatgttct attgtcattg ggaaattttg ctttctaacc | 6240 |
| cagtggaggt tagaaagaag ttatattctg gtagcaaatt aactttacat ccttttcct | 6300 |
| acttgttatg gttgtttgga ccgataagtg tgcttaatcc tgaggcaaag tagtgaatat | 6360 |
| gttttatatg ttatgaagaa agaattgtt gtaagttttt gattctactc ttatatgctg | 6420 |
| gactgcattc acacatggca tgaaataagt caggttcttt acaaatggta ttttgataga | 6480 |
| tactggattg tgtttgtgcc atatttgtgc cattccttta agaacaatgt tgcaacacat | 6540 |
| tcatttggat aagttgtgat ttgacgactg atttaaataa aatatttgct tcacttaaaa | 6600 |
| aaaaaaaa | 6608 |

<210> SEQ ID NO 59
<211> LENGTH: 1703
<212> TYPE: DNA
<213> ORGANISM: Homo sapiens

<400> SEQUENCE: 59

| | |
|---|---|
| aagcttgtgg cttcttctcc ttactcttcc tccttggtgt ctctatgtta gagggccgtt | 60 |
| agcatctgct ggggcctggt cgcattcacc ctgctctgcc actcactggc tgtgtgactc | 120 |
| tggacaaatt aacttctctg gacctggcag tttctcctct ctacaatgag aatactggag | 180 |
| agtccttatc ttatgggttg ctacagaatt aagtgacatc tcacacacaa cacacttcct | 240 |
| acagtccctg ttcacacgcta aaagtactca actagcttcg gatacgtcat cagcaaccac | 300 |
| cccacgggtt actgtgatgc tgcacaatta ttaagccctg gctgctacag agttgtaacc | 360 |
| tgtctgcact tccaaccggc gccgcaagca gcattcccag tcccgctttc acccgcgcgc | 420 |
| taacggctca ggttcgagta caggacagga gggaggggag ctgtgcacac ggcggaggcg | 480 |
| cacggcgtgg gcacccagca cccggtacac tgtgtcctcc cgctgcaccc agccccttca | 540 |
| gcccgaggcg tccccgaggc gcaagtgggc cgccttcagg gaactgaccg cccgcggccc | 600 |
| gtgtgcagag ccgggtgcgc ccggcccagt gcgcgcggcc gggtgttcg cttggagccg | 660 |
| caagtgactt ctagcgcggg gcgtgtgcag gcacggccgg ggcggggctt ttgcactcgt | 720 |
| cccggctctt tctagctata aacactgctt gccgcgctgc actccaccac gcctcctcca | 780 |
| agtcccagcg aacccgcgtg caacctgtcc cgactctagc cgcctcttca gcacgccatg | 840 |
| gatcccaact gctcctgcgc cgccggtaag aggctgggga tgcccagtgt agactgtagc | 900 |

-continued

```
gctagagaag caatttctga cccctctttc tttctctggt cactcaattt caggcacagg        960
agttgctctt cccaaagagt tttggtatct ttctctccat tctaggttat tcggagcccc       1020 cttttttaccg ttaaggagat ctgagttaat ggcttgctca agtcccagg aatcggttgt       1080 ggactgagga actcggcccc gggtcttagt acgcgtccct tgttcaggta tccaggagt       1140 tctcacctct gtcttttctc cttcaggtga ctcctgcacc tgcgccggct cctgcaaatg      1200
caaagagtgc aaatgcacct cctgcaagaa aagtaagtgg gatcctctct ttcctctacc      1260
ccttccctgt cctccagcct gtcccctctc caccatcctc aggggaatta aagcagtctg      1320
gggatgcccc attgcgcgga aattgttgcc tcctcagtga tcttatcagg gagagcagga     1380
atccttattc ccggtgtcgc tagtactcat ctctgcgcct cctgtctgcc cccaggctgc     1440
tgctcctgct gccctgtggg ctgtgccaag tgtgcccagg gctgcatctg caaaggggcg     1500
tcggacaagt gcagctgctg cgcctgatgc tgggacagcc ccgctcccag atgtaaagaa     1560
cgcgacttcc acaaacctgg attttttatg tacaaccctg accgtgaccg tttgctatat     1620
tcctttttct ataaaataat gtgaatgata ataaacagc tttgacttga ttctgtctct      1680
ggttttcttt atatgcctta aaa                                            1703
```

<210> SEQ ID NO 60
<211> LENGTH: 2932
<212> TYPE: DNA
<213> ORGANISM: Homo sapiens

<400> SEQUENCE: 60

```
aggcccggtt cgccgccgct tcctgctgcc gccatgctcg acttcttcac cattttctcc        60
aagggcgggc ttgtgctctg gtgcttccag ggcgttagcg actcatgcac cggacccgtt       120
aacgcgttga ttcgttccgt gctgctgcag gaacggggag gtaacaactc cttcacccat       180
gaggcactga cactcaagta taaactggac aaccagtttg agctggtgtt tgtggttggt       240
tttcagaaga tcctgacact gacatatgta gacagattga tagatgacgt gcatcggctg       300
tttcgggaca gtaccgcac agagatccaa cagcaaagtg ctttaagttt attaaatggc       360
acttttgatt tccaaaatga cttcctgcgg ctccttcgtg aagcagagga gagcagtaag       420
atccgtgctc ccactaccat gaagaaattt gaagattctg aaaaggccaa gaaacctgtg       480
aggtccatga ttgagacacg gggggaaaag cccaaggaaa aagcaaagaa tagcaaaaaa       540
aagggggcca agaaggaagg ttctgatggt cctttggcta ccagcaaacc agtccctgca       600
gaaaagtcag gtcttccagt gggtcctgag aacgaggtag aactttccaa agaggagctg       660
atccgcagga agcgcgagga gttcattcag aagcatggga ggggtatgga gaagtccaac       720
aagtccacga agtcagatgc tccaaaggag aagggcaaaa agcaccccg ggtgtgggaa       780 ctgggtggct gtgctaacaa agaagtgttg gattacagta ctcccaccac caatggaacc       840
cctgaggctg ccttgtctga ggacatcaac ctgattcgag ggactgggtc tgggggcag     900 cttcaggatc tggactgcag cagctctgat gacgaagggg ctgctcaaac tctcaccaaa       960
cctagtgcga ccaagggaac actgggtggc atgtttggta tgctgaaggg ccttgtgggt     1020
tcaaagagct tgagtcgtga agacatggaa tctgtgctgg acaagatgcg tgatcatctc     1080
attgctaaga acgtggctgc agacattgcc gtccagctct gtgaatctgt tgccaacaag     1140
ttggaaggga aggtgatggg gacgttcagc acggtgactt ccacagtaaa gcaagcccta     1200
caggagtccc tggtgcagat tctgcagcca cagcgtcgtg tagacatgct ccgggacatc     1260
```

-continued

```
atggatgccc agcgtcgcca gcgcccttat gtcgtcacct tctgcggcgt taatggagtg    1320
gggaaatcta ctaatcttgc caagatttcc ttctggttgt tagagaatgg cttcagtgtc    1380
ctcattgctg cctgtgatac atttcgtgct ggggccgtgg agcagctgcg tacacacacc    1440
cggcgtttga gtgccctaca ccctccagag aagcatggtg gccgcaccat ggtgcagttg    1500
tttgaaaagg gctatggcaa ggatgctgct ggcattgcca tggaagccat tgcttttgca    1560
cgtaaccaag gctttgacgt ggtgctggtg gacacggcag gccgcatgca agacaatgcc    1620
cctctgatga ctgccctggc caaactcatt actgtcaata cacctgattt ggtgctgttt    1680
gtaggagaag ccttagtagg caatgaagcc gtggaccagc tggtcaagtt caacagagcc    1740
ttggctgacc attctatggc tcagacacct cggctcattg atggcattgt tcttaccaaa    1800
tttgatacca ttgatgacaa ggtgggagct gctatttcta tgacgtacat cacaagcaaa    1860
cccatcgtct ttgtgggcac cggccagacc tactgtgacc tacgcagcct caatgccaag    1920
gctgtggtgg ctgccctcat gaaggcttaa cgtggctctt gcccaatacc aaatcgccgc    1980
tttccccaca agcccttctt cctgtatcaa gaatgtgctt tagagtatgt gagcaacctg    2040
tcttaagtgt agtacaaagg cagagtgagg gggcttgtgg ctccttccaa ccccactccc    2100
cgttcagcac agccgccatt tgcaaggaag gcctaatcat gttacaatca ctgcccgact    2160
gaccctctcc cagcggcctc ccccttccta ctcaggcacc cccttcactc tgcctacaga    2220
ctcagtctta ttacagcttt gaccaatggt tggaacccaa caccagagct ttgctaataa    2280
tgagtgtggt caagagccgt ctgagcctaa tgagtcccag ctgcattagg ttaagagact    2340 cttccgagc cagcgccagg tcttgaatgg cacctctccc taggatacac agcctgcagg     2400
tccccaggac ctgatgacac ccgcctcact gtggcagtgt attgcctgtt aattgctgct    2460
aattctaatt ctgatgatga ctcctactcc attgtttacc ccaaagcatc agctaggctg    2520
gagtgatttg ttacaaatga gcaaaagatg agtccttgct tccctcagaa ataaaagtag    2580
cccagctgca gcgttgcatt ggcttcttgg cctcccaact cttccactcc cagaatcaga    2640
agtaagctct gcatgttccc ttcctggagg aaaccaattg tcagaaggtg tatgatgacc    2700 ccctccctc ccatccttca cctcctaagc agtcctggct tttcctcatc actcccctct     2760
acagtgcctg gtagacaagt gctacattga agaaacaaaa cctcttgtta agacttgtcc    2820
tgtagcttga tattacaggt gtgctattag tgcaataagg tgaaggctgt ctgcccagag    2880
aaataagtaa tttatataag aaaataaatt tcataaataa attggaaatt cc             2932
```

<210> SEQ ID NO 61
<211> LENGTH: 2165
<212> TYPE: DNA
<213> ORGANISM: Homo sapiens

<400> SEQUENCE: 61

```
cccgccttcc atacctcccc ggctccgctc ggttcctggc caccccgcag cccctgccca     60
ggtgccatgg ccgcattgta ccgccctggc ctgcggctta actggcatgg gctgagcccc    120
ttgggctggc catcatgccg tagcatccag accctgcgag tgcttagtgg agatctgggc    180
cagcttccca ctggcattcg agattttgta gagcacagtg cccgcctgtg ccaaccagag    240
ggcatccaca tctgtgatgg aactgaggct gagaatactg ccacactgac cctgctggag    300
cagcagggcc tcatccgaaa gctccccaag tacaataact gctggctggc ccgcacagac    360
cccaaggatg tggcacgagt agagagcaag acggtgattg taactccttc tcagcgggac    420
acggtaccac tccgcctggg tggggcctgt gggcagctgg gcaactggat gtccccagct    480
```

```
gatttccagc gagctgtgga tgagaggttt ccaggctgca tgcagggccg caccatgtat      540
gtgcttccat tcagcatggg tcctgtgggc tccccgctgt cccgcatcgg ggtgcagctc      600
actgactcag cctatgtggt ggcaagcatg cgtattatga cccgactggg gacacctgtg      660
cttcaggccc tgggagatgg tgactttgtc aagtgtctgc actccgtggg ccagcccctg      720
acaggacaag gggagccagt gagccagtgg ccgtgcaacc cagagaaaac cctgattggc      780
cacgtgcccg accagcggga gatcatctcc ttcggcagcg gctatggtgg caactccctg      840
ctgggcaaga agtgctttgc cctacgcatc gcctctcggc tggcccggga tgagggctgg      900
ctggcagagc acatgctgat cctgggcatc accagccctg cagggaagaa ggcgctatgt      960
gcagccgcct ccctagtgc ctgtggcaag accaacctgg ctatgatgcg gcctgcactg     1020
ccaggctgga agtggagtg tgtgggggat gatattgctt ggatgaggtt tgacagtgaa     1080
ggtcgactcc gggccatcaa ccctgagaac ggcttctttg gggttgcccc tggtacctct     1140
gccaccacca atcccaacgc catggctaca atccagagta acactatttt taccaatgtg     1200
gctgagacca gtgatggtgg cgtgtactgg gagggcattg accagcctct ccacctggt     1260 gttactgtga cctcctggct gggcaaaccc tggaaacctg gtgacaagga gccctgtgca     1320
catcccaact ctcgattttg tgccccggct cgccagtgcc ccatcatgga cccagcctgg     1380
gaggccccag agggtgtccc cattgacgcc atcatctttg gtggccgcag acccaagggg     1440
gtacccctgg tatacgaggc cttcaactgg cgtcatgggg tgtttgtggg cagagccatg     1500
cgctctgagt ccactgctgc agcagaacac aaagggaaga tcatcatgca cgacccattt     1560
gccatgcggc cctttttggg ctacaacttc gggcactacc tggaacactg gctgagcatg     1620
gaagggcgca agggggccca gctgccccgt atcttccatg tcaactggtt ccggcgtgac     1680
gaggcagggc acttcctgtg gccaggcttt ggggagaatg ctcgggtgct agactggatc     1740
tgccggcggt tagaggggga ggacagtgcc cgagagacac ccattgggct ggtgccaaag     1800
gaaggagcct tggatctcag cggcctcaga gctatagaca ccactcagct gttctccctc     1860
cccaaggact tctgggaaca ggaggttcgt gacattcgga gctacctgac agagcaggtc     1920
aaccaggatc tgcccaaaga ggtgttggct gagcttgagg ccctggagag acgtgtgcac     1980
aaaatgtgac ctgaggccta gtctagcaag aggacatagc accctcatct gggaataggg     2040
aaggcacctt gcagaaaata tgagcaattg atattaacta acatcttcaa tgtgccatag     2100
accttcccac aaagactgtc caataataag agatgcttat ctattttaaa aaaaaaaaa     2160 aaaaa                                                                2165
```

<210> SEQ ID NO 62
<211> LENGTH: 660
<212> TYPE: DNA
<213> ORGANISM: Homo sapiens

<400> SEQUENCE: 62

```
gccgccycg aggattcagc agcctccccc ttgagccccc tcgcttcccg acgttccgtt       60
cccccctgcc cgccttctcc cgccaccgcc gccgccgcct tccgcagccg tttccaccga      120
ggaaaaggaa tcgtatcgta tgtccgctat ccagaacctc cactctttcg accccttgc      180 tgatgcaagt aagggtgatg acctgcttcc tgctggcact gaggattata tccatataag      240
aattcaacag agaaacggca ggaagaccct tactactgtc caagggatcg ctgatgatta      300
cgataaaaag aaactagtga aggcgtttaa gaaaaagttt gcctgcaatg gtactgtaat      360
```

```
tgagcatccg gaatatggag aagtaattca gctacaggt gaccaacgca agaacatatg    420
ccagttcctc gtagagattg gactggctaa ggacgatcag ctgaaggttc atgggtttta    480
agtgcttgtg gctcactgaa gcttaagtga ggatttcctt gcaatgagta gaatttccct    540
tctctccctt gtcacaggtt taaaaacctc acagcttgta taatgtaacc atttggggtc    600
cgcttttaac ttggactagt gtaactcctt catgcaataa actgaaaaga gccatgcaaa    660

<210> SEQ ID NO 63
<211> LENGTH: 794
<212> TYPE: DNA
<213> ORGANISM: Homo sapiens

<400> SEQUENCE: 63
cccccccccc cccccccagc cagtgggttc ccgcgcgtgc cgagactctg aggccttgca     60
cccccacgat cccgtacgat ggccgtcaag aagatcgcga tcttcggcgc cactggccag    120
accgggctca ccaccctggc gcaggcggtg caagcaggtt acgaagtgac agtgctggtg    180
cgggactcct ccaggctgcc atcagagggg ccccggccgg cccacgtggt agtgggagat    240
gttctgcagg cagccgatgt ggacaagacc gtggctgggc aggacgctgt catcgtgctg    300
ctgggcaccc gcaatgacct cagtcccacg acagtgatgt ccgagggcgc ccggaacatt    360
gtggcagcca tgaaggctca tggtgtggac aaggtcgtgg cctgcacctc ggcttttcctg    420 ctctgggacc ctaccaaggt gcccccacga ctgcaggctg tgactgatga ccacatccgg    480
atgcacaagg tgctgcggga atcaggcctg aagtacgtgc tgtgatgcc gccacacata    540 ggagaccagc cactaactgg ggcgtacaca gtgaccctgg atggacgagg ccctcaagg    600 gtcatctcca aacatgacct gggccatttc atgctgcgct gcctcaccac cgatgagtac    660
gacggacaca gcacctaccc ctcccaccag taccagtagc actctgtccc catctgggag    720
ggtggcattc tgggacatga ggagcaaagg aaggggcaa taaatgttga gccaagagct    780
tcaaattact ctag                                                     794

<210> SEQ ID NO 64
<211> LENGTH: 851
<212> TYPE: DNA
<213> ORGANISM: Homo sapiens

<400> SEQUENCE: 64
cgggaacgca acatgaaggt gctccttgcc gccgccctca tcgcgggtc cgtcttcttc     60 ctgctgctgc cgggaccttc tgcggccgat gagaagaaga aggggcccaa agtcaccgtc    120
aaggtgtatt ttgacctacg aattggagat gaagatgtag gccgggtgat cttttggtctc    180 ttcggaaaga ctgttccaaa aacagtggat aattttgtgg ccttagctac aggagagaaa    240
ggatttggct acaaaaacag caaattccat cgtgtaatca aggacttcat gatccagggc    300
ggagacttca ccaggggaga tggcacagga ggaaagagca tctacggtga gcgcttcccc    360
gatgagaact tcaaactgaa gcactacggg cctggctggg tcagcatggc caacgcaggc    420
aaagacacca acggctccca gttcttcatc acgacagtca agacagcctg gctagatggc    480
aagcatgtgg tgtttggcaa agttctagag ggcatggagg tggtgcgaaa ggtggagagc    540
accaagacag acagccggga taaaccctg aaggatgtga tcatcgcaga ctgcggcaag    600
atcgaggtgg agaagccctt tgccatcgcc aaggagtagg gcacaggac atctttcttt    660 gagtgaccgt ctgtgcaggc cctgtagtcc ggcacaggg tctgagctgc actggccccg    720
gtgctggcat ctggtggagc ggacccactc ccctcacatt ccacaggccc atggactcac    780
```

-continued

| | |
|---|---|
| ttttgtaaca aactcctacc aacactgacc aataaaaaaa aatgtgggtt tttttttttt | 840 |
| ttaataaaaa a | 851 |

<210> SEQ ID NO 65
<211> LENGTH: 1941
<212> TYPE: DNA
<213> ORGANISM: Homo sapiens

<400> SEQUENCE: 65

| | |
|---|---|
| tctcttgatt cctagtctct cgatatggca cctccgtcag tctttgccga ggttccgcag | 60 |
| gcccagcctg tcctggtctt caagctcact gccgacttca gggaggatcc ggaccccgc | 120 |
| aaggtcaacc tgggagtggg agcatatcgc acggatgact gccatccctg gttttgcca | 180 |
| gtagtgaaga aagtggagca gaagattgct aatgacaata gcctaaatca cgagtatctg | 240 |
| ccaatcctgg gcctggctga gttccggagc tgtgcttctc gtcttgccct tgggatgac | 300 |
| agcccagcac tcaaggagaa gcgggtagga ggtgtgcaat ctttggggg aacaggtgca | 360 |
| cttcgaattg gagctgattt cttagcgcgt tggtacaatg gaacaaacaa caagaacaca | 420 |
| cctgtctatg tgtcctcacc aacctgggag aatcacaatg ctgtgttttc cgctgctggt | 480 |
| tttaaagaca ttcggtccta tcgctactgg gatgcagaga agagaggatt ggacctccag | 540 |
| ggcttcctga atgatctgga gaatgctcct gagttctcca ttgttgtcct ccacgcctgt | 600 |
| gcacacaacc caactgggat tgacccaact ccggagcagt ggaagcagat tgcttctgtc | 660 |
| atgaagcacc ggtttctgtt ccccttcttt gactcagcct atcagggctt cgcatctgga | 720 |
| aacctggaga gagatgcctg gccattcgc tattttgtgt ctgaaggctt cgagttcttc | 780 |
| tgtgcccagt ccttctccaa gaacttcggg ctctacaatg agagagtcgg gaatctgact | 840 |
| gtggttggaa aagaacctga gagcatcctg caagtccttt cccagatgga gaagatcgtg | 900 |
| cggattactt ggtccaatcc ccccgcccag ggagcacgaa ttgtggccag caccctctct | 960 |
| aaccctgagc tctttgagga atggacaggt aatgtgaaga caatggctga ccggattctg | 1020 |
| accatgagat ctgaactcag ggcacgacta gaagccctca aaaccctgg gacctggaac | 1080 |
| cacatcactg atcaaattgg catgttcagc ttcactgggt tgaacccaa gcaggttgag | 1140 |
| tatctggtca atgaaaagca catctacctg ctgccaagtg gtcgaatcaa cgtgagtggc | 1200 |
| ttaaccacca aaaatctaga ttacgtggcc acctccatcc atgaagcagt caccaaaatc | 1260 |
| cagtgaagaa acaccacccg tccagtacca ccaaagtagt tctctgtcat gtgtgttccc | 1320 |
| tgcctgcaca aacctacatg tacataccat ggattagaga cacttgcagg actgaaagct | 1380 |
| gctctggtga ggcagcctct gtttaaaccg gccccacatg aagagaacat cccttgagac | 1440 |
| gaatttggag actgggatta gagcctttgg aggtcaaagc aaattaagat tttatttaa | 1500 |
| gaataaaaga gtactttgat catgagacat aggtatcttg tccctctcac taaaaaggag | 1560 |
| tgttgtgtgt ggcggccacg tgcttctatg tggtgtttga ctctgtacaa attctagtcc | 1620 |
| caaagatcaa gttgtctgaa ggagccaaag tgtaatgtg ggtgtcggct gcggcattaa | 1680 |
| attcatcatc tcaacccaga gtgtctggtc tccctgctct ttctgcatgg ttgtgtccct | 1740 |
| agtcctaagc tttggttctt tagggtgact gtggtaagaa ggatatttaa tcatgacatg | 1800 |
| cacggacacg tacatattta actgaaacaa gttttaccaa acagtattta ctcgtgatgt | 1860 |
| gcgtagtgca ttctgatatt tttgagccat tctattgtgt tctacttcac ctaaaaaaat | 1920 |
| aaaataaaaa tgttgatcaa g | 1941 |

<210> SEQ ID NO 66
<211> LENGTH: 2736
<212> TYPE: DNA
<213> ORGANISM: Homo sapiens

<400> SEQUENCE: 66

| | | | | | |
|---|---|---|---|---|---|
| ttgcactctc | ccacacccctt | ttcttttcgt | ccgctcttcg | cttatttctc | ccgccgtctc | 60 |
| ctctgcataa | gaaggggaac | gaaagatggc | ggcggaaacg | ctgctgtcca | gtttgttagg | 120 |
| actgctgctt | ctgggactcc | tgttacccgc | aagtctgacc | ggcggtgtcg | ggagcctgaa | 180 |
| cctggaggag | ctgagtgaga | tgcgttatgg | gatcgagatc | ctgccgttgc | ctgtcatggg | 240 |
| agggcagagc | caatcttcgg | acgtggtgat | tgtctcctct | aagtacaaac | agcgctatga | 300 |
| gtgtcgcctg | ccagctggag | ctattcactt | ccagcgtgaa | agggaggagg | aaacacctgc | 360 |
| ttaccaaggg | cctgggatcc | ctgagttgtt | gagcccaatg | agagatgctc | cctgcttgct | 420 |
| gaagacaaag | gactggtgga | catatgaatt | ctgttatgga | cgccacatcc | agcaatacca | 480 |
| catggaagat | tcagagatca | aaggtgaagt | cctctatctc | ggctactacc | aatcagcctt | 540 |
| cgactgggat | gatgaaacag | ccaaggcctc | caagcagcat | cgtcttaaac | gctaccacag | 600 |
| ccagacctat | ggcaatgggt | ccaagtgcga | ccttaatggg | aggccccggg | aggccgaggt | 660 |
| tcggttcctc | tgtgacgagg | gtgcaggtat | ctctgggac | tacatcgatc | gcgtggacga | 720 |
| gcccttgtcc | tgctcttatg | tgctgaccat | tcgcactcct | cggctctgcc | ccacccctct | 780 |
| cctccggccc | ccacccagtg | ctgcaccaca | ggccatcctc | tgtcacccctt | ccctacagcc | 840 |
| tgaggagtac | atggcctacg | ttcagaggca | agccgactca | aagcagtatg | agataaaat | 900 |
| catagaggag | ctgcaagatc | taggccccca | agtgtggagt | gagaccaagt | ctggggtggc | 960 |
| accccaaaag | atggcaggtg | cgagcccgac | caaggatgac | agtaaggact | cagatttctg | 1020 |
| gaagatgctt | aatgagccag | aggaccaggc | cccaggaggg | gaggaggtgc | cggctgagga | 1080 |
| gcaggaccca | agccctgagg | cagcagattc | agcttctggt | gctcccaatg | attttcagaa | 1140 |
| caacgtgcag | gtcaaagtca | ttcgaagccc | tgcggattg | attcgattca | tagaggagct | 1200 |
| gaaaggtgga | acaaaaaagg | ggaagccaaa | tataggccaa | gagcagcctg | tggatgatgc | 1260 |
| tgcagaagtc | cctcagaggg | aaccagagaa | ggaaagggt | gatccagaac | ggcagagaga | 1320 |
| gatggaagaa | gaggaggatg | aggatgagga | tgaggatgaa | gatgaggatg | aacggcagtt | 1380 |
| actgggagaa | tttgagaagg | aactggaagg | gatcctgctt | ccgtcagacc | gagaccggct | 1440 |
| ccgttcggag | gtgaaggctg | gcatggagcg | ggaactggag | aacatcatcc | aggagacaga | 1500 |
| gaaagagctg | gacccagatg | ggctgaagaa | ggagtcagag | cgggatcggg | caatgctggc | 1560 |
| tctcacatcc | actctcaaca | aactcatcaa | aagactggag | gaaaacaga | gtccagagct | 1620 |
| ggtgaagaag | cacaagaaaa | agagggttgt | ccccaaaaag | cctcccccat | caccccaacc | 1680 |
| tacagaggag | gatcctgagc | acagagtccg | ggtccgggtc | accaagctcc | gtctcggagg | 1740 |
| ccctaatcag | gatctgactg | tcctcgagat | gaaacgggaa | aacccacagc | tgaaacaaat | 1800 |
| cgagggcctg | gtgaaggagc | tgctggagag | ggagggactc | acagctgcag | ggaaaattga | 1860 |
| gatcaaaatt | gtccgcccat | gggctgaagg | gactgaagag | ggtgcacgtt | ggctgactga | 1920 |
| tgaggacacg | agaaacctca | aggagatctt | cttcaatatc | ttggtgccgg | agctgaaga | 1980 |
| ggcccagaag | gaacgccagc | ggcagaaaga | gctggagagc | aattaccgcc | gggtgtgggg | 2040 |
| ctctccaggt | ggggagggca | caggggacct | ggacgaattt | gacttctgag | accaacacta | 2100 |
| cacttgaccc | ttcacggaat | ccagactctt | cctggactgg | cttgcctcct | ccccaccctcc | 2160 |

| | |
|---|---|
| ccaccctgga acccctgagg gccaaacagc agagtggagc tgagctgtgg acctctcggg | 2220 |
| caactctgtg ggtgtggggg ccctgggtga atgctgctgc ccctgctggc agccaccttg | 2280 |
| agacctcacc gggcctgtga tatttgctct cctgaactct cactcaatcc tcttcctctc | 2340 |
| ctctgtggct tttcctgtta ttgtcccta atgataggat attccctgct gcctacctgg | 2400 |
| agattcagta ggatcttttg agtggaggtg ggtagagaga gcaaggaggg caggacactt | 2460 |
| agcaggcact gagcaagcag gcccccacct gcccttagtg atgtttggag tcgttttacc | 2520 |
| ctcttctatt gaattgcctt gggatttcct tctccctttc cctgcccacc ctgtccccta | 2580 |
| caatttgtgc ttctgagttg aggagccttc acctctgttg ctgaggaaat ggtagaatgc | 2640 |
| tgcctatcac ctccagcaca atcccagcga aaaggtgtg aagcacccac catgttcttg | 2700 |
| aacaatcagg tttctaaata aacaactgga ccatca | 2736 |

<210> SEQ ID NO 67
<211> LENGTH: 1860
<212> TYPE: DNA
<213> ORGANISM: Homo sapiens

<400> SEQUENCE: 67

| | |
|---|---|
| cgtgaacggt cgttgcagag attgcgggcg gctgagacgc cgcctgcctg gcacctagga | 60 |
| gcgcagcgga gccccgacac cgccgccgcc gccatggagt ccgagaccga acccgagccc | 120 |
| gtcacgctcc tggtgaagag ccccaaccag cgccaccgcg acttggagct gagtggcgac | 180 |
| cgcggctgga gtgtgggcca cctcaaggcc cacctgagcc gcgtctaccc cgagcgtccg | 240 |
| cgtccagagg accagaggtt aatttattct gggaagctgt tgttggatca ccaatgtctc | 300 |
| agggacttgc ttccaaagca ggaaaaacgg catgttttgc atctggtgtg caatgtgaag | 360 |
| agtccttcaa aaatgccaga atcaacgcc aaggtggctg aatccacaga ggagcctgct | 420 |
| ggttctaatc ggggacagta tcctgaggat tcctcaagtg atggtttaag gcaaagggaa | 480 |
| gttcttcgga acctttcttc ccctggatgg gaaaacatct caaggcctga agctgcccag | 540 |
| caggcattcc aaggcctggg tcctggtttc tccggttaca caccctatgg gtggcttcag | 600 |
| cttttcctggt tccagcagat atatgcacga cagtactaca tgcaatattt agcagccact | 660 |
| gctgcatcag gggcttttgt tccaccacca agtgcacaag agatacctgt ggtctctgca | 720 |
| cctgctccag cccctattca caaccagttt ccagctgaaa accagcctgc caatcagaat | 780 |
| gctgctcctc aagtggttgt taatcctgga gccaatcaaa atttgcggat gaatgcacaa | 840 |
| ggtggcccta ttgtggaaga agatgatgaa ataaatcgag attggttgga ttggaccctat | 900 |
| tcagcagcta cattttctgt ttttctcagt atcctctact tctactcctc cctgagcaga | 960 |
| ttcctcatgg tcatgggggc caccgttgtt atgtacctgc atcacgttgg gtggtttcca | 1020 |
| tttagaccga ggccggttca gaacttccca aatgatggtc ctcctcctga cgttgtaaat | 1080 |
| caggacccca caataactt acaggaaggc actgatcctg aaactgaaga ccccaaccac | 1140 |
| ctccctccag acagggatgt actagatggc gagcagacca gccctccttt atgagcaca | 1200 |
| gcatggcttg tcttcaagac tttctttgcc tctcttcttc cagaaggccc cccagccatc | 1260 |
| gcaaactgat ggtgtttgtg ctgtagctgt tggaggcttt gacaggaatg gactggatca | 1320 |
| cctgactcca gctagattgc ctctcctgga catggcaatg atgagttttt aaaaaacagt | 1380 |
| gtggatgatg atatgctttt tgtgagcaagc aaaagcagaa acgtgaagcc gtgatacaaa | 1440 |
| ttggtgaaca aaaaatgccc aaggcttctc atgtgtttat tctgaagagc tttaatatat | 1500 |

-continued

| | | | | |
|---|---|---|---|---|
| actctatgta | gtttaataag | cactgtacgt | agaaggcctt | aggtgttgca tgtctatgct | 1560 |
| tgaggaactt | ttccaaatgt | gtgtgtctgc | atgtgtgttt | gtacatagaa gtcatagatg | 1620 |
| cagaagtggt | tctgctggta | agatttgatt | cctgttggaa | tgtttaaatt acactaagtg | 1680 |
| tactacttta | tataatcaat | gaaattgcta | gacatgtttt | agcaggactt ttctaggaaa | 1740 |
| gacttatgta | taattgcttt | ttaaaatgca | gtgctttact | ttaaactaag gggaactttg | 1800 |
| cggaggtgaa | aacctttgct | gggttttctg | ttcaataaag | ttttactatg aatgaccctg | 1860 |

<210> SEQ ID NO 68
<211> LENGTH: 3082
<212> TYPE: DNA
<213> ORGANISM: Homo sapiens

<400> SEQUENCE: 68

| | | | | |
|---|---|---|---|---|
| agggagtcgt | gtcggcgcca | ccccggcccc | cgagcccgca | gattgcccac cgaagctcgt | 60 |
| gtgtgcaccc | ccgatcccgc | cagccactcg | cccctggcct | cgcgggccgt gtctccggca | 120 |
| tcatgtgtgg | tatatttgct | tacttaaact | accatgttcc | tcgaacgaga cgagaaatcc | 180 |
| tggagaccct | aatcaaaggc | cttcagagac | tggagtacag | aggatatgat tctgctggtg | 240 |
| tgggatttga | tggaggcaat | gataaagatt | gggaagccaa | tgcctgcaaa acccagctta | 300 |
| ttaagaagaa | aggaaaagtt | aaggcactgg | atgaagaagt | tcacaagcaa caagatatgg | 360 |
| atttggatat | agaatttgat | gtacaccttg | aatagctca | tacccgttgg gcaacacatg | 420 |
| gagaacccag | tcctgtcaat | agccaccccc | agcgctctga | taaaaataat gaatttatcg | 480 |
| ttattcacaa | tggaatcatc | accaactaca | aagacttgaa | aaagtttttg gaaagcaaag | 540 |
| gctatgactt | cgaatctgaa | acagacacag | agacaattgc | caagctcgtt aagtatatgt | 600 |
| atgacaatcg | ggaaagtcaa | gataccagct | ttactaccct | ggtggagaga gttatccaac | 660 |
| aattggaagg | tgcttttgca | cttgtgttta | aaagtgttca | ttttcccggg caagcagttg | 720 |
| gcacaaggcg | aggtagccct | ctgttgattg | gtgtacggag | tgaacataaa ctttctactg | 780 |
| atcacattcc | tatactctac | agaacaggca | agacaagaa | aggaagctgc aatctctctc | 840 |
| gtgtggacag | cacaacctgc | cttttccgg | tggaagaaaa | agcagtggag tattactttg | 900 |
| cttctgatgc | aagtgctgtc | atagaacaca | ccaatcgcgt | catctttctg gaagatgatg | 960 |
| atgttgcagc | agtagtggat | ggacgtcttt | ctatccatcg | aattaaacga actgcaggag | 1020 |
| atcaccccgg | acgagctgtg | caaacactcc | agatggaact | ccagcagatc atgaagggca | 1080 |
| acttcagttc | atttatgcag | aaggaaatat | ttgagcagcc | agagtctgtc gtgaacacaa | 1140 |
| tgagaggaag | agtcaacttt | gatgactata | ctgtgaattt | gggtggtttg aaggatcaca | 1200 |
| taaaggagat | ccagagatgc | cggcgtttga | ttcttattgc | ttgtggaaca agttaccatg | 1260 |
| ctggtgtagc | aacacgtcaa | gttcttgagg | agctgactga | gttgcctgtg atggtggaac | 1320 |
| tagcaagtga | cttcctggac | agaaacacac | cagtctttcg | agatgatgtt tgctttttcc | 1380 |
| ttagtcaatc | aggtgagaca | gcagatactt | tgatgggtct | tcgttactgt aaggagagag | 1440 |
| gagctttaac | tgtggggatc | acaaacacag | ttggcagttc | catatcacgg gagacagatt | 1500 |
| gtggagttca | tattaatgct | ggtcctgaga | ttggtgtggc | cagtcaaaag gcttatacca | 1560 |
| gccagtttgt | atcccttgtg | atgtttgccc | ttatgatgtg | tgatgatcgg atctccatgc | 1620 |
| aagaaagacg | caaagagatc | atgcttggat | tgaaacggct | gcctgatttg attaaggaag | 1680 |
| tactgagcat | ggatgacgaa | attcagaaac | tagcaacaga | actttatcat cagaagtcag | 1740 |
| ttctgataat | gggacgaggc | tatcattatg | ctacttgtct | tgaaggggca ctgaaaatca | 1800 |

-continued

| | |
|---|---|
| aagaaattac ttatatgcac tctgaaggca tccttgctgg tgaattgaaa catggccctc | 1860 |
| tggctttggt ggataaattg atgcctgtga tcatgatcat catgagagat cacacttatg | 1920 |
| ccaagtgtca gaatgctctt cagcaagtgg ttgctcggca ggggcggcct gtggtaattt | 1980 |
| gtgataagga ggatactgag accattaaga acacaaaaag aacgatcaag gtgccccact | 2040 |
| cagtggactg cttgcagggc attctcagcg tgatcccttt acagttgctg gctttccacc | 2100 |
| ttgctgtgct gagaggctat gatgttgatt tcccacggaa tcttgccaaa tctgtgactg | 2160 |
| tagagtgagg aatatctata caaaatgtac gaaactgtat gattaagcaa cacaagacac | 2220 |
| cttttgtatt taaaaccttg atttaaaata tcacccctttg aagcctttttt ttagtaaatc | 2280 |
| cttatttata tatcagttat aattattcca ctcaatatgt gattttttgtg aagttacctc | 2340 |
| ttacattttc ccagtaattt gtggaggact ttgaataatg gaatctatat tggaatctgt | 2400 |
| atcagaaaga ttctagctat tattttctttt aaagaatgct gggtgttgca tttctggacc | 2460 |
| ctccacttca atctgagaag acaatatgtt tctaaaaatt ggtacttgtt tcaccatact | 2520 |
| tcattcagac cagtgaaaga gtagtgcatt taattggagt atctaaagcc agtggcagtg | 2580 |
| tatgctcata cttggacagt tagggaaggg tttgccaagt tttaagagaa gatgtgatttt | 2640 |
| attttgaaat ttgtttctgt tttgtttttta aatcaaactg taaaacttaa aactgaaaaaa | 2700 |
| ttttattggt aggatttata tctaagtttg gttagcctta gtttctcaga cttgttgtct | 2760 |
| attatctgta ggtggaagaa atttaggaag cgaaatatta cagtagtgca ttggtgggtc | 2820 |
| tcaatcctta acatatttgc acaatttttat agcacaaact ttaaattcaa gctgctttgg | 2880 |
| acaactgaca atatgatttt aaatttgaag atgggatgtg tacatgttgg gtatcctact | 2940 |
| actttgtgtt ttcatctcct aaaagtgttt tttatttcct tgtatctgta gtcttttatt | 3000 |
| ttttaaatga ctgctgaatg acatatttta tcttgttctt taaaatcaca acacagagct | 3060 |
| gctattaaat taatattgat at | 3082 |

<210> SEQ ID NO 69
<211> LENGTH: 1815
<212> TYPE: DNA
<213> ORGANISM: Homo sapiens

<400> SEQUENCE: 69

| | |
|---|---|
| aaaccaacgc ctggctcgga gcagcagcct ctgaggtgtc cctggccagt gtccttccac | 60 |
| ctgtccacaa gcatggggaa catcttcgcc aacctcttca agggccttttt tggcaaaaaa | 120 |
| gaaatgcgca tcctcatggt gggcctggat gctgcaggga agaccacgat cctctacaag | 180 |
| cttaagctgg gtgagatcgt gaccaccatt cccaccatag gcttcaacgt ggaaaccgtg | 240 |
| gagtacaaga acatcagctt cactgtgtgg gacgtgggtg ccaggacaa gatccggccc | 300 |
| ctgtggcgcc actacttcca gaacacacaa ggcctgatct tcgtggtgga cagcaatgac | 360 |
| agagagcgtg tgaacgaggc ccgtgaggag ctcatgagga tgctggccga ggacgagctc | 420 |
| cgggatgctg tcctcctggt gttcgccaac aagcaggacc tccccaacgc catgaatgcg | 480 |
| gccgagatca cagacaagct ggggctgcac tcactacgcc acaggaactg gtacattcag | 540 |
| gccacctgcg ccaccagcgg cgacgggctc tatgaaggac tggactggct gtccaatcag | 600 |
| ctccggaacc agaagtgaac gcgaccccccc tccctctcac tcctcttgcc ctctgcttta | 660 |
| ctctcatgtg gcaaacgtgc ggctcgtggt gtgagtgcca gaagctgcct ccgtggtttg | 720 |
| gtcaccgtgt gcatcgcacc gtgctgtaaa tgtggcagac gcagcctgcg gccaggcttt | 780 |

-continued

| | |
|---|---|
| ttatttaatg taaatagttt ttgtttccaa tgaggcagtt tctggtactc ctatgcaata | 840 |
| ttactcagct ttttttattg taaaaagaaa aatcaactca ctgttcagtg ctgagagggg | 900 |
| atgtaggccc atgggcacct ggcctccagg agtcgctgtg ttgggagagc cggccacgcc | 960 |
| cttggctttta gagctgtgtt gaaatccatt ttggtggttg gttttaacc caaactcagt | 1020 |
| gcatttttta aaatagttaa gaatccaagt cgagaacact tgaacacaca gaagggagac | 1080 |
| cccgcctagc atagatttgc agttacggcc tggatgccag tcgccagccc agctgttccc | 1140 |
| ctcgggaaca tgaggtggtg gtggcgcagc agactgcgat caattctgca tggtcacagt | 1200 |
| agagatcccc gcaactcgct tgtccttggg tcaccctgca ttccatagcc atgtgcttgt | 1260 |
| ccctgtgctc ccacggttcc caggggccag gctgggagcc cacagccacc ccactatgcc | 1320 |
| gcaggccgcc ctacccacct tcaggcagcc tatgggacgc agggccccat ctgtccctcg | 1380 |
| gtcgccgtgt ggccagagtg ggtccgtcgt ccccaacact cgtgctcgct cagacacttt | 1440 |
| ggcaggatgt ctggggcctc accagcagga gcgcgtgcaa gccgggcagg cggtccacct | 1500 |
| agacccacag cccctcggga gcaccccacc tctgtgtgtg atgtagcttt ctctccctca | 1560 |
| gcctgcaagg gtccgatttg ccatcgaaaa agacaacctc tactttttc ttttgtattt | 1620 |
| tgataaacac tgaagctgga gctgttaaat ttatcttggg gaaacctcag aactggtcta | 1680 |
| tttggtgtcg tggaacctct tactgctttc aatacacgat tagtaatcaa ctgttttgta | 1740 |
| tacttgtttt cagttttcat ttcgacaaac aagcactgta attatagcta ttagaataaa | 1800 |
| atctcttaac tattt | 1815 |

<210> SEQ ID NO 70
<211> LENGTH: 2462
<212> TYPE: DNA
<213> ORGANISM: Homo sapiens

<400> SEQUENCE: 70

| | |
|---|---|
| gctccccatt gtccttgtca atactgtgag actcatccaa tatcctatcc acctctacgt | 60 |
| agtctggatt aaagggctct tcatcctcat ggaagaagtg tctcatctga gccagggggg | 120 |
| gcggcgattt catcatgctc cgagccggcg gcgcgcgccg cttccgtcgc caccctctct | 180 |
| ggacagccca gggccgcacg tcatgccctc tccgcgtcca gtgctgctta gaggtgctcg | 240 |
| cgccgctctg ctgctgctgc tgccgccccg gctcttagcc cgaccctcgc tcctgctccg | 300 |
| ccggtccctc agcgcggcct cctgcgcccc gatctccttg cccgccgccg cctcccggag | 360 |
| cagcatggac ggcgcggggg ctgaggaggt gctggctcct ctgaggctag cagtgcgcca | 420 |
| gcagggagat cttgtgcgaa aactcaaaga agataaagca ccccaagtag acgtagacaa | 480 |
| agcagtggct gagctcaaag cccgcaagag ggttctggaa gcaaaggagc tggcgttaca | 540 |
| gcccaaagat gatattgtag accgagcaaa aatggaagat accctgaaga ggaggttttt | 600 |
| ctatgatcaa gcttttgcta tttatggagg tgttagtggt ctgtatgact ttgggccagt | 660 |
| tggctgtgct ttgaagaaca atattattca gacctgagg cagcacttta tccaaggaga | 720 |
| acagatcctg gagatcgatt gcaccatgct caccctgag ccagttttaa agacctctgg | 780 |
| ccatgtagac aaatttgctg acttcatggt gaaagacgta aaaaatggag atgttttcg | 840 |
| tgctgaccat ctattaaaag ctcatttaca gaaattgatg tctgataaga agtgttctgt | 900 |
| cgaaaagaaa tcagaaatgg aaagtgtttt ggcccagctt gataactatg acagcaaga | 960 |
| acttgcggat cttttttgtga actataatgt aaaatctccc attactggaa atgatctatc | 1020 |
| ccctccagtg tcttttaact taatgttcaa gactttcatt gggcctggag gaaacatgcc | 1080 |

```
tgggtacttg agaccagaaa ctgcacaggg gattttcttg aatttcaaac gacttttgga    1140
gttcaaccaa ggaaagttgc cttttgctgc tgcccagatt ggaaattctt ttagaaatga    1200
gatctcccct cgatctggac tgatcagagt cagagaattc acaatggcag aaattgagca    1260
ctttgtagat cccagtgaga aagaccaccc caagttccag aatgtggcag accttcacct    1320
ttatttgtat tcagcaaaag cccaggtcag cggacagtcc gctcggaaaa tgcgcctggg    1380
agatgctgtt gaacagggtg tgattaataa cacagtatta ggctatttca ttggccgcat    1440
ctacctctac ctcacgaagg ttggaatatc tccagataaa ctccgcttcc ggcagcacat    1500
ggagaatgag atggcccatt atgcctgtga ctgttgggat gcagaatcca aaacatccta    1560
cggttggatt gagattgttg gatgtgctga tcgttcctgt tatgacctct cctgtcatgc    1620
acgagccacc aaagtcccac ttgtagctga aaacctctg aaagaaccca aaacagtcaa    1680
tgttgttcag tttgaaccca gtaagggagc aattggtaag gcatataaga aggatgcaaa    1740
actggtgatg gagtatcttg ccatttgtga tgagtgctac attacagaaa ttgagatgct    1800
gctgaatgag aaagggggaat tcacaattga aactgaaggg aaaacatttc agttaacaaa    1860
agacatgatc aatgtgaaga gattccagaa aacactatat gtggaagaag ttgttccgaa    1920
tgtaattgaa ccttccttcg gcctgggtag gatcatgtat acggtatttg aacatacatt    1980
ccatgtacga gaaggagatg aacagagaac attcttcagt ttccctgctg tagttgctcc    2040
attcaaatgt tccgtcctcc cactgagcca aaaccaggag ttcatgccat ttgtcaagga    2100
attatcggaa gccctgacca ggcatggagt atctcacaaa gtagacgatt cctctgggtc    2160
aatcggaagg cgctatgcca ggactgatga gattggcgtg gcttttggtg tcaccattga    2220
ctttgacaca gtgaacaaga cccccacac tgcaactctg agggaccgtg actcaatgcg    2280
gcagataaga gcagagatct ctgagctgcc cagcatagtc caagacctag ccaatggcaa    2340
catcacatgg gctgatgtgg aggccaggta tcctctgttt gaagggcaag agactggtaa    2400
aaaagagaca atcgaggaat gaggacaatt ttgacaactt ttgaccactt gcgctaataa    2460
aa                                                                   2462
```

<210> SEQ ID NO 71
<211> LENGTH: 2415
<212> TYPE: DNA
<213> ORGANISM: Homo sapiens

<400> SEQUENCE: 71

```
cggcgccgcg agcttctcct ctcctcacga ccgaggcaga gcagtcatta tggcgaacct      60
tggctgctgg atgctggttc tctttgtggc cacatggagt gacctgggcc tctgcaagaa     120
gcgcccgaag cctggaggat ggaacactgg gggcagccga tacccggggc agggcagccc     180
tggaggcaac cgctacccac ctcagggcgg tggtggctgg gggcagcctc atggtggtgg     240 ctggggcag cctcatggtg gtggctgggg gcagccccat ggtggtggct gggacagcc      300 tcatggtggt ggctggggtc aaggaggtgg cacccacagt cagtggaaca agccgagtaa     360
gccaaaaacc aacatgaagc acatggctgg tgctgcagca gctggggcag tggtgggggg     420
ccttggcggc tacatgctgg gaagtgccat gagcaggccc atcatacatt tcggcagtga     480
ctatgaggac cgttactatc gtgaaaacat gcaccgttac cccaaccaag tgtactacag     540
gcccatggat gagtacagca accagaacaa ctttgtgcac gactgcgtca atatcacaat     600
caagcagcac acggtcacca caaccaccaa ggggggagaac ttcaccgaga ccgacgttaa     660
```

-continued

```
gatgatggag cgcgtggttg agcagatgtg tatcacccag tacgagaggg aatctcaggc    720
ctattaccag agaggatcga gcatggtcct cttctcctct ccacctgtga tcctcctgat    780
ctctttcctc atcttcctga tagtgggatg aggaaggtct tcctgttttc accatctttc    840
taatcttttt ccagcttgag ggaggcggta tccacctgca gccctttag tggtggtgtc    900 tcactctttc ttctctcttt gtcccggata ggctaatcaa tacccttggc actgatgggc    960
actggaaaac atagagtaga cctgagatgc tggtcaagcc cctttgatt gagttcatca   1020 tgagccgttg ctaatgccag gccagtaaaa gtataacagc aaataaccat tggttaatct   1080
ggacttattt ttggacttag tgcaacaggt tgaggctaaa acaaatctca gaacagtctg   1140
aaataccttt gcctggatac ctctggctcc ttcagcagct agagctcagt atactaatgc   1200
cctatcttag tagagatttc atagctattt agagatattt tccatttaa gaaacccga    1260 caacatttct gccaggtttg ttaggaggcc acatgatact tattcaaaaa atcctagag    1320 attcttagct cttgggatgc aggctcagcc cgctggagca tgagctctgt gtgtaccgag   1380
aactggggtg atgttttact tttcacagta tgggctacac agcagctgtt caacaagagt   1440
aaatattgtc acaacactga acctctggct agaggacata ttcacagtga ataactgt    1500 aacatatatg aaaggcttct gggacttgaa atcaaatgtt tgggaatggt gcccttggag   1560
gcaacctccc attttagatg tttaaaggac cctatatgtg gcattccttt ctttaaacta   1620
taggtaatta aggcagctga aaagtaaatt gccttctaga cactgaaggc aaatctcctt   1680
tgtccattta cctggaaacc agaatgattt tgacatacag gagagctgca gttgtgaaag   1740
caccatcatc atagaggatg atgtaattaa aaaatggtca gtgtgcaaag aaagaactg    1800 cttgcattc tttatttctg tctcataatt gtcaaaaacc agaattaggt caagttcata   1860
gtttctgtaa ttggcttttg aatcaaagaa tagggagaca atctaaaaaa tatcttaggt   1920
tggagatgac agaaatatga ttgatttgaa gtggaaaaag aaattctgtt aatgttaatt   1980
aaagtaaaat tattccctga attgtttgat attgtcacct agcagatatg tattactttt   2040
ctgcaatgtt attattggct tgcactttgt gagtatctat gtaaaaatat atatgtatat   2100
aaaatatata ttgcatagga cagacttagg agttttgttt agagcagtta acatctgaag   2160
tgtctaatgc attaactttt gtaaggtact gaatacttaa tatgtgggaa accctttgc    2220 gtggtcctta ggcttacaat gtgcactgaa tcgtttcatg taagaatcca agtggacac    2280 cattaacagg tctttgaaat atgcatgtac tttatatttt ctatatttgt aacttgcat   2340 gttcttgttt tgttatataa aaaattgta aatgttaat atctgactga aattaaacga     2400
gcgaagatga gcacc                                                    2415
```

<210> SEQ ID NO 72
<211> LENGTH: 3869
<212> TYPE: DNA
<213> ORGANISM: Homo sapiens
<400> SEQUENCE: 72

```
aagcttggct ccagaactgg cttttgaagg tggaggtggg ggtagtgaga actgaaacag     60
gctggctgga caactggcag cttggtgtgg ccttagaagc atgagtgagg gtggccggga    120
gacgatttgt ctgactgtt gtgatttcac cctgactttt cctgccttca gcctctgcag    180
agatgtgggc agctggtcag gatggccatt cgggctcagc acagcaacgc agcccagact    240
cagactgggg aagcaaacag gggctggaca ggccaggaga gcctgtcgga cagtgatcct    300
gagatgtggg agttgctgca gagggagaag gacaggcagt gtcgtggcct ggagctcatt    360
```

```
gcctcagagg tgggactggg gagatgggca ggggttgggc caccatgggt acaggaagta    420
acaaagttat cttaactgat atttctccaa aacccccttt cacactcagg acctttcttt    480
gggctttatc ttcctttctt atctccctca agcaaaggca gtgcaagtcc agtttatggg    540
gttgggacat ttagggagcc tccagggtcc ctacagtttc atctgatccc ttccttcctc    600
ctatgaggaa ggaggagcct agaagcacaa gtttgagtgg gtaggtggca ttgaggggcc    660
actgctcatg gcagatgggt ttctgagaat gctgcctctg gctttgcccc aggcctggtg    720
ctgagtgaat ggagctttct gcagggagta ctcccgcttt cagctctggc tctggcaggg    780
agggactgtg ggagtccagg ggaagggget caataccttc tgacattgcc ccccaccacc    840
ccagaacttc tgcagccgag ctgcgctgga ggccctgggg tcctgtctga acaacaagta    900
ctcggagggt tatcctggca agaggtgagg gctggagggc agtgtcaggg atggtgctcc    960
cagtggggga acccacctgt accttcccag tgttcattga ggagtgaact tcccagtcct   1020
ttgctgatgg ttgagagtcc tttctctgtg ccctcattac ccctctccca cggcagatac   1080 tatggggag cagaggtggt ggatgaaatt gagctgctgt gccagcgccg ggccttggaa    1140
gcctttgacc tggatcctgc acagtgggga gtcaatgtcc agccctactc cgggtcccca   1200
gccaacctgg ccgtctacac agcccttctg caacctcacg accggatcat ggggctggac   1260
ctgcccgatg ggggccagtg agtatggatg ggctggctga tggtcttggc ggcaggattg   1320
gtgtgggaaa ggagttattt attgaatacc tactgtggac catacagatg gaacaggcct   1380
tgccctgtcc tgcatgtcac agtggatgag gaagataaga tcccagttat agtgcctacc   1440
acagagtgga cagagcagtg aggcggtgtg tcctaggact ggtgttctgg ggacagagaa   1500
ctgtggagtt gaagggagtg gttaagtccg ggggtccttc cacccaggcc ttcttacttc   1560
ctctcacttc gcagtctcac ccacggctac atgtctgacg tcaagcggat atcagccacg   1620
tccatcttct tcgagtctat gccctataag ctcaacgtga gtgctctagg gtgtggggag   1680
gggctcttgg ccctggtggt ggtcctcccc tggagaagct gagggcctgg agcgccgggc   1740
cgtccttagg gttaaggagg agagtgagct gccctgcttc cttctcaggg ctttagctgt   1800
ttgtgtgtct gtccagccca aaactggcct cattgactac aaccagctgg cactgactgc   1860
tcgactttcc cggccacggc tcatcatagc tggcaccagc gcctatgctc gcctcattga   1920
ctacgcccgc atgagagagg ttggtggggg gggctgagga ctgggcacct ccccagggg    1980 tggtgaggag gtgtgggagg agggcagcct tgggcaggcc tctccgggcc ctccccaggc   2040
tgaggccttg cctctgtacc tgcccaggtg tgtgatgaag tcaaagcaca cctgctggca   2100
gacatggccc acatcagtgg cctggtgget gccaaggtga ttccctcgcc tttcaagcac   2160
gcggacatcg tcaccaccac tactcacaag actcttcgag gggccaggtc aggtcctgag   2220
gtcgggcttg cctttccctg ccttcaggcc tattcctggg gcactgttgg cctggacctg   2280
agaggaattc attcccacct gcagccctta agactcctgc ccagtctgtg agagttctcc   2340
ttctcttgcc catggtggcc atgccctggc aggggatttg tggatgggat tgaggggctg   2400
attccctcta ccactggaat ccagtgtacc aagcccacgt gagctgtgcc cttggggccc   2460
aggtccgcca gcttcctctg ccttctctgt cccttgtcct tcttttcagc ttagactctg   2520
accatccacc tctcacacag gtcagggctc atcttctacc ggaaagggt gaaggctgtg    2580 gaccccaaga ctgccggga gatcccttac acatttgagg accgaatcaa ctttgccgtg   2640
ttcccatccc tgcaggggg ccccccacaat catgccattg ctgcagtagc tgtggcccta   2700
```

-continued

```
aagcaggttg gggatcctgt ctttgtaggg tgtgggggg caatggcctg gaggcttaga      2760
ccctgcacct tgctaactga tgctggggct gatggaaggg aaatgccagg atggaaggag     2820
tcaaggctgg ggtcacagag ctatgctgag ggtgcagggc cagagggtag tgcagggctt     2880
gggtccaggc ctagggtgac agctgctact gtctcatctc caggcctgca ccccatgtt     2940
ccgggagtac tccctgcagg ttctgaagaa tgctcgggcc atggcagatg ccctgctaga    3000
gcgaggctac tcactggtat caggtaagcc agcaggtgat gggtgagggc ctctgtagct    3060
tcaggcagag gcccaggact caccactccc catttcttac ccaccttagg tggtactgac    3120
aaccacctgg tgctggtgga cctgcggccc aagggcctgg atggagctcg ggctgagcgg    3180
gtgctagagc ttgtatccat cactgccaac aagaacacct gtcctggaga ccgaagtgcc   3240
atcacaccgg gcggcctgcg gcttgggcc ccagccttaa cttctcgaca gttccgtgag    3300
gatgacttcc ggagagttgt ggactttata gatgaagggg tcaacattgg cttagaggtg   3360
aagagcaaga ctggtgagtg agcaagaagg agccccgggc cagccagttc ccactcactg    3420
tctgctccct ccccagctg atctcactgc cttccctaga gctctgacca cttgtttcct    3480
cacctctct ctctagccaa gctccaggat ttcaaatcct tcctgcttaa ggactcagaa    3540
acaagtcagc gtctgccaa cctcaggcaa cgggtggagc agtttgccag ggccttcccc    3600
atgcctggtt ttgatgagca ttgaaggcac ctggaaaatg aggcccacag actcaaagtt   3660
actctccttc cccctacctg ggccagtgaa atagaaagcc tttctatttt ttggtgcggg    3720
agggaagacc tctcacttag ggcaagagcc aggtatagtc tcccttccca gaatttgtaa   3780
ctgagaagat cttttctttt tccttttttt ggtaacaaga cttagaagga gggcccaggc    3840
actttctgtt tgaaccctg tcatgatca                                        3869
```

<210> SEQ ID NO 73
<211> LENGTH: 3344
<212> TYPE: DNA
<213> ORGANISM: Homo sapiens

<400> SEQUENCE: 73

```
ggtacagctg cgcgtctgcg ggaataggtg cagcgggccc ttggcggggg actctgaggg     60
aggagctggg gacggcgacc ctaggagagt tctttggggt gactttcaag atggactcta   120
ctctaacagc aagtgaaatc cggcagcgat ttatagattt cttcaagagg aacgagcata   180
cgtatgttca ctcgtctgcc accatcccat tggatgaccc cactttgctc tttgccaatg   240
caggcatgaa ccagtttaaa cccatttttcc tgaacacaat tgacccatct caccccatgg   300
caaagctgag cagagctgcc aatacccaga agtgcatccg ggctgggggc aaacaaaatg   360
acctggacga tgtgggcaag gatgtctatc atcacacctt cttcgagatg ctgggctctt   420
ggtcttttgg agattacttt aaggaattgg catgtaagat ggctctggaa ctcctcaccc   480
aagagtttgg cattcccatt gaaagacttt atgttactta ctttggcggg gatgaagcag   540
ctggcttaga agcagatctg gaatgcaaac agatctggca aaatttgggg ctggatgaca   600
ccaaaatcct cccaggcaac atgaaggata acttctggga gatgggtgac acgggcccct   660
gtggtccttg cagtgagatc cactacgacc ggattggtgg tcgggacgcc gcacatcttg    720
tcaaccagga cgaccctaat gtgctggaga tctggaacct tgtgttcatc cagtataaca    780
gggaagctga tggcattctg aaacctcttc ccaagaaaag cattgacaca gggatgggcc    840
tggaacgact ggtatctgtg ctgcagaata agatgtccaa ctatgacact gacctttttg    900
tcccttactt tgaagccatt cagaagggca caggtgcccg accatacact gggaaagttg    960
```

```
gtgctgagga tgccgatggg attgacatgg cctaccgggt gctggctgac catgctcgga    1020
ccatcactgt ggcactggct gatggtggcc ggcctgacaa cacagggcgt ggatatgtgt    1080
tgagacggat tctccgccga gctgtccgat acgcccatga aaagctcaat gccagcaggg    1140
gcttctttgc tacgttagtg gatgttgtcg tccagtccct gggagatgca tttcctgagc    1200
tgaagaagga cccagacatg gtgaaggaca tcattaatga agaagaggtg cagtttctca    1260
agactctcag cagagggcgt cgcatcctgg acaggaaaat tcagagcctg ggagacagca    1320
agaccattcc cggagacact gcttggctcc tctatgacac ctatgggttt ccagtggatc    1380
tgactggact gattgctgaa gagaagggcc tggtggtaga catggatggc tttgaagagg    1440
agaggaaact ggcccagctg aaatcacagg gcaagggagc tggtggggaa gacctcatta    1500
tgctggacat ttacgctatc gaagagctcc gggcacgggg tctggaggtc acagatgatt    1560 cccccaaagta caattaccat ttggactcca gtggtagcta tgtatttgag aacacagtgg    1620
ctacggtgat ggctctgcgc agggagaaga tgttcgtgga agaggtgtcc acaggccagg    1680
agtgtggagt ggtgctggac aagacctgtt tctatgctga gcaaggaggc cagatctatg    1740
acgaaggcta cctggtgaag gtggatgaca gcagtgaaga taaaacagag tttacagtga    1800
agaatgctca ggtccgagga gggtatgtgc tacacattgg aaccatctac ggtgacctga    1860
aagtggggga tcaggtctgg ctgtttattg atgagccccg acgaagaccc atcatgagca    1920
accacacagc tacgcacatt ctgaacttcg ccctgcgctc agtgcttggg gaagctgacc    1980
agaaaggctc attggttgct cctgaccgcc tcagatttga ctttactgcc aagggagcca    2040
tgtccaccca acagatcaag aaggctgaag agattgctaa tgagatgatt gaggcagcca    2100
aggccgtcta tacccaggat tgcccccctgg cagcagcgaa agccatccag ggcctacggg    2160
ctgtgtttga tgagacctat cctgaccctg tgcgagtcgt ctccattggg gtcccggtgt    2220
ccgagttgct ggatgacccc tctgggcctg ctggctccct gacttctgtt gagttctgtg    2280
ggggaacgca cctgcggaac tcgagtcatg caggagcttt tgtgatcgtg acggaagaag    2340
ccattgccaa gggtatccgg aggattgtgg ctgtcacagg tgccgaggcc cagaaggccc    2400
tcaggaaagc agagagcttg aagaaatgtc tctctgtcat ggaagccaaa gtgaaggctc    2460
agactgctcc aaacaaggat gtgcagaggg agatcgctga ccttggagag gccctggcca    2520
ctgcagtcat cccccagtgg cagaaggatg aattgcggga gactctcaaa tccctaaaga    2580
aggtcatgga tgacttggac cgagccagca agccgatgt ccagaaacga gtgttagaga    2640
agacgaagca gttcatcgac agcaaccccca accagcctct tgtcatcctg gagatggaga    2700
gcggcgcctc agccaaggcc ctgaatgaag ccttgaagct cttcaagatg cactcccctc    2760
agacttctgc catgctcttc acggtggaca atgaggctgg caagatcacg tgcctgtgtc    2820
aagtccccca gaatgcagcc aatcgggct taaaagccag cgagtgggtg cagcaggtgt    2880
caggcttgat ggacggtaaa ggtggtggca aggatgtgtc tgcacaggcc acaggcaaga    2940
acgttggctg cctgcaggag gcgctgcagc tggccacttc cttcgcccag ctgcgcctcg    3000
gggatgtaaa gaactgagtg gggaaggagg aggctccccac tggatccatc cgtccagcca    3060
agagctcttc atctgctaca agaacatttg aatcttggga cctttaaaga gcccctccta    3120
acccagcagt aactggaaca cacttgggag cagtcctatg tctcagtgcc ccttaaattt    3180
ctgccctgag ccctccacgt cagtgccatc ggtctagaac cactaacccc gcattgctgt    3240
tgatcgtcac gctcgcatct atagataacg gctctccaga cctgagcttt ccgcgtcagc    3300
```

-continued aagtaggaat cgttttgct gcagagaata aaaggaccac gtgc      3344

<210> SEQ ID NO 74
<211> LENGTH: 1902
<212> TYPE: DNA
<213> ORGANISM: Homo sapiens

<400> SEQUENCE: 74
gcccctttct ttctcctcgt cggcccgaga gcaggaacac gataacgaag gaggcccaac      60
ttcattcaat aaggagcctg acggatttat cccagacggt agaacaaaag gaagaatatt     120
gatggatttt aaaccagagt ttttaaagag cttgagaata cggggaaatt aatttgttct     180
cctacacaca tagataggqt aaggttgttt ctgatgcagc tgagaaaaat gcagaccgtc     240
aaaaaggagc aggcgtctct tgatgccagt agcaatgtgg acaagatgat ggtccttaat     300
tctgctttaa cggaagtgtc agaagactcc acaacaggtg aggacgtgct tctcagtgaa     360
ggaagtgtgg ggaagaacaa atcttctgca tgtcggagga acgggaatt cattcctgat     420
gaaaagaaag atgctatgta ttgggaaaaa aggcggaaaa ataatgaagc tgccaaaaga     480
tctcgtgaga agcgtcgact gaatgacctg gttttagaga acaaactaat tgcactggga     540
gaagaaaacg ccactttaaa agctgagctg cttcactaa aattaaagtt tggtttaatt      600
agctccacag catatgctca agagattcag aaactcagta attctacagc tgtgtacttt     660
caagattacc agacttccaa atccaatgtg agttcatttg tggacgagca cgaaccctcg     720
atggtgtcaa gtagttgtat ttctgtcatt aaacactctc cacaaagctc gctgtccgat     780
gtttcagaag tgtcctcagt agaacacacg caggagagct ctgtgcaggg aagctgcaga     840
agtcctgaaa acaagttcca gattatcaag caagagccga tggaattaga gagctacaca     900
agggagccaa gagatgaccg aggctcttac acagcgtcca tctatcaaaa ctatatgggg     960
aattctttct ctgggtactc acactctccc ccactactgc aagtcaaccg atcctccagc    1020
aactccccgg gaacgtcgga aactgatgat ggtgtggtag aaagtcatc tgatggagaa    1080
gacgagcaac aggtccccaa gggccccatc cattctccag ttgaactcaa gcatgtgcat    1140
gcaactgtgg ttaaagttcc agaagtgaat tcctctgcct tgccacacaa gctccggatc    1200
aaagccaaag ccatgcagat caaagtagaa gcctttgata tgaatttgat ggccacgcaa    1260
aaactttcct cacctattga catgacatct aaaagacatt tcgaactcga aaagcatagt    1320
gccccaagta tggtacattc ttctcttact cctttctcag tgcaagtgac taacattcaa    1380
gattggtctc tcaaatcgga gcactggcat caaaaagaac tgagtggcaa aactcagaat    1440
agtttcaaaa ctggagttgt tgaaatgaaa gacagtggct acaaagtttc tgacccagag    1500
aacttgtatt tgaagcaggg gatagcaaac ttatctgcag aggttgtctc actcaagaga    1560
cttatagcca cacaaccaat ctctgcttca gactctgggt aaattactac tgagtaagag    1620
ctgggcatt agaaagatgt catttgcaat agagcagtcc attttgtatt atgctgaatt    1680
ttcactggac ctgtgatgtc atttcactgt gatgtgcaca tgttgtctgt ttggtgtctt    1740
tttgtgcaca gattatgatg aagattagat tgtgttatca ctctgcctgt gtatagtcag    1800
atagtccatg cgaaggctgt atatattgaa cattattttt gttgttctat tataaagtgt    1860
gtaagttacc agtttcaata aaggattggt gacaaacaca ga                      1902

<210> SEQ ID NO 75
<211> LENGTH: 1560
<212> TYPE: DNA
<213> ORGANISM: Homo sapiens

<400> SEQUENCE: 75

```
ctccataagg cacaaacttt cagagacagc agagcacaca agcttctagg acaagagcca      60
ggaagaaacc accggaagga accatctcac tgtgtgtaaa catgacttcc aagctggccg     120
tggctctctt ggcagccttc ctgatttctg cagctctgtg tgaaggtgca gttttgccaa     180
ggagtgctaa agaacttaga tgtcagtgca taaagacata ctccaaacct ttccacccca     240
aatttatcaa agaactgaga gtgattgaga gtggaccaca ctgcgccaac acagaaatta     300
ttgtaaagct ttctgatgga agagagctct gtctggaccc caaggaaaac tgggtgcaga     360
gggttgtgga gaagttttg aagagggctg agaattcata aaaaaattca ttctctgtgg      420
tatccaagaa tcagtgaaga tgccagtgaa acttcaagca atctacttc aacacttcat      480
gtattgtgtg ggtctgttgt agggttgcca gatgcaatac aagattcctg gttaaatttg     540
aatttcagta acaatgaat agttttcat tgtaccatga aatatccaga acatacttat       600
atgtaaagta ttatttattt gaatctacaa aaacaacaa ataattttta aatataagga      660
ttttcctaga tattgcacgg gagaatatac aaatagcaaa attgggccaa gggccaagag     720
aatatccgaa ctttaatttc aggaattgaa tgggtttgct agaatgtgat atttgaagca     780
tcacataaaa atgatgggac aataaatttt gccataaagt caaatttagc tggaaatcct     840
ggatttttt ctgttaaatc tggcaaccct agtctgctag ccaggatcca caagtccttg      900
ttccactgtg ccttggtttc tcctttattt ctaagtggaa aaagtattag ccaccatctt     960
acctcacagt gatgttgtga ggacatgtgg aagcacttta agttttttca tcataacata    1020
aattattttc aagtgtaact tattaaccta tttattattt atgtatttat ttaagcatca    1080
aatatttgtg caagaatttg gaaaaataga agatgaatca ttgattgaat agttataaag    1140
atgttatagt aaatttattt tatttagat attaaatgat gttttattag ataaatttca     1200
atcagggttt ttagattaaa caaacaaaca attgggtacc cagttaaatt ttcatttcag    1260
atatacaaca ataattttt tagtataagt acattattgt ttatctgaaa ttttaattga     1320
actaacaatc ctagtttgat actcccagtc ttgtcattgc cagctgtgtt ggtagtgctg    1380
tgttgaatta cggaataatg agttagaact attaaaacag ccaaaactcc acagtcaata    1440
ttagtaattt cttgctggtt gaaacttgtt tattatgtac aaatagattc ttataatatt    1500
atttaaatga ctgcattttt aaatacaagg ctttatattt ttaactttaa aaaaaaccgg    1560
```

<210> SEQ ID NO 76
<211> LENGTH: 642
<212> TYPE: DNA
<213> ORGANISM: Homo sapiens

<400> SEQUENCE: 76

```
tcgtgttcat gggagctcgt tttcttttcc tctaggcaga gaagaggcga tggcggcgat      60
ggcatctctc ggcgccctgg cgctgctcct gctgtccagc ctctcccgct gctcagccga     120
ggcctgcctg gagccccaga tcacccttc ctactacacc acttctgacg ctgtcatttc      180
cactgagacc gtcttcattg tggagatctc cctgacatgc aagaacaggg tccagaacat     240
ggctctctat gctgacgtcg gtggaaaaca attccctgtc actcgaggcc aggatgtggg    300
gcgttatcag gtgtcctgga gcctggacca caagagcgcc cacgcaggca cctatgaggt    360
tagattcttc gacgaggagt cctacagcct cctcaggaag gctcagagga ataacgagga    420
catttccatc atcccgcctc tgtttacagt cagcgtggac catcggggca cttggaacgg    480
```

| | | |
|---|---|---|
| gccctgggtg tccactgagg tgctggctgc ggcgatcggc cttgtgatct actacttggc | 540 | |
| cttcagtgcg aagagccaca tccaggcctg agggcggcac cccagccctg cccttgcttc | 600 | |
| cttcaataaa catcacagga cctgggactg cacaggaaaa aa | 642 | |

<210> SEQ ID NO 77
<211> LENGTH: 2647
<212> TYPE: DNA
<213> ORGANISM: Homo sapiens

<400> SEQUENCE: 77

| | | |
|---|---|---|
| gccgcgctgg tggcggcggc gcgtcgttgc agttgcgcca tctgtcagga gcggagccgg | 60 | |
| cgaggagggg gctgccgcgg gcgaggagga ggggtcgccg cgagccgaag gccttcgaga | 120 | |
| cccgcccgcc gcccggcggc gagagtagag gcgaggttgt tgtgcgagcg gcgcgtcctc | 180 | |
| tcccgcccgg gcgcgccgcg cttctcccag cgcaccgagg accgcccggg cgcacacaaa | 240 | |
| gccgccgccc gcgccgcacc gcccggcggc cgccgcccgc gccagggagg gattcggccg | 300 | |
| ccgggccggg gacaccccgg cgccgccccc tcggtgctct cggaaggccc accggctccc | 360 | |
| gggcccgccg gggaccccccc ggagccgcct cggccgcgcc ggaggagggc ggggagagga | 420 | |
| ccatgtgagt gggctccgga gcctcagcgc gcgcagtttt ttttgaagaa gcaggatgct | 480 | |
| gatctaaacg tggaaaaaga ccagtcctgc ctctgttgta aagacatgt ggtgtatata | 540 | |
| aagtttgtga tcgttggcgg aaattttgga atttagataa tgggctgtgt gcaatgtaag | 600 | |
| gataaagaag caacaaaact gacggaggag agggacggca gcctgaacca gagctctggg | 660 | |
| taccgctatg gcacagaccc cacccctcag cactacccca gcttcggtgt gacctccatc | 720 | |
| cccaactaca acaacttcca cgcagccggg ggccaaggac tcaccgtctt tggaggtgtg | 780 | |
| aactcttcgt ctcatacggg gaccttgcgt acgagaggag gaacaggagt gacactcttt | 840 | |
| gtggcccttt atgactatga agcacggaca gaagatgacc tgagttttca caaggagaa | 900 | |
| aaatttcaaa tattgaacag ctcggaagga gattggtggg aagcccgctc cttgacaact | 960 | |
| ggagagacag gttacattcc cagcaattat gtggctccag ttgactctat ccaggcagaa | 1020 | |
| gagtggtact ttggaaaact tggccgaaaa gatgctgagc gacagctatt gtcctttgga | 1080 | |
| aacccaagag gtaccttttct tatccgcgag agtgaaacca ccaaaggtgc ctattcactt | 1140 | |
| tctatccgtg attgggatga tatgaaagga gaccatgtca acattataa aattcgcaaa | 1200 | |
| cttgacaatg gtggatacta cattaccacc cgggcccagt ttgaaacact tcagcagctt | 1260 | |
| gtacaacatt actcagagag agctgcaggt ctctgctgcc gcctagtagt tccctgtcac | 1320 | |
| aaagggatgc aaggcttac cgatctgtct gtcaaaacca agatgtctg ggaaatccct | 1380 | |
| cgagaatccc tgcagttgat caagagactg ggaaatgggc agtttgggga agtatggatg | 1440 | |
| ggtacctgga tgaaacac aaaagtagcc ataaagactc ttaaaccagg cacaatgtcc | 1500 | |
| cccgaatcat tccttgagga agcgcagatc atgaagaagc tgaagcacga caagctggtc | 1560 | |
| cagctctatg cagtggtgtc tgaggagccc atctacatcg tcaccgagta tatgaacaaa | 1620 | |
| ggaagtttac tggatttctt aaaagatgga gaaggaagag ctctgaaatt accaaatctt | 1680 | |
| gtggacatgg cagcacaggt ggctgcagga atggcttaca tcgagcgcat gaattatatc | 1740 | |
| catagagatc tgcgatcagc aaacattcta gtggggaatg gactcatatg caagattgct | 1800 | |
| gacttcggat tggcccgatt gatagaagac aatgagtaca cagcaagaca aggtgcaaag | 1860 | |
| ttccccatca gtggacggc ccccgaggca gccctgtacg ggaggttcac aatcaagtct | 1920 | |
| gacgtgtggt ctttttggaat cttactcaca gagctggtca ccaaaggaag agtgccatac | 1980 | |

-continued

```
ccaggcatga caaccggga ggtgctggag caggtggagc gaggctacag gatgccctgc    2040
ccgcaggact gccccatctc tctgcatgag ctcatgatcc actgctggaa aaaggaccct   2100
gaagaacgcc ccacttttga gtacttgcag agcttcctgg aagactactt taccgcgaca   2160
gagccccagt accaacctgg tgaaaacctg taaggcccgg gtctgcggag agaggccttg   2220
tcccagaggc tgccccaccc ctccccatta gctttcaatt ccgtagccag ctgctcccca   2280
gcagcggaac cgcccaggat cagattgcat gtgactctga agctgacgaa cttccatggc   2340
cctcattaat gacacttgtc cccaaatccg aacctcctct gtgaagcatt cgagacagaa   2400
ccttgttatt tctcagactt tggaaaatgc attgtatcga tgttatgtaa aaggccaaac   2460
ctctgttcag tgtaaatagt tactccagtg ccaacaatcc tagtgctttc ctttttaaa    2520
aatgcaaatc ctatgtgatt ttaactctgt cttcacctga ttcaactaaa aaaaaaagt    2580
attattttcc aaaagtggcc tctttgtcta aaacaataaa attttttttc atgttttaac   2640
aaaaacc                                                              2647

<210> SEQ ID NO 78
<211> LENGTH: 1826
<212> TYPE: DNA
<213> ORGANISM: Homo sapiens

<400> SEQUENCE: 78
tacctgaccc cagccatttc ccttctagaa attgttctac agacatatgt aataacatat      60
acaaaaggtt attctttcag cagtgtttgt cagagcgaga acattccaga gagctgttgc     120
gcagccattg gtacctgtat tggggaaaca tagcatacaa tcaagaagct tacagcctca    180
gtggcgaaaa tttttcatg tcagagaccg agaactcttg cagtcgttta tgtcatccct     240
tcttctccag acagaagata ccaaaaagtt gcaatcaaag atctcttcat cttattgata    300
aagccactaa taagccaaaa tgtctgtcaa tgtcaaccgc agcgtgtcag accagttcta    360
tcgctacaag atgccccgtc tgattgccaa ggttgagggc aaaggcaatg gaatcaagac    420
agttatagtc aacatggttg acgttgcaaa ggcgcttaat cggcctccaa cgtatcccac    480
caaatatttt ggttgtgagc tgggagcaca gacccagttt gatgttaaga atgaccgtta    540
cattgtcaat ggatctcatg aggcgaataa gctgcaagac atgttggatg gattcattaa    600
aaaatttgtt ctctgtcctg aatgtgagaa tcctgaaaca gatttgcatg tcaatccaaa    660
gaagcaaaca ataggtaatt cttgtaaagc ctgtggctat cgaggcatgc ttgacacaca    720
tcataaactc tgcacattca ttctcaaaaa cccacctgag aatagtgaca gtggtacagg    780
aaagaaagaa aaagaaaaga aaacagaaa gggcaaagac aaggaaaatg gctccgtatc     840
cagcagtgag acaccaccac caccaccacc accaaatgaa attaatcctc ctccacatac    900
aatggaagaa gaggaggatg atgactcggg agaagataca actgaggaag ctcaaaggcg    960
tcgaatggat gaaatcagtg accatgcaaa agttctgaca ctcagtgatg atttggaaag   1020
aacaattgag gagagggtca atatcctctt tgattttgtt aagaaaaaga aagaagaggg   1080
tgttattgat tcatctgaca agaaatcgt tgctgaagca gaaagactgg atgtaaaagc    1140
catgggccct cttgttctaa ctgaagttct tttaatgag aagattagag aacagattaa     1200
gaaatacagg cgccatttcc tacgattttg tcacaacaac aaaaaagccc aacggtacct    1260
tcttcatggt ttggagtgtg tggtagcaat gcatcaagct cagcttatct ccaagattcc    1320
acatatcttg aaggagatgt acgatgcaga ccttttagaa gaagaggtca tcatcagctg    1380
```

```
gtcggaaaag gcctctaaga aatatgtctc caaagaactt gccaaagaga ttcgtgtcaa    1440
agcagaacca tttataaaat ggttgaagga ggcagaggaa gaatcttctg gtggcgaaga    1500
agaagatgaa gatgagaaca ttgaggtggt gtattcgaag gctgccagtg taccgaaagt    1560
tgagactgta aagtcagaca caaggatga cgacatcgat attgatgcca tttaaaggga    1620
tggatgcaac ctagcttaac agtataatgc tgcaaatttt cctccattat cagccagaag    1680
tgcaacatgt atgtgcaaaa gctaaaatgg cttaacatca tgctacactt tacactaaaa    1740
atctattact gtgagtgtga aaaactagtg gtggacacat ttggatcaca tttatacagt    1800
tataaaaata aaggtttgat tttggt                                         1826

<210> SEQ ID NO 79
<211> LENGTH: 5857
<212> TYPE: DNA
<213> ORGANISM: Homo sapiens

<400> SEQUENCE: 79
cggcgcaggc ggcggcgtcc gaggagattt aatccagaga ctgacttcac tatagaaccc      60
acagttgtat caatggttgg ggaaagatag tgcaacagg caaaggagaa acagctctga     120
catacaaaga aaatgagtat gctaaagcca agtgggctta aggcccccac caagatcctg     180
aagcctggaa gcacagctct gaagacacct acggctgttg tagctccagt agaaaaaacc     240
atatccagtg aaaaagcatc aagcactcca tcatctgaga ctcaggagga atttgtggat     300
gactttcgag ttggggagcg agtttgggtg aatggaaata gcctggatt tatccagttt     360 cttggagaaa cccagtttgc accaggccag tgggctggaa ttgtttaga tgaacccata     420 ggcaagaacg atggttcggt ggcaggagtt cggtatttcc agtgtgaacc tttaaagggc     480
atatttaccc gaccttcaaa gttaacaagg aaggtgcaag cagaagatga agctaatggc     540
ctgcagacaa cgcccgcctc ccgagctact tcaccgctgt gcacttctac ggccagcatg     600
gtgtcttcct cccccctccac ccccttcaaac atccctcaga accatcaca gccagcagca     660 aaggaacctt cagctacgcc tccgatcagc aaccttacaa aaactgccag tgaatctatc     720
tccaaccttt cagaggctgg ctcaatcaag aaaggagaaa gagagctcaa aatcggagac     780
agagtattgg ttggtggcac taaggctggt gtagtccggt tcttggggga gaccgacttt     840
gccaaggggg agtggtgtgg cgtggagtta gatgagccac ttgggaagaa tgatggcgct     900
gttgctggaa caaggtattt tcagtgtcaa cccaaatatg gcttgttcgc tcctgtccac     960
aaagttacca agattggctt cccttccact acaccagcca agccaaggc caacgcagtg    1020 aggcgagtga tggcgaccac gtccgccagc ctgaagcgca gcccttctgc ctcttccctc    1080
agctccatga gctcagtggc ctcctctgtg agcagcaggc ccagtcggac aggactattg    1140
actgaaacct cctcccgtta cgccaggaag atctccggta ccactgccct ccaggaggcc    1200
ctgaaggaga agcagcagca cattgagcag ctgctggcgg aacgggatct ggagagggcg    1260
gaggtggcca aggccacgag ccacgtgggg gagatagagc aggagctagc tctgccccgg    1320
gacggacatg accagcatgt cctggaattg gaagccaaaa tggaccagct gcgaacaatg    1380
gtggaagctg ctgacaggga gaaggtggag cttctcaacc agcttgaaga ggagaaaagg    1440
aaggttgagg accttcagtt ccgggttgaa gaagaatcaa ttaccaaagg tgatcttgag    1500
acgcagacca aactggagca tgcccgcatt aaggagcttg aacagagcct gctctttgaa    1560
aagaccaaag ctgacaaaact ccagagggag ttagaagaca ctagggtggc tacagtttca    1620
gaaaagtcac gtataatgga actggagaaa gacctagcat tgagagtaca ggaagtagct    1680
```

```
gagctccgaa gaaggctaga gtccaataag cctgctgggg atgtggacat gtcactttcc   1740
cttttgcaag agataagctc tttgcaagaa aagttagaag tcacccgtac tgaccaccag   1800
agagaaataa cttctctgaa ggagcatttt ggagcccggg aagaaactca tcagaaggag   1860
ataaaggctc tgtataccgc cacgaaaag cttccaaag agaacgagtc attgaaaagc    1920
aagctggagc atgccaacaa agagaactca gatgtgatag ctctatggaa gtccaaactg   1980
gagactgcca tcgcatccca ccagcaggcg atggaagaac tgaaggtatc tttcagcaaa   2040
gggcttggaa cagagacggc agaatttgct gaactaaaaa cacaaataga gaaatgaga    2100 ctagattacc aacacgaaat agaaaatttg cagaatcaac aagactctga acgggctgcc   2160
catgctaaag agatggaagc cttgaggct aaactgatga aagttattaa agaaaaggaa    2220
aacagtctgg aagccatcag gtcgaaactg acaaagcag aagaccagca tctcgtagaa    2280
atggaagaca cgttaaacaa attacaggaa gctgaaataa aggtaaagga ctagaggta    2340 ctgcaagcca aatgcaatga acaaaccaag gttattgata attttacatc acagctcaag   2400
gctactgaag aaaagctctt ggatcttgat gcacttcgga aagccagttc cgaaggtaaa   2460
tcggaaatga agaaacttag acagcagctt gaggcagctg agaaacagat taaacattta   2520
gagattgaaa agaatgctga agtagcaag gctagtagca ttaccagaga gctccagggg    2580
agagagctaa agcttactaa ccttcaggaa aatttgagtg aagtcagtca agtgaaagag   2640
actttggaaa aagaacttca gattttgaaa gaaaagtttg ctgaagcttc agaggaggca   2700
gtctctgttc agagaagtat gcaagaaact gtaaataagt tacaccaaaa ggaggaacag   2760
tttaacatgc tgtcttctga cttggagaag ctgagagaaa acttagcaga tatggaggca   2820
aaatttagag agaaagatga gagagaagag cagctgataa aggcaaagga aaaactggaa   2880
aatgacattg cagaaataat gaagatgtca ggagataact cttctcagct gacaaaaatg   2940
aacgatgaat acgtctgaa agaaagagat gtagaagaat tacagctaaa acttacaaag    3000
gctaatgaaa atgcaagttt tctgcaaaaa agtattgagg acatgactgt caaagctgaa   3060
cagagccagc aagaagcagc taaaaagcat gaggaagaaa agaaagaatt ggagaggaaa   3120
ttgtcggacc tggaaaagaa aatgcaaaca agccacaacc agtgtcagga gctgaaagcc   3180
aggtatgaga gagccacttc tgagacaaaa accaagcatg aagaaatcct acagaacctc   3240
cagaagacgc tgctggacac agaggacaag ctgaagggcg cacggaggga aacagtggc    3300 ttgctgcagg agctggagga gctgagaaag caagccgaca agccaaagc tgctcaaaca    3360 gcggaagatg ccatgcagat aatgaacag atgaccaaag agaagactga gactctggcc    3420
tccttggagg acaccaagca aacaaatgca aaactacaga atgaattgga cacacttaaa   3480 gaaacaact tgaaaaatgt ggaagagctg aacaaatcaa agaactcct gactgtagag    3540 aatcaaaaa tggaagaatt taggaaagaa atagaacccc taaagcaggc agcagctcag   3600
aagtcccagc agctttcagc gttgcaagaa gagaacgtta aacttgctga ggagctgggg   3660 agaagcagg acgaagtcac aagtcatcaa agctggaag aagaaagatc tgtgctcaat    3720
aatcagttgt tagaaatgaa aaaaagagaa tccaagttca taaaagacgc agatgaagag   3780
aaagcttcct tgcagaaatc catcagtata actagtgcct tactcacaga aaaggatgcc   3840
gagctggaga aactgagaaa tgaggtcaca gtgctcaggg gagaaaacgc ctctgccaag   3900
tccttgcatt cagttgttca gactctagag tctgataagg tgaagctcga gctcaaggta   3960
aagaacttgg agcttcaact caaagaaaac aagaggcagc tcagcagctc ctcaggtaat   4020
```

```
acagacactc aggcagacga ggatgaaaga gcccaggaga gtcagattga tttcctaaat    4080
tcagtaatag tggaccttca aaggaagaat caagacctca agatgaaggt ggagatgatg    4140
tcagaagcag ccctgaatgg gaacggggat gacctaaaca attatgacag tgatgatcag    4200
gagaaacagt ccaagaagaa acctcgcctc ttctgtgaca tttgtgactg ctttgatctc    4260
cacgacacag aggattgtcc tacccaggca cagatgtcag aggaccctcc ccattccaca    4320
caccatggca gtcggggtga ggaacgccca tactgtgaaa tctgtgagat gtttggacac    4380
tgggccacca actgcaatga cgacgaaacc ttctgatgaa gcctccagtg gagaactggg    4440
cttgctcaga cgcactcgca ttgacacaac gtaacaccag cattgtgtgt gcagacttca    4500
ggagaactca tgttatttttt taaccccgtc aacaaatcta ggaaaatatt ttgatcttca    4560
acaaattgcc ctttagtctc cccgtatgag ttagaataat aaatatttag taggtgagtt    4620
ttcacctcga atttttgtttt cttgattttt acgtttgaag acattgcacc agatgccatt    4680
acatttattg gccccccgac cttgtagaaa aacccctacc ctcacaatac cttatttaag    4740
taactttaaa ttatgccgtt acttttcata tttgcaccta agatatttcc aggctgcatt    4800
tgtatattta gattttttgg ttaagctttg acactggaat gagttgaaaa aatgtgccat    4860
tttgcatttt catctactca tttaaagtat tttattctta ttcaaagaaa tatctgagct    4920
ctttgcacta cctgttatca gtagtgcctt tacttcaggc ttgataatac ttaggtgtga    4980
ttataaaatc atgaagcagg taaagggagg ggcaagcccc aaactgctgt ggggacattt    5040
tataatctat atgctgcacc cacttaatct actgtggtgt tttgtttatt agttttgcat    5100
aatttcagct tctatatatt gtatgtatat attttttaaa aatctatatt ttgggaaaaa    5160
aacatacaca atgtgtcttt cttttttggac atttacctttt ttgaaaaaga aaacacttaa    5220
aatgatcatt aggacataac agactaggcc agacatagca tcttgtggct ttgcaaccat    5280
tttcatttgt ttgttttcct tttatttctt caccagattt aaataaaagg aggaattttc    5340
tccaattttt ttttccttct ctggcaggta tccccagcag tcaattaaca ataagccagt    5400
ataaaacacc taaataacca atctacaatc tcccttcaca agttttttta ctgttttttag    5460 atgaatgtac gatgagaaat tcaacgttaa taattctgga ttttcttatc acaaaaaaga    5520
aaatgaagga cctcaaagca cctgaacagt ttatcgacca gtttgaatct atttatcttc    5580
atttgaatgt cttctagata tgtaaaaagt cataaaatgt atcttccatg ctacatgtac    5640
aataagaact tctataattg tatatatgcc tttgatgtat tttcccctca agattatcaa    5700
ctgtgtgttc gacagtgaat attcaatctg gtaccagttg aaattttttgg ttataaatgt    5760 aatacgaatt gtttcacaaa cagaaaacat gtaaagcagt attaaaattt ggccaaacaa    5820
gtgttctgta tctactttta ataaatggtt attcttt                             5857
```

<210> SEQ ID NO 80
<211> LENGTH: 2634
<212> TYPE: DNA
<213> ORGANISM: Homo sapiens

<400> SEQUENCE: 80

```
gccgccgccg ccgccgccgc cgcgggcttc gttcgtaagg aagggggcct aggccgggcc      60
tgcggtggtg ggggttgctg cgcgccgggg gtcgctcctg ctgtgtcttc cgctccagct     120
tcgcccactt ccccttacca gcggggtggg cgcggagaag acctgccgga gccatggagg     180
acgaagtggt ccgctttgcc aagaagatgg acaagatggt gcagaagaag aacgcggctg     240
gagcattgga tttgctaaag gagcttaaga atattcctat gacccgtgga atactgcagt     300
```

```
ccacaagaat cggaatgtca gttaatgcta ttcgcaagca gagtacagat gaggaagtta    360
catctttggc aaagtctctc atcaaatcct ggaaaaaatt attagatggg ccatcaactg    420
agaaagacct tgacgaaaag aagaaagaac ctgcaattac atcgcagaac agccctgagg    480
caagagaaga aagtacttcc agcggcaatg taagcaacag aaaggatgag acaaatgctc    540
gagatactta tctttcatcc tttcctcggg caccaagcac ttctgattct gtgcggttga    600
agtgtaggga gatgcttgct gcagctcttc gaacagggga tgactacatt gcaattggag    660
ctgatgagga agaattagga tctcaaattg aagaagctat atatcaagaa ataaggaata    720
cagacatgaa atacaaaaat agagtacgaa gtaggatatc aaatcttaaa gatgcaaaaa    780
atccaaattt aaggaaaaat gtcctctgtg ggaatattcc tcctgactta tttgctagaa    840
tgacagcaga ggaaatggct agtgatgagc tgaaagagat gcggaaaaac ttgaccaaag    900
aagccatcag agagcatcag atggccaaga ctggtgggac ccagactgac ttgttcacat    960
gtggcaaatg taaaaagaag aattgcactt acacacaggt acaaacccgt agtgctgatg   1020
aaccaatgac aacatttgtt gtctgtaatg aatgtggaaa tcgatggaag ttctgttgag   1080
ttggaagaat tggcaaaata tctggaccat taagaaaacg gattttgtaa ctagctttaa   1140
actaggccaa gcaactagtt ttcctgcaaa tcaaattttt aaagcaactt gggttagact   1200 ttgttttttga cctaacatcc cttccttaaa tgccttctgt agtttcagat cagtagggag   1260
accatataat aattgtatgg tacctgtttc aaaacatatt ttttctgttt ttataagtaa   1320
gttgatatta attaaactct tggcaatatt tcttctttct taaaggaaaa tataccttaa   1380 cttttttttct tttacactgt gaaacataca cagtagaaat tctgttactc tctgttatta   1440
atacataaat gaaaatacat ttttttccat attggcatgt agctacaaat attaaaggag   1500 gagaaaggt aatataattt taggtttacc aaatatggtg tgtattcaaa taatacttga    1560
ccagcttatc taaaatgtac ataattttga ggtagcttat gaatttgatt ttaattatta   1620
tgttcacaag cttggaatat tagatattat tttgcatctg taactaaccg tgatcatcat   1680
ttcttgtaat ttcttgtaca tgtatattac ttgttcttaa tagattttttg gaaacaagac   1740 tttattgaga tcagttttggt tttcctgtta atttacctgt ttgactttat aatgtgtttt   1800
agttttgcag aagaacactg ttgtagttta gaaggctttt cataaatccc ctcataggca   1860
aagatgaaaa cttcccacta tttttttttccc ctcttaggaa gacatactgg aaagaaaatg   1920
tttagcatct tagtgtagta tagctattgt aaacagttca tgactagatt ttgattcgga   1980
aatctatact gaccaaggat taatcttaag gattgtataa ttcattaaag ctgtggtctt   2040
tccatgtgga gactgataga aaataatttt gtcccaagtc ttatttgctg acttttttctg   2100 tcatgagtga gattgttgaa caaactgaat atatgggcta tagcaagtag ctttacagta   2160
cagatcttac aattaagttt tgcttttgtt aaagtgtgta ccatttttttc tgtttggagt   2220 aagacaaaaa ttgttttgac ataggttccc tagggtacac ttgctctagc atactttaaa   2280
ggccactgtt gcaaagtcta cattttatgc tgaatctgca ttctgtcagg cacccataga   2340
aagacctcag tacatgcttt gcactctcct ttgctcccctt tttccaattt cttattgcat   2400
atcattttgt tgtaatacag aaagcagcat ttttaaatgt ccgtgttaag aattggcccg   2460
ctggtaccaa ctcacctcta ttttgtcagt tcatagttga agattttgtt ttatttcaaa   2520
aagaaagtac atttttgaaa taatgtttca gaataaaata atctcacttt taagtgatcc   2580
attttaaaat ttgtaattca ataaagtttt ttttgttgtt aaacataaaa aaaa          2634
```

<210> SEQ ID NO 81
<211> LENGTH: 351
<212> TYPE: DNA
<213> ORGANISM: Homo sapiens
<220> FEATURE:
<221> NAME/KEY: misc_feature
<222> LOCATION: (1)...(351)
<223> OTHER INFORMATION: n = A,T,C or G

<400> SEQUENCE: 81

```
caatctgctt ccnctaatat ancoccagtc taaggcattt aaaattaaac agctcttcaa      60
cgccccaagt tattncatca ggctaagaac ttctccgaga aacgcacaag anggcaggca     120
aacaggtggg taggtgagag gtcacggggc tccatctgca agctccatct acaaggcatc     180
aatctgcgtt gtggcatcaa cgttaaaatg ttctacagct tagggatctt cttgaagcaa     240
ggttccaagc acaaaactag gtatgaccgg aggcttcaat ttagaagatg cagcatctga     300
aaacctttac cccgggnaag gagggtgcc tgctggcatt tcatggggct c               351
```

<210> SEQ ID NO 82
<211> LENGTH: 1682
<212> TYPE: DNA
<213> ORGANISM: Homo sapiens

<400> SEQUENCE: 82

```
atgctcagtc ctccaggcgt cggtgctcag cggtgttgga acttcgttgc ttgcttgcct      60
gtgcgcgcgt gcgcggacat ggcctcaaac gattataccc aacaagcaac ccaaagctat     120
ggggcctacc ccacccagcc cgggcagggc tattcccagc agagcagtca gccctacgga     180
cagcagagtt acagtggtta tagccagtcc acggacactt caggctatgg ccagagcagc     240
tattcttctt atggccagag ccagaacaca ggctatggaa ctcagtcaac tccccaggga     300
tatggctcga ctgcggcta tggcagtagc cagagctccc aatcgtctta cgggcagcag     360
tcctcctacc ctggctatgg ccagcagcca gctcccagca gcacctcggg aagttacggt     420
agcagttctc agagcagcag ctatgggcag ccccagagtg ggagctacag ccagcagcct     480
agctatggtg gacagcagca agctatggga cagcagcaaa gctataatcc ccctcagggc     540
tatggacagc agaaccagta caacagcagc agtggtggtg gaggtggagg tggaggtgga     600
ggtaactatg gccaagatca atcctccatg agtagtggtg gtggcagtgg tggcggttat     660
ggcaatcaag accagagtgg tggaggtggc agcggtggct atggacagca ggaccgtgga     720
ggccgcggca ggggtggcag tggtggcggc ggcggcggcg gcggtggtgg ttacaaccgc     780
agcagtggtg gctatgaacc cagaggtcgt ggaggtggcc gtgaggcag aggtggcatg     840
ggcggaagtg accgtggtgg cttcaataaa tttggtgtgt tcaagaagga agtgtatctt     900
catacatcac cacacctgaa agcagatgtg cttttccaga ctgatccaac tgcagagatg     960
gcagctgagt cattgccttt ctccttcggg acactgtcca gctgggagct ggaagcctgg    1020
tatgaggacc tgcaagaggt cctgtcttca gatgaaaatg ggggtaccta tgtttcacct    1080
cctggaaatg aagaggaaga atcaaaaatc ttcaccactc ttgaccctgc ttctctggct    1140
tggctgactg aggaggagcc agaaccagca gaggtcacaa gcacctccca gagccctcac    1200
tctccagatt ccagtcagag ctccctggct caggaggaag aggaggaaga ccaagggaga    1260
accaggaaac ggaaacagag tggtcattcc ccagccgggg ctggaaagca gcgcatgaag    1320
gagaaagaac aggagaatga aaggaagtg gcacagctag ctgaagagaa tgaacggctc    1380
aagcaggaaa tcgagcgcct gaccagggaa gtagaggcga ctcgccgagc tctgattgac    1440
```

-continued

```
cgaatggtga atctgcacca agcatgaaca attgggagca tcagtccccc acttgggcca    1500
cactacccac ctttcccaga agtggctact gactaccctc tcactagtgc caatgatgtg    1560
accctcaatc ccacatacgc aggggaagg cttggagtag acaaaaggaa aggtctcagc    1620
ttgtatatag agattgtaca tttatttatt actgtcccta tctattaaag tgactttcta    1680
tg                                                                   1682
```

<210> SEQ ID NO 83
<211> LENGTH: 1791
<212> TYPE: DNA
<213> ORGANISM: Homo sapiens

<400> SEQUENCE: 83

```
ggcggacgga gcgagccctg ggcgagtgaa ttgtggctgt ggttgacgg tggagacacc      60 ccccggagag gcggagggaa gggaggcgag gctgcacctg catgcttccc gcctcccact    120
ccccagcgcc cccggaccgt gcagttctct gcaggaccag gccatggagc tcgaagtccg    180
gcgggtccga caggcgttcc tgtccggccg gtcgcgacct ctgcggtttc ggctgcagca    240
gctggaggcc ctgcggagga tggtgcagga gcgcgagaag gatatcctga cggccatcgc    300
cgccgacctg tgcaagagtg aattcaatgt gtacagtcag gaagtcatta ctgtccttgg    360
ggaaattgat tttatgcttg agaatcttcc tgaatgggtt actgctaaac cagttaagaa    420
gaacgtgctc accatgctgg atgaggccta tattcagcca cagcctctgg gagtggtgct    480
gataatcgga gcttggaatt ccccttcgt tctcaccatt cagccactga taggagccat    540
cgctgcagga aatgctgtga ttataaagcc ttctgaactg agtgaaaata cagccaagat    600
cttggcaaag cttctccctc agtatttaga ccaggatctc tatattgtta ttaatggtgg    660
tgttgaggaa accacggagc tcctgaagca gcgatttgac cacattttct atacgggaaa    720
cactgcggtt ggcaaaattg tcatggaagc tgctgccaag catctgaccc ctgtgactct    780
tgaactggga gggaaaagtc catgttatat tgataaagat tgtgacctgg acattgtttg    840
cagacgcata acctggggaa atacatgaa ttgtggccaa acctgcattg cacccgacta    900
tattctctgt gaagcatccc tccaaaatca aattgtatgg aagattaagg aaacagtgaa    960
ggaattttat ggagaaaata taaaagagtc tcctgattat gaaaggatca tcaatcttcg   1020 tcatttaag aggatactaa gtttgcttga aggacaaaag atagcttttg gtggggagac   1080
tgatgaggcc acacgctaca tagccccaac agtacttacc gatgttgatc ctaaaaccaa   1140
ggtgatgcaa gaagaaattt ttggaccaat tcttccaata gtgcctgtga aaatgtaga   1200 tgaggccata aatttcataa atgaacgtga aaagcctctg ctctctttatg tattttcgca   1260 taaccataag ctcatcaaac ggatgattga tgagacatcc agtggaggtg tcacaggcaa   1320
tgacgtcatt atgcacttca cgctcaactc tttcccattt ggaggagtgg gttccagtgg   1380
gatgggagct tatcacggaa acatagtttt tgatacttt tctcatcagc gtccctgttt   1440
attaaaaagt ttaaagagag aaggtgctaa caaactcaga tatcctccca acagccagtc   1500
aaaggtggat tgggggaaat ttttcctctt gaaacggttc aacaaagaaa aactcggtct   1560
cctgttgctc actttcctgg gtattgtagc cgctgtgctt gtcaaggcag aatattactg   1620
aagaatgatc ctgttcaacc tcctagtgcc tctactgaat tattcctctt ttaaatggtt   1680
aatgaaccaa taatttttaa atcataccaa aaatagtaag aaaatatgca aacactctgt   1740
gatcaaactt aaaagtcatt gccattcatc attaataaaa gttgccattt c             1791
```

-continued

<210> SEQ ID NO 84
<211> LENGTH: 3520
<212> TYPE: DNA
<213> ORGANISM: Homo sapiens

<400> SEQUENCE: 84

| | | | | | |
|---|---|---|---|---|---|
| tctagagaag | ccaatcagtg | tcgccgggt | cccagttcta | aagtccccac | gcacccaccc | 60 |
| ggactcagaa | tctcctcaga | cgccgagatg | cgggtcacgg | cgccccgaac | cgtcctcctg | 120 |
| ctgctctggg | gggcagtggc | cctgaccgag | acctgggccg | tgagtgcgg | ggtcgggagg | 180 |
| gaaatggcct | ctgtggggag | gagcgagggg | accgcaggcg | ggggcgcagg | acctgaggag | 240 |
| ccgcgccggg | aggagggtcg | gcggtctc | agccctcct | cgcccccagg | ctcccactcc | 300 |
| atgaggtatt | tctacaccgc | catgtcccgg | cccggccgcg | gggagccccg | cttcatcgca | 360 |
| gtgggctacg | tggacgacac | ccagttcgtg | aggttcgaca | cgacgccgc | gagtccgagg | 420 |
| acggagcccc | gggcgccatg | gatagagcag | gaggggccgg | agtattggga | cggggagaca | 480 |
| cggaacatga | aggcctccgc | gcagacttac | cgagagaacc | tgcggatcgc | gctccgctac | 540 |
| tacaaccaga | gcgaggccgg | tgagtgaccc | cggcccgggg | cgcaggtcac | gactccccat | 600 |
| cccccacgta | cggcccgggg | tcgccccgag | tctccgggtc | cgagatccgc | ctccctgagg | 660 |
| ccgcgggacc | cgcccagacc | ctcgaccggc | gagagcccca | ggcgcgttta | cccggtttca | 720 |
| ttttcagttg | aggccaaaat | ccccgcgggt | tggtcgggc | gggcgggc | tcggggacg | 780 |
| gggctgaccg | cggggccggg | gccagggtct | cacatcatcc | agaggatgta | tggctgcgac | 840 |
| ctggggcccg | acggcgcct | cctccgcggg | catgaccagt | ccgcctacga | cggcaaggat | 900 |
| tacatcgccc | tgaacgagga | cctgagctcc | tggaccgcgg | cggacaccgc | ggctcagatc | 960 |
| acccagcgca | agtgggaggc | ggcccgtgtg | gcggagcagc | tgagagccta | cctggagggc | 1020 |
| ctgtgcgtgg | agtggctccg | cagatacctg | gagaacggga | aggagacgct | gcagcgcgcg | 1080 |
| ggtaccaggg | gcagtgggga | gccttcccca | tctcctatag | gtcgccgggg | atggcctccc | 1140 |
| acgagaagag | gaggaaaatg | ggatcagcgc | tagaatgtcg | ccctcccttg | aatgagaat | 1200 |
| ggcatgagtt | ttcctgagtt | tcctctgagg | gccccctctt | ctctctagga | caattaaggg | 1260 |
| atgacgtctc | tgaggaaatg | gaggggaaga | cagtccctag | aatactgatc | aggggtcccc | 1320 |
| tttgacccct | gcagcagcct | tgggaaccgt | gacttttcct | ctcaggcctt | gttctctgcc | 1380 |
| tcacactcag | tgtgtttggg | gctctgattc | cagcacttct | gagtcacttt | acctccactc | 1440 |
| agatcaggag | cagaagtccc | tgttccccgc | tcagagactc | gaactttcca | atgaatagga | 1500 |
| gattatccca | ggtgcctgcg | tccaggctgg | tgtctgggtt | ctgtgcccct | tcccacacc | 1560 |
| aggtgtcctg | tccattctca | ggctggtcac | atgggtggtc | ctagggtgtc | ccatgagaga | 1620 |
| tgcaaagcgc | ctgaattttc | tgactcttcc | catcagaccc | cccaaagaca | cacgtgaccc | 1680 |
| accacccgt | ctctgaccat | gaggccaccc | tgaggtgctg | ggccctgggc | ttctaccctg | 1740 |
| cggagatcac | actgacctgg | cagcgggatg | gcgaggacca | aactcaggac | actgagcttg | 1800 |
| tggagaccag | accagcagga | gatagaacct | tccagaagtg | ggcagctgtg | gtggtgcctt | 1860 |
| ctggagaaga | gcagagatac | acatgccatg | tacagcatga | ggggctgccg | aagcccctca | 1920 |
| ccctgagatg | gggtaaggag | ggggatgagg | ggtcatatct | cttctcaggg | aaagcaggag | 1980 |
| cccttctgga | gccttcagc | agggtcaggg | cccctcgtct | tcccctcctt | tcccagagcc | 2040 |
| atcttcccag | tccaccatcc | ccatcgtggg | cattgttgct | ggcctggctg | tcctagcagt | 2100 |
| tgtggtcatc | ggagctgtgg | tcgctactgt | gatgtgtagg | aggaagagct | caggtaggga | 2160 |

```
agggggtgagg ggtggggtct gggttttctt gtcccactgg gggtttcaag ccccaggtag    2220
aagtgttccc tccctcatta ctgggaagca gcatccacac aggggctaac gcagcctggg    2280
accctgtgtg ccagcactta ctcttttgtg cagcacatgt gacaatgaag gacggatgta    2340
tcaccttgat ggttgtggtg ttggggtcct gatttcagca ttcatgagtc agggggaaggt   2400 ccctgctaag gacagacctt aggagggcag ttggtccagg acccacactt gctttcctcg    2460
tgtttcctga tcctgccttg ggtctgtagt catacttctg gaaattcctt ttgggtccaa    2520
gacgaggagg ttcctctaag atcttaaggc cctgcttcct cccagtcccc tcacaggaca    2580
ttttcttccc acaggtggaa aaggagggag ctactctcag gctgcgtgta agtggtgggg    2640
gtgggagtgt ggaggagctc acccacccca taattcctcc tgtcccacgt ctcctgcggg    2700
ctctgaccag gtcctgtttt tgttctactc cagccagcga cagtgcccag ggctctgatg    2760
tgtctctcac agcttgaaaa ggtgagattc ttggggtcta gagtgggtcg ggtggcgggt    2820 ctggggggtgg gtggggcaga ggggaaaggc ctgggtaatg gggattcttt gattgggatg   2880
tttcgcgtgt gtggtgggct gtttacagtg tcatcgctta ccatgactaa ccagaatttg    2940
ttcatgactg ttgttttctg tagcctgaga cagctgtctt gtgagggact gagatgcagg    3000
atttcttcac gcctcccctt tgtgacttca agagcctctg gcatctcttt ctgcaaaggc    3060
acctgaatgt gtctgcgtcc ctgttagcat aatgtgagga ggtggagaca cagcccaccc    3120
ttgtgtccac tgtgacccct gttcccatgc tgacctgtgt ttcctcccca gtcatctttc    3180
ctgttccaga gaggtggggc tggatgtctc catctctgtc tcaactttac gtgcactgag    3240
ctgcaacttc ttacttccct actgaaaata agaatctgaa tataaatttg ttttctcaaa    3300
tatttgctat gagaggttga tggattaatt aaataagtca attcctggaa tttgagagag    3360
caaataaaga cctgagaacc ttccagaatc tgcatgttcg ctgtgctgag tctgttgcag    3420
gtggggtgtg gagaaggctg tgggggggccg agtgtggacg gggcctgtgc ccatttggtg    3480
ttgagtccat catgggcttt atgtggttag tcctcagctg                          3520
```

<210> SEQ ID NO 85
<211> LENGTH: 1923
<212> TYPE: DNA
<213> ORGANISM: Homo sapiens

<400> SEQUENCE: 85

```
gctgagcatc gccagggcgg gcggcagggc gcggcctctc cgccgggtgt acctcctgtc      60
gcggcgcgag acctctggtg aaagaaaaga tgttgtcccg gttaagagta gtttccacca    120
cttgtacttt ggcatgtcga catttgcaca taaaagaaaa aggcaagcca cttatgctga    180
acccaagaac aaacaaggga atggcattta ctttacaaga acgacaaatg cttggtcttc    240
aaggacttct acctcccaaa atagagacac aagatattca agccttacga tttcatagaa    300
acttgaagaa aatgactagc cctttggaaa aatatatcta cataatggga atacaagaaa    360
gaaatgagaa attgttttat agaatactgc aagatgacat tgagagttta atgccaattg    420
tatatacacc gacggttggt cttgcctgct cccagtatgg acacatcttt agaagaccta    480
agggattatt tatttcgatc tcagacagag gtcatgttag atcaattgtg gataactggc    540
cagaaaatca tgttaaggct gttgtagtga ctgatggaga gagaattctg ggtcttggag    600
atctgggtgt ctatggaatg ggaattccag taggaaaact ttgtttgtat acagcttgtg    660
caggaatacg gcctgataga tgcctgccag tgtgtattga tgtgggaact gataatatcg    720
```

-continued

```
cactcttaaa agacccattt tacatgggct tgtaccagaa acgagatcgc acacaacagt      780
atgatgacct gattgatgag tttatgaaag ctattactga cagatatggc cggaacacac      840
tcattcagtt cgaagacttt ggaaatcata atgcattcag gttcttgaga agtaccgag       900
aaaaatattg tactttcaat gatgatattc aagggacagc tgcagtagct ctagcaggtc      960
ttcttgcagc acaaaaagtt attagtaaac caatctccga acacaaaatc ttattccttg     1020
gagcaggaga ggctgctctt ggaattgcaa atcttatagt tatgtctatg gtagaaaatg     1080
gcctgtcaga acaagaggca caaagaaaa tctggatgtt tgacaagtat ggtttattag      1140
ttaagggacg gaaagcaaaa atagatagtt atcaggaacc atttactcac tcagccccag     1200
agagcatacc tgatactttt gaagatgcag tgaatatact gaagccttca actattattg     1260
gagttgcagg tgctggccgt cttttcactc ctgatgtaat cagagccatg gcctctatca     1320
atgaaaggcc tgtaatattt gcattaagta atcctacagc acaggcagag tgcacggctg     1380
aagaagcata tacttaca gagggcaggt gtttgtttgc cagtggcagt ccatttgggc       1440
cagtgaaact tacagatggg cgagtctta caccaggtca aggaaacaat gtttatattt      1500
ttccaggtgt ggctttagct gttattctct gtaacacccg gcatattagt gacagtgttt    1560
tcctagaagc tgcaaaggcc ctgacaagcc aattgacaga tgaagagcta gcccaaggga     1620
gactttaccc accgcttgct aatattcagg aagtttctat taacattgct attaaagtta    1680
cagaatacct atatgctaat aaaatggctt ccgataccc agaacctgaa acaaggcca       1740
aatatgttaa agaagaaca tggcggagtg aatatgattc cctgctgcca gatgtgtatg     1800
aatggccaga atctgcatca agccctcctg tgataacaga atagaagcac tcccctgata    1860
aatactttct gtgctccagg gaacccctt tttcagacaa gaagagataa tgtcttcagt      1920
ttt                                                                    1923
```

<210> SEQ ID NO 86  
<211> LENGTH: 286  
<212> TYPE: DNA  
<213> ORGANISM: Homo sapiens  
<220> FEATURE:  
<221> NAME/KEY: misc_feature  
<222> LOCATION: (1)...(286)  
<223> OTHER INFORMATION: n = A,T,C or G

<400> SEQUENCE: 86

```
ctcttttctg aaaaccagtt gcaaatagtt ttactcaact tttcacactc aaaaacactt       60
taaattttaa aagctaaaaa ctattnacaa attatccatt ttaattttaa aaatgtttgt      120
tgttggtttc attgttccat gttaaaaaaa aaaatcggc ctcgtccaac aaccatacct      180
cagctgctac caccattaac ttctggctgc cgtgaagagt acttagaatt ggccccttac     240
aacttttcag aggtccaaca tatattctgt tccacggccc atgata                    286
```

<210> SEQ ID NO 87  
<211> LENGTH: 1029  
<212> TYPE: DNA  
<213> ORGANISM: Homo sapiens

<400> SEQUENCE: 87

```
gaattcggca cgaggaaata aaccaagaaa ctcctgggtc tgaaaaatat tcacctgaaa       60
cgtatcaaga aatacctggg cttgaagaat attcacctga aatataccaa gaaacatccc     120
agcttgaaga atattcacct gaaatatacc aagaaacacc ggggcctgaa gacctctcta     180
ctgagacata taaaaataag gatgtgccta agaatgcttt ccagaaacca caccaagaaa    240
```

```
caggtgggcc ccaaggccag gatcctaaag cacaccagga agatgctaaa gatgcttata      300
cttttcctca agaaatgaaa gaaaaaccca agaagagcc aggaatacca gcaattctga       360
atgagagtca tccagaaaat gatgtctata gttatgtttt gttttaacaa tgctcaacca      420
taaagttgtg gtccaatgga acatacagct taatagttta tgcgtgattt tctcaaaata     480
ttgtaaaact tttgacaatg ctcattaata ttatttttc tatttgtaga ccatatctga     540
aagaaataac atttttaag gctctaccac atagacaata tcatgctaga atgtgtgtgt      600
gtgtgtgtgt gtgtgtgtgt gtatgtatgt ataggtcggg gagaggatag tggtgggaac    660
agacaaataa ggaagcgggg aggactggat aattggtttt ccccctaag aacatttatt     720 tacgtcttaa gagcagataa gtgactaaga ctgaacacat acattttgtg gagtatatag    780
ttttcttgta aatgctgttc aattattaat gtaacagtag catcaaaatt ttattcaggc    840
tttagttgac tctttggtc agttttaaca attctcctta aaagatattt tggagtgatg    900
aatgtagttt acttttgtat ttgaattttg attttctatt tttatttttt aaatattgta   960
tttgtgcaca atgtacatta aatcattatt acatgcttaa aaaaaaaaaa aaaaaaaga    1020 tgcggccgc                                                            1029

<210> SEQ ID NO 88
<211> LENGTH: 268
<212> TYPE: DNA
<213> ORGANISM: Homo sapiens

<400> SEQUENCE: 88
ttaaattcaa gtggaaaagc gtatcgaaat cttactgcta aaagttctag gtcctcaaat     60
gtgtattcat taatcataag atgatatcat ttgggaatca ttttattcct ttatgttttc   120
aataaatacc tgtggttggt gccaaacact actcttgaca ataggcattc aagcagttaa   180
taatgtcagt accattttta gatatcttag ttttggattt gagcagaaac ttatgaactt    240
ttttaaacag tcattaatcc atattgca                                       268

<210> SEQ ID NO 89
<211> LENGTH: 930
<212> TYPE: DNA
<213> ORGANISM: Homo sapiens

<400> SEQUENCE: 89
gaattcggca cgagctgtct tcggccttct cttcccaaaa taatggatga ctttttttt    60 tccactatta gaggctgtta gcactcagac ttcatcctga acctggatta gtgatcggtt   120
ttgttttaag atcctaagag cacaaacaat gagacagaaa caggctccat tcgctaatgc   180
actgctcatt gaggaatgtc agtgatgaca tacatgtgga aaatttgggg ctaccagacc   240
tctccccagt ctcatctcag tctcaggccc agaatgaggt gaaaattgga gagagggccc   300
tggagcagag aaaggggggat tcctgggaca tgtagggcca tgtcactgag gcaacttcca   360
gcaatgattt acaggaagcg tttagctcat gcatatattg gggccaatct gaaaggaat   420 caagggttat gaaactctca actgtgacat tttataggt atggcgcaac cagagttagc    480
taagtacaga tatcattagc tatatgttca tttgattgct attacatatt ctctctctct   540
gacacacaca tacacacaca cacacacacg cacacacaca cgactgaatt atattcagca   600
gtattttatg ctcttggaa actgttactt attcagatac agggtgtttt gtttttgctt   660
tttgctgatt ctctactaat tttattattc ccaatactct ctttcatttt gaattatgga   720
```

```
gtttattgca gtattgtatt ttttgagatg taaaaactat tataattaga actaaatttt    780
tcaaaaatgg aaacatgcag gttaaatgat aaaaatagtg tatttgtgaa atttgggttc    840
cgttttgttt tgtcatcata gcaaatagaa aaaaatgag ttgattacag aaaaaaaaaa     900
aaaaaaaaag atctttaatt aagcggccgc                                     930

<210> SEQ ID NO 90
<211> LENGTH: 410
<212> TYPE: DNA
<213> ORGANISM: Homo sapiens
<220> FEATURE:
<221> NAME/KEY: misc_feature
<222> LOCATION: (1)...(410)
<223> OTHER INFORMATION: n = A,T,C or G

<400> SEQUENCE: 90 ccttttttt tttttttttac taagaggtct ttgctttaag ntcactgcga tgataccagn    60
ganaattaac tttnagtctt ttaagtanna ctgcaccctc gcgcaggcca ccagccanaa   120
tnctgataag tcgaagtatg gcagntgtgc tgatatanga tgaagtacaa ctgatcagaa   180
atgaaaagcg tgtctttttc cancatgcat naggccgaan tccttttgct ctcgntccgc   240
ccacatctnc ngctacacac atacacacac acacacacac acacacacac acatacacac   300
actcctagcg ctcagtctct ctctctctcc tcttctctca tgataaatca agcaagtggc   360
cctaggcagc ccttcaggag gagaagcctt taagtgcaga acaaaatcag              410

<210> SEQ ID NO 91
<211> LENGTH: 1568
<212> TYPE: DNA
<213> ORGANISM: Homo sapiens

<400> SEQUENCE: 91
aagcttggca cgagggtaga tttctaggaa tgaagtgggg cagatcttat ctttgtggat    60
tacaggcact gtactaaaaa caggtttcct atttaatata aaagaaagt gaatcttctt    120 ttggatagaa tcatccattc ccatcgccgc accccctacc ccccaaacac acacacacac   180
acacacacac acacacacac acacacacgc cctactcttc atttgctagg ggaaggtcac   240
agcacaacta aatccaggac aggacattgt gaccatgacc cagccacagt caataccaga   300
aagatgattc agagtctgaa gtggtgcccc aggtgccaac aggataacct ctaccccccg   360
actttgtctc tggggtcctg ttccttcctg caaagcccaa tccaagactg gcatggctca   420
gaggttgtga gaaaggcatg gactggaaca atcatgtcca gaggggtctg gagctttgtt   480
tcctgttcac cagcaaaaaa tgtctctccc attttctga aagtggctga tgtaagaaca   540
ggcagaagga aaacctttt tgtcaataac tctgtcctta aggaatggtc ctctgggagg   600
gctgtgctgc tagtgggtac ctcagtcaca caccccaac cccaggcagc ctctagagcc    660
ttcttgcttt cattttcctt gaatgtacat aggaacaagg gggaaagtct cttactgaag   720
tgcctgaaac ccaaagctag agcttctaga gacgccgttc ttcctgtctc agcttggcca   780
gcctttcaac aatgttctct agtttcaagc tccagcttct cagaaagaat taagaactt   840 gctgttccaa attaagtaga aagtgagact caataataac tgaactacag caaaaggcag   900
agaattacag ggagaaaaaa cttgtactta ccagcccaat tctactctcc tcaaactgac   960
acacacacac acacacacac acacacacac acacactctc ttttagggga ctaagagaga  1020
gaagcatgtt attacatttt actcatccaa acagtaatgc aaaaataaaa cggtagaata  1080
tgaaaagctc aggatctctc ccaaggctac ctactgcagg agggccaaca ggtgagatgg  1140
```

-continued

```
gaagaatgga aacagggacc gattttgtag ctcatacaat taggacacct taggaatagc    1200
attgtagtaa tggtgatgaa tatgctctgc caaattcatc cagtctgcac catcttatag    1260
ctgcccagca cactcgactg ttcatgtggt ctctttgtag tgtgagtttg gagtgtccta    1320
ttagcctgtt ctggttagga atgagttaac ggctctttcc ctcaacctta gtctagtccc    1380
agggctgagg attcagctgg atccacatgg tcttgagggt tggcatgagg aggggaagc     1440 tttttttgaat cgcttttttga tcacataatc tgccatttta agagtaagat ttgctttatg   1500
gaaatcaatt cattaataaa aaatgatatt caagttgcaa aaaaaaaaa aaaaaaattc     1560 ctgcggcc                                                            1568
```

<210> SEQ ID NO 92
<211> LENGTH: 747
<212> TYPE: DNA
<213> ORGANISM: Homo sapiens

<400> SEQUENCE: 92

```
agaattcggc acgagggaga cccagctggc ctggggtctg ctttccgaca ttttgcctct     60
ctcactggtc atgtatttat tccatattta tatggtctac ttcctgtggc tgggagcagc    120
agctcctgaa ggttccgtgg gggtgcgggg ggttggacag gacactcctt cttggaaggc    180
accaattttc ccagccccac tcccattaca cacacacaca cacacacaca cacacacaca    240
cacacacaca cacacacaca cactgattca ggccttgaga gtcaagccca agagctccct    300
tggccctgtt ccccactccc tccactggcc tctgctgttc ctgtctttgc tcacaccctc    360
acagctgctc tctggcagag gttggcatag cctaggagca gctgcaattg cacctgaggg    420
acaggcccta gagtttggtg gcccaagtcc tgaacccctc ttagaccagg tgaggtgcag    480
aggtggttgc tgcttccagt ttcccttcag acttagctgt gtgaacccca ctcctatcct    540
ttggccttag ttttcccatc tgtaaaactc agaaacgcag ttggaaagtc cttattcatt    600
tagtaagcga atatattata atatgtatag agcgcctttt gtgtaagtca ctggtcagaa    660
tcctcactga gctcccagtc cagagagaag ccagacaatt aaaacagtaa tgacaatgaa    720 aaaaaaaaa aaaaaagtg cggccgc                                         747
```

<210> SEQ ID NO 93
<211> LENGTH: 1820
<212> TYPE: DNA
<213> ORGANISM: Homo sapiens

<400> SEQUENCE: 93

```
gaattcggcc gagttttttt gttagaccct tgaagctgtt tttgagaata cagattccaa     60
tacaaccaca aaaaccttac cacatctaag aaaattaata ctgattctat cttatgtaat    120
atctgttctt tatttaagtt tcccgaaata tccccaaaat atcttttata gctttcattt    180
ttttccaaac caggcaaggt ttatacattc attgcatgcg ttatgtctc tttcatctct     240 ttcaatctag aatagcccac cccatcatct tttcttctgt tggacagtta tactaatatg    300
cagagatgat gtcatatttt tcactacaga aaaagcactc ataaatatgt ataaatgtat    360
atcgatcata atgcttgaga aggaatgggc attggaccca tacctctgca ctctggcttg    420
aaggaagatg aaaagtttct agatacaaca gaggaaatga taatatagag aagtccagga    480
ggtacaaagt ctgtgtgaca aagatagaaa gtagaggaat gtgatacaaa gggagaaata    540
aaacctttga atcttggagc tatataataa atgttaagat tcttcatact gaggttgtga    600
```

| | |
|---|---|
| agcaggacaa tagtgaagag gaatactgaa gaaattatag gagttttaaa aatgattaca | 660 |
| agatatatcc tatatagaga gaatattaca atttctggtg aaaactatca aatataaggg | 720 |
| gatattctcc agaacgaaaa ggtgaaagaa acacctcat tggcactatg tagaagaaat | 780 |
| gggttgtaat tatccaccac tgcacctgcc agccacgaat ggctgtttaa acttcagtta | 840 |
| aactagttaa aattacataa aataaaaaat ctagtccctc agtcacactg accacatttc | 900 |
| aagtgctcaa tagctataca tagctagtgg ctccatatta gagtgttttc atcatcgaaa | 960 |
| aaagtttaac tggccatcac tgcaatagat tcaatataaa ggtatgctgg cttttagggt | 1020 |
| acacattcaa ggtttggtag ggagcctatt aaaactgatc aaaatccttg attgttattt | 1080 |
| agtctggatg aatcacatag gggataatga cagtgaggaa gagaacacgg aagcatattt | 1140 |
| agagtcctca caaaaaatct ggatgtgctg gaataatag gttgtgtgtg tgtgtgtgtg | 1200 |
| tgtgtgtgtg tgtgtgtgtg tgtgactcct tattgttgat tgacacagtg gaacaatgaa | 1260 |
| ggaagatagt agaagacaag taatctagtt ttacctgtgc tcttctctct tgcaaggtag | 1320 |
| aaggctaagc ctttgatcca ggctggaggc cctgaaactg ggattgatag gatgggctta | 1380 |
| ttactgtggc cctgaactga gcccagttg agggcggcct gggaagcaag gcatgaacac | 1440 |
| agccttgata aacaaaatga gtaaaggatg cacagttaag agccaaaaag agaatagcct | 1500 |
| gaacgtgtag aaggaaacta aagctacaag ggagttaaaa gctggttgaa gtgagtgttt | 1560 |
| tgggggtttt ctgtgaatta ataattttga agaggaaaca gccctggtgc gtggggcaca | 1620 |
| ttttcgtaga gaacacaaag aaaagaaaac ctctttggta catattttct ttcagtattt | 1680 |
| ttgggcaagg agaatgatgt acttttttact gacaagagta taactaaagt tgccattaac | 1740 |
| agaaataaag cccagttatc ataaaggaac tgaagtccaa gattaaagaa aaaaaaaaa | 1800 |
| agatctttaa ttaagcggcc | 1820 |

<210> SEQ ID NO 94
<211> LENGTH: 1497
<212> TYPE: DNA
<213> ORGANISM: Homo sapiens
<220> FEATURE:
<221> NAME/KEY: misc_feature
<222> LOCATION: (1)...(1497)
<223> OTHER INFORMATION: n = A,T,C or G

<400> SEQUENCE: 94

| | |
|---|---|
| gaattcggca cgagctgtta tatgaacaca cacacacaca cacacacaca cacacacaca | 60 |
| cacacgcaca cacataccac atttcaataa gtcttcattg ttctgggtcc ttaccttttcc | 120 |
| tgtcctcctg ttatatgaac acacacacac acacacacac acacacgc acaccacatt | 180 |
| tcaatgtctg catggttctg ggggtaacaa aggcaagaag ttaaagtaag accacatttg | 240 |
| ragtattact tactctgtmg mayywwramm kmrtwkwkaa mmccmmwtww ksmaamywmy | 300 |
| ttttttttttc mgsmwraarg ggrarsykrm mwkrwymaaa wycmwkgktt tymaaawkgr | 360 |
| amykgraaar rgsmwtyccr smmmmwytww wammmmawtt wawtttymar ktycmrggsy | 420 |
| tkrmmrgscc ykgggggsmwt yywarsmarg rwtgsmwwaa wtkggymawy ytgkkgraar | 480 |
| rktkggkwmy tttkgytyma wttttwawtw mccmawyytt yyyykgattg taattacctc | 540 |
| caytactttc atgatccccc tacaaatatt ttttaaatg atatatttat tcactgaatc | 600 |
| aaatgtcatt aatgagttat cttcttgtgg aggatgactg ttctctttgt taatgttcac | 660 |
| aatcaagatc ttgggctgag aagaggccct tcacccaag agtttgaagt atcacagcgt | 720 |
| gtggggaagg tgggaaccag ggataccat tcatttccma ccgagacaca ggaggaagtg | 780 |

```
gagtcacaga attttgagcc cgctctcttt gactgcccag ccagagacac ttgattyykg      840
taacctcttc acttggatcc tgcctyttna agcwttaaaa ccattctcct taaacctctg      900
agtgttttgt gggttctggg tgttttgtac attttagcca agctaaccac ttgtctgcaa      960
gtacttgact ttcctatgaa ttctttgaag attattgagt cagaaaggaa aaatatagcc     1020
ccaaattccc aggcttttaa tgcattacat taactgccta ttgaaatgag aagttcttca     1080
caaacttgta tacccactaa caagattgca cataaacatg caktaaagta tatactraga     1140
wrccmtctgt ccaacggctc atgcatatgn aastccswwc atgggagytt gccaattgca     1200
ttcatcaagt cgttttgcgg agtcagatcc ctgatggaag agctcacagg ctctgccttc     1260
caagtcctgg gttcctaact ggtgaccttar gcctggggtc tgtggggaga ccaaccctgg     1320
cttccaagaa aaccacattc catggactat cagaaataga cacagatttg ggtgacaaag     1380
ctggctctgt atttgcattt tatttttgtg twmwatgtca gtttgggaat gattaatatt     1440
aaacatttat ttgagaaaca aaaaaaaaaa aaaaaaaga tctttaatta agcggcc        1497
```

<210> SEQ ID NO 95
<211> LENGTH: 583
<212> TYPE: DNA
<213> ORGANISM: Homo sapiens
<220> FEATURE:
<221> NAME/KEY: misc_feature
<222> LOCATION: (1)...(583)
<223> OTHER INFORMATION: n = A,T,C or G

<400> SEQUENCE: 95

```
cccacgaggg tgcaatcctc gtaggctgat cggtcccatt tcaacactgt gagactgagg       60
gtacattaga ggaaatggtg tatatgatcc ctatgaaacg attctttggc ttttgtttaa      120
aaacaaaacg ggtttgttct cataatctat agaactatga agattactgg atcatatttt      180
tttctcttaa ccaggagtgc ctcagagatt ctgctatgac tttggacttc tctgagtctg      240
tgcaatcatt ttctggagaa gcatggggaa aggtggtaga ctgctgcact ttttcattaa      300
aatgagggta gctctttctc caccccccca tctcctttat cccgaagaca taaatgttca      360 attacgagg catttaaatc aagttgtgac cacctccatt ggagggcagg actcttgatt      420
gtgtaattga taatgcactt tctcaatggg ctgtatagtc attattaacg tgtcttccct      480
cttccccaca aggacatata aggncatttc tgccttcaag tttggccaac taacaaatca      540
gaatctgagg ggcatgttct atttcccagg aatgattgac act                       583
```

<210> SEQ ID NO 96
<211> LENGTH: 943
<212> TYPE: DNA
<213> ORGANISM: Homo sapiens

<400> SEQUENCE: 96

```
gaattcggca cgaggggatt ttttaaagct tttctgttca ccctcctgcc aggaaaatcc       60
cagaaagctt aatgataccc caaatgatt acacccaggg aggaaaaaaa ggagcgcttt      120
ctagggtcag aatcgtggag agaatactca gaaatgaacc tctttaaagc cttgcaggaa      180
tgagtcactc ttacttaatg aaatgttaaa gccaattaaa aagcatgctg tgatgcccag      240 cttcccttt cacagggtgc atgcgtctcc tgctggtgaa tcacatgcgg caagaggcaa      300
ctggctccac agcctgggat gctgccgtac caagaggaaa gaagcagcaa aatgcccttta    360 cgttgttcta aacccccgac gcataaagtg tagaggaggg atggccaagg gtgggtggta      420
```

-continued

```
gaaagtgtgt tcaggctgac actggcaatg agtacagata atttcacttt cctcttctag    480
gggcaaaggc tgatggcctc tacctttgta tccaggagaa actgcagagc agccctgtga    540
ctttacaaaa tatgctacct caaagtgcta ccgataaacc tttctaattg taagtgccct    600
tactaagggc acatgtctta atcaaagtta gttttttgtt ttctggtttg ttttttttt    660 ttgtatattg atgaatgaga tcttacctat taaatatatt attggattat ggttcctgaa    720
ggtcattaga gtgtgtgtgt gtgtgtgtgt gtgtgtgtgt tttatgactt aaatatcttt    780
acgtgtgttt tttagagctt ggttctttaa agatttggag aagatatgta aattaccaag    840
gcacttggtt tttctgtttt atatactaat aatcagggcc taagttaaat aaaaatatgt    900
gtgcatgtat tttaaaaaaa aaaaaaaaaa aaattgcggc cgc                     943
```

<210> SEQ ID NO 97
<211> LENGTH: 566
<212> TYPE: DNA
<213> ORGANISM: Homo sapiens
<220> FEATURE:
<221> NAME/KEY: misc_feature
<222> LOCATION: (1)...(566)
<223> OTHER INFORMATION: n = A,T,C or G

<400> SEQUENCE: 97

```
agggantaag cttgcggccg cttaattaaa naanatttag cgtaaaatta cacttaaaca     60
ttatcagctg ctgctgggaa aaaatggaca aattgcccag gcagccacat tagaagaaga    120
aagtcattng aatacagnta tatacttatt tttattgaga cacatcttgc tgngtcaccc    180
agggttttgc tctgttgcca cagcttactg cagccgtgac ccaggctcaa gtgatccctc    240
ccacctcagg cccctctccc cgaccagtag ccgagactac aggcaggcac agactggcac    300
caccacactc ggctaatttt ttttttttga ggcagggtct cactatgttg tccaggctgg    360
tcttgaactc ctgagctcaa gtgatcctct naccttggct tccaaagtgc tgggattaca    420
gacaagtcat ggcanctggc tgagtacagt tattcancat aagcataaca aatacagaat    480
ggcagcccag ttcctttgnt aatgaaatng taagggggtgt actagggcaa gctggccctg    540
attatgtcac atgagtttgg tttaga                                         566
```

<210> SEQ ID NO 98
<211> LENGTH: 454
<212> TYPE: DNA
<213> ORGANISM: Homo sapiens

<400> SEQUENCE: 98

```
gttcatcacc atggactgga cctggaggtt cctctttgtg gtggcagcag ctacaggtgt     60
ccagtcccag gtgcagctgg tgcagtctgg ggctgaggtg aagaagcctg gtcctcggt    120 gaaggtctcc tgcaaggctt ctggaggcac cttcagcagc tatgctatca gctgggtgcg    180
acaggcccct ggacaagggc ttgagtggat gggagggatc atccctatct ttggtacagc    240
aaactacgca cagaagttcc agggcagagt cacgattacc gcggacgaat ccacgagcac    300
agcctacatg gagctgagca gcctgagatc tgaggacacg gccgtgtatt actgtgcgag    360
ggggccaaga ctattagccg acgtattact atggttcggg gagttatccg agtttgacta    420
ctggggccag ggaaccctgg tcaccgtctc ctca                                454
```

<210> SEQ ID NO 99
<211> LENGTH: 122
<212> TYPE: DNA
<213> ORGANISM: Homo sapiens

```
<220> FEATURE:
<221> NAME/KEY: misc_feature
<222> LOCATION: (1)...(122)
<223> OTHER INFORMATION: n = A,T,C or G

<400> SEQUENCE: 99
agggcgaatt gggccctcta tatggatcgc actttttttt ttnttttttt ccattcacta     60
attgtaatta atttagcata agcaaagaaa tgaccttagg aacatacccca ggttttaaga   120 ta                                                                   122

<210> SEQ ID NO 100
<211> LENGTH: 967
<212> TYPE: DNA
<213> ORGANISM: Homo sapiens

<400> SEQUENCE: 100
gaattcggca cgaggctgga agtggcagaa ctgagatttg cgttccaacg tccattccca     60
tccttccata tcaccctgat tttctcgggt tcagagtcct ggttcatttc ctggctgttc    120
cgcagacatg tcacaaactc cagaaccttc atttctccat ctgcaaatgg caattgtaat    180
tcttgctctg tcaacctcac agatttctct cgaaggcata cacacacaca cacacacaca    240
cacacacaca cacacacaca ctagaaaact gtaaagagat gtaaacctta ccgaataatt    300
acagggtatt ttgattggta ttttttactat gattattttt gctaatcaaa gaaaccagac    360
aggtagtgtc agggaattgt ctaaagcaat gagacattct tgaaaagtct gtatcagatc    420
tccacttctt gccagagaaa atcgccttaa ggtgtccata ggtgtcctgg cttccagtga    480
ggcaacctag caattaggaa agaaatgcat ggtgagtgct tcgtatgggc actcatcaaa    540
tgagcctttc agagctcaat agaaaccct atcccagtga atcttctgtt gtgctgaaga    600
ttgcagctga agattgttgt cccacacagc acagtgatgt tagaattggt tgagctccta    660
atgtggcaag accccacaca tttctagatc cacccagaat gaggtaaacc cttccaaaga    720
aaaagagaaa tatcgaatgc tgtatttttga gtcttcttac tctgtgggat tgatagagca    780
agaattacaa gaattctttt gagtctaaga caccactgat tttaaattac acttaaagtc    840
ataccagtga tttttggaga ggaggaaaga aaataccaca tttaacaagt atatcaattg    900
ttagaagtag cctaatttca aaaatgttaa aaatgtaaaa aaaaaaaaaa aaaattcctg    960
cggccgc                                                              967

<210> SEQ ID NO 101
<211> LENGTH: 588
<212> TYPE: DNA
<213> ORGANISM: Homo sapiens
<220> FEATURE:
<221> NAME/KEY: misc_feature
<222> LOCATION: (1)...(588)
<223> OTHER INFORMATION: n = A,T,C or G

<400> SEQUENCE: 101 ttttttttcag agtaaacngc atgtttattt tgaacattca agtttacaaa aacaaaaagg     60 tnttttnaacc atgacacann tcacacacat acacacacac acacacgcac acacacgcac    120
acatgttgca gctcatgtca atttatgtac aaaacaggga gaggagaaag gggcaaggct    180 ggggagggt tgtcagtagg gtgcactaat gtcacagtgt cagacaactt gacatgctca    240
ctcacactca gcctgggccc atgtgagccc cttccccacc caggggtcgg gggtcagggt    300 ggggaggtggg ggtctggggt ggcaggcagt ggaataaagg ggtgaagaga gtagtcccctt    360
```

```
ctctgggagg gagccccttt ccaagtttac tcaggccaag ggtgctggga cacacaaagg      420 agggggact caatgctggg gagaggctgg ctgcgtccta naagagggct gaatgcagtc      480
agaaggctgg gcttaagttt nccgtgtcag ctgggtggcc ttgaggtcgc tcccctcccg      540
gcttnacttc ctcatctgta aaatgganggc tttggccttt tttaaaac                 588
```

<210> SEQ ID NO 102
<211> LENGTH: 553
<212> TYPE: DNA
<213> ORGANISM: Homo sapiens
<220> FEATURE:
<221> NAME/KEY: misc_feature
<222> LOCATION: (1)...(553)
<223> OTHER INFORMATION: n = A,T,C or G

<400> SEQUENCE: 102

```
ntccttttt ttttttttaa tagtatcatt catttgtaca gagaaatcat ttggatggat       60
ctatttacag tcttttctga ttatcatttc cactggccaa atatttcaca gaatagtcaa     120
cactgacttg aattgatcac cattataatc gggcttttac tcctcctccc cccttttcaaa   180 gatgatgatc ccatttttaac agaaacattt tgtaataaaa gattcaccag tctttttcca    240
tcttatgact aaatccacca aaatttatct aatatggtca aattttttaac acatttcatt    300 gtttcttttc aaactcatta tttgcaggta ttgcaaacca aggcaaataa gtccacgtcc     360
cctcgagcct tctacaactt actacacgcc ctcaagttga gcttctccta tctcctttca     420
cacttgtgaa atgtctggca caaccagaca ttttacttga agacaaaact actctctttt     480
cctctctttt tcttttaact cactaccaat caccttccct cttgcatttc agacaacact    540
aaaactttca aca                                                        553
```

<210> SEQ ID NO 103
<211> LENGTH: 1650
<212> TYPE: DNA
<213> ORGANISM: Homo sapiens

<400> SEQUENCE: 103

```
aagcttggca cgaggtggat ccactagcta cactggctga gaatgctctc accccaggat     60 ttcatttta ttttaccaca tcattgttgg tatcttaaga tcaatgtact ggagcagcgg     120
ggtctcacaa agaggatacc tggtgacacg cccaggcttt cagaatgcac tatagggctt    180
tagtgacttg tccaggttca gctgaaatgt gccatctggg acctactaat gcttgttgaa    240
ctttactgga tctcagaagc tgggtctcag aagctcagat gttcctcaga gctacgatat    300
caacaacctg tgatgacaga gagaaggttg ctccatgatg gatttggaaa cttactggct    360
agctaaacct gactgaatgg gaaggaatgt ggatagcttt ggaactctag tttcactaga    420
tgagctggaa tttgtatttt gacaaattgc acgttatgat tattaagtaa tgcaactgat    480
ttttttttcc cttaaaacaa acaatctaga atctgtgtaa tcaaaataat ttctctaaaa    540
ggctgcaagt atatgcttaa agtgttgggg cattcagagc atttggaaca ttacattctt    600
ttgaatgtca attggtagat gaaaatacca gcttttaagt catacatttg attttttgaa    660
acaatatgca tttagagttt gtaagtcaag tgaataactg ataaggtaaa aaaaagggggg    720 agttcattgt tgagtatgaa tttaaagtaa ccagactgcc ttttgtccag tggctgtcag    780
taatttactt cagcaggcat tttttttttt ttgaggctgt tctatgatat catgacccctt   840 cttgtaggga tgagcttcca gtggtgaggc agtctgagaa tgtgtgaagc agtataatga    900
agccagacca agatggaagc ttggcctggg atttgagcat caggaaaact gttgaagggt    960
```

-continued

```
tatgtataca tcacacacac acacacacac acacacacac acacacacac actctcttcc      1020
atactcctat aacaacgtat agtatttact atacctggtg acaggtattt actatacatt      1080
gttgaagatc tataacatgg aatgcctagt gctaagtgca gtgtccttag tgaaattgta      1140
ttggtttgga attatttatg agtttgggat tatttgtcac tacccttaaa tgatcttgac      1200
actcacctat ttgaaaagat attgaggatt tgccatttga tattgaccag ggtgtattgt      1260
gcacaaatat tgtaatata catctgtctg tccttaaatc actgtaagtt ttaactggaa      1320
tagatttgct ccacattact cggtagggct gatatttcat gcctcatgga tgagaaaaga      1380
ataggcaaaa attatatctc gggctgcctc acacatcttt taacaggata agggaaaaat      1440
aaatataaga cctatgagtt atggcatcag gcttgaactt taatttatga attaaaccaa      1500
caatattatt gattattgca attatctatc ttaatttcat ttgttctcct tttaaaaatt      1560
aattatgttt attttaccta ttgtgaataa agtcactcct cccatgtgct taaaaaaaaa      1620
aaaaaaaaaa aaaaaattc ctgcggccgc                                        1650

<210> SEQ ID NO 104
<211> LENGTH: 590
<212> TYPE: DNA
<213> ORGANISM: Homo sapiens

<400> SEQUENCE: 104
ggaatccttt ttttttttt ggaattataa aacaaggctg agtctgaagt taaatgtgtg        60
attatgctag aaatattttg ctagactctt tgcatctctc cctgattgcc tactttctct      120
ccattctgta cttgcacagg agaaatgaaa acacaattct tgtggcacgt ttggtggaaa      180
aatttctttg aatgtatttg ctaaaccaag agatcttaca aaacatggta aaatactttg      240
gctatatttc catcagccca ctgaagtgag ggcttgagaa gcttagtgca ccttgttttg      300
tgagggagga ggcaatgccc ttttatgaca atattcttga attcaatgtt tgtttattcc      360
cttacttcta aatatgcatg tatctacgtg tgtatatatc tgtatgtaca tgtatatacc      420
acacacacac acacacacac atgcatgcac gtgcacacac acacatacac acacacac       480 acacagtgat tccttgcaag agttccttaa ctgatttcaa attttttattt acttatgtct      540 ttattttgta gaaggtggtg tgggtagatg acagggtgtg agaggcgaaa                 590

<210> SEQ ID NO 105
<211> LENGTH: 541
<212> TYPE: DNA
<213> ORGANISM: Homo sapiens
<220> FEATURE:
<221> NAME/KEY: misc_feature
<222> LOCATION: (1)...(541)
<223> OTHER INFORMATION: n = A,T,C or G

<400> SEQUENCE: 105
tccagggaat aagcttgcgg ccgcttaatt aaacgatctt tttttttttt tttttttcc        60 tctcatttag tctcagagcc taaaagaaa tgcctccagt ctctgttagc cccgatgttt      120
ggaatgaaat taacaagatt ctaccttaaa agagaaaact tatgtgggct tttcaaattg      180
tgaaaatttg ttccctctta taaaatataa tctttcccct gctgctggtt tataaatatg      240
ggcatatagc ccagagccat tataaagaaa aaacaaccaa ccacaataaa ctaaggagcc      300
tcatctgatg gctaaggttc tcaggaaaaa atgagaagag caccttgatc aggaaaggaa      360
aaaaggatag aggataaaaa cagtaacctt taacttctat gccctnactc agccagtaac      420
```

| | |
|---|---|
| ttacggcagg tgttgctggc aaggccttag ctgnatttct tcattaagtt gaacatcctg | 480 |
| tctgccactc ctaccaaccc agctgctnat aagctgccct gagcacccan gaaaagaagg | 540 |
| g | 541 |

<210> SEQ ID NO 106
<211> LENGTH: 776
<212> TYPE: DNA
<213> ORGANISM: Homo sapiens

<400> SEQUENCE: 106

| | |
|---|---|
| gaattcggca cgagcactac tgaatcttga aactataaat atattattga tatggaccac | 60 |
| aattgctgtt ttggaaatca gtgttcacac atcatgttca agcagttaca agatttttat | 120 |
| gtagataatc agtcagctga tatattttca tgagtcatta attttaagat actctatgag | 180 |
| tcacatctgt gatttttcagc aagctatatt tatgataaat gatggacaga ttttgagtag | 240 |
| tacagattga aaattttttga ttaactcaaa gtgaagtatg ctgagagatc aaggacacag | 300 |
| acatactctt tctctagcat gtgcgcgcgc gcgcacacac acacacacac acacacacac | 360 |
| cactcattgt atttgaggtg aagcagttgt taatgtgtgc tttgtacctc acctaggaaa | 420 |
| atcctaaact ttcttttttaa ctattttaca aaattggggc acatacttaa gacatttcat | 480 |
| taggtggtgg tgataatcat tatataaaaa tctaaagcct gaagtgaggt tttaggcttt | 540 |
| gcatagatta taatatgggg aaatgtttgc aatgtgataa catatacatg atgtccacta | 600 |
| ctcacctgta attagtctga ggtagtgggt tgatgttaag ttctctattc aggcttcaag | 660 |
| atactgtttg ggggctggcg gggagggaag gtgcagccca cttttcaaaa gaggaagaat | 720 |
| tggttgtaat gttggaaaaa aaaaaaaaaa aaaaagatct ttaattaagc ggccgc | 776 |

<210> SEQ ID NO 107
<211> LENGTH: 468
<212> TYPE: DNA
<213> ORGANISM: Homo sapiens
<220> FEATURE:
<221> NAME/KEY: misc_feature
<222> LOCATION: (1)...(468)
<223> OTHER INFORMATION: n = A,T,C or G

<400> SEQUENCE: 107

| | |
|---|---|
| attaaccctc actaaaggga ataagcttgc ggccgcttaa ttaaagatct tttttttttt | 60 |
| ttttttttga gggttttctg ttatttcttt attggggtgg gggtggggtg catcattcag | 120 |
| atctttgtgc tggtgcctac gtgcatacaa gtacacacac acacacacac acaggcatgt | 180 |
| gttcacgtat gtatacatat acacacaagg ccagagctct agtgtgctgg aggaggggca | 240 |
| agctcttttt ccaagagggt attagaaaga ggttgattcc agaggatgag tggtctctga | 300 |
| ggctatagcc ccccactggg tgggcagcca gctctgtgag aatgccaggg tgcagctgac | 360 |
| agcgctggag gcctggggac tggactctga gaggagcttg gcagacaca gcagcctccg | 420 |
| gccccaanac tgccctgggt tggcaggccc aaccctggtc ctgacagg | 468 |

<210> SEQ ID NO 108
<211> LENGTH: 515
<212> TYPE: DNA
<213> ORGANISM: Homo sapiens
<220> FEATURE:
<221> NAME/KEY: misc_feature
<222> LOCATION: (1)...(515)
<223> OTHER INFORMATION: n = A,T,C or G

<400> SEQUENCE: 108

-continued

```
tccttttttt ttttttttaa attgaattta tactttatta aaatcaaaca atacaagcct        60
taaaatttga ttttntaaca ttataaaact atgcatcctt tatgaagttt cagttgatat       120
ctgattaaaa aacactttgt ttcataagtg ttcagtgatt tatgaaactt ttaaaacaaa       180
ttaagatggg atttattaca tcttatagcc attattggac ccattctaca ttttgaaaga       240
ctaagagaat agggttagct atgggaaatg ctggctcact ggaagaatcc tgcattttcc       300
aacttcccca ctcctagaag ttttgctaac aggaattgca actaggaatg cctcacctga       360
aaaactaatt tcatacaact ttcattaagt agtttgacaa tctgtgaccc acaaatactt       420
ccatagaatg gtagaattat ttataatcag aaatggatgg tgggggtata aagggaatca       480
agagaggana gaaganggct aatggtggtt cttca                                  515
```

<210> SEQ ID NO 109
<211> LENGTH: 1179
<212> TYPE: DNA
<213> ORGANISM: Homo sapiens
<220> FEATURE:
<221> NAME/KEY: misc_feature
<222> LOCATION: (1)...(1179)
<223> OTHER INFORMATION: n = A,T,C or G

<400> SEQUENCE: 109

```
aagcttggca cgaggaattt cttaaagcaa acaacaaaaa tgtacatttc tgttttttcct       60 tttaataaac aggtgtactc tttatcatgg ttggtatgat ggaccattct ttggggcgga      120
ggattgatta tgttactctc tttaaaatct gttcccatat tgaacaggca gattggaaaa      180
gctatggttc gatttctcag aagaaatgtt taggtcttag tcaatagttt taactatgcc      240
atttgtttaa atgagtgcat ttgcttcgag ggtagtgtct tactaaaagt taggaacaga      300
gacctagtgg gtgtgtccaa ggccgtgtca ctttcccctt cagcacaccc cagcttctga      360
cctcagagcc caggagctgc gtggacagtg tggggtgcca ggaggagggg cggtggctgg      420
tcctcaggca cgctgcactc ccagccagac atggtctttc cgtttcttaa gtagcaagtg      480
taggtttcag ctggcagttc cacctgcatg ttctctgctt cgctgccttg gaaggggcca      540
cattccccat tcctcttctc cttacagcgc ctgcctcctt tttcaagcag gcggaaagct      600
gctgtttctc acgtttcagg gagagggtg agcggaggga gacctgtgtc cgtgccgtcc       660
ggctccctgg gtgggaacag gcaagggatc agatgcccct gacaccacgc ctctggccac       720
accagatgcc tctgcagtcc tcgacagcct cttcagtgtc cctcctgcgg tgatgtcctt      780
actgtcccca gccagggccg gggaccggtg tttcactgag gacctgcatt agaaacatt       840 tttaaattgt tgtacaggaa gagatgtgtc taaaacagca tcttaaagct gagtgtattt      900
ctttgcacaa ggggtcatgc tgatgaattc ttctttcatt ctgatctttg ttcagccaac      960
aggagcgtcc ttttctaatg tcttccattc ctaccccccca cccaaaaaca aagaaatat      1020 ttgtagcttg ctatctgtat ttgaattttt agcaatttta tatttagata ctttgaaaaa      1080
tgtaaatgac taatttggtc attaaatctt gtgacatatt cgatattaaa atgatattaa      1140
aataaaagtc atataaatca aaaaaaaaaa aaaaaannc                             1179
```

<210> SEQ ID NO 110
<211> LENGTH: 510
<212> TYPE: DNA
<213> ORGANISM: Homo sapiens
<220> FEATURE:
<221> NAME/KEY: misc_feature
<222> LOCATION: (1)...(510)

-continued

<223> OTHER INFORMATION: n = A,T,C or G

<400> SEQUENCE: 110

| | | | |
|---|---|---|---|
| ccnggggaata agcttgcggc cgcttaatta aagatctttt ttttttttt tttttgagga | 60 |
| gataaaccaa ttttatgtct atcatgttat acaaaaatct agaataata gatttgtaca | 120 |
| gaaaaaaatg ataataaatg agaacacaaa acatataatt taaatttggt attttttccc | 180 |
| ccatgatatt aggatgataa tcatttcaaa gcacatgtct agcttcagag taggatttgt | 240 |
| tcactggcca aagcctgcca tgaaactatg gctttcagca tctgtctgct ctactggctc | 300 |
| ttgacaaaac tcttgaggtc ttcaagaaaa gtaatgtact cctggtgctc cagggctgtg | 360 |
| ctgagctcca ccagctcatc tgcaaaagtg ttgtccaccc ctnggtcggc aaggaaatcc | 420 |
| attaggtggt catataaggc ccagtccaag gaatctgtgt tgagtgtata attagtattc | 480 |
| ttccattcag actcgccagt ggactaaaag | 510 |

<210> SEQ ID NO 111
<211> LENGTH: 1634
<212> TYPE: DNA
<213> ORGANISM: Homo sapiens

<400> SEQUENCE: 111

| | |
|---|---|
| aagcttggca cgagggcctt tgtaacaata aatagtgata gtgttgtttt cattcatctc | 60 |
| atccatttat aagtctaggt attagatcta agagaagata ccctctgcat ccaactgcta | 120 |
| aagcagggaa ctgggcaagg agctacatcc ttcatcaact atccagtcaa atgcaaggga | 180 |
| aagggctgaa gcagcaagca aatgaactca gaagaggtga aatcaatgaa tttcatgttc | 240 |
| tttccattac catttgctag gtcagcctag ctatcctcat ggtcaaagat taataaacag | 300 |
| aaataaaaac aaattcacca ttgctaggca ctacaggaag ctaaaaagga aatacttgaa | 360 |
| gattcagaaa aaaataaaag gaacacttac agtgatttac taccaaaata aaacatttg | 420 |
| tgtttctcga taagtattgt attcccggct cctaaaatct ttgtatgaca gatggtcagc | 480 |
| attcaataaa tatacattga attagtgaat aatcttttag aaaatgattc catatcctca | 540 |
| gtgggtggca agaagtcttt gaatccataa agcatgaatg taaggctata gaaagaataa | 600 |
| actgagacca aaaatatat agagagagaa agagagaaaa gaaagaaag caagaaggca | 660 |
| agcaagaaag aaaaaaacag aaacaaaaga gaaagaaatg aaaacaatgt acaaagtaag | 720 |
| aaaatatgaa aatgaaagt gcaattgagg gattaataga tgcgtgtaaa taaaattttc | 780 |
| cacatatata agaattttc catagataga tagatagata gatagataga cagacagata | 840 |
| gatagataga tagatagatc ctactctagg tctataattt gtcttttgat gtcatgttat | 900 |
| tttttaataa acaggaatat ttattatata aaaaaatctc tctctccccc catggcccct | 960 |
| tcttcctggt ttctagtttt tatgtctgac ttagaaaaac ccttatcaaa ctaaaattat | 1020 |
| ctttctgatt ttccctaatt ttatatcata ttttaatt taatctttt aacctaactg | 1080 |
| aaatttttta ttatgtctga tgagcaattt gtgtttaata aatgatatta agaaagaaa | 1140 |
| ctttggaaga agtcactgat ggtggcttgt aattacagac taagtaattt ggatcatgat | 1200 |
| tccttccaaa gacatcttaa aagctgaaaa attataaaaa taatctcttt gtaggctttg | 1260 |
| gagaattaag aagatggtga gaaatagtg ggcaatgatc cataagaaga taaacatctc | 1320 |
| aggccgggag cggtggctca cacctgtaat gtcagcactt tgggaggccg aggtgggcag | 1380 |
| atgcttgagc tcagaagttc aagatcaccc tggctaacat ggtgaaaccc tgtctctact | 1440 |
| aaaaatacaa aaattagcca ggtatggtgg caggtgcctg taattccatc tacttgagag | 1500 |

| | |
|---|---|
| gcttaggtag gagaagtgct tgaactgggg aggcagaggt tgtagtgagc caagattgtg | 1560 |
| ccattgcact ccagcctggg caacagagtg agactccatc tcaaaaaaaa aaaaaaaaa | 1620 |
| tttcctgcgg ccgc | 1634 |

<210> SEQ ID NO 112
<211> LENGTH: 426
<212> TYPE: DNA
<213> ORGANISM: Homo sapiens
<220> FEATURE:
<221> NAME/KEY: misc_feature
<222> LOCATION: (1)...(426)
<223> OTHER INFORMATION: n = A,T,C or G

<400> SEQUENCE: 112

| | |
|---|---|
| nnttttttt ttttcctatg gatgtttagt tctaaaaagc accatttctc aaaaaaacta | 60 |
| tccttcctcc attgaactgc ttttgcacct ctgtcaaaaa tcaattgggc atatttgtgt | 120 |
| gagtctattt ctgggttctt tattctgttc cattgatcta cgtgtctatc cctctgtcaa | 180 |
| taccacagtc ttgattactg tcactaaaaa gaaagtctta aaatagggta gacagactac | 240 |
| ttccaattca ttcttctttt ttaaaattgt tttatctatt ttggtttctg tgcctttata | 300 |
| tataantttt agaacaagct tgtctgtatc tataagaaat cttgctgtga ttctaatagg | 360 |
| aattgcatta nacctataat cactttgggg agaattgaca tctttacgat gttgattntt | 420 |
| ccaacc | 426 |

<210> SEQ ID NO 113
<211> LENGTH: 727
<212> TYPE: DNA
<213> ORGANISM: Homo sapiens

<400> SEQUENCE: 113

| | |
|---|---|
| agaattcggc acgaggcact aagatgtgtc ttaagaatca cagtgcgtgc ttcatccctt | 60 |
| tattgaagaa cagaaaatta tgactactct acaaggtgga taatattttg gtacctgtgc | 120 |
| ttgccacagc cctgttcctc aaagctgaat tgatagattt ctctttgact tccaagacct | 180 |
| agcagttata aggcaccttg aaataaattg tttgtgcctg gaaatgcagg gagggcaata | 240 |
| gctttgtaaa ttggtttaca ttttttctcct tgaatttttc tagggtccta gtgcttccga | 300 |
| atcatttaat ggcattgtcg gatatctttt acatttcaat tgcaatccat gaaattacat | 360 |
| ttagaagatt cttagtactt aactgtagtc ttctccatga attacacgtt agaatagact | 420 |
| ggcagcaact gaatatgcag caagtaagcc tctagcttat agtttcatcc ctacccctca | 480 |
| tgcctgcgtg agtctgtaca gggatatgtg tgtgtgtgtg tgtgtgtgtg tgttagagag | 540 |
| gaagaggaag agcagaatgt ctgtatacta catgctgcta aggtagtgaa taaatcagta | 600 |
| atgcaatatt gtgggtccaa actactcttt gcactacttt atttacagta gtaaataaaa | 660 |
| ttatttttat acaattgact accaaaaaaa aaaaaaaaa aaaaaaaaa aaaaagatg | 720 |
| cggccgc | 727 |

<210> SEQ ID NO 114
<211> LENGTH: 2291
<212> TYPE: DNA
<213> ORGANISM: Homo sapiens

<400> SEQUENCE: 114

| | |
|---|---|
| gaacaatgaa gaaagcccca cagccactgt tgctgagcag ggagaggata ttacctccaa | 60 |

-continued

```
aaaagacagg ggagtattaa agattgtcaa aagagtgggg aatggtgagg aaacgccgat      120
gattggagac aaagtttatg tccattacaa aggaaaattg tcaaatggaa agaagtttga      180
ttccagtcat gatagaaatg aaccatttgt ctttagtctt ggcaaaggcc aagtcatcaa      240
ggcatgggac attggggtgg ctaccatgaa gaaaggagag atatgccatt tactgtgcaa      300
accagaatat gcatatggct cggctggcag tctccctaaa attccctcga atgcaactct      360
cttttttgag attgagctcc ttgatttcaa aggagaggat ttatttgaag atggaggcat      420
tatccggaga accaaacgga aaggagaggg atattcaaat ccaaacgaag gagcaacagt      480
agaaatccac ctggaaggcc gctgtggtgg aaggatgttt gactgcagag atgtggcatt      540
cactgtgggc gaaggagaag accacgacat tccaattgga attgacaaag ctctggagaa      600
aatgcagcgg gaagaacaat gtattttata tcttggacca agatatggtt ttggagaggc      660
agggaagcct aaatttggca ttgaacctaa tgctgagctt atatatgaag ttacacttaa      720
gagcttcgaa aaggccaaag aatcctggga gatggatacc aaagaaaaat tggagcaggc      780
tgccattgtc aaagagaagg gaaccgtata cttcaaggga ggcaaataca tgcaggcggt      840
gattcagtat gggaagatag tgtcctggtt agagatggaa tatggtttat cagaaaagga      900
atcgaaagct tctgaatcat ttctccttgc tgcctttctg aacctggcca tgtgctacct      960
gaagcttaga gaatacacca aagctgttga atgctgtgac aaggcccttg gactggacag      1020
tgccaatgag aaaggcttgt ataggagggg tgaagcccag ctgctcatga acgagtttga      1080
gtcagccaag ggtgactttg agaaagtgct ggaagtaaac ccccagaata aggctgcaag      1140
actgcagatc tccatgtgcc agaaaaaggc caaggagcac aacgagcggg accgcaggat      1200
atacgccaac atgttcaaga agtttgcaga gcaggatgcc aaggaagagg ccaataaagc      1260
aatgggcaag aagacttcag aagggggtcac taatgaaaaa ggaacagaca gtcaagcaat      1320
ggaagaagag aaacctgagg gccacgtatg acgccacgcc aaggagggaa gagtcccagt      1380
gaactcggcc cctcctcaat gggctttccc ccaactcagg acagaacagt gtttaatgta      1440
aagtttgtta tagtctatgt gattctggaa gcaaatggca aaaccagtag cttcccaaaa      1500 acagccccc tgctgctgcc cggagggttc actgaggggt ggcacgggac cactccaggt      1560
ggaacaaaca gaaatgactg tggtgtggag ggagtgagcc agcagcttaa gtccagctca      1620
tttcagtttc tatcaacctt caagtatcca attcagggtc cctggagatc atcctaacaa      1680 tgtgggctg ttaggtttta cctttgaact ttcatagcac tgcagaaacc ttttaaaaaa      1740
aaatgcttca tgaatttctc cttcctaca gttgggtagg gtagggaag gaggataagc      1800 ttttgttttt taaatgactg aagtgctata aatgtagtct gttgcatttt taaccaacag      1860
aacccacagt agagggtct catgtctccc cagttccaca gcagtgtcac agacgtgaaa      1920
gccagaacct cagaggccac ttgcttgctg acttagcctc ctcccaaagt cccctcctc      1980 agccagcctc cttgtgagag tggctttcta ccacacacag cctgtccctg ggggagtaat      2040
tctgtcattc ctaaaacacc cttcagcaat gataatgagc agatgagagt ttctggatta      2100
gcttttccta ttttcgatga agttctgaga tactgaaatg tgaaagagc aatcagaatt      2160 gtgcttttc tcccctcctc tattccttt agggaataat attcaataca cagtacttcc      2220
tcccagaaaa aaaaaaaaa aaaaaaaaaa aaaaaaaaaa aaaaaaaaaa aaaaaaaaaa      2280
aaaaaaaaaa a                                                          2291
```

<210> SEQ ID NO 115
<211> LENGTH: 637

```
<212> TYPE: DNA
<213> ORGANISM: Homo sapiens

<400> SEQUENCE: 115
gcggccgcct tttttttttt tttttttttag tttgtaaaag tcttttattg tatccgtgcc    60
acacatagtg aaaaataaca ctcctaaaaa aagaatgcta cctttccac aacattttat     120 tttaaataaa acttcaagta ctcttacgta ggtacaaaaa aaatctgatc tatttgcctc    180
caacaggcca ccacaacaca cagtagataa aacacagtgg ttacaaacgt cttttaaatt    240
tatttctgag gcaaggcaaa tgggagggaa atgtttctat gaaaaaatac tgtgtgcgta    300
ggaaattgtc acaattttat tccacatgga tacaaatgat tatactttaa tttaggccct    360
ggtggcttaa aattatataa caaaatagaa aaatggaaaa ctaatatccc ctacaccctg    420
tttcaaaggc aggcactacc aagattaagg agacgccaca gtgttggtag aggataatta    480
ctgtacagac tgtatagcta tcattacctt cagacgaaaa taaaatgcta caatcctcta    540
aggcatgaac aataatgtct gcaaacaata tatacacata atacatattt taaaacaaga    600
cttaatataa acaagaatga accctcgtgc cgaattc                              637

<210> SEQ ID NO 116
<211> LENGTH: 664
<212> TYPE: DNA
<213> ORGANISM: Homo sapiens

<400> SEQUENCE: 116
gaattcggca cgagggcaga cacaactcag ctcccttact gtcctcaggc ccggctattt    60
caagaattcc agaaaaagag tgcaccggcg tgtgcgggcc ggtgctgccc ggaaaacccg    120
tgaagcaggc acgcacggcc cggatgcaag cacatctgtc ccctccccca aaggtctccc    180
cagctttatt gatcgcgtgg gtgcgggtag ggatctaaat ttgtctccca gattttctct    240
gaaatcgagt ctcttgggag tgaaggtcca tatgattaca ccacgtcctt agcagtcgcg    300
ttgtgttcaa aatgggcatg ggtgctcgcg gcgcggatac tgagttcccc agagacgcgg    360
agtcttttgc cccaggggct tattcttgtt ttctcaatgg aacaggtctt ctaatctccc    420
caggaacatc tcagtaagta ggggtgtgcg tgtttgtgtg tgtgtcagtg tgtgtgtgta    480
aatggttcct atgagctgac agtttggtat ttaaagaaca aatggacata agcacagaag    540
tcatgacttt tctatggata agattgagat ttctgagatt tccaagacaa ggttgacctg    600
tcacgggata gtattttcaa tccttctcat ttaaaaaaaa aaaaaaaaaa attcctgcgg    660
ccgc                                                                  664

<210> SEQ ID NO 117
<211> LENGTH: 515
<212> TYPE: DNA
<213> ORGANISM: Homo sapiens
<220> FEATURE:
<221> NAME/KEY: misc_feature
<222> LOCATION: (1)...(515)
<223> OTHER INFORMATION: n = A,T,C or G

<400> SEQUENCE: 117 tcctttttt ttttttttaa attgaattta tactttatta aaatcaaaca atacaagcct      60
taaaatttga ttttntaaca ttataaaact atgcatcctt tatgaagttt cagttgatat    120
ctgattaaaa aacactttgt ttcataagtg ttcagtgatt tatgaaactt ttaaaacaaa    180
ttaagatggg atttattaca tcttatagcc attattggac ccattctaca ttttgaaaga    240
```

```
ctaagagaat agggttagct atgggaaatg ctggctcact ggaagaatcc tgcattttcc    300
aacttcccca ctcctagaag ttttgctaac aggaattgca actaggaatg cctcacctga    360
aaaactaatt tcatacaact ttcattaagt agtttgacaa tctgtgaccc acaaatactt    420
ccatagaatg gtagaattat ttataatcag aaatggatgg tgggggtata aagggaatca    480
agagaggana gaganggct aatggtggtt cttca                                515
```

<210> SEQ ID NO 118
<211> LENGTH: 580
<212> TYPE: DNA
<213> ORGANISM: Homo sapiens

<400> SEQUENCE: 118

```
tttttttttt gcaacttgaa tatcatttt tattaatgaa ttgatttcca taaagcaaat     60
ctttctctta aaatggcaga ttatgtgatc aaaaagcgat tcaaaaaagc ttccccctcc    120
tcatgccaac cctcaagacc atgtgggatc cagctgaatc ctcagccctg ggactagact    180
aaggttgagg gaaagagccg ttaactcatt cctaaccaga acaggctaat aggacactcc    240
aaactcacac tacaaagaga ccacatgaac agtcgagtgt gctgggcagc tataagatgg    300
tgcagactgg atgaatttgg cagagcatat tcatcaccat tactacaatg ctattcctaa    360
ggtgtcctaa ttgtatgagc tacaaaatcg gtccctgttt ccattcttcc catctcacct    420
gttggccctc ctgcagtagg tagccttggg agaagatcct gagcttttca tattctaccg    480
ttttattttt gcattactgt ttggatgagt aaaatgtaat aacatgcttc tctctcttaa    540
gtcccctaaa gagagtgtgt gtgtgtgtgt gtgtgtgtgt                          580
```

<210> SEQ ID NO 119
<211> LENGTH: 928
<212> TYPE: DNA
<213> ORGANISM: Homo sapiens

<400> SEQUENCE: 119

```
gcggccgcag gaattttttt tttttttttt ttcttttcca taaattggtt tatttaaaca     60
ttacccgaaa tcgtgaagga aaaatattg gaaattacca aatgcccctta acaggcgaa    120 tgattaggta acattttgtg catatgtatt aggttacgtt aataaagaaa ttttaaggat    180
ataaagaaaa tgcttattga taaaggtaaa ggcaaaatag agaaagcaaa attatgtgaa    240
cagtgtgaac tcaattccat aaaatgtata tgcatagaat atgaaaagaa attatagcaa    300
aatatttatt attggttatc tcctggtctt aagattatac accatttttc cttttcttct    360
tacttttttt ctgtgttata aatatgtaaa ataactaaag acatcctaag tagtaaaaat    420
aatttgacct aaattgtgta tgtgtgtgtg tgtgtgtgtg tgtgtgtgta tcaatgaaga    480
attttttttt gttttattt atgttttctt taggaaaata aaacatgtct agtaagaaag    540
atgaaacaaa gaaagagttg gggtaagttc acattttca aaccaacttg tgcttctaaa    600
ataaaattct gcctctccac acactgggtt cctggaagct aaccaaaatc tgctcagtaa    660
tattaactcc acttaaaaaa aggaagagaa catattgaac tgcattcact tatggtctgg    720
gtgcttggaa gaaatcagct ggtgagtacc aaagtgatga ctgcatgttt ctatttgcat    780
tttgaaaatt gacagataat tgaaaggaat cagcatatga aatttctcca aggaagccag    840
ctgagaagcc cgaggaaccc tgcctacgga ggcctcctgg tgcctgaagt ctggttgcag    900
aatgttctag aaccctcgtt ccgaattc                                       928
```

<210> SEQ ID NO 120
<211> LENGTH: 1853
<212> TYPE: DNA
<213> ORGANISM: Homo sapiens

<400> SEQUENCE: 120

| | | | | | |
|---|---|---|---|---|---|
| gcggccgcag | gaatttttt | tttttttttt | tttttatgt | tacaaatatt | ttattgcaat | 60 |
| ttttccctt | taacaatgtc | tggatatttt | ggaattaata | tctcggactt | ctttctaatc | 120 |
| cacattggtt | catcttgttc | attatgaaca | gaggattcta | ctttacaatg | tactaaaatg | 180 |
| ttgttatgta | tttcaggacc | attgaacatt | caagttgttt | atcattttct | ttgaccacca | 240 |
| acattgctgt | aatgaatagg | gatttaagag | caaaagtaac | gagaatactt | gcttaaccac | 300 |
| ttatgaaaac | atatcataaa | agtagaacaa | tcaaatggt | ggatgccata | gagaaagcaa | 360 |
| ggtaacaaaa | taggaagcct | agggaccaat | aaagtatata | tacaaggatt | tcctatatca | 420 |
| caaagtaac | acttcaggta | catggaaaaa | gaatttcagt | accaaaaggc | acctcagtct | 480 |
| cacatccaca | cattcaaaaa | taattaaaat | tttacatgaa | aagttggaaa | cacaaaatga | 540 |
| actagaaaaa | caatatataa | attaggacaa | acactgcttt | gcaatgggag | gacctttgta | 600 |
| aatctgacag | taaagtgaa | gaaggagttt | actagggatc | tgtttgacat | tacagaagca | 660 |
| ttcatattca | taccataa | aacctcatat | acaacattat | aagacaaaca | acagatttgg | 720 |
| gggaaaaaca | ctccaccatc | tgtgaaagac | tgtatgtcaa | tagtcaaaaa | gacttaatca | 780 |
| gaaaatgata | gcacccaaca | gaagaaagac | cttaatgggc | ttggcccagt | taaaaaatac | 840 |
| caatcgatgc | ctaagatacc | tataaaaata | tgtgcaaact | ggataactaa | aataatgcaa | 900 |
| attaaagcaa | tttaatgcca | ttattttcc | tgtatctgaa | aggcaaagat | ttaaaagaac | 960 |
| cataatccct | ggtgcaggcc | caggcataga | tcagcagccc | ctcatctgtg | gccggtggga | 1020 |
| gggagagttg | cctggtctat | ctggaagagt | ggccacccgg | gccatttgga | ccaaaggccc | 1080 |
| taaagcatat | atgcctttgg | ggcattttcc | tttgtttggc | agtttcccct | gacttttccg | 1140 |
| cagtagacgt | gggctctgga | ctcctctcct | gatgttcccc | aggtcccgcc | agcctgccca | 1200 |
| ccacttgggc | cgttaacttc | tctacatgac | gtggggtctc | aagggactgg | aggtcccaca | 1260 |
| gacatcactg | agacaactag | cagggctccc | cagaagctcc | caaacagtct | ctcatgtgcg | 1320 |
| tcccttgcac | cgcccccccg | accccaata | ccatgcccat | ttctcggagt | gacaatcgag | 1380 |
| gctagtctga | attccctgag | cctcactgag | cgtgcccagt | cctgtgccac | tcttccaagc | 1440 |
| cctaaccccc | acgggtgccc | acctggtgcc | tcccacctct | gcacccagat | gagaatcatg | 1500 |
| tcatgtgcat | cagcgactgc | cggggacagg | cagcccacac | aagtcctcaa | cacaaccagc | 1560 |
| cgaatctcag | tctgataagg | ctcagctcag | acctcagccc | cactctcata | ataaatcagt | 1620 |
| gaaaaagaa | ggaagaaaaa | tggcaaaagc | aaggaaacct | gattaaaaaa | atgaggggga | 1680 |
| gatggaatga | gtatatctag | aaagttctaa | taatgcagaa | cctacaaata | agttaacctg | 1740 |
| acaggaaaaa | tgtgtgcatg | tacgtgtgtg | tgtgtgtgtc | tgtgtgagcg | cagggagaga | 1800 |
| agtgatttgc | tgaaggtcaa | ggggccgga | gcaaggctcc | tcgtgccgaa | ttc | 1853 |

<210> SEQ ID NO 121
<211> LENGTH: 709
<212> TYPE: DNA
<213> ORGANISM: Homo sapiens

<400> SEQUENCE: 121

| | | | | | |
|---|---|---|---|---|---|
| gtttggagac | tgtgtccaag | gcgactggtg | ccccatctct | ggggactat | gctcggcccg | 60 |

```
cctacatcgt cacgccctac tggccacctg tccagagcat caggtcacct gggaccccat     120
cgatggacgc gttatcggct cagctctaca attccttatc cctcgactcc cttccttccc     180
cacccagaga acctctaaga ccctcaaagt cctcaccccg ccgaccactc atacaacccc     240
caacattcca ccctccttct tccaagccat gcgaaaccat tcccccttcc gcaacggata     300
tatggagccc accctcgggc agcagctccc agccttgtct ttccccgacc ccggcctccg     360
gccccaaaac ttatacaccc tctggggaag ctccgttgtc tgcatgtacc tctatcagct     420
ctcccccccc atcacctggc ccctcctgcc ccatgtaatc ttctgccacc ctggtcagct     480
cggggccttc ctcactaagg tccctataa gcgaatggag gagcttctct ataaaatctt      540
ccttaatacc ggggccctta taatactacc tgaagattgc ctgcccacca ccttttccca    600
gcccacaagg gcgcccgcca cgttaacagc ctggcaaaat ggcctccttc ctttccaagc    660
tgcaatcacc accccaggcc ttatttggac atttaccgat ggtacaccc                709
```

<210> SEQ ID NO 122
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 122

```
agggaggctg gggccaggtg tcagccctag gcctccatcc aacaccgtgg aaatgttgct      60
gccctcttct tggcgctgac cccaagattg gggtttcctt tctgccgctc cctccactgt     120
tgtttatcta actgggcccc cactccaggt ccagagggac tgtgctcact gcacagacat     180
cactcagctt ccgctcccca gtcctgcaga gctgttgcca ggtgccagtg ggggagngga    240
g                                                                     241
```

<210> SEQ ID NO 123
<211> LENGTH: 448
<212> TYPE: DNA
<213> ORGANISM: Homo sapiens

<400> SEQUENCE: 123

```
ctcgaggcca agaattcggc acgaggtttc ttctacctct gttatctaag cagagggaag      60
taaacttctc accgcccccc acccctcact gcccccgatt acactagaat tgctttcgcc     120
aaattgtagt tgaagctaag gaaggggaat ctggcccctg ctgggagagg gaactggaat    180
gccacacaag gcaaggcctg cttccttcct tcccctctgc tgctgctgcc tcggaacgct    240
gcagcccagg cttcctccca cagtggccct tggaagcagg ccgcagagta gacagctgct    300
ccttttggaa gagtcagtcc cctgtgtttt ctgaactgtt tttcctagca tgtatgtggg    360
tagagctttc atgcatctct agtaataata agctgaaatt agtttttttt ttaattctcc   420
aatttaaaac ttttaattaa gcggccgc                                         448
```

<210> SEQ ID NO 124
<211> LENGTH: 1821
<212> TYPE: DNA
<213> ORGANISM: Homo sapiens

<400> SEQUENCE: 124

```
gaattcggaa cgagggaggc attttgtggc cttaaacgg ggtgttcagg gtcagccctc       60
agggtgctgg ggcccttcca tcccttgtcc ccttcaggtt ggtgaaaagg actccggggg    120
```

-continued

| | |
|---|---|
| ccaggtgctg tatagcagct tatggaagtc tcagctgggc tatcctgccc ttgggagcac | 180 |
| agacaggctc ctagggtgct gagtgaagcc tgaagaccaa gcccctcct cctggaatgc | 240 |
| tccttccacc cctacctctc agagatgggc ctgacacctc tttctcattc attctccttt | 300 |
| tccctgtgct ctgggaaagc ccctggctca ggctgtcaga gtgaggatgg acctcaaaag | 360 |
| tttgatcccc tcgtgcagat gaagaagctg aagcccagag tgcggaaggg gagtggccca | 420 |
| aggtcacaca gctagtttga gtagagccag tcttgggaga gccaagtact acagccctgg | 480 |
| gggtgtcaca ccgcttgtca ctgccctga gtctcctgc caaacaactg cagggagttt | 540 |
| ggctaacagt cctgtgtcca gggtgccggt ggggatgtta tagatgttgc tgggatcctg | 600 |
| ccctcggctc caaattctgg cctctcatcc caggctgcag accttctgc cccatgacag | 660 |
| gcctgggtgc cacacagagg tggccaccct ccaccacag tgtctgcagc tgctgccctt | 720 |
| ctcccaggcc cccagacaga agagaccctg tttcccctcc tctccctgt gacttcacaa | 780 |
| gagcttgggc ttggagtgaa ggtcagcatg ttctcatgtg ctcatcctct tggtttcccc | 840 |
| aaagaccggg agggtcacgg atgggcgtg cagaatcctt gtgttttttc tcgctgggca | 900 |
| gcttgagggg ctggggagta ttcccagggt cttgctctg gagagtccct gcagagccac | 960 |
| tggctgaggt tgggttcagg gttcagcgga gtcctccatg cttccaaagg ccgggaagca | 1020 |
| cccgcctctc tatcgagtca gtgctgtgcg tgtgtgtctg agaatgtgtg tgatgtgtgg | 1080 |
| agtgtgcgtg tgtttgtgtg tgtgtgtgtg tgtgttgggg cagaaggacc actctttcct | 1140 |
| ggggatccct tgacccttat aactagaagg gaccttaggg agcatctaag ctggtgcccc | 1200 |
| cattgtacag gcgaggtcca gagggatggc atctgcccac cccaccccctt gccctcttgt | 1260 |
| tgcctgcact catttcccag ggaccctcct aggataggaa tgccctcctt cctggcccc | 1320 |
| tcccgccatc ctcccagcca cccacataat caccatctca gcccaactct ggtgccctc | 1380 |
| taggtctcca tgcattcttc ctgccctaga gtagccagct caccaaggcc tttatcccca | 1440 |
| gcccaggaga agggtcaggg agggaagggg ctgcaccagc cctgagacct caaagacttg | 1500 |
| ggagaaaagc caaaactcct catgcccagg cccacatgtc tgaccacccc agcccacccc | 1560 |
| gccaccaagg taaaagcaca acaggagacc cccttattaa tgggtgaaat gattggggtt | 1620 |
| gttttttttag tcacacagcc ccatcctcac cccttgcct tgctgtctgt ctccaccca | 1680 |
| gcctctgttc cccatttgcc tctctttcac ctccaagccc ccaaatgtaa cctctagttg | 1740 |
| cggacgcggt tgttctatca ataaagctgc agtgttctag caaaaaaaaa aaaaaaaaa | 1800 |
| aaaaaaaaa agcgcggccg c | 1821 |

<210> SEQ ID NO 125
<211> LENGTH: 540
<212> TYPE: DNA
<213> ORGANISM: Homo sapiens
<220> FEATURE:
<221> NAME/KEY: misc_feature
<222> LOCATION: (1)...(540)
<223> OTHER INFORMATION: n = A,T,C or G

<400> SEQUENCE: 125

| | |
|---|---|
| tttttttttt tcnttcataa ttgtaattaa tttagcataa gcaaagaaat gaccttagga | 60 |
| acatatttag gttttaagat agatttctat ntaatgggcc tgaaaggcat tttgatctga | 120 |
| atttattttc caacgatttc aaatataatt tgtcatctgt gtgtagacat atacgggcat | 180 |
| gaacacacat tcacccacac atacaaaaac acttgctttc tatcagatca gggtaatttt | 240 |

```
tttattgcag gtctctttta atattggcta gcagaaaacc tatccccaac ctaacagatt      300
acacacacac acacacacac acacacacac acacagagct atttttccac acttcctcac      360
agtgaaaagc tctctaacaa gataccagaa ggtcgagaga gacaatgctt ttatggctgg      420
gccttgagga caattctggt tgcatttaaa tctcagtgcc aaatgcacta ggttccctgc      480
cgttataatt tttggatcag tctcttctga aatcangtca cagagaaaac aggatgattt      540
```

<210> SEQ ID NO 126
<211> LENGTH: 2490
<212> TYPE: DNA
<213> ORGANISM: Homo sapiens

<400> SEQUENCE: 126

```
gttcgtagtt cggctctggg gtcttttgtg tccgggtctg gcttggcttt gtgtccgcga       60 gttttttgttc cgctccgcag cgctcttccc gggcaggagc cgtgaggctc ggaggcggca     120
gcgcggtccc cggccaggag caagcgcgcc ggcgtgagcg gcggcggcaa aggctgtggg     180 gaggggctt cgcagatccc cgagatgccg gagttcctgg aagaccctc ggtcctgaca      240 aaagacaagt tgaagagtga gttggtcgcc aacaatgtga cgctgccggc cggggagcag     300
cgcaaagacg tgtacgtcca gctctacctg cagcacctca cggctcgcaa ccggccgccg     360
ctccccgccg gcaccaacag caaggggccc ccggacttct ccagtgacga agagcgcgag     420
cccaccccgg tcctcggctc tggggccgcc gccgcgggcc ggagccgagc agccgtcggc     480
aggaaagcca caaaaaaaac tgataaaccc agacaagaag ataaagatga tctagatgta     540
acagagctca ctaatgaaga tcttttggat cagcttgtga atacggagt gaatcctggt      600 cctattgtgg gaacaaccag gaagctatat gagaaaaagc ttttgaaact gagggaacaa     660
ggaacagaat caagatcttc tactcctctg ccaacaattt cttcttcagc agaaaataca     720
aggcagaatg gaagtaatga ttctgacaga tacagtgaca atgaagaagg aaagaagaaa     780
gaacacaaga agtgaagtc cactagggat attgttcctt tttctgaact tggaactact     840
ccctctggtg gtggattttt tcagggtatt tcttttcctg aaatctccac ccgtcctcct      900
ttgggcagta ccgaactaca ggcagctaag aaagtacata cttctaaggg agacctacct     960
agggagcctc ttgttgccac aaacttgcct ggcaggggac agttgcagaa gttagcctct    1020
gaaaggaatt tgtttatttc atgcaagtct agccatgata ggtgtttaga gaaaagttct    1080
tcgtcatctt ctcagcctga acacagtgcc atgttggtct ctactgcagc ttctccttca    1140
ctgattaaag aaaccaccac tggttactat aaagacatag tagaaaatat ttgcggtaga    1200
gagaaaagtg gaattcaacc attatgtcct gagaggtccc atatttcaga tcaatcgcct    1260
ctctccagta aaaggaaagc actagaagag tctgagagct cacaactaat ttctccgcca    1320
cttgcccagg caatcagaga ttatgtcaat tctctgttgg tccagggtgg ggtaggtagt    1380
ttgcctggaa cttctaactc tatgccccca ctggatgtag aaaacataca gaagagaatt    1440
gatcagtcta gtttcaaga aactgaattc ctgtctcctc caagaaaagt ccctagactg    1500
agtgagaagt cagtggagga aagggattca ggttcctttg tggcatttca gaacatacct    1560
ggatccgaac tgatgtcttc ttttgccaaa actgttgtct ctcattcact cactacctta    1620
ggtctagaag tggctaagca atcacagcat gataaaatag atgcctcaga actatcttttt    1680 cccttccatg aatctatttt aaagtaatt gaagaagaat ggcagcaagt tgacaggcag    1740
ctgccttcac tggcatgcaa atatccagtt tcttccaggg aggcaacaca gatattatca    1800
gttccaaaag tagatgatga aatcctaggg tttatttctg aagccactcc actaggaggt    1860
```

```
attcaagcag cctccactga gtcttgcaat cagcagttgg acttagcact ctgtagagca    1920
tatgaagctg cagcatcagc attgcagatt gcaactcaca ctgcctttgt agctaaggct    1980
atgcaggcag acattagtca agctgcacag attcttagct cagatcctag tcgtacccac    2040
caagcgcttg ggattctgag caaaacatat gatgcagcct catatatttg tgaagctgca    2100
tttgatgaag tgaagatggc tgcccatacc atgggaaatg ccactgtagg tcgtcgatac    2160
ctctggctga aggattgcaa aattaattta gcttctaaga ataagctggc ttccactccc    2220
tttaaaggtg gaacattatt tggaggagaa gtatgcaaag taattaaaaa gcgtggaaat    2280
aaacactagt aaaattaagg acaaaaagac atctatctta tctttcaggt actttatgcc    2340
aacattttct tttctgttaa ggttgtttta gtttccagat agggctaatt acaaaatgtt    2400
aagcttctac ccatcaaatt acagtataaa agtaattgcc tgtgtagaac tacttgtctt    2460
ttctaaagat ttgcgtagat aggaagcctg                                     2490

<210> SEQ ID NO 127
<211> LENGTH: 1478
<212> TYPE: DNA
<213> ORGANISM: Homo sapiens

<400> SEQUENCE: 127
aagcttggca cgaggataac ttctacattt tgaaaatttt atgtcaatta tttaatagaa     60
tatctctaaa tttaggtttg tctcattttt caatgtaatt ggattcaggt tacgcatttt    120
tgatagatta gagtggtgct gtgttattct tattgcacag gtctgttggg ttgagtgggg    180
tgagttaaat cattcctttt tggcctctca taatactgaa tcaagtgaaa gttggcctga    240
gtcatcagaa gacttgtctc ggctgaatgt acaaggtgct cactgacata cagatccaaa    300
gttgagtcgg actggtctga ctgttggctg aaagctcacc tggggctgcc agaggtcttc    360
aacctagcgt ctccacgtaa cttaagcttc ttatatcatg tgcctaaatt ctgagacaga    420
ggaatagaga agagagaaag gaagagcaag agagagaagg ggagttccga gtgtccattc    480
caagaaactg aggtggaaac tgcaaggctt cttataccag agcattactt tttgtaccag    540
aacattactt ccagtgtatt ctatctgtaa agcaagttat atttagttca catcttgatg    600
tgagaaatag cattgtgtac agggaaaaag aacttgatag ctattttgt agactatctg     660 ataaagatgt ttctgggctg agttaataat gctatgttgg ctatttattt ctgattttct    720
agttctgtca tttcttctac atttattagt tagtctttgt gtcagttggg gttccctagg    780
gaaacagaac caataggata tatctatatc tttacctatg tcccatacag atacacacac    840
acacacacac acacacacac acatccaatc cacacacaca tgtacattca atctgttgat    900
agcctgacta gaacaatagg caaaggcaag gggaaattcg tatctctacc tgactgcttc    960
agctgaaata tcaatcagtc tcttcctgcc ctacactggg accaacatca tgagccctct   1020
ggttcccaga actgtaacac tggctttcct cttccgggg tctccagctt cagacagta    1080 gaatcatgag acttctcagc ctccttaacc atgtgagcca atgccttata acaaatatcc   1140
tacaaacata tatatataaa tgtatacata caaatataat aatatcatac aaatatatat   1200
atttatatgt atacatgtaa ttacatttaa gaacatttaa ggctatttac atgtaaagaa   1260
aggaaaaata atgtaaatat ttgttttcac ctgaaataaa tgtcagacac tgtctttgtt   1320
taaagaaata gtcctcttaa actttgggca atgctgccaa ttcattaac ttacaatgtt    1380 atttcaattg catcaccaga gtaaaatctt agagtattat ttttatctaa taaattaata   1440
```

```
acatccaaaa aaaaaaaaaa aaaaattcct gcggccgc                            1478
```

<210> SEQ ID NO 128
<211> LENGTH: 376
<212> TYPE: DNA
<213> ORGANISM: Homo sapiens
<220> FEATURE:
<221> NAME/KEY: misc_feature
<222> LOCATION: (1)...(376)
<223> OTHER INFORMATION: n = A,T,C or G

<400> SEQUENCE: 128

```
catcactata gggcgaattg gcgtaccggg ccccccctcg agttttttt tttttttttt       60
tttttaacc aagctaaggc actaccagaa atttcaagga taatgattct ggccactaga     120
gaatgaaaac agcattggca atacttattt ttaatcatat ctagttgaca tagaaacaaa    180
caatctttt ctagggaaaa aaaagccaat tctgtgttac atccttgtta gaacattgtg     240
caattcaaat aagcgagtct gcctcatctt taatagaaat tctctcaaaa agggtttagt    300
gaccactaca gtcaatttta aaacaaatt agctgaattc cctcttactc tgaagtgnta    360
tttcaagtct gggggt                                                    376
```

<210> SEQ ID NO 129
<211> LENGTH: 903
<212> TYPE: DNA
<213> ORGANISM: Homo sapiens

<400> SEQUENCE: 129

```
gaattcggca cgaggtgtca gctcagtgca tcccaggcag ctcttagtgt ggagcagtga     60
actgtctgtg gttccttcta cttggggatc atgcagagag cttcacgtct gaagagagag   120
ctgcacatgt tagccacaga gccacccca ggcatcacat gttggcaaga taaagaccaa    180
atggatgacc tgcgagctca aatattaggt ggagccaaca cacctatga gaaaggtgtt    240
tttaagctag aagttatcat tcctgagagg tacccatttg aacctcctca gatccgattt    300
ctcactccaa tttatcatcc aaacattgat tctgctggaa ggatttgtct ggatgttctc   360
aaattgccac caaaggtgc ttggagacca tccctcaaca tcgcaactgt gttgacctct    420
attcagctga tcatgtcaga acccaaccct gatgacccgc tcatggctga catatcctca   480
gaatttaaat ataataagcc agccttcctc aagaatgcca gacagtggac agagaagcat   540
gcaagacaga aacaaaaggc tgatgaggaa gagatgcttg ataatctacc agaggctggt   600
gactccagag tacacaactc aacacagaaa aggaaggcca gtcagctagt aggcatagaa   660
aagaaatttc atcctgatgt ttaggggact tgtcctggtt catcttagtt aatgtgttct   720
ttgccaaggt gatctaagtt gcctaccttg aatttttttt taaatatatt tgatgacata   780
attttgtgt agtttatta tcttgtacat atgtattttg aaatctttta aacctgaaaa    840
ataaatagtc atttaatgtt gaaaaaaaaa aaaaaaaaa aagatcttta attaagcggc     900
cgc                                                                  903
```

<210> SEQ ID NO 130
<211> LENGTH: 1140
<212> TYPE: DNA
<213> ORGANISM: Homo sapiens
<220> FEATURE:
<221> NAME/KEY: misc_feature
<222> LOCATION: (1)...(1140)
<223> OTHER INFORMATION: n = A,T,C or G

<400> SEQUENCE: 130

```
ctggcgctgc tggggctcgg cgncggcctt tgtctgcggg cacggccgct gcggtgctca      60
ggaacagccc atggaagaat catatgaaga ggtggtgact gaggtcgtaa gcaggagtgg     120
acatgtttgg atttccaaca gctaccctgc tggactgtca tggaagatat gcccagaatg     180
tagcgttctt caatgtgatg actgaagccc accacaaata tgaccactct gaggctacag     240
gatcctcaag ctgggatatc caaaattctt tcagaagaga aagctggaa caaaaatccc      300 cagattcgaa gacactacag gaagattcac ctggagtgag acaaagggtc tatgagtgcc     360
aggagtgtgg aaaatccttc cggcaaaaag gtagtctaac gttacatgag agaatccaca     420
ctggtcaaaa gccttttgag tgcacccact gtggaaaaag cttcagggcc aaaggcaatc     480
ttgttacaca tcaacggata cacgggagag aagcctta tcagtgcaag gagtgtggga      540
aaagcttcag tcaacgaggt agtctcgctg tccacgagag actccacact ggacagaaac     600
cctacgagtg tgctatttgt cagagaagct tcaggaatca gagtaacctt gctgttcaca     660
ggagagttca cagtggtgag aagccctata gatgtgatca gtgtggaaaa gccttcagtc     720 agaaggaag cttaattgtt cacatcgag tccacacagg cctgaagccc tatgcctgta      780
cccagtgcag gaagagtttc cacaccaggg ggaattgtat tctgcatggc aaaatccaca     840
caggagagac accctatctg tgcggccagt gtggaaaaag cttcacccag agagggagtc     900
tggctgtgca ccagcgaagc tgctcacaga ggctcaccct ttgaccactt tcctgaagag     960
aagttctctt tatgaattaa gagtacaaaa tcctctgaga tgaagcaacc tatccagttc    1020
tatggaatga atggagaatc tttcagaaag accatcattg ggtagggcaa actgattttt    1080 ttccttccc ccaaaagagt atgaaaaata aggtcttgt ttattatcat taaaaaaaaa     1140

<210> SEQ ID NO 131
<211> LENGTH: 1337
<212> TYPE: DNA
<213> ORGANISM: Homo sapiens

<400> SEQUENCE: 131
aagcttggca cgagggcagt ctcatgataa tccaagtaac tctctgtgtg aagcacctttt    60 gaacatttca cgtgatactt tgtgttcaga tgaatacttt gctggtggct tacactcatc     120
ttttgatgat ctttgtggaa actcaggatg tggaaatcag gaaaggaagt tggaaggatc     180
cattaatgac attaaaagtg atgtgtgtat ttcttcactt gtattgaaag caaataatat     240
tcattcatca ccatctttca ctcacctcga taatcaagt cctcagaaat ttctgagtaa      300
tctttcaaag gaagaaataa acttgcaaag aaatattgca ggtaaagtag tcaccccctca    360 ccaaaagcag gctgcaggta tgtctcagga gacgtttgaa gagaagtatc gtttgtctcc     420
taccttatct tcaacaaaag gccaccttttt gatacattca agacccagga gttcctcagt     480
aaagagaaaa agagtatcac atggctccca ttcacctccg aaggaaaaat gcaagagaaa     540
gaggagcacc aggagatcta tcatgccgag gctgcagctg tgcaggtcgg aaggcaggct     600
gcagcacgtg gcgggacctg ccctggaggc tcttagctgt ggggagtctt catatgatga     660 ctattttca cctgataatc ttaaggaaag gtattcagag aatcttcctc ctgaatctca     720
gctgccatca agccctgctc agttgagctg cagaagtctt tctaagaagg agagaacaag     780
catatttgaa atgtctgatt tttcctgcgt tggcaaaaaa accagaacag ttgacattac     840
caatttcaca gcaaaaacca tctccagtcc tcggaaaact ggaaatggtg aaggccgtgc     900
aacttcgagt tgcgtgactt ctgcccctga agaagcccta aggtgtttgta gacaggctgg    960
```

-continued

| gaaagaagac gcatgcccag agggaaatgg cttttcttac accattgagg accctgctct | 1020 |
| tccaaaagga catgatgatg atttaactcc tttggaagga agccttgaag aaatgaaaga | 1080 |
| agcggttggt ctgaaaagca cacagaacaa aggtaccact tccaaaatat caaactcctc | 1140 |
| tgaaggcgaa gcccagagtg aacatgagcc atgttttata gttgactgta acatggagac | 1200 |
| atctacagaa gagaaggaaa acttacccgg aggatacagt ggaagtatgt gaatctcctt | 1260 |
| ttccaagtca ccttcgctaa ataaacatgt aacagtgcat ccataaaaaa aaaaaaaaaa | 1320 |
| aaaattcctg cggccgc | 1337 |

<210> SEQ ID NO 132
<211> LENGTH: 492
<212> TYPE: DNA
<213> ORGANISM: Homo sapiens
<220> FEATURE:
<221> NAME/KEY: misc_feature
<222> LOCATION: (1)...(492)
<223> OTHER INFORMATION: n = A,T,C or G

<400> SEQUENCE: 132

| aataagcttg cggccgcgan nccggagcct gcccgcgcgc ccccggaacc cgcgcccccg | 60 |
| gccgaggcca ccggggaccc ggcnccgtcc cgcccctgct gccccgagc cggcggcctc | 120 |
| ncccgnnggg ccggaggganc ctggagagcc cgcggggctg ggggagctcg gggagcctgc | 180 |
| gggaccgggg gagcccgaag ggccanggga tcccgcggng gngccagcgg aggcggagga | 240 |
| gcaggcggtg gaggcgaggc aggaagagga gcaggacttg gatggtgaga aggggccatc | 300 |
| atcggaaggg cctgacgagg angacngaga aggcttctcc ttnaaataca gccccggnaa | 360 |
| gctnanggga aaccagtacn ngaagatgat gaccaaagag ganctggang aggagcagat | 420 |
| gatnganctg acctntgacc tcacttccct gtagcaagtt ccttangtcc tgagccacaa | 480 |
| atattcttgc aa | 492 |

<210> SEQ ID NO 133
<211> LENGTH: 693
<212> TYPE: DNA
<213> ORGANISM: Homo sapiens

<400> SEQUENCE: 133

| ctcgaggcca agaattcggc acgaggctga gagggtgggt ctgagtcccc acaatgtctg | 60 |
| aagctgcccc tgggattctc aggccaacct gccaacagca agcggatttt cttgcaagat | 120 |
| cagggacccc atttctgcag ccagtgtctc ctgggtgcct tctgaggact cccaccccca | 180 |
| tcccagtatc tcatctgtcc cctctcctgg ggcttaagtg ggttgcttcc aggcagaagc | 240 |
| agccaaggac cgattccagg cactttctgt agcaaatgac tgtgaattac gacttctctt | 300 |
| gcccttcttc tagcagtctg tgcctcctct ctgaccagtt tggagggcac tgaagaaagg | 360 |
| caagggccgt gctgctgctg gcggggcag gagaggagcc tggccagtgt gccacattaa | 420 |
| atacccgtgc aggcgcggag aagcaaccgg cacccccttc cggcctgaaa gccctccctg | 480 |
| caagaaggtg tgcaggagag aagaggcccc ggcatgggga tctggttct agagggcatg | 540 |
| tgatgactgt aaatgttcac tgggtgggta gggagtggta tccagtgttc aagtgcagaa | 600 |
| atctttggct ttgctaccag ttccatatga tgagaaataa acgttcgctg aggttttgtt | 660 |
| tcaaaaaaaa aaaaaaaaaa aaaggcggc cgc | 693 |

<210> SEQ ID NO 134
<211> LENGTH: 1855

<212> TYPE: DNA
<213> ORGANISM: Homo sapiens

<400> SEQUENCE: 134

| | | | | | |
|---|---|---|---|---|---|
| cctcaggccg | gctgtgaacg | tagttcctga | gagatagcaa | acatgcccaa | cagtgagccc | 60 |
| gcatctctgc | tggagctgtt | caacagcatc | gccacacaag | gggagctcgt | aaggtccctc | 120 |
| aaagcgggaa | atgcgtcaaa | ggatgaaatt | gattctgcag | taaagatgtt | ggtgtcatta | 180 |
| aaaatgagct | acaaagctgc | cgcgggggag | gattacaagg | ctgactgtcc | tccagggaac | 240 |
| ccagcaccta | ccagtaatca | tggcccagat | gccacagaag | ctgaagagga | ttttgtggac | 300 |
| ccatggacag | tacagacaag | cagtgcaaaa | ggcatagact | acgataagct | cattgttcgg | 360 |
| tttggaagta | gtaaaattga | caaagagcta | ataaaccgaa | tagagagagc | caccggccaa | 420 |
| agaccacacc | acttcctgcg | cagaggcatc | ttcttctcac | acagagatat | gaatcaggtt | 480 |
| cttgatgcct | atgaaaataa | gaagccattt | tatctgtaca | cgggccgggg | ccctcttct | 540 |
| gaagcaatgc | atgtaggtca | cctcattcca | tttatttca | caaagtggct | ccaggatgta | 600 |
| tttaacgtgc | ccttggtgat | ccagatgacg | gatgacgaga | agtatctgtg | gaaggacctg | 660 |
| accctggacc | aggcctatag | ctatgctgtg | gagaatgcca | aggacatcat | cgcctgtggc | 720 |
| tttgacatca | acaagacttt | catattctct | gacctggact | catggggat | gagctcaggt | 780 |
| ttctacaaaa | atgtggtgaa | gattcaaaag | catgttacct | tcaaccaagt | gaaaggcatt | 840 |
| tcggcttca | ctgacagcga | ctgcattggg | aagatcagtt | ttcctgccat | ccaggctgct | 900 |
| ccctccttca | gcaactcatt | cccacagatc | ttccgagaca | ggacggatat | ccagtgcctt | 960 |
| atcccatgtg | ccattgacca | ggatccttac | tttagaatga | caagggacgt | cgcccccagg | 1020 |
| atcggctatc | ctaaaccagc | cctgttgcac | tccaccttct | tcccagccct | gcaggcgcc | 1080 |
| cagaccaaaa | tgagtgccag | cgaccccaac | tcctccatct | tcctcaccga | cacggccaag | 1140 |
| cagatcaaaa | ccaaggtcaa | taagcatgcg | ttttctggag | ggagagacac | catcgaggag | 1200 |
| cacaggcagt | ttgggggcaa | ctgtgatgtg | gacgtgtctt | tcatgtacct | gaccttcttc | 1260 |
| ctcgaggacg | acgacaagct | cgagcagatc | aggaaggatt | acaccagcgg | agccatgctc | 1320 |
| accggtgagc | tcaagaaggc | actcatagag | gttctgcagc | ccttgatcgc | agagcaccag | 1380 |
| gcccggcgca | aggaggtcac | ggatgagata | gtgaaagagt | tcatgactcc | ccggaagctg | 1440 |
| tccttcgact | ttcagtagca | ctcgttttac | atatgcttat | aaaagaagtg | atgtatcagt | 1500 |
| aatgtatcaa | taatcccagc | ccagtcaaag | caccgccacc | tgtaggcttc | tgtctcatgg | 1560 |
| taattactgg | gcctggcctc | tgtaagcctg | tgtatgttat | caatactgtt | tcttcctgtg | 1620 |
| agttccatta | tttctatctc | ttatgggcaa | agcattgtgg | gtaattggtg | ctggctaaca | 1680 |
| ttgcatggtc | ggatagagaa | gtccagctgt | gagtctctcc | ccaaagcagc | cccacagtgg | 1740 |
| agcctttggc | tggaagtcca | tgggccaccc | tgttcttgtc | catggaggac | tccgagggtt | 1800 |
| ccaagtatac | tcttaagacc | cactctgttt | aaaaatatat | attctatgta | tgcgt | 1855 |

<210> SEQ ID NO 135
<211> LENGTH: 2559
<212> TYPE: DNA
<213> ORGANISM: Homo sapiens

<400> SEQUENCE: 135

| | | | | | |
|---|---|---|---|---|---|
| ggaattccgg | aattccgaat | gcgtcggaaa | gagcgggagt | gtgcgccgcg | cgagagtggg | 60 |
| aggcgaaggg | ggcaggccag | ggagaggcgc | aggagccttt | gcagccacgc | gcgcgcgctt | 120 |

```
ccctgtcttg tgtgcttcgc gaggtagagc gggcgccggc agcggcgggg attactttgc    180
tgctagtttc ggttgccggc agcggcgggt gtagtctcgg cggcagcggc ggagacacta    240
gcactatgtc ggaggagcag ttcggcggga cggggcggcg gcacgcgaac ggcggcggta    300
ggcgctcggc gggcgacgag gagggagcca tggtggcggc gacacagggg gcagcggcgg    360
cgcgggaagc ggacgcggga ccggggcgg aaccgcgtct ggaggcaccg aagggcagcg    420
ccgagtcgga gggggcgaag attgacgcca gtaagaacga ggaggatgaa gggaaaatgt    480
ttataggagg ccttagctgg gacactacaa agaaagatct gaaggactac ttttccaaat    540
ttggtgaagt tgtagactgc actctgaagt tagatcctat cacagggcga tcaaggggtt    600
ttggctttgt gctatttaaa gaatcggaga gtgtagataa ggtcatggat caaaagaac    660
ataaattgaa tgggaaggtg attgatccta aaagggccaa agccatgaaa acaaaagagc    720
cggttaaaaa aatttttgtt ggtggccttt ctccagatac acctgaagag aaaataaggg    780
agtactttgg tggttttggt gaggtggaat ccatagagct ccccatggac aacaagacca    840
ataagaggcg tgggttctgc tttattacct ttaaggaaga agaaccagtg aagaagataa    900
tggaaaagaa ataccacaat gttggtctta gtaaatgtga aataaaagta gccatgtcga    960
aggaacaata tcagcaacag caacagtggg gatctagagg aggatttgca ggaagagctc    1020
gtgggaatt ccggaattcc tcagaggcag gagaaggctt ggagctaccc ccaaactcaa    1080
tccactgttg gcagctgagc gtgtagtagg gtggtcctag ccatacagaa ccacttctct    1140
gtctccctcc tcttccctgg ttcgtccagc cccagtccat cagggaccac ctgggcagcc    1200
tcccagagat gggatcgggt tggggctaag ggcatcgggt ctgtcgcagc cagggtgca    1260
ggaggatcgc tgtgctgtga ccgttcagc tggctcccga cgaaggaggc acggaaccag    1320
acagcgcggc gagggcgaga gcgctgcagg caaggcgtag gccccgcggc ggatcttgcc    1380
gaagagcagg acaggctccg agtcctggaa ggggtagtgg ccggccagca tggtgaagag    1440
cgccacgccc aggctccaga catcggctgc cttgcccgag tatgaggccc gtgagctgag    1500
tatctcaggt cccacgtagg ctggcgacgc gtgcttgtcc acagggaatc atctggccca    1560
gtcagcacgc aggagtcctc caggttctcc agcaccagct tcttcctggg acatggggag    1620
aaacagaagg tcaggtcct acccagaacc cccatgctat cacccttgtg gcacccactt    1680
tccaagtcgc tgctggcctt tgacagacac aagccagtcc tgtgatgtct gatcctgttt    1740
tacagatacc caagcccagg ctcagagagg ttaagtcatt taaggccaca gagcaattaa    1800
atttaaacta aaattctgaa aggaatacat ttttcaacag agtccttggg gagggggctg    1860
atggggctga gagggttaag cctctcttaa accagctaca aacttagggt ccaggcaggt    1920
aataagatga gagaaacagg aagtgtgcct gacatctcag cacaagcgct acctaaaaag    1980
ggtacacaac gcattctagg gtttaccaag tgcctgctgt gttcctggcc cttgacccag    2040
ctcattacct ggctcacctc attctatcta gctacagcct gcaaggaaga caccatttta    2100
cagctgtaga gcatgggcct gggatgggaa cgctggctgg cagatactca gagccagtgc    2160
tgtgacccac cctctcagtt cccaagatgg ccccacattc ccattgtttt ccccaagaga    2220
agccaggaat tgtattttaa tgaaaaggtc cccatttaaa aaatattggc aaaccagttt    2280
atataaaaaa cacaaacagg taagcagggc aaaaaaaaaa gtgtgtaagg ctgggcgcgg    2340
tgctcatgcc cggtaatcct agcactttgg gagcgcgagg caggggatc acttgagttc    2400
aggagttcaa gaccagcctg gcaacacgg taaaaaccta tctctacaaa aaatacgaaa    2460
attagcaggc atggtgattc gcacctgtag tcccagctac ttgggaggct gatcttgaac    2520
```
tcctgaactc aagtgatccc cctgcctcgg ccggaattc                          2559

<210> SEQ ID NO 136
<211> LENGTH: 895
<212> TYPE: DNA
<213> ORGANISM: Homo sapiens

<400> SEQUENCE: 136
agagacttaa gtctaaggca ctgagcgtat catgttaaag atgagcggt ggcagcgaca      60
gagccaaaat cagagctgga acctgaggag agagtgttca agaaggaagt gtatcttcat    120
acatcaccac acctgaaagc agatgtgctt ttccagactg atccaactgc agagatggca    180
gctgagtcat tgcctttctc ttcggacact gtcagctggg agctggaagc ctggtatgag    240
gacctgcaag aggtcctgtc ttcagatgaa atgggggta cctatgtttc acctcctgga     300
aatgaagagg aagaatcaaa atcttcacc actcttgacc ctgcttctct ggcttggctg     360
actgaggagg agccagaacc agcagaggtc acaagcacct cccagagccc tcactctcca    420
gattccagtc agagctccct ggctcaggag gagaggagg aagaccaagg gagaaccagg     480
aaacggaaac agagtggtca ttccccagcc cgggctggaa agcagcgcat gaaggagaaa    540
gaacaggaga atgaaaggaa agtggcacag ctagctgaag agaatgaacg gctcaagcag    600
gaaatcgagc gcctgaccag ggaagtagag gcgactcgcc gagctctgat tgaccgaatg    660
gtgaatctgc accaagcatg aacaattggg agcatcagtc ccccacttgg gccacactac    720
ccacctttcc cagaagtggc tactgactac cctctcacta gtgccaatga tgtgaccctc    780
aatcccacat acgcagggg aaggcttgga gtagacaaaa ggaaaggtct cagcttgtat     840
atagagattg tacatttatt tattactgtc cctatctatt aaagtgactt tctat         895

<210> SEQ ID NO 137
<211> LENGTH: 1860
<212> TYPE: DNA
<213> ORGANISM: Homo sapiens

<400> SEQUENCE: 137
cgtgaacggt cgttgcagag attgcgggcg gctgagacgc cgcctgcctg gcacctagga     60
gcgcagcgga gccccgacac cgccgccgcc gccatggagt ccgagaccga acccgagccc    120
gtcacgctcc tggtgaagag ccccaaccag cgccaccgcg acttggagct gagtggcgac    180
cgcggctgga gtgtgggcca cctcaaggcc cacctgagcc gcgtctaccc cgagcgtccg    240
cgtccagagg accagaggtt aatttattct gggaagctgt tgttggatca ccaatgtctc    300
agggacttgc ttccaaagca ggaaaaacgg catgttttgc atctggtgtg caatgtgaag    360
agtccttcaa aaatgccaga atcaacgcc aaggtggctg aatccacaga ggagcctgct    420
ggttctaatc ggggacagta tcctgaggat tcctcaagtg atggtttaag gcaaagggaa    480
gttcttcgga acctttcttc ccctggatgg gaaaacatct caaggcctga agctgcccag    540
caggcattcc aaggcctggg tcctggtttc tccggttaca cacctatgg gtggcttcag    600
cttttcctggt tccagcagat atatgcacga cagtactaca tgcaatattt agcagccact    660
gctgcatcag gggcttttgt tccaccacca agtgcacaag atacctgt ggtctctgca      720
cctgctccag ccctattca caaccagttt ccagctgaaa accagcctgc caatcagaat     780
gctgctcctc aagtggttgt taatcctgga gccaatcaaa atttgcggat gaatgcacaa    840
ggtggcccta ttgtggaaga agatgatgaa ataaatcgag attggttgga ttggacctat    900

-continued

```
tcagcagcta catttctgt ttttctcagt atcctctact tctactcctc cctgagcaga      960
ttcctcatgg tcatgggggc caccgttgtt atgtacctgc atcacgttgg gtggtttcca    1020
tttagaccga ggccggttca gaacttccca aatgatggtc ctcctcctga cgttgtaaat    1080
caggacccca acaataactt acaggaaggc actgatcctg aaactgaaga ccccaaccac    1140
ctccctccag acagggatgt actagatggc gagcagacca gcccctcctt tatgagcaca    1200
gcatggcttg tcttcaagac tttctttgcc tctcttcttc cagaaggccc cccagccatc    1260
gcaaactgat ggtgtttgtg ctgtagctgt tggaggcttt gacaggaatg gactggatca    1320
cctgactcca gctagattgc ctctcctgga catggcaatg atgagttttt aaaaaacagt    1380
gtggatgatg atatgctttt gtgagcaagc aaaagcagaa acgtgaagcc gtgatacaaa    1440
ttggtgaaca aaaaatgccc aaggcttctc atgtgtttat tctgaagagc tttaatatat    1500
actctatgta gtttaataag cactgtacgt agaaggcctt aggtgttgca tgtctatgct    1560
tgaggaactt ttccaaatgt gtgtgtctgc atgtgtgttt gtacatagaa gtcatagatg    1620
cagaagtggt tctgctggta agatttgatt cctgttggaa tgtttaaatt acactaagtg    1680
tactacttta tataatcaat gaaattgcta gacatgtttt agcaggactt ttctaggaaa    1740
gacttatgta taattgcttt ttaaaatgca gtgctttact ttaaactaag gggaactttg    1800
cggaggtgaa aacctttgct gggttttctg ttcaataaag ttttactatg aatgaccctg    1860
```

<210> SEQ ID NO 138
<211> LENGTH: 2074
<212> TYPE: DNA
<213> ORGANISM: Homo sapiens

<400> SEQUENCE: 138

```
gaattcggca cgaggcgcgg cggctgcgac cgggacggcc catttccgc cagctcgccg       60
ctcgctatgg cgtcgctcac cgtgaaggcc taccttctgg gcaaggagga cgcggcgcgc     120
gagattcgcc gcttcagctt ctgctgcagc cccgagcctg aggcggaagc cgaggctgcg     180
gcgggtccgg gaccctgcga gcggctgctg agccgggtgg ccgccctgtt ccccgcgctg     240
cggcctggcg gcttccaggc gcactaccgc gatgaggacg gggacttggt tgccttttcc     300
agtgacgagg aattgacaat ggccatgtcc tacgtgaagg atgacatctt ccgaatctac     360
attaaagaga aaaagagtg ccggcgggac caccgcccac cgtgtgctca ggaggcgccc     420
cgcaacatgg tgcaccccaa tgtgatctgc gatggctgca atgggcctgt ggtaggaacc     480
cgctacaagt gcagcgtctg cccagactac gacttgtgta gcgtctgcga gggaaagggc     540
ttgcaccggg gcacaccaa gctcgcattc cccagcccct tcgggcacct gtctgagggc     600
ttctcgcaca gccgctggct ccggaaggtg aaacacggac acttcgggtg ccaggatgg     660
gaaatgggtc caccaggaaa ctggagccca cgtcctcctc gtgcagggga ggcccgccct     720
ggccccacgg cagaatcagc ttctggtcca tcggaggatc cgagtgtgaa tttcctgaag     780
aacgttgggg agagtgtggc agctgcccctt agcctctgg gcattgaagt tgatatcgat    840
gtggagcacg gaggaaaag aagccgcctg accccgtct ctccagagag ttccagcaca     900
gaggagaaga gcagctcaca gccaagcagc tgctgctctg accccagcaa gccgggtggg     960
aatgttgagg gcgccacgca gtctctggcg gagcagatga ggaagatcgc cttggagtcc    1020
gaggggcgcc ctgaggaaca gatggagtcg gataactgtt caggaggaga tgatgactgg    1080
acccatctgt cttcaaaaga agtggaccg tctacaggtg aactccagtc cctacagatg    1140
ccagaatccg aagggccaag ctctctggac ccctcccagg agggacccac agggctgaag    1200
```

```
gaagctgcct tgtacccaca tctcccgcca gaggctgacc cgcggctgat tgagtccctc   1260
tcccagatgc tgtccatggg cttctctgat gaaggcggct ggctcaccag gctcctgcag   1320
accaagaact atgacatcgg agcggctctg gacaccatcc agtattcaaa gcatccccg    1380 ccgttgtgac acttttgcc cacctcttct gcgtgcccct cttctgtctc atagttgtgt    1440
taagcttgcg tagaattgca ggtctctgta cgggccagtt tctctgcctt cttccaggat   1500
caggggttag ggtgcaagaa gccatttagg gcagcaaaac aagtgacatg aagggagggt   1560
ccctgtgtgt gtgtgtgctg atgtttcctg ggtgccctgg ctccttgcag cagggctggg   1620
cctgcgagac ccaaggctca ctgcagcgcg ctcctgaccc ctccctgcag gggctacgtt   1680
agcagcccca cacatagctt gcctaatggc tttcactttc tcttttgttt taaatgactc   1740
ataggtccct gacatttagt tgattatttt ctgctacaga cctggtacac tctgattta    1800 gataaagtaa gcctaggtgt tgtcagcagg caggctgggg aggccagtgt tgtgggcttc   1860
ctgctgggac tgagaaggct cacgaagggc atccgcaatg ttggtttcac tgagagctgc   1920
ctcctggtct cttcaccact gtagttctct catttccaaa ccatcagctg cttttaaaat   1980
aagatctctt tgtagccatc ctgttaaatt tgtaaacaat ctaattaaat ggcatcagca   2040
ctttaaccaa taaaaaaaaa aaaaaaaaa aaaa                                2074

<210> SEQ ID NO 139
<211> LENGTH: 3500
<212> TYPE: DNA
<213> ORGANISM: Homo sapiens

<400> SEQUENCE: 139
ttgtgaaggg cgcgggtggg gggcgctgcc ggcctcgtgg gtacgttcgt gccgcgtctg     60
tcccagagct ggggccgcag gagcggaggc aagaggggca ctatggcaga caaagttagg   120
aggcagaggc cgaggaggcg agtctgttgg gccttggtgg ctgtgctctt ggcagacctg   180
ttggcactga gtgatacact ggcagtgatg tctgtggacc tgggcagtga gtccatgaag   240
gtggccattg tcaaacctgg agtgcccatg gaaattgtct tgaataagga atctcggagg   300
aaaacaccgg tgatcgtgac cctgaaagaa atgaaagat tctttggaga cagtgcagca   360
agcatggcga ttaagaatcc aaaggctacg ctacgttact tccagcacct cctggggaag   420
caggcagata ccccccatgt agctctttac caggcccgct tcccggagca cgagctgact   480
ttcgacccac agaggcagac tgtgcacttt cagatcagct cgcagctgca gttctcacct   540
gaggaagtgt tgggcatggt tctcaattat tctcgttctc tagctgaaga ttttgcagag   600
cagcccatca aggatgcagt gatcaccgtg ccagtcttct tcaaccaggc cgagcgccga   660
gctgtgctgc aggctgctcg tatggctggc ctcaaagtgc tgcagctcat caatgacaac   720
accgccactg ccctcagcta tggtgtcttc cgccggaaag atattaacac cactgcccag   780
aatatcatgt tctatgacat gggctcaggc agcaccgtat gcaccattgt gacctaccag   840
atggtgaaga ctaaggaagc tgggatgcag ccacagctgc agatccgggg agtaggattt   900
gaccgtaccc tggggggcct ggagatggag ctccggcttc gagaacgcct ggctgggctt   960
ttcaatgagc agcgcaaggg tcagagagca aaggatgtgc gggagaaccc gcgtgccatg   1020
gccaagctgc tgcgtgaggc taatcggctc aaaaccgtcc tcagtgccaa cgctgaccac   1080
atggcacaga ttgaaggcct gatggatgat gtggacttca aggcaaaagt gactcgtgtg   1140
gaatttgagg agttgtgtgc agacttgttt gagcgggtgc ctgggcctgt acagcaggcc   1200
```

-continued

```
ctccagagtg ccgaaatgag tctggatgag attgagcagg tgatcctggt gggtggggcc    1260
actcgggtcc ccagagttca ggaggtgctg ctgaaggccg tgggcaagga ggagctgggg    1320
aagaacatca atgcagatga agcagccgcc atggggcag tgtaccaggc agctgcgctc    1380
agcaaagcct ttaaagtgaa gccatttgtc gtccgagatg cagtggtcta ccccatcctg    1440
gtggagttca cgagggaggt ggaggaggag cctgggattc acagcctgaa gcacaataaa    1500
cgggtactct tctctcggat ggggcctac cctcaacgca aagtcatcac ctttaaccgc    1560
tacagccatg atttcaactt ccacatcaac tacggcgacc tgggcttcct ggggcctgaa    1620
gatcttcggg tatttggctc ccagaatctg accacagtga agctaaaagg ggtgggtgac    1680
agcttcaaga agtatcctga ctacgagtcc aagggcatca aggctcactt caacctggat    1740
gagagtggcg tgctcagtct agacaggtg gagtctgtat ttgagacact ggtagaggac    1800
agcgcagaag aggaatctac tctcaccaaa cttggcaaca ccatttccag cctgtttgga    1860
ggcggtacca caccagatgc caaggagaat ggtactgata ctgtccagga ggaagaggag    1920
agccctgcag aggggagcaa ggacgagcct ggggagcagg tggagctcaa ggaggaagct    1980
gaggccccag tggaggatgg ctctcagccc ccaccccctg aacctaaggg agatgcaacc    2040
cctgagggag aaaaggccac agaaaaagaa aatggggaca gtctgaggc ccagaaacca    2100 agtgagaagg cagaggcagg gcctgagggc gtcgctccag ccccagaggg agagaagaag    2160
cagaagcccg ccaggaagcg gcgaatggta gaggagatcg gggtggagct ggttgttctg    2220
gacctgcctg acttgccaga ggataagctg gctcagtcgg tgcagaaact tcaggacttg    2280
acactccgag acctggagaa gcaggaacgg gaaaaagctg ccaacagctt ggaagcgttc    2340
atatttgaga cccaggacaa gctgtaccag cccgagtacc aggaagtgtc cacagaggag    2400
cagcgtgagg agatctctgg gaagctcagc gccgcatcca cctggctgga ggatgagggt    2460
gttggagcca ccacagtgat gttgaaggag aagctggctg agctgaggaa gctgtgccaa    2520
gggctgtttt ttcgggtaga ggagcgcaag aagtggcccg aacggctgtc tgccctcgat    2580
aatctcctca accattccag catgttcctc aaggggggcc ggctcatccc agagatggac    2640
cagatcttca ctgaggtgga gatgacaacg ttagagaaag tcatcaatga gacctgggcc    2700
tggaagaatg caactctggc cgagcaggct aagctgcccg ccacagagaa gcctgtgttg    2760
ctctcaaaag acattgaagc taagatgatg gccctggacc gagaggtgca gtatctgctc    2820
aataaggcca agtttaccaa gccccggccc cggcctaagg acaagaatgg gacccgggca    2880
gagccacccc tcaatgccag tgccagtgac caggggggaga aggtcatccc tccagcaggc    2940
cagactgaaa tgcagagcc catttcagaa cctgagaaag tagagactgg atccgagcca    3000
ggagacactg agcctttgga gttaggaggt cctggagcag aacctgaaca gaaagaacaa    3060
tcgacaggac agaagcggcc tttgaagaac gacgaactat aaccccccacc tctgttttcc    3120 ccattcatct ccaccccctt ccccccaccac ttctatttat ttaacatcga gggttggggg    3180
aggggttggt cctgccctcg gctggagttc ctttctcacc cctgtgattt ggaggtgtgg    3240 agaagggaa gggagggaca gctcactggt tccttctgca gtacctctgt ggttaaaaat    3300
ggaaactgtt ctcctcccca gccccactcc ctgttcccta cccatatagg ccctaaattt    3360
gggaaaaatc actattaatt tctgaatcct ttgcctgtgg gtaggaagag aatggctgcc    3420
agtggctgat gggtcccggt gatgggaagg gtatcaggtt gctggggagt ttccactctt    3480
ctctggtgat tgttccttcc                                              3500
```

<210> SEQ ID NO 140
<211> LENGTH: 5468
<212> TYPE: DNA
<213> ORGANISM: Homo sapiens

<400> SEQUENCE: 140

| | | | | | |
|---|---|---|---|---|---|
| cccggggtca | ctcctgctgg | acctactccg | accccctagg | ccgggagtga | aggcgggact | 60 |
| tgtgcggtta | ccagcggaaa | tgcctcgggg | tcagaagtcg | caggagagat | agacagctgc | 120 |
| tgaaccaatg | ggaccagcgg | atggggcgga | tgttatctac | cattggtgaa | cgttagaaac | 180 |
| gaatagcagc | catgaatcag | ctgggggggc | ggagcagtga | cgtttattgc | ggagggggcc | 240 |
| gcttcgaatc | ggcggcggcc | agcttggtgg | cctgggccaa | tgaacggcct | ccaacgagca | 300 |
| gggccttcac | caatcggcgg | cctccacgac | ggggctgggg | gagggtatat | aagccgagta | 360 |
| ggcgacggtg | aggtcgacgc | cggccaagac | agcacagaca | gattgaccta | ttggggtgtt | 420 |
| tcgcgagtgt | gagagggaag | cgccgcggcc | tgtatttcta | gacctgccct | tcgcctggtt | 480 |
| cgtggcgcct | tgtgaccccg | ggcccctgcc | gcctgcaagt | cgaaattgcg | ctgtgctcct | 540 |
| gtgctacggc | ctgtggctgg | actgcctgct | gctgcccaac | tggctggcaa | gatgaagctc | 600 |
| tccctggtgg | ccgcgatgct | gctgctgctc | agcgcggcgc | gggccgagga | ggaggacaag | 660 |
| aaggaggacg | tgggcacggt | ggtcggcatc | gacttgggga | ccacctactc | ctggtaagtg | 720 |
| gggttgcgga | tgaggggggac | ggggcgtggc | gctggctggc | gtgagaagtg | cggtgctgat | 780 |
| gtccctctgt | cgggttttttg | cagcgtcggc | gtgttcaaga | acggccgcgt | ggagatcatc | 840 |
| gccaacgatc | agggcaaccg | catcacgccg | tcctatgtcg | ccttcactcc | tgaaggggaa | 900 |
| cgtctgattg | gcgatgccgc | caagaaccag | ctcacctcca | accccgagaa | cacggtcttt | 960 |
| gacgccaagc | ggctcatcgg | ccgcacgtgg | aatgacccgt | ctgtgcagca | ggacatcaag | 1020 |
| ttcttgccgt | tcaaggttcg | accggttttc | ctcatccagt | tagagaacgg | gtgggtggtg | 1080 |
| ggagtattta | gagttataag | tctctggaaa | agtgttgaga | caacagttga | aggttataga | 1140 |
| catgatgtat | gtaataactt | taatactatt | agtatgttac | aaaacttaag | acagttgctg | 1200 |
| tcgtactgtc | tacgatagtt | taggaataaa | agaccgatta | aaactgaact | ttgtaagaca | 1260 |
| cctatactcc | ctgaagtatt | tctagtcaat | ttgcagcccc | aagggaccaa | aataaaccaa | 1320 |
| attgtgggga | tggtagtggg | tcttttaaac | tttgagatgt | cattgtatct | gtgtctgaaa | 1380 |
| acaataattc | tttaaaatag | gtggttgaaa | agaaaactaa | accatacatt | caagttgata | 1440 |
| ttggaggtgg | gcaaacaaag | acatttgctc | ctgaagaaat | ttctgccatg | gttctcacta | 1500 |
| aaatgaaaga | aaccgctgag | gcttatttgg | gaaagaaggt | aaatatttct | agaacaatgt | 1560 |
| taagtatttt | ttgatcatta | gtattctcgg | ttggctgtta | tgtatagaag | ccttcgtgaa | 1620 |
| gggtttcaaa | aattttaatc | agaatggtat | tcatgcttgt | cacggtttaa | ttattgagtc | 1680 |
| cctttactat | aagccaaaca | aaaatagact | tttcatgtat | tatttaatgc | ttacattcca | 1740 |
| ggaacaataa | aattttatat | gttgtattca | tcaataattg | gcttaaaaac | taaagtgatg | 1800 |
| gtttgactgt | aatttttttt | ttttgagatg | gagtcttgct | ctgttgccca | ggctggactg | 1860 |
| cagtggcacg | atctcagctc | actgcaacct | ctgcctcccg | ggttaagcag | ctctcctgcc | 1920 |
| tcagcctcca | agtaatggaa | cgacaggcac | accaccacag | ctggctaatt | ttttttttt | 1980 |
| tttttaattt | tcagtagaga | cagggtttct | ccacattgcc | aggctggtct | tgaaatcctg | 2040 |
| ccctcaggtt | gatcctcctg | cctagcctcc | caaagtgctg | gattataggc | agaagccacc | 2100 |
| gcctggccag | actgtaattt | aaataagggt | taaactatgt | gacaatacac | ttaattatct | 2160 |

```
ttatccttttt aggttaccca tgcagttgtt actgtaccag cctatttaa tgatgcccaa    2220 cgccaagcaa ccaaagacgc tggaactatt gctggcctaa atgttatgag gatcatcaac    2280
gagccgtaag tatgaaattc agggatacgg catatttgcc aaatagtgga aatgtgaagt    2340
actgacaaaa cttttcctt tttcaatcta atagtacggc agctgctatt gcttatggcc    2400
tggataagag ggagggggag aagaacatcc tggtgtttga cctgggtggc ggaaccttcg    2460
atgtgtctct tctcaccatt gacaatggtg tcttcgaagt tgtggccact aatggagata    2520
ctcatctggg tggagaagac tttgaccagc gtgtcatgga acacttcatc aaactgtaca    2580 aaagaagac gggcaaagat gtcaggaagg acaatagagc tgtgcagaaa ctccggcgcg    2640
aggtagaaaa ggccaaggcc ctgtcttctc agcatcaagc aagaattgaa attgagtcct    2700
tctatgaagg agaagacttt tctgagaccc tgactcgggc caaatttgaa gagctcaaca    2760
tggtatgttc cttgttttct gctttgctaa tgagatctcc ttagactctg aattcaggac    2820
attgcatcta gatacttaga taacagacat cacagtaacc atgtcttttt tctaggatct    2880
gttccggtct actatgaagc ccgtccagaa agtgttggaa gattctgatt tgaagaagtc    2940
tgatattgat gaaattgttc ttgttggtgg ctcgactcga attccaaaga ttcagcaact    3000
ggttaaagag ttcttcaatg gcaaggaacc atcccgtggc ataaacccag atgaagctgt    3060
agcgtatggt gctgctgtcc aggctggtgt gctctctggt gatcaagata caggtaggtc    3120
atcatcgcag catctttctt agtgattcag tagcttgatg gaagagctcg gtaccctat    3180 tgctttagaa ataccagaa tatgagcaac aaggtcacac agctagtaaa gggtataagt    3240
gaagacaaga ctggggtagt ctccaagatc attagcaact gtttaattca ctgcctttaa    3300
aatgtgtgtg ttagaaccta accaaatgtt agagagataa actttacata gctcataggg    3360
agaacttgaa ttaaaagtta aataacttat ccttacaggt gacctggtac tgcttcatgt    3420 atgtccctt acacttggta ttgaaactgt aggaggtgtc atgaccaaac tgattccaag    3480
taatacagtg gtgcctacca agaactctca gatcttttct acagcttctg ataatcaacc    3540
aactgttaca atcaaggtct atgaaggtaa ttaccttaag tttggttaat atcatggctt    3600 ttttttttgag atgaagtctt gctctgttgc ccaggctgga ctgcagtggc acgatctcgg    3660
ctcactgcaa attctgtctc ccgggttcaa gtgattctcc tgcctcagcc tccagagtag    3720
ctggattaca gcctgaccac cacacctggc taatttctgt attttagta gaggatgggc    3780 tttcaccatg tttcccaggc tggtctccaa ctcctgacct caggtcatct gcctgcctcc    3840
accgtcccga aagtactggg attatagcgt gagccaccac gccagatcta tctatcatgg    3900
catattttaa aagaacatga cttaatatgt cctattgaaa tggctaggga actaagtaac    3960
tgctgttttc agatggaggt cttaatttga ataatgttga tattagatat ttagcattct    4020
tttttttttt tttttaatgg agtcttgctc tgtcgcctag gctggggtgc agtggcatga    4080
cttgcaacct ctgcctcccg aatagctggg attacaggtg cccaccatca cgcccggcta    4140
agttttgtat tttagtaga ggcgagtttc gccatgttgg ccaggctggt cttgaacccc    4200
taacctcagt gatcccacgg tcaccgacct ggcctcccaa aagtactgta cccagccaat    4260
gattagcatt ctcactaata atagcatctg agctggctcc tagagtacaa gaaaaaggag    4320
ttcacagtac tttaaaatag ataaaattca gttgagttag taacctaact cattgttagt    4380
actagttgct gctccttgta gaccaatatg aaattacttt tagctcgata aaaccaaaag    4440 tgtcactta tgcttcagac tgaaatgcgg ggatctagat gtgctaatgc ttgtcagtaa    4500
caactaacaa gttttctgt atgtaacttc taggtgaaag acccctgaca aaagacaatc    4560
```

```
atcttctggg tacatttgat ctgactggaa ttcctcctgc tcctcgtggg gtcccacaga    4620
ttgaagtcac ctttgagata gatgtgaatg gtattcttcg agtgacagct gaagacaagg    4680
gtacagggaa caaaaataag atcacaatca ccaatgacca gaatcgcctg acacctgaag    4740
aaatcgaaag gatggttaat gatgctgaga agtttgctga ggaagacaaa aagctgaagg    4800
agcgcattga tactagaaat gagttggaaa gctatgccta ttctctaaag aatcagattg    4860
gagataaaga aaagctggga ggtaaacttt cctctgaaga taaggagacc atggaaaaag    4920
ctgtagaaga aaagattgaa tggctggaaa gccaccaaga tgctgacatt gaagacttca    4980
aagctaagaa gaaggaactg gaagaaattg ttcaaccaat tatcagcaaa ctctatggaa    5040
gtgcaggccc tccccaact ggtgaagagg atacagcaga aaaagatgag ttgtagacac    5100
tgatctgcta gtgctgtaat attgtaaata ctggactcag gaacttttgt taggaaaaaa    5160
ttgaaagaac ttaagtctcg aatgtaattg gaatcttcac ctcagagtgg agttgaaact    5220
gctatagcct aagcggctgt ttactgcttt tcattagcag ttgctcacat gtctttgggt    5280
gggggggaga agaagaattg gccatcttaa aaagcgggta aaaaacctgg gttagggtgt    5340
gtgttcacct tcaaaatgtt ctatttaaca actgggtcat gtgcatctgg tgtaggaggt    5400
tttttctacc ataagtgaca ccaataaatg tttgttattt acactggtct aatgtttgtg    5460
agaagctt                                                            5468

<210> SEQ ID NO 141
<211> LENGTH: 1990
<212> TYPE: DNA
<213> ORGANISM: Homo sapiens

<400> SEQUENCE: 141
gaattccggg ggtattggca gctgaggagt ggaggctggg cagctccgac tccctgacgc      60
cagcgcgacc agatcaatcc aggctccagg agaaagcagg cgggcgggcg gagaaaggag     120
aggccgagcg gctcaacccg ggccgaggct cggggagcgg agagtggcgc accgcccggc     180
cgtccggacc cgggccgcga gaccccgctc gcccggccac tcgtgctccc gcacggacgg     240
gcgcgccgcc aacccggtgc tgactgggtt acttttttaa acactaggaa tggtaatttc     300
tactcttctg gacttcaaac taagaagtta aagagacttc tctgtaaata aacaaatctc     360
ttctgctgtc cttttgcatt tggagacagc tttatttcac catatccaag gagtataact     420
agtgctgtca ttatgaatgt gacaagttta ttttccttta caagtccagc tgtgaagaga     480
cttcttgggt ggaaacaggg cgatgaagaa gaaaaatggg cagagaaagc tgttgatgct     540
ttggtgaaaa aactgaagaa aaagaaaggt gccatggagg aactggaaaa ggccttgagc     600
tgcccagggc aaccgagtaa ctgtgtcacc attccccgct ctctggatgg caggctgcaa     660
gtctcccacc ggaagggact gcctcatgtc atttactgcc gtgtgtggcg ctggcccgat     720
cttcagagcc accatgaact aaaaccactg gaatgctgtg agtttccttt tggttccaag     780
cagaaggagg tctgcatcaa tccctaccac tataagagag tagaaagccc tgtacttcct     840
cctgtgctgg ttccaagaca cagcgaatat aatcctcagc acagcctctt agctcagttc     900
cgtaacttag gacaaaatga gcctcacatg ccactcaacg ccacttttcc agattctttc     960
cagcaaccca acagccaccc gtttcctcac tctcccaata gcagttaccc aaactctcct    1020
gggagcagca gcagcaccta ccctcactct cccaccagct cagacccagg aagccctttc    1080
cagatgccag ctgatacgcc cccacctgct tacctgcctc ctgaagaccc catgacccag    1140
```

-continued

```
gatggctctc agccgatgga cacaaacatg atggcgcctc ccctgccctc agaaatcaac      1200
agaggagatg ttcaggcggt tgcttatgag gaaccaaaac actggtgctc tattgtctac      1260
tatgagctca acaatcgtgt gggtgaagcg ttccatgcct cctccacaag tgtgttggtg      1320
gatggtttca ctgatccttc caacaataag aaccgtttct gccttgggct gctctccaat      1380
gttaaccgga attccactat tgaaaacacc aggcggcata ttggaaaagg agttcatctt      1440
tattatgttg gagggaggt gtatgccgaa tgccttagtg acagtagcat ctttgtgcaa       1500
agtcggaact gcaactacca tcatggattt catcctacta ctgtttgcaa gatccctagt      1560
gggtgtagtc tgaaaatttt taacaaccaa gaatttgctc agttattggc acagtctgtg      1620
aaccatggat ttgagacagt ctatgagctt acaaaaatgt gtactatacg tatgagcttt      1680
gtgaagggct ggggagcaga ataccaccgc caggatgtta ctagcacccc ctgctggatt      1740
gagatacatc tgcacggccc cctccagtgg ctggataaag ttcttactca aatgggttca      1800
cctcataatc ctatttcatc tgtatcttaa atggccccag catctgcctc tggaaaacta      1860
ttgagccttg catgtacttg aaggatggat gagtcagaca cgattgagaa ctgacaaagg      1920
agccttgata atacttgacc tctgtgacca actgttggat tcagaaattt aaacaaaaaa      1980
aaaaaaaaaa                                                             1990
```

<210> SEQ ID NO 142
<211> LENGTH: 576
<212> TYPE: DNA
<213> ORGANISM: Homo sapiens

<400> SEQUENCE: 142

```
tgggggagat tgggactggg gaaatggccc ttgagtgaag gaaagggaga taaagctgag       60
gaagaggcct caggactcag cacagggtgg caacactacc attcactgtc cctgtgccat      120
ttcttcagac tctgggccgc caccaccacc agatggccaa gagcagataa cctttgtcc       180 acagccaggt agagatgggc aacttacatg gccttgagaa gaggtataga aaaggagtg       240 cttttgaggg ctaccccctg ttgtgaccat tcctgaagtg cagagaccac accagcaaaa      300
catgcccagt cttagtagtg gggacgaaga attgatgagt ggatccagtc agctccggca      360
gacaggccac agggttgcca ggtttgatga gccaaccagg tgagcacaca gcttcggagc      420
actgccctga atcctgtctt ctccctcagg actgcccttt cctggccaca ccaagtttgg      480
cacctctcca gaaagttggc agggagcaag tggcagacag caccctctc tccctagcct       540 attaacacac agagccgcca atggcagggc agagcg                                576
```

<210> SEQ ID NO 143
<211> LENGTH: 1932
<212> TYPE: DNA
<213> ORGANISM: Homo sapiens

<400> SEQUENCE: 143

```
gcggccgcac caattttttt tttttatt tttttttt ttttttttt ttcaaatatt           60 cagggaactt tatttttaaa gaataaatca agtaagacac agctttcgtt tacctaaaca      120
tgcataatcc aacctgaata taaactgcac ttaattggtg aattacacat gaatacaaa       180 gggaatgcaa ttttacatat gtaaaatgat tgctagctat agcaatttaa cagtcaaatt      240
tatcagaaca ttgtacatta aaaacacaa acaacaactt aaagccaaat atctatagta       300
aaccaaggaa aattctgata tggaatggtt tgactaaaag caaagaataa ggcacctgct      360
atgaatttag cacaaccata aaacagaatt agttaaccaa gacacttgtt tcaaaaaggg      420
```

```
aaacaagtac agagactgat taactgggtg agaaaggcaa gtaacaattt agttaaaaac      480
ctgctggccc aagtcagtt gattcattcc ttattccaga atagttaagt tcctgaaagt       540
ccttaaccac tctgctccct tactgttctc catgtttgag ggtatcagaa gcccctgtg       600 aggttcacgc tgtgtataga ctaggtagca gatttcccctt ctgttcctct taaaacagct    660
tattttaaaa gaaatatcct gaggcaatta acaaagcaaa cacaagcagc tttctttcca      720
acgcattaat acatagacac tgctcaggtt ttttttcacc aagttatggc taagtataca     780
aatagccaat acttgcagtt ttcaacagta ctagaaaacc caaaacctgc cctatgaccc      840
tcacccttac cattagtaaa acgtaaattt gatcaatcat aacctataaa gtcatataac     900
aaagggaaga ctaaagactg atcattatca gtaaatccat tcaattccag atgccacttt     960
aggctgatgt gtctagtacc ctaatgattg aaaaatcatt aatctagaaa aagcatttgc     1020
aaactaagga taacttcgca gttgatgtgc cttttttgc tattaaaagt gctatttaac      1080
atgctaaaat gtcttatggc acattggact caacagcatg ttctgatgag gcatccattt     1140
ttagcagtat ttttccctag aattttgttt ggcatagtaa accccttga tatattaaaa      1200 tagttctggt gaaataaatg taacataaac aaaccttccc tgactgactt cactccacca    1260
cggtagcttt tagtgaaacc acagtaactg attaagtcag aaaacgatca agttttttt     1320 ttatggcatc ttgggttact atactcactc atgcaaaatc caaggtagtg taatggaaac    1380
aatattggta aaatagatgt tgtggctata agcatctccc tttatattag acatttagaa    1440
gcttttaaaa cttttagat gctaaaggtt gtggcaaaac taggctgtgt agttgttcca     1500
tttataagca ccttattaca ggacagttac atgaacctat aagggagtgt gctttcagtt    1560
caaaagagta ataaagtgcc tagctatata aaaccacaa gacttcaaat tgtaatttaa     1620
gctaactgca gttatacatt tgggttaaca aaatctagac cctgtctatg cagagttaga    1680
ctaattgttc atactgtttt aataaccaca taaaaaaact tactcttaat tgactgaata    1740
agtagggtcc actactgtat cttaacaatc aaatttatt gctttattca tgtggtgttt    1800
tttgcaaggc actgtggtat ggactagaaa acttggaatg actcatgaag aaaccttgga    1860
atgacacatg aagcatgata ggaaagtcat tctgaggcag gatgctttac tgaattgcct    1920
cgtgccgaat tc                                                        1932

<210> SEQ ID NO 144
<211> LENGTH: 1846
<212> TYPE: DNA
<213> ORGANISM: Homo sapiens

<400> SEQUENCE: 144
gcagtgcggc ggtcacaggc tgagtgctgc ggcgcgatcc ttgcttccct gagcgttggc       60 ccggaggaa agaagatggt gctggatctg gatttgtttc gggtggataa aggaggggac      120
ccagccctca tccgagagac gcaggagaag cgcttcaagg acccgggact agtggaccag      180
ctggtgaagg cagacagcga gtggcgacga tgtagatttc gggcagacaa cttgagcaag     240
ctgaagaacc tatgcagcaa gacaatcgga gagaaatga agaaaaaaga gccagtggga      300
gatgatgagt ctgtcccaga gaatgtgctg agtttcgatg accttactgc agacgcttta    360
gctaacctga agtctcaca atcaaaaaa gtccgactcc tcattgatga agccatcctg       420
aagtgtgacg cggagcggat aaagttggaa gcagagcggt tgagaaccct ccgagagatt     480
gggaaccttc tgcaccctc tgtacccatc agtaacgatg aggatgtgga caacaaagta     540
```

```
gagaggattt gggggcgattg tacagtcagg aagaagtact ctcatgtgga cctggtggtg      600
atggtagatg gctttgaagg cgaaaagggg gccgtggtgg ctgggagtcg agggtacttc      660
ttgaaggggg tcctggtgtt cctggaacag gctctcatcc agtatgccct tcgcaccttg      720
ggaagtcggg gctacattcc catttatacc ccctttttca tgaggaagga ggtcatgcag      780
gaggtggcac agctcagcca gtttgatgaa gaactttata aggtgattgg caaaggcagt      840
gaaaagtctg atgacaactc ctatgatgag aagtacctga ttgccacctc agagcagccc      900
attgctgccc tgcaccggga tgagtggctc cggccggagg acctgcccat caagtatgct      960
ggcctgtcta cctgcttccg tcaggaggtg ggctcccatg gccgtgacac ccgtggcatc     1020
ttccgagtcc atcagtttga aagattgaa cagtttgtgt actcatcacc ccatgacaac      1080
aagtcatggg agatgtttga agagatgatt accaccgcag aggagttcta ccagtccctg     1140
gggattcctt accacattgt gaatattgtc tcaggttctt tgaatcatgc tgccagtaag     1200
aagcttgacc tggaggcctg gtttccgggc tcaggagcct tccgtgagtt ggtctcctgt     1260
tctaattgca cggattacca ggctcgccgg cttcgaatcc gatatgggca aaccaagaag     1320
atgatggaca aggtggagtt tgtccatatg ctcaatgcta ccatgtgcgc cactacccgt     1380
accatctgcg ccatcctgga gaactaccag acagagaagg gcatcactgt gcctgagaaa     1440
ttgaaggagt tcatgccgcc aggactgcaa gaactgatcc cctttgtgaa gcctgcgccc     1500
attgagcagg agccatcaaa gaagcagaag aagcaacatg agggcagcaa aaagaaagca     1560
gcagcaagag acgtcacccct agaaaacagg ctgcagaaca tggaggtcac cgatgcttga     1620
acattcctgc ctccctattt gccaggcttt catttctgtc tgctgagatc tcagagcctg     1680
cccaacagca gggaagccaa gcacccattc atcccctgc ccccatctga ctgcgtagct     1740
gagaggggaa cagtgccatg taccacacag atgttcctgt ctcctcgcat gggcataggg     1800
acccatcatt gatgactgat gaaaccatgt aataaagcat ctctgg                    1846

<210> SEQ ID NO 145
<211> LENGTH: 2131
<212> TYPE: DNA
<213> ORGANISM: Homo sapiens

<400> SEQUENCE: 145
ctctttataa tttagtttcc atagaagtta tatgtgcatt taaaaaaatt caatgctgga       60
gcgaccgtgt ctggggagcc gagccccgct tctcgctgcg gtgagcccgg actgggcac      120 gcactgcgca gactccccgc tgcagtgggc ggagtccac aggccccgcc cctcctccca      180
ccctcgttca gccgtccag acagaagctg gggcccagcg gaggtagcag cagacgcctg      240
agagcgaggc cgaggcctc agggtttgga gacccctgaca cacccaccttt ctcacctggg     300 ctctgcgtat cccccagcct tgagggaaga tgaagcctaa actgatgtac caggagctga      360
aggtgcctgc agaggagccc gccaatgagc tgcccatgaa tgagattgag gcgtggaagg      420
ctgcggaaaa gaaagcccgc tggtcctgc tggtcctcat tctggcggtt gtgggcttcg      480
gagcctgatg actcagctgt ttctatggga atacggcgac ttgcatctct ttgggcccaa      540
ccagcgccca gccccctgct atgacccttg cgaagcagtg ctggtggaaa gcattcctga      600
gggcctggac ttccccaatg cctccacggg gaacccttcc accagccagg cctggctggg      660
cctgctcgcc ggtgcgcaca gcagcctgga catcgcctcc ttctactgga ccctcaccaa      720
caatgacacc cacacgcagg agccctctgc ccagcagggt gaggagtcc tccggcagct      780 gcagaccctg gcaccaaagg gcgtgaacgt ccgcatcgct gtgagcaagc ccagcgggcc      840
```

-continued

```
ccagccacag gcggacctgc aggctctgct gcagagcggt gcccaggtcc gcatggtgga      900
catgcagaag ctgacccatg gcgtcctgca taccaagttc tgggtggtgg accagaccca      960
cttctacctg ggcagtgcca acatggactg gcgttcactg acccaggtca aggagctggg     1020
cgtggtcatg tacaactgca gctgcctggc tcgagacctg accaagatct ttgaggccta     1080
ctggttcctg ggccaggcag gcagctccat cccatcaact tggccccggt tctatgacac     1140
ccgctacaac caagagacac caatggagat ctgcctcaat ggaacccctg ctctggccta     1200
cctggcgagt gcgcccccac ccctgtgtcc aagtggccgc actccagacc tgaaggctct     1260
actcaacgtg gtggacaatg cccggagttt catctacgtc gctgtcatga actacctgcc     1320
cactctggag ttctccccacc ctcacaggtt ctggcctgcc attgacgatg gctgcggcg     1380
ggccacctac gagcgtggcg tcaaggtgcg cctgctcatc agctgctggg acactcgga     1440
gccatccatg cgggccttcc tgctctctct ggctgccctg cgtgacaacc atacccactc     1500
tgacatccag gtgaaactct ttgtggtccc cgcggatgag gcccaggctc gaatcccata     1560
tgcccgtgtc aaccacaaca gtacatggt gactgaacgc gccacctaca tcggaacctc     1620
caactggtct ggcaactact tcacggagac ggcgggcacc tcgctgctgg tgacgcagaa     1680
tgggagggc ggcctgcgga gccagctgga ggccattttc ctgagggact gggactcccc     1740
ttacattcat gaccttgaca cctcagctga cagcgtgggc aacgcctgcc gcctgctctg     1800
aggcccgatc cagtgggcag gccaaggcct gctgggcccc cgcggaccca ggtgctctgg     1860
gtcacggtcc ctgtccccgc accccgcctt ctgtctgccc cattgtggct cctcaggctc     1920
tctcccctgc tctcccacct ctacctccac cccaccggc ctgacgctgt ggccccggga      1980
cccagcagag ctgggggagg atcagcccc caaagaaatg ggggtgcatg ctggcctgcc     2040
ccctggccca cccccacttt ccagggcaaa aggggcccag ggttataata agtaaataac     2100
ttgtctgtaa aaaaaaaaaa aaaaaaaaa a                                    2131
```

<210> SEQ ID NO 146
<211> LENGTH: 1044
<212> TYPE: DNA
<213> ORGANISM: Homo sapiens

<400> SEQUENCE: 146

```
ttaattaaag atcttttttt tttttttttt tgccagtgcc aggataaaaa gcaaatttt       60
aaattggaaa atgtctagca ctttacacag tggaatgaaa gaatacgaaa ttcaaaaaca     120
ttattaaaag tccatatgcc gcagcagcac gcgccatgat gagagctccc cttccgaggc     180
gcttctggag cagcttcctc aacctgtccg ggagacgggc tcagaagagc agggccccca     240
tgctgccaac ctcgctttgc tccttaacga agatctcaaa gtactggtag atgattgtga     300
ctgcgagcag gatcccggtt ccagacccaa tggcgcctag gaagtcagcc aggaccgaga     360
gggccccgat gcacagccca ccaaaggccg cggctgtggg gatgtaccgg ttgagttcat     420
ggaccatggg aggtctctcg gtggcctctc atcaccatct gctgctcctt cagctgcttt     480
gcaacatctt tggcagagga acctgagacc tcaatccacg ttttggagaa gaatgcacag     540
gagcccagca tgaacactat gtatacaact gcatggaccg gtcttctaa cacgagcca      600
aaagattctg gagggacag gtaatagcaa aggccaccaa ctggataagc acgtgctgac     660
cagcaagttg ccactgaagc gagctgagag catttgggag atgacataaa ggttggacac     720
cagggcagac tgcaggatga tgggatgtt ggacgtatag aagagcttga tgggataggt     780
```

| | |
|---|---|
| gttgtactgg ccacggtagc gggccgactt gattggcagg tccactcgga agccctggaa | 840 |
| atagatgacc actgcaaaga caaagatggt ggcgatgaga ttcatgaggt tgggaagatt | 900 |
| ctggcggtag aacgcctccc gaagggctcg gaccttgtct gtgcgtgtgg ccagcagatg | 960 |
| gaaaagtgcg atgatagcac cttcaaattc cattcctcgg ccagtgttga cagtagtggg | 1020 |
| gctgaatgcc ctcgtgccga attc | 1044 |

<210> SEQ ID NO 147
<211> LENGTH: 526
<212> TYPE: DNA
<213> ORGANISM: Homo sapiens
<220> FEATURE:
<221> NAME/KEY: misc_feature
<222> LOCATION: (1)...(526)
<223> OTHER INFORMATION: n = A,T,C or G

<400> SEQUENCE: 147

| | |
|---|---|
| aacnaagatc tttttttttt tttttttttt gcttgatttt attttattaa aaaagactgg | 60 |
| aactcagtcc nttnttccta ttaagtccat tttcccaaga gatgtcactg tttgagataa | 120 |
| taacttaaat attcttgatg tggaggtagt ctctctcttc ctagtgggat gtcttcttag | 180 |
| ctccttccc aaacttggca tcaagaccaa gacccaggaa cacaagcaca gtgcccaccc | 240 |
| actgcatggg gctgatggga ttggcgaaga ggatcacaga ggccaaaatt gtgaagaact | 300 |
| ttcgagttgt agtgatgatg gagcaggtca ggggaccaaa atacacaacc gtcataaaga | 360 |
| tgaagctctg acccagggca ctggtcagcc caaagagcag ggatgttata gatgatggca | 420 |
| gggtaccttt cagcaaagct caagaactcc cagagctccc cagtgaacag gattcccatt | 480 |
| cccagcagca aatgtcgcca aaggtttga tgttcagcat catggt | 526 |

<210> SEQ ID NO 148
<211> LENGTH: 1923
<212> TYPE: DNA
<213> ORGANISM: Homo sapiens

<400> SEQUENCE: 148

| | |
|---|---|
| gccgggcagg aggaaggagc ctccctcagg gtttcgggaa ccagatctct caccaggaaa | 60 |
| gactgataca gaacgatcga tacagaaacc acgctgccgc caccacacca tcaccatcga | 120 |
| cagaacagtc cttaatccag aaacctgaaa tgaaggaaga ggagactctg cgcagagcac | 180 |
| tttgggtccg gagggcgaga ctccggcgga agcattcccg ggcgggtgac ccagcacggt | 240 |
| ccctcttgga attggattcg ccattttatt tttcttgctg ctaaatcacc gagcccggaa | 300 |
| gattagagag ttttatttct gggattcctg tagacacacc cacccacata catacattta | 360 |
| tatatatata tattatatat atataaaaat aaatatctct atttatata tataaaatat | 420 |
| atatattctt ttttaaatt aacagtgcta atgttattgg tgtcttcact ggatgtattt | 480 |
| gactgctgtg gacttgagtt gggagggaa tgttcccact cagatcctga cagggaagag | 540 |
| gaggagatga gagactctgg catgatcttt tttttgtccc acttggtggg gccagggtcc | 600 |
| tctcccctgc ccaggaatgt gcaaggccag ggcatggggg caaatatgac ccagttttgg | 660 |
| gaacaccgac aaacccagcc ctggcgctga gcctctctac cccaggtcag acggacagaa | 720 |
| agacagatca caggtacagg gatgaggaca ccggctctga ccaggagttt ggggagcttc | 780 |
| aggacattgc tgtgctttgg ggattccctc cacatgctgc acgcgcatct cgcccccagg | 840 |
| ggcactgcct ggaagattca ggagcctggg cggccttcgc ttactctcac ctgcttctga | 900 |
| gttgcccagg aggccactgg cagatgtccc ggcgaagaga agagacacat tgttggaaga | 960 |

-continued

```
agcagcccat gacagctccc cttcctggga ctcgccctca tcctcttcct gctcccctcc    1020
ctggggtgca gcctaaaagg acctatgtcc tcacaccatt gaaaccacta gttctgtccc    1080
cccaggagac ctggttgtgt gtgtgtgagt ggttgacctt cctccatccc ctggtccttc    1140
ccttcccttc ccgaggcaca gagagacagg gcaggatcca cgtgcccatt gtggaggcag    1200
agaaaagaga aagtgtttta tatacggtac ttatttaata tcccttttta attagaaatt    1260
aaaacagtta atttaattaa agagtagggt ttttttttcag tattcttggt taatatttaa    1320
tttcaactat ttatgagatg tatctttgc tctctcttgc tctcttattt gtaccggttt     1380
ttgtatataa aattcatgtt tccaatctct ctctccctga tcggtgacag tcactagctt    1440
atcttgaaca gatatttaat tttgctaaca ctcagctctg ccctcccga tcccctggct     1500 ccccagcaca cattcctttg aaataaggtt tcaatataca tctacatact atatatatat    1560
ttggcaactt gtatttgtgt gtatatatat atatatatgt ttatgtatat atgtgattct    1620
gataaaatag acattgctat tctgtttttt atatgtaaaa acaaaacaag aaaaaataga    1680
gaattctaca tactaaatct ctctcctttt ttaattttaa tatttgttat catttattta    1740
ttggtgctac tgtttatccg taataattgt ggggaaaaga tattaacatc acgtctttgt    1800
ctctagtgca gtttttcgag atattccgta gtacatattt attttttaaac aacgacaaag   1860 aaatacagat atatcttaaa aaaaaaaaaa gcattttgta ttaaagaatt taattctgat   1920
ctc                                                                 1923
```

<210> SEQ ID NO 149
<211> LENGTH: 157
<212> TYPE: DNA
<213> ORGANISM: Homo sapiens
<220> FEATURE:
<221> NAME/KEY: misc_feature
<222> LOCATION: (1)...(157)
<223> OTHER INFORMATION: n = A,T,C or G

<400> SEQUENCE: 149

```
ttttttttcnt gatcaaangt actcttttat tcttaaataa aaatcttaat tngctttgac     60
ctccaaaggc tctaatccca ntctccaaat tcnnntnaag ggatgntctn ttcatgtggg    120
gccggtttaa acagaggctg cctcaccaga gcagcct                             157
```

<210> SEQ ID NO 150
<211> LENGTH: 1220
<212> TYPE: DNA
<213> ORGANISM: Homo sapiens

<400> SEQUENCE: 150

```
ctcgaggcca agaattcggc acgaggcaat cagcatacag tacagactga aaatagattt     60
catggatcta gcaagcactg caggactgtc actcaacgaa gaggaaatat ggttactaca    120
tacactgact gttcaggaca gtagttctta ttctattctc actaaatcca actggttgac    180
tcttcctcat tatctttgat gctaaacaat tttctgtgaa ctattttgac aagtgcatga    240
tttcacttta aacaatttga tatagctatt aagtatattt aagggttttt ttttttgaca    300
aattcaacat tcaacgagta gacaaaatgc taattatttc cctgattagg aaagtttctt    360
taaaaaacac gtaattttgc ctagtgcttt ttctctacct gcccttgggc tcactaatat    420
caccagtatt attaccaaga aaatattgag tttacctgat taaactttaa aagttaattg    480
tagatttaaa ttgtgtgaac ctaatgattt ttgcagtgaa acctttacta attcaaagtt    540
```

-continued

```
gcatgttcta tgacatctgt gacttgcgtt gcagagtgta catgaaactg tataattgag      600
tcattcagta aaggagaaca gtatcttggt taattgctac tgaaaggttg agaaaggaat      660
ggtttgatat ttaccacagc gctgtgcctt tctacagtag aactgggta aaggaaatgg       720 ttttattgcc catagtcatt taggctggaa aaagttgaa aacttaacga atatattgcca      780 agagattgtt atgtgtttgg ttccagccta aaaatgattt tgtagtgttg aaatcatagc      840
tacttacata gcttttttcat atttctttct tagttgttgg cactcttagg tcttagtatg     900
gatttatgtg tttgtgtgtg tgtagtttat cctctctctc atctttatct agagattgac      960
tgatacctca ttctgtttgt aaaaccagcc agtaatttct gtgcaacctt actatgtgca      1020
atatttttaa atcctgagaa atgtgtgctt ttgttttcgg atagacttat ttctttagtt      1080
ctgcactttt ccacattata ctccatatga gtattaatcc tatggataca tattaaaaca     1140
agtgtctcat acaacattgt atgtgagaga aatataaata tttacaacct gaaaaaaaaa      1200
aaaaaaaaaa tggcggccgc                                                  1220
```

<210> SEQ ID NO 151
<211> LENGTH: 546
<212> TYPE: DNA
<213> ORGANISM: Homo sapiens
<220> FEATURE:
<221> NAME/KEY: misc_feature
<222> LOCATION: (1)...(546)
<223> OTHER INFORMATION: n = A,T,C or G

<400> SEQUENCE: 151

```
ctttttttt tttttaaaaa acaaactgca aatggtatt tatttacatt aaaacatgaa        60
ttgcctgtat tnacacaaat ataagaggaa caatctgtta tgcacaataa ctgtaatatt     120
tagtacatgt tatacacagc agtatctgtt aagtcagtgg tttgagtgaa aacacagtac    180 caaacattc ctgatacaaa ataagttact cattcacata ttctaatcat acaagacact     240
taatatttta aaagttacat acttcaaata acactggcta aatgtacaac taaagtttat    300 taatttttt tatgaaaaga cttcagattg ttattcataa atgatccctt tcaggatgca      360
ttatctttta aataaataaa ctaaattgac ttcaagacta tttataaata gcccactaaa    420
atatgattga agacattcct tcatttttatt aaaggtgtag ctatatacta gagaaatatgc  480 tcaactactg cctccaaatt ccaacactgt cattctaatt tgcaaatagg aattatttaa    540
attcca                                                                546
```

<210> SEQ ID NO 152
<211> LENGTH: 543
<212> TYPE: DNA
<213> ORGANISM: Homo sapiens
<220> FEATURE:
<221> NAME/KEY: misc_feature
<222> LOCATION: (1)...(543)
<223> OTHER INFORMATION: n = A,T,C or G

<400> SEQUENCE: 152

```
tttttttttt tttcaaatct anatacttat tttacttcat cagttccaat cacntttctc      60
atcatacatc caatgacaat atacatatct tcatgggtnc taccattttg canaggcatc    120
atttactaat gcaattatcc aattgattta atgatnctag ctttattctg ggttattata    180
ttccatatta tacaatgata ggatatttga agagacatat aatttttgtaa gacaagactc  240 attacatgat tgtattattt tctatgacat atttaaagag tttaataaca tgtataagta    300
aaancaaatt taggagaaga gtcaagatat ttcatgtatt ccaaagaact gatnctagta    360
```

```
ttgaggaagc taatagccta aaattatatc caaggcatgg ccacatnttt ttcccaaaat    420
gtctgaatga tcagggcaac ttcttatggt tcccttaggc tgtcagtctt gnccttctct    480
tctgggagct ntggggtaaa agtttggtct acagcagaag tgaaacatng gttgggctgg    540
gtt                                                                 543
```

```
<210> SEQ ID NO 153
<211> LENGTH: 516
<212> TYPE: DNA
<213> ORGANISM: Homo sapiens
<220> FEATURE:
<221> NAME/KEY: misc_feature
<222> LOCATION: (1)...(516)
<223> OTHER INFORMATION: n = A,T,C or G

<400> SEQUENCE: 153
tttttttttt gacngttttt aattgtgcct ttattcaact tagttcatta aaaatgtttt     60
aaagatcntt taaataaagt gaccactnac atgggatata ggtcacccct cagcatgtta    120
ttttttttct taaaaagcag tatttcttac aggaatctta ctgatcacac ggtagttaca    180
ataatgtcag atatgatgta tacagtctaa acgagacagt ccagttaaga atatacataa    240
tgtaaaaata cacatattaa aagttagcca agtggacaga cgcatgcggg ggtgggggga    300
gcaggtgaca ggaactcctt taacaatcag tagagggccc agatgcaaag aatctggttt    360
tccccgttac agtaaacagc tttcactaac gtatacaggt atttcataca catctaaaca    420 cacaagggt aagttgtgac ctgctacaca tagggtctaa agtggtgtaa ttgtgatttt     480
cccctcgtgc cgaattcttg gcctcgaggg ccaaat                              516
```

```
<210> SEQ ID NO 154
<211> LENGTH: 985
<212> TYPE: DNA
<213> ORGANISM: Homo sapiens

<400> SEQUENCE: 154
gaattcggca cgaggctgtt caggggatcc ttctgtttct cacggggtga acatgtctt      60 tagttcctca tgttaacacg aagccagagc ccacatgaac tgttggatgt cttccttaga    120
aagggtaggc atggaaaatt ccacgaggct cattctcagt atctcattaa ctcattgaaa    180
gattccagtt gtatttgtca cctggggtga caagaccaga caggctttcc caggcctggg    240
tatccaggga ggctctgcag ccctgctgaa gggccctaac tagagttcta gagtttctga    300 ttctgttct cagtagtcct tttagaggct tgctatactt ggtctgcttc aaggaggtcg     360
accttctaat gtatgaagaa tgggatgcat ttgatctcaa gaccaaagac agatgtcagt    420
gggctgctct ggccctggtg tgcacggctg tggcagctgt tgatgccagt gtcctctaac    480
tcatgctgtc cttgtgatta aacacctcta tctcccttgg gaataagcac atacaggctt    540
aagctctaag atagataggt gtttgtcctt ttaccatcga gctacttccc ataataacca    600
ctttgcatcc aacactcttc acccacctcc catacgcaag gggatgtgga tacttggccc    660
aaagtaactg gtggtaggaa tcttagaaac aagaccactt atactgtctg tctgaggcag    720
aagataacag cagcatctcg accagcctct gccttaaagg aaatctttat taatcacgta    780
aggttcacag ataattcttt ttttaaaaaa acccaacctc ctagagaagc acaactgtca    840
agagtcttgt acacacaact tcagctttgc atcacgagtc ttgtattcca agaaaatcaa    900
agtggtacaa tttgtttgtt tacactatga tactttctaa ataaactctt tttttttaaa    960
```

| aaaaaaaaaa aaaaaaggcg gccgc | 985 |

<210> SEQ ID NO 155
<211> LENGTH: 1280
<212> TYPE: DNA
<213> ORGANISM: Homo sapiens

<400> SEQUENCE: 155

| ctcgaggcca agaattcggc acgagggaaa ggagaagatg aaaaagagga agaagacaga | 60 |
| aaagaaacag gagatggaaa agagaatgaa gatggaaaag agaagggaga taaaaaagag | 120 |
| gggaaagatg taaaagtcaa agaagatgaa aaagagagag aagatggaaa agaagatgaa | 180 |
| ggtggaaatg aggaagaagc tggaaaagag aaagaagatt taaagaagaa ggaagaagga | 240 |
| aaagaggaag atgagatcaa agaagatgat ggaaaaaaag aggagccaca gagtattgtt | 300 |
| taaaactgcc ctatgtagtt tcataatttg gtaacatgta ccttcatgtt gtaaagttaa | 360 |
| tagagataaa tattttatc aaaaatttta taaacacagc ctttctttag cattgattta | 420 |
| atttcagaac atcttcatat tgattattag ccataaagtt tctaacatga aacatttatc | 480 |
| tataaatttt gtgattatag tagtggaata catagaaaaa aatatgcttt caactttgtg | 540 |
| agtgaatttc gtgttgtgta agttatatgt caaatctttg aattttaatt ttactctttt | 600 |
| atacatgtga taatttcata aagtgaggga tcccaaaaaa agagtttcat ccaacattct | 660 |
| tgttctgcag gttgctttta taagaaggt gaactatttt catgtaatgt taagagttaa | 720 |
| acttatcttt cccaaatata actttattat tagcttggga aaaatgaaat tgtattccca | 780 |
| tttttaaaat aaatacaaat gtttatttca gaagggcagt tttgattata tgtgaataca | 840 |
| caaattttac tggatttatc ttaataaaaa gactctgacg atgattgtgt tttgttatat | 900 |
| cttcaaaaat atagctagtg aaatattgtg cttaattttt ttctattgtg ttattcatga | 960 |
| aaatatttaa tattcactga cataaaatta atataaagta aaattcacca ttttaattat | 1020 |
| aataaaaata aagtatataa ttcaatggtt gtcagtatat tcacaatgtt gtgtccactg | 1080 |
| tttaattcca gagaattttt atcacccaaa taagaaacaa agcaccaatt agcagtctct | 1140 |
| tcccattttc gcccaactta tcccccacct ccatcccttg gcaaccacta atctgccttc | 1200 |
| tatctctatg gatttgccta ttctgaacat ttattataaa tggaatcaca taaaaaaaaa | 1260 |
| aaaaaaaaaa aggcggccgc | 1280 |

<210> SEQ ID NO 156
<211> LENGTH: 604
<212> TYPE: DNA
<213> ORGANISM: Homo sapiens
<220> FEATURE:
<221> NAME/KEY: misc_feature
<222> LOCATION: (1)...(604)
<223> OTHER INFORMATION: n = A,T,C or G

<400> SEQUENCE: 156

| gnnttgtang nactnctnng gnaatccaga tcttttttt ttttttttta cgttacctct | 60 |
| gnggtgattn atattctacc agtnaggata caaaatttac annancatct acnagtncca | 120 |
| aaccattnat gaccttataa ttttatcgng catgaaaang gncnangaca ggantncaaa | 180 |
| tggantntat gtntaaagag ttacntagta atnngtnctt gantatggtg ataaaatctg | 240 |
| ctanacangt aacaggaatg tnatnaagcc tanctagaca ttatgaacac aatctgacac | 300 |
| cgaagcattt ccnggttgta tcctnagctt aacaggcact ggagacngnc aggttcntca | 360 |
| aatggtccat gaacacctgc aggctaacan catcnnttag gatgggtgct ncnnttgtcc | 420 |

```
tgtccnnaag catacaggtg attggcntgt ctgagatggg ttgactcttg gacaccggaa      480
tccagcctga ctgcctacat gctccgtgtt gatgtaacga ggcatcgcga agcgagcttg      540
cagaatgnnt ngagcntcat ccaatggngc ntgcngaagg ngcttgaggt tagcatnctn      600
ggcc                                                                   604
```

<210> SEQ ID NO 157
<211> LENGTH: 476
<212> TYPE: DNA
<213> ORGANISM: Homo sapiens
<220> FEATURE:
<221> NAME/KEY: misc_feature
<222> LOCATION: (1)...(476)
<223> OTHER INFORMATION: n = A,T,C or G

<400> SEQUENCE: 157

```
taatccaaga tctttttttt tttttttttt ttttcttggt tccaatattt attattctga       60
caggttagga atactntgat aaataagtaa tattttctct tacagaaaat tgtaatgata      120
ccattgagta caattaaaca ctctgagaat ttcacagaaa catcagaatt ttaatagaca      180
gtagccagcg tccttgtggc cagtgtgagt gacttctcac agctgcaaac accctgggcc      240
agatttctta aaacagctac atgacaaaaa caatgctatt gacatccaat aatgctaaag      300
cctgggtacc acccaggctc cactgactgg tggtttccaa acatctctcc actgactggt      360
ggttttcaac cacaaggaaa ggaaaatgga atattctttg gctcttccag cctagacaca      420
actcctgacc taagactttg agtggagagt cctaacccct gggaagttga actttc         476
```

<210> SEQ ID NO 158
<211> LENGTH: 1782
<212> TYPE: DNA
<213> ORGANISM: Homo sapiens

<400> SEQUENCE: 158

```
cggtgagccg gccgtattcc cgctctcgct taggggcac aggcgcaggc atcggcccgg       60
ccactccaag ccttcggtgc gcgggcgcgt ctgggatacg ggcccgggag gcgccgccct     120
ccgtccgccc ggtgcctctc aggaacagcg aaccggagag agcgccggag agttgggctc     180
agtgcggagc tcggcgccgg ggcccatgcc cgtgcgcccc cgcaggccgg cgccatggcc     240
tccgggagtg tggccgagtg cctgcagcag gagaccacct gccccgtgtg cctgcagtac     300
ttcgcagagc ccatgatgct cgactgcggc cataacatct gttgcgcgtg cctcgcccgc     360
tgctggggca cggcagagac taacgtgtcg tgcccgcagt gccggagac cttcccgcag     420 aggcacatgc ggcccaaccg gcacctggcc aacgtgaccc aactggtaaa gcagctgcgc     480
accgagcggc cgtcggggcc cggcggcgag atgggcgtgt gcgagaagca ccgcgagccc     540
ctgaagctgt actgcgagga ggaccagatg cccatcgcg tggtgtgcga ccgctcccgc     600
gagcaccgcg ccacagcgt gctgccgctc gaggaggcgg tggagggctt caaggagcaa     660
atccagaacc agctcgacca tttaaaaaga gtgaaagatt taagaagag acgtcgggcc     720 cagggggaac aggcacgagc tgaactcttg agcctaaccc agatggagag ggagaagatt     780
gtttgggagt tgagcagct gtatcactcc ttaaaggagc atgagtatcg cctcctggcc     840
cgccttgagg agctagactt ggccatctac aatagcatca atggtgccat cacccagttc     900
tcttgcaaca tctcccacct cagcagcctg atcgctcagc tagaagagaa gcagcagcag     960
cccaccaggg agctcctgca ggacattggg gacacattga gcagggctga aagaatcagg    1020
```

```
attcctgaac cttggatcac acctccagat ttgcaagaga aaatccacat ttttgcccaa    1080
aaatgtctat tcttgacgga gagtctaaag cagttcacag aaaaaatgca gtcagatatg    1140
gagaaaatcc aagaattaag agaggctcag ttatactcag tggacgtgac tctggaccca    1200
gacacggcct accccagcct gatcctctct gataatctgc ggcaagtgcg gtacagttac    1260
ctccaacagg acctgcctga caaccccgag aggttcaatc tgtttccctg tgtcttgggc    1320
tctccatgct tcatcgccgg gagacattat tgggaggtag aggtgggaga taaagccaag    1380
tggaccatag tgtctgtga  agactcagtg tgcagaaaag gtggagtaac ctcagccccc    1440
cagaatggat tctgggcagt gtctttgtgg tatgggaaag aatattgggc tcttacctcc    1500
ccaatgactg ccctacccct gcggaccccg ctccagcggg tggggatttt cttggactat    1560
gatgctggtg aggtctcctt ctacaacgtg acagagaggt gtcacacctt cactttctct    1620
catgctacct tttgtgggcc tgtccggccc tacttcagtc tgagttactc gggagggaaa    1680
agtgcagctc ctctgatcat ctgccccatg agtgggatag atgggttttc tggccatgtt    1740
gggaatcatg gtcattccat ggagacctcc ccttgaggag gt                      1782
```

<210> SEQ ID NO 159
<211> LENGTH: 1465
<212> TYPE: DNA
<213> ORGANISM: Homo sapiens

<400> SEQUENCE: 159

```
gaattcggca cgagggtgcc ttttaggaga aataaagagg aagatttgca atcaactaaa      60
gaagagagat ttccagcgat ccacaagtcg attgctattg gctctcagcc agtgctcact     120
gttgggacaa cccacatatc caaattgaca gatgaccaac tcataaaaga gtttcttagt     180
ggttcttact gctttcgtgg gggtgtcggt tggtggaaat atgaattctg ctatggcaaa     240
catgtacatc aataccatga ggacaaggat agtggggaaa cctctgtggt tgtcgggaca     300
tggaaccaag aagagcatat tgaatgggct aagaagaata ctgctagagc ttatcatctt     360
caagacgatg gtacccagac agtcaggatg gtgtcacatt tttatggaaa tggagatatt     420
tgtgatataa ctgacaaacc aagacaggtg actgtaaaac taaagtgcaa agaatcagat     480
tcacctcatg ctgttactgt atatatgcta gagcctcact cctgtcaata tattcttggg     540
gttgaatctc cagtgatctg taaaatctta gatacagcag atgaaaatgg acttcttttct    600 ctccccaact aaaggatatt aaagttaggg gaaagaaaag atcattgaaa gtcatgataa     660
tttctgtccc actgtgtctc attatagagt tctcagccat tggacctctt ctaaaggatg     720
gtataaaatg actctcaacc actttgtgaa tacatatgtg tatataagag gttattgata     780
aacttctgag gcagacattt gtctcgcttt ttttcatttt tgttgtgtct tataaactga     840 ctgttttttct ttgcttggat actgtgattc caaaataaat ctcatccaag caagttagag     900
tccagcctaa tcaaatgtca taattgttgt acctattgaa agtttttaaa taatagattt      960
attatgtaaa ttatagtata tgtaagtagc taatgaagta aagatcatga agaaagaaat    1020
tgataggtgt aaatgagaga ccatgtaaaa tatgtaaatt ctagtacctg aaatcctttc    1080
aacagatttt tatatagcaa ctgctctctg caagtagtta aactagaaac tgggcacatg    1140
gtagaggctc acatgggagt tgtcctcacc cttgttaatc tcaagaaact cttatttata    1200
ataggttgct tctctctcag aacttttatc tattactttt ttcttcttat gagtatgttt    1260
actctcagag tatctatctg atgtagacag ttggtgatgc ttctgagact cagaatggtt    1320
tactctaaca aaacactgtg ctgtctatcc cttgtacttg cctactgtaa tatggatttc    1380
```

```
acttctgaac agtttacagc acaatattta ttttaaagtg aataaaatgt ccacaagcaa    1440
aaaaaaaaaa aaaaaaggcg gccgc                                         1465
```

<210> SEQ ID NO 160
<211> LENGTH: 657
<212> TYPE: DNA
<213> ORGANISM: Homo sapiens

<400> SEQUENCE: 160

```
cgcggggtaa cgcggagtag cacgccatga aggcctcggg cacgctacga gagtacaagg     60
tagtgggtcg ctgcctgccc acccccaaat gccacacgcc gcccctctac cgcatgcgaa    120
tctttgcgcc taatcatgtc gtcgccaagt cccgcttctg gtactttgtg tctcagttaa    180
agaagatgaa gaagtcttca ggggagattg tctactgtgg caggtgtttg agaagtcccc    240
cctgcgggtg aagaacttcg ggatctggct gagctatgac tcccggagcg gcacccacaa    300
catgtaccgg gaataccggg acctgaccac cgcaggcgct gtcacccagt gctaccgaga    360
catgggtgcc cggcaccgcg cccgagccca ctccattcag atcatgaagg tggaggagat    420
cgcggtcagc aagtgccgcc ggccggctgt caagcagttc cacgactcca agatcaagtt    480
cccgctgccc caccgggtcc tgcgccgtca gcacaagcca cgcttcacca ccaagaggcc    540
caacaccttc ttctaggtgc agggccctcg tccggggtgt gccccaaata aactcaggaa    600
cgcccggtga aaaaaaaaa aaaaaacat aaaaaaaac catcaaaaaa aataaaa         657
```

<210> SEQ ID NO 161
<211> LENGTH: 483
<212> TYPE: DNA
<213> ORGANISM: Homo sapiens
<220> FEATURE:
<221> NAME/KEY: misc_feature
<222> LOCATION: (1)...(483)
<223> OTHER INFORMATION: n = A,T,C or G

<400> SEQUENCE: 161

```
nntttttttt tgttttaaa aagaattgtt tatttaccga acctggggca tattagatac     60
aaccattttt aaatttacat cttttaaatc agttttgaag tgtttcacac acacaaaaaa    120
cttggcatgc aacagttgtc ctaaggtgaa agtcacctca ttaataaact gttgcaagtg    180
ttctcaccca aggtggaagt atggtttatc ctgaacatga aaacctgtaa caaatttaaa    240
ttaattatat aaaactcgtt acttgtagtt ttgcccttgc aaagatccaa aaaaaaaaa    300 aaaagcaca agtaactaat atgtatcagt cacaacataa tcctggatca tncccatacc    360
aaaaccggat gctcttttaa ttttaaaccc atcatcagag aacaagagaa agtaatttca    420
ttttacacaa aacaagattn acatgtgcca aaaagaaat accccaaaag aaacaaaaac    480
caa                                                                 483
```

<210> SEQ ID NO 162
<211> LENGTH: 956
<212> TYPE: DNA
<213> ORGANISM: Homo sapiens
<220> FEATURE:
<221> NAME/KEY: misc_feature
<222> LOCATION: (1)...(956)
<223> OTHER INFORMATION: n = A,T,C or G

<400> SEQUENCE: 162

```
gacgggagct gcatgaaagc cgaagttatg gaccgctagc atctgtcact ggccaccggt     60
```

-continued

```
ttccgggagt aagcggcnta ccttacagcc ctgacacgag ccgggtgctc tctcttctca      120
ccgcggccca cgtctcctcg ntggctccgg tggcctcgct gggtcgcgag gaggcngagg      180
actgtactct gaggccaaaa gccagagtcg gccctgaacg cccacgactc tcagggtcca      240
gaggccgtga daccggccgc ggctgaaagg taaagaaacc aagtggaaga gtgtttcctc      300
ctctggccgt aaagcatgct gtcnccgccc tactcnggac cgccccaaag actcnatggg      360
atggacctga gtcagccgaa tccttagccc cttccctttg gggcctgctg tggtgctcga      420
catcagtgac agacggaagc agcagaccat caaggctaag gggaggnccg gggnttttt      480 ttttaccagt catctacaac acatttattt gtacaatcca gaaactagca ggaccaaaat      540
tagcagcaat gtgagacatt tactggcagc tttgccttct acccnaaggt caaagtactt      600
gagacattgc ctgtgtgcct aaggaggcat cacacaagga aagccccacc ccctacttcc      660
ttcatctgag caaaggaacc tgtttacatg cacagtgctt agtgggtggg actctccaaa      720
gcagtggaaa ttcatcttta acctaattta tacaggtctg cgtcacgatg gcaaattgaa      780
ggtgccatga tttagctggt ttcnctggaa cattcctttc aggngcccan actttgtcac      840
actttcatgc cccaagggga ttcaggtgct ctgggatgtc taccctggaa tacanccttg      900
cctccttttc cngaggtatt gggctccagt aanccaccgg ggggttttgg aaatca          956
```

<210> SEQ ID NO 163
<211> LENGTH: 560
<212> TYPE: DNA
<213> ORGANISM: Homo sapiens
<220> FEATURE:
<221> NAME/KEY: misc_feature
<222> LOCATION: (1)...(560)
<223> OTHER INFORMATION: n = A,T,C or G

<400> SEQUENCE: 163

```
tttttttttt ctgaaaacaa gttttattta aataagggtt taaatacatt acacataaca       60
ttaaaacttt aggggaaaaa aaaccaaaa accagtttgt tacttcacat ggcattgggc       120
agctgctgct attaagttgc aagctctaca gctagctaca tgactgatgg atcagtttga      180
gatttgttcc cttgtcaaaa gtttaactct gatagaaggt tggcctcaca ttctgatgtt      240
tggacatccc ttagctagga tatgtctggt cgaacagacc tttgtggcaa gccagatgtc      300
ctatcacctc gctagcggta agagggcctc tttgagctct gtccacctag tcaggttgga      360
gacaccaggg gatctaccac caaaagctcc cttctagtag tacagctggt gcttctgcct      420
taccccatcc tctcctctca gattcaccga ggactgttca gggtggtaac attctcttag      480
ggtagggaac tctgcagagg gagagctgan gaggttccgg cctagttgtt tgtaatctta      540
gggctctggg cttggctgaa                                                  560
```

<210> SEQ ID NO 164
<211> LENGTH: 526
<212> TYPE: DNA
<213> ORGANISM: Homo sapiens
<220> FEATURE:
<221> NAME/KEY: misc_feature
<222> LOCATION: (1)...(526)
<223> OTHER INFORMATION: n = A,T,C or G

<400> SEQUENCE: 164

```
tttttttttt ttggaagaat acacgaaata tgtttaatac ttagtatcaa actaaaaagt       60
aatataaaat ttnaaaactt cttttttttc atgcacaggc ttttctggt aaggaccgct       120 gggattgaac agaagcttcc ggtaaataag ggccccgtcg gcaagacagc atactgctgt      180
```

| cacaagtgca aacacccctc caccaactgt caatgttgtg gtttctggta tcagtgccaa | 240 |
| cacagatacg atgagcatga atactgttgt taccagtgag ttgataatat ccagccgcag | 300 |
| catcttcacg tggcctttca cactgaagca gaaggggccg atgttttatt ttcggctgca | 360 |
| cgttatccat cgcgtctgca gacccagcag cagcactttc cctcaactct tctcagctgg | 420 |
| ctgcctgagt aggttctgcg aagcgatagc aaccgccacc gcggcggagc accgccctcc | 480 |
| cctacttctc ggcctcgtgc cgaattcttg gcctcgaggg ccaaat | 526 |

<210> SEQ ID NO 165
<211> LENGTH: 3205
<212> TYPE: DNA
<213> ORGANISM: Homo sapiens

<400> SEQUENCE: 165

| cgactcgtcg ccattcccgg agcaggtcgg cctcggccca ggggcgagta tccgttgctg | 60 |
| tgtcggagac actagtcccc gacaccgaga cagccagccc tctcccctgc ctcgcggcgg | 120 |
| gagagcgtgt ccgccggcc ggccggcggg gctcgcgcaa cctccctcgc ctccccttcc | 180 |
| cccgcagcct ccgccccgcc aggcccggcc cggactcccg agccccggcc tcctcgtcct | 240 |
| cggtcgccgc tgccgccggg cttaacagcc ccgtccgccg cttctcttcc tagtttgaga | 300 |
| agccaaggaa ggaaacaggg aaaaatgtcg ccatgaaggc cgagaaccgc tgccgccgcc | 360 |
| gaccccccgcc ggccctgaac gccatgagcc tgggtccccg ccgcgcccgc tccgctccga | 420 |
| ctgccgtcgc cgccgaggcc cccgttgatg ccgctgagct cccccaacgc cgccgccacc | 480 |
| gcctccgaca tggacaagaa cagcggctcc aacagctcct ccgcctcttc gggcagcagc | 540 |
| aaagggcaac agccgccccg ctccgcctcg gcggggccag ccggcgagtc taaacccaag | 600 |
| agcgaattac taatttcagc tggattcaat ttgttgtcag ttgattctgt agtaaggcca | 660 |
| tatgttgccc ctctggaggt gcttgtcaac tactctggat gatggatgga aagaactcca | 720 |
| gtggatccaa gcgttataat cgcaaacgtg aactttccta ccccaaaaat gaaagtttta | 780 |
| acaaccagtc ccgtcgctcc agttcacaga aaagcaagac ttttaacaag atgcctcctc | 840 |
| aaagggggcgg cggcagcagc aaactctttta gctcttcttt taatggtgga agacgagatg | 900 |
| aggtagcaga ggctcaacgg gcagagttta gccctgccca gttctctggt cctaagaaga | 960 |
| tcaacctgaa ccacttgttg aatttcactt tgaacccccg tggccagacg ggtcactttg | 1020 |
| aaggcagtgg acatggtagc tggggaaaga ggaacaagtg gggacataag ccttttaaca | 1080 |
| aggaactctt tttacaggcc aactgccaat ttgtggtgtc tgaagaccaa gactacacag | 1140 |
| ctcattttgc tgatcctgat acattagtta actgggactt tgtggaacaa gtgcgcattt | 1200 |
| gtagccatga agtgccatct tgcccaatat gcctctatcc acctactgca gccaagataa | 1260 |
| cccgttgtgg acacatcttc tgctgggcat gcatcctgca ctatcttttca ctgagtgaga | 1320 |
| agacgtggag taaatgtccc atctgttaca gttctgtgca taagaaggat ctcaagagtg | 1380 |
| ttgttgccac agagtcacat cagtatgttg ttggtgatac cattacgatg cagctgatga | 1440 |
| agagggagaa agggggtgttg gtggctttgc ccaaatccaa atggatgaat gtagaccatc | 1500 |
| ccattcatct aggagatgaa cagcacagcc agtactccaa gttgctgctg gcctctaagg | 1560 |
| agcaggtgct gcaccgggta gttctggagg agaaagtagc actagagcag cagctggcag | 1620 |
| aggagaagca cactcccgag tcctgcttta ttgaggcagc tatccaggag ctcaagactc | 1680 |
| gggaagaggc tctgtcggga ttggccggaa gcagaaggga ggtcactggt gttgtggctg | 1740 |

-continued

```
ctctggaaca actggtgctg atggctccct tggcgaagga gtctgttttt caacccagga    1800
agggtgtgct ggagtatctg tctgccttcg atgaagaaac cacggaagtt tgttctctgg    1860
acactccttc tagacctctt gctctccctc tggtagaaga ggaggaagca gtgtctgaac    1920
cagagcctga ggggttgcca gaggcctgtg atgacttgga gttagcagat gacaatctta    1980 aagagggac catttgcact gagtccagcc agcaggaacc catcaccaag tcaggcttca    2040
cacgcctcag cagctctcct tgttactact tttaccaagc ggaagatgga cagcatatgt    2100
tcctgcaccc tgtgaatgtg cgctgcctcg tgcgggagta cggcagcctg agaggagcc    2160 ccgagaagat ctcagcaact gtggtggaga ttgctggcta ctccatgtct gaggatgttc    2220
gacagcgtca cagatatctc tctcacttgc cactccactg tgagttcagc atctgtgaac    2280
tggctttgca acctcctgtg gtctctaagg aaaccctaga gatgttctca gatgacattg    2340
agaagaggaa acgtcagcgc caaaagaagg ctcgggagga acgccgccga gagcgcagga    2400
ttgagataga ggagaacaag aaacagggca agtacccaga agtccacatt cccctcgaga    2460
atctacagca gtttcctgcc ttcaattctt atacctgctc ctctgattct gctttgggtc    2520
ccaccagcac cgagggccat ggggccctct ccatttctcc tctcagcaga agtccaggtt    2580
cccatgcaga ctttctgctg acccctctgt cacccactgc cagtcagggc agtccctcat    2640
tctgcgttgg gagtctggaa gaagactctc ccttcccttc ctttgcccag atgctgaggg    2700
ttggaaaagc aaaagcagat gtgtggccca aactgctcc aaagaaagat gagaacagct    2760
tagttcctcc tgcccctgtg gacagcgacg gggagagtga taattcagac cgtgttcctg    2820
tgcccagttt tcaaaattcc ttcagccaag ctattgaagc agccttcatg aaactggaca    2880
caccagctac ttcagatccc ctctctgaag agaaggagg aaagaaaaga aaaaacaga    2940 aacagaagct cctgttcagc acctcagtcg tccacaccaa gtgacactac tggcccaggc    3000
taccttctcc atctggtttt tgttttgtt tttttttccc ccatgctttt gtttggctgc    3060
tgtaattttt aagtatttga gtttgaacag attagctctg gggggagggg gtttccacaa    3120 tgtgagggg aaccaagaaa attttaaata cagtgtattt ccagcttcc tgtctttaca    3180 ccaaaataaa gtattgacac aagag                                         3205
```

<210> SEQ ID NO 166
<211> LENGTH: 1143
<212> TYPE: DNA
<213> ORGANISM: Homo sapiens

<400> SEQUENCE: 166

```
ctcgaggcca agaattcggc acgagggctc caaacagcag tctgaggagg acctgctcct      60
gcaggatttc agccgcaatc tctcggccaa gtcctccgcg ctcttcttcg gaaacgcgtt     120
catcgtgtct gccatcccca tctggttata ctggcgaata tggcatatgg atcttattca     180
gtctgctgtt ttgtatagtg tgatgaccct agtaagcaca tatttggtag cctttgcata     240
caagaatgtg aaatttgttc tcaagcacaa agtagcacag aagagggaag atgctgtttc     300
caaagaagtg actcgaaaac tttctgaagc tgataataga aagatgtctc ggaaggagaa     360
agatgaaaga atcttgtgga agaagaatga agttgctgat tatgaagcta acattttc     420 catcttctat aacaacactc tgttcctggt cgtggtcatt gttgcttcct tcttcatatt     480
gaagaacttc aaccccacag tgaactacat attgtccata agtgcttcat caggactcat     540
cgccctcctg tctactggct ccaaatagac catgtcagct tcaccccctg gctttgtgtc     600
tatgggtggc ctgtggtata tggaaaagta gcagggtggt caggtgggga gacacaagat     660
```

```
gtttttatag tctagagcct ttaaaaaaac ccagcagaat gtaattcagt atttgtttat    720
tggctgtttt ttgacagatt gttgaaatta aatgaattga aagggaaact cagagtacta    780
ggacgtttat taaaaggaaa aaaatgtctt gcaatgtgct gtaatcacaa gaggagaaaa    840
taacttgttt ccttgatctg tcagaggtca cagtaacctg ggccgagctg ttattattta    900
ttatataata gtagtaggaa gttaataact ggttctctgt gttccaagca caatattaca    960
acttcctttg aaccgtaaat atcagaatga atcctcttcc cagggattg aacagaagct    1020 taatgtttac aagtgtttga atttgtgatc tgaaataaca caaaattaaa aacatgattt    1080
ctctaatttt ccaactagag gaagagaaaa aaaaaaaaaa aaaaaaaaaa aaactgcggc    1140
cgc                                                                 1143

<210> SEQ ID NO 167
<211> LENGTH: 560
<212> TYPE: DNA
<213> ORGANISM: Homo sapiens
<220> FEATURE:
<221> NAME/KEY: misc_feature
<222> LOCATION: (1)...(560)
<223> OTHER INFORMATION: n = A,T,C or G

<400> SEQUENCE: 167
ttcctttttt tttttttttt tgccgttgac tgctaatcaa aaataagcct tacctagaaa     60
acagaaactg aattttcaaa cacagagaca gannaaaaaa aaaaaaccca ccaatgctac    120
ctctgtaaaa taaaactaga agcaaaatga atagtttcaa gacagtcggc taaccaacaa    180
accaaatgca caagagaata ctaaacaggg ttttactgtc atcaagttcg aaggcaggaa    240
gacagactag aaaaggtctt aggagagatg ggctaccatg gacaaatgaa gccacactct    300
atctgttaaa tctaaattct aacattaaaa ctcctgaatc ctggagttag tttaatgtca    360
ctgacattaa ctagctttag ttattgtcat tttattcaaa tggatgccat ttgattaggt    420
aagtattgag cattattta ggagaaaaac caaacccaac tcctatttgc ttaggtacca    480
tgtcccatga acaaaaaaga agaagagagc aaagtatttt tgagacagtc tttaagtgaa    540
gccataagaa ctaagttatt                                               560

<210> SEQ ID NO 168
<211> LENGTH: 9573
<212> TYPE: DNA
<213> ORGANISM: Homo sapiens

<400> SEQUENCE: 168
ggatcctaca tgatggctac agatacagct gttgttcaag gttttagcct ggaatctctg     60
ccaattcaat aacggaggca ataaaaatag acactagtat tataaagaca gaattcattt    120
attttgaaag ttttgaaagc tatgaatatc taccaagaat aaaataaatt gtactgaaaa    180
tatattagaa tgaattaaaa aatgccaaat tcacaactaa taaaatttat tataaagtta    240
aaaattctta tattttctg tctcagtata aaaataaac atttaatgta tctattagaa    300
aataattagc aattttgtaa atgatatcaa agaaaatttg aacaaatggt gaaatatttt    360
cttatctgcg gacaccaaat taaaaaaatt caggccaggt gcagtggctc acacctgtaa    420
tcccaactac tttgggaggc caaggcagga ggatctcttg atccaaggag tttaagacca    480
gcctgggcag ggacgggtgc agtggctcat gcctgtaatc ccagcatttt gggaggctga    540
gacggcagat catgaggtca agagatcaag accatcctgg ccaacatggt gaaaccctgt    600
```

-continued

| | | | | | |
|---|---|---|---|---|---|
| ctctactaaa | aatacaaaaa | ttagctgtac | atggtgacgc | atgcactcct | gtagtcccag | 660 |
| ctacttggga | ggctgaggca | ggagaatcac | ttgaaccggg | gaggcggagg | ttgcagtgag | 720 |
| ccagatcgca | ccactgcact | ccagcctggt | gacagagcga | gacccatct | caaaaaaaaa | 780 |
| ttagccaggc | atggcttcat | gtgcctatag | tcctagctac | tagggaggct | gaggtcggag | 840 |
| gattgcttga | gcctgggagg | tcgaggctgc | tgtgaaccga | gattgtgcta | ctggactcca | 900 |
| gcctgggtga | caaagtgaga | ccctgtctca | aacaaacaaa | caaacaaaaa | accaaaaaaa | 960 |
| ccccaaaata | aaacaaaaat | tcaacagcat | gtagattagt | aatgttagtg | ctttattttt | 1020 |
| aaaaattatt | gttaacttat | atgggttttc | ctctgagaag | gtgcactgga | aggtgtcagc | 1080 |
| agagcagata | gcacaaactc | ctcagatttc | agaagcaggg | gtttatggta | aatgaaaaat | 1140 |
| gccagtcact | tgtcagcatg | cacaggtggc | tatgcccgcc | ctgtgtcagg | ctctgtgtca | 1200 |
| gtagtagggt | gctccatgcg | tccttttcag | agtcctacat | gccatctatg | ctcactcagc | 1260 |
| caggcctgtc | acctggaagt | aacaggcaac | tcctcctgca | ctggaattag | cagcagagtc | 1320 |
| aggtgaataa | tgtggcctgg | ccacaccacc | tctcagcaaa | tgtccccagt | ggtgatgccc | 1380 |
| gatagttccc | aatcctcctt | aagtaattaa | ttcacttcaa | ttgaattaaa | aaaatcaatc | 1440 |
| acttccctat | gacacacaag | gacattcact | ctctggcttt | aactatcctt | gcctgccttg | 1500 |
| ttattatcat | tccatgtgcc | caatactgtc | aaaagatgta | tttttgccat | accctccaca | 1560 |
| tgcatttcat | atgtgtgatt | tttattttca | aattctatat | ctcttctagg | aatatggtgt | 1620 |
| gttttatttg | tcctgctgca | ggactcccct | ctccactcag | attaaattat | taaattccag | 1680 |
| ataaaaaatt | aacttggaat | actgttgaat | caatagtaga | agtaaccaaa | ataataaaga | 1740 |
| tatttcaaaa | tgaagattga | tttttaaaag | taaaaatgtc | acatactcca | cctagaagat | 1800 |
| aagagactgt | actacaaatt | cattagaaca | tccccttcat | gtcatgggcc | agtcatgtcc | 1860 |
| ctgaacttaa | cctctgtctt | ctcgggtgat | gttacaggcc | aatgcagcat | cagctgccca | 1920 |
| cactcctagt | ggtggaatct | gggagcacag | gcaggagtct | gcgcctgtgg | ccttggctgg | 1980 |
| gtgaaagatg | acatttccaa | gacttcttgc | ttggcagcca | tcctcacgtg | caggtggtct | 2040 |
| ggcagcagca | ctgcaaaacc | caggcaaggg | atgccccact | gcaaggccca | gtggtaactg | 2100 |
| tggtggccat | tggcattggg | ggcagatgca | gccatgtgag | ttggtgggct | gtggcagcca | 2160 |
| ccctaatgat | ggtttccacc | cctcccagct | ggtggtggct | aaaaccaccc | ggtaggagtt | 2220 |
| tcaaaagcag | tggcaccatt | aagcggagct | cctggaggag | gactggaagc | aactgcttgc | 2280 |
| attgaaggaa | tgtagctata | gtggaattat | tgaaccacat | catatttgca | agatgcaga | 2340 |
| atgtattaca | gattacgaga | tatggaagtt | gaggttaatc | tggtagagag | cagtgaatat | 2400 |
| gaggaggaag | ctctctattg | ggcgggtgct | atcatagctg | cagaaggtga | tggtgcaatg | 2460 |
| cttctgccag | tgagtaaagt | cttgtacaaa | cttaaaccag | ttacgggta | aaatctgatc | 2520 |
| caggactacc | tgagggtcac | ttatgttggc | ctgttcaata | cacacatttc | tttccaggag | 2580 |
| ccttaccaaa | ggtctatagt | agtgagttca | gtatggaggc | agtaatcaga | tcatatctgg | 2640 |
| aaggaactgg | cataaactcc | aatcctgtgg | gacatcatgg | acagcaacta | aattcgaatc | 2700 |
| aacagagtag | agcccttgac | attggacaag | ttcgtggtga | aagatctgag | gctttaggac | 2760 |
| tccgacattt | gtgaatgaca | gcactaaatg | aagtctttac | tggtgaacgt | ctatccagaa | 2820 |
| taccttatgc | ttgggctgtg | gcagtggata | atttaagtag | acccactcta | tttatttatt | 2880 |
| tattttgaga | cggagtcttg | ctctgttgcc | caggctggag | tgcagtggcg | tgatctaggt | 2940 |
| tcactgcaag | ctccgcctcc | caggttcacg | ccattctcct | gcctcagcct | cccaagtagg | 3000 |

-continued

```
tgggactata ggcacccatc accacacctg gctaattttt tgtattttta gtagagacag   3060
ggtttcaccg tgttagccag gatggtctcg atctcctgac ctggtgatcc atccgccttg   3120
gtctcccaaa gtgctgggat tacaggtgtg agcctctgcg cctggctaag tagacccact   3180
ctaaaagact ggtttcttac tgtgagattt cagttggtaa tggtccatgg gaaaaatgga   3240
agacttcagg gctcaatttg tgaactggag caagatcaaa ggcaacaggg ttgcaagtca   3300
ggctgtggag catgattaaa atattgcaaa tgacaaggac gttggagtct tgcattcaac   3360
tgtaaaatga cagaataaca aataaatata atgaatcatt gttctagagt ccaaaaaggg   3420
ccaaaagtaa ttttcagtat tcaagaacta aaaagcaagc agttttctcg agcacccatg   3480
agcattgttt ctcctgagag atttgtcctc gttttcattg ctggaacacc tgcatggttg   3540
tagatggagg aatgtctttt gatgttccta tttttatatc agacaagctt taaagcaaca   3600
acagttataa aagacaaaga aggaaatttt ataatgataa aaggatcggt ccaacagaac   3660
aatatcacaa tcctaaatat atatgcacct aatactggag ctcccaaatt tataaaacaa   3720
ttattactag acctaagaaa tgggatagat ggcaccacaa taatagtagg ggacttcaat   3780
actccatgga cagcactaga caggacatca aggcagaaag tcaataaaga aaaaattgac   3840
tttaattata tcctagaaca aatagattta gcagatattt acctaacatt ctacccaaca   3900
acttcagaat ataccatatt ttaatcagca catagaacgt tctccaagat aaatcataag   3960
ataggccaca aaacaagtct caacaaattt aagaaaattg aaattatgtc aagtacctt t   4020 tcagaccaca atggaataaa actggaaatt aactccaaaa agaaccctta aaactataca   4080
aatacatgaa aattaaataa tctgctcctg aatgaccttt gggttaacaa tgaaatcaag   4140
aaggaaattt aaaaattgct tgaactgaac aataatagtg acacaaccta ttaaaacctc   4200
tgagatacag caaaactaag aggacagttc atagcattaa atagtctgaa acagcatgaa   4260
cagacaatct aaggtgacac ctcaaggaac tcaagaaaca agaaccaacc aaactcaaac   4320
ccagaagaaa agaaataaca aagatcagag cagaactaaa taaaattgaa acaaaaaata   4380
caaaagataa atgaaacaaa aactggttat ttgaagagat aaacaaaatt gacagaccgt   4440
tagtgagatt aaccaagaaa aaagggaga cgatccaaat aagctcaatt agaaatgaaa   4500
tgggaaatat tacaaccaat accacagaaa tatgaaagat attcaaggct actatgaaca   4560
cccttatgca cacagactag aaaatctaga agagatggat aaattcctgg aaaataagtt   4620
attatttgaa aaagacactt gtatggccgg gcacggtggc tcatgcctgt aatcccagca   4680
ctttgggagg ataagcgggc ggatcatctg aggttaggag ttcaagacca gcctggccaa   4740
catgttgaaa ctccatctct actaaaaata caaaattagc tggacatggt ggtgcatgcc   4800
tgtaatcccc gctactctgg aggctgaggc aggagaatcg cttgaaccca ggaggtggag   4860
gttgcagtga gccaagattg caccattgca ctccagcctg ggcaacaaga gcgaaattct   4920
gtctcaaaaa aaaaaaaaa aaaaaaaga agaaagaaa aagacacttg cacacatgtt   4980
tatagcagta caatttgcaa ttgcaaaaat atgcaaacga tataaatata catcaaccaa   5040
tgagtgaata agaaaacgt tatttttta tttttagacg gaatttcgct tttgttgccc   5100
aggctggagt gcaatggtat gatctaggtt taccgcaacc tctgcctcct gggttcaagt   5160
gattctcttg cctcagcttc ccgagtagct gggattacag gcatgtacca ccacgtccag   5220
ctaattttgt attttagta gagacagggt ttctccatgt tggtcaggct ggtctcgaac   5280
tcctgacctc agatgatctg cctaccttgg cctcccaaag tgctgggatt atgggcatca   5340
```

```
gccactgcac ccagccaaaa atgtgatttt atatatatat atataatata caccatgaaa      5400
tactactcag acctaaaaag gaataaaata atggaatttg cagcaacctg gatggagttg      5460
gcctcgttta ctactctggg tttctgtctg aggatgaggg tgatgattgc tgatcaggat      5520
gcggaaggaa cccagtgcta acccacagca tctgccccac agggaaataa ggcacaagtc      5580
tcttgtttga tcccacgcta tgacctctag acctactctt ccctcttgtc accaaaacca      5640
caatcaggaa aaatttctgc aggcatttca ccatcctgga caaggatct gagactcttc       5700 actgaatttg tgaccttcta tccagccaat atttatactg agctattaag attaacatct      5760
tagcctggtc attgccacac aggcaggcaa ggcagctcag gtggaaaata cttttggtca      5820
tcccatgtgt ctgggcatat ggccttgatg tgagtttatg ttcatgctca ggacaagtta      5880
tgggtcaggg gactagtcag cttatgggcc aggaaaaggt gctaaggttt gtggagtcaa      5940
agagggaatt cacacatatt aatgctcctt gtttccacct aaggcagttt gtgaagtctg      6000
tgggttctgt gactgtccac aaatggagca ggaacattcc ttagaacgga tgattgggac      6060
cccacaaagg aaaagacaag aggaagcaca ggctacacaa tgaaaataca cttggtcatg      6120
ccaaaggcta ggtcatgcca aaggctaatg aaagagcttt gagtataatt cagtgccttt      6180
ggggttgagt ggaaaataca aaaccatct ttgccctgct ctcacaccac aacaatcaac        6240
acgtttccat gaccaaatgt gtaggatttc tccccacccc ctagaaagca agccattggt      6300
tttgcagcgg acaccacaca ggtgccctct cattgaatgc aattctgaca ctatccacat      6360
ggagacaggg tcagatctta cagtttgagg gctacttccc caagactgtg ccccactact      6420
tacgccaatc ccaagcctca gattgcttta cctgtgcttc tgtccaaata gctgtaagtt      6480
gaagatttca caacatctcc ttggcttcta ttaatttgct agaatggctc acagagctca      6540
gtagacactt acaggtttat taaaaaggat acaaccaagc atatagatga agacatgcat      6600
agcacaaggt atgggaagtg gtgcaccacc gtccagtaat cttcatgtgt tcagccttcc      6660
agaagttctc ccagcctagc tccatttggg ttattttatg gacgcttcct caccgaggct      6720
ttatggagta aaccactgcc cattggtgaa taatcggcag cccctctccc ctccacagag      6780
gttgggagat gaggctgaaa gtcccatccc tctaacactg ccttggtctt tcttgtgacc      6840
tgcccccatc ctgaagttac ctagggactg tcagccaaca gtcatctcat tagcatacaa      6900
aaagactctg gtgattttaa gtattttagg agttgtataa caagaaatgg ggtcaaagac      6960 caaaccata atttataata acacagggat gaaaagaaa gtagaggttg atgatttcaa        7020
gcccacacta gtcctcatta tgacagatgt ggatttccaa cccataagag gcaggaggct      7080
gaagagctga gacgaaacct gtgaaaagca gggacagggg acatttctca atttcttgtt      7140
actgaagtga tagagctcca ccaggcctca cttggattga caaactaaat taaaagatac      7200 actcttaaa taaaaagcac ttctgagcat acatccaaaa gaatgaaaat caggatattg       7260
cagaaatatt tgcacatttt tattcatgca gcattaatca caatttcaaa gacatggaga      7320
cagcataagg tccactaatc attgaatgtt tacagaaaat gtggtgtata gctgcaatgg      7380
atgctgttca aattcaagaa gaattaggcc gggcacggtg gctcccgcct gtaatcccgg      7440
cactttggga ggccaaggcg ggcggatcac aaggtcagga gttcaagacc agcctgacca      7500
atatggtgaa accccgcccc tactaaaaat accaaaatta ctgggtgtg gtggcagaag       7560 cctgtaattc tagatactca ggaggctgag gcaggagaat ctcttgaatc cgggaggcag      7620
aggttgcagt gagctgagat tgcgccactg cactccagct gggtgacag agtgagactc       7680 tgtctctcaa aaaaaaaga ataattaaat tttgccatat gcagcaacag ggaaaacct        7740
```

```
ggaggatatt acactgagtg aaataagcca atcttagaag gggaaatgct gcacggcctc      7800
atttatatga ggtatctaat ttttttttt cgagacagag ttttgctctt gtcacccagg       7860
ttggagtgca atggcgcgat ctcagctcat tgcaacctcc gcctcccggg ttcaagcgat      7920
tctcctgcct cagcctcctg agtagctggt attacaagtg cctgccacca cacctggcta     7980 attttttgtat ttttagtaga gacacagttt caccatgttg gccaagctgg tctcgaactc    8040
ctgacctcag gtgatccgcc tgcctcgacc tcccaaagtg ctgggattac aggcatgagc     8100
caccacgtcc ggcctatagg aggtgtctaa tatactcaac cgagcagaaa tggagtagaa     8160
tgctggttgc caggggtagg gagagaagga aatggggagt cactgctcaa gggctatgaa     8220
gctttaggtt tgcaaaatga acaagttcta gagatgtgct gtacaacact gtgcttacag     8280
ctgacaacac tgtattatgt acttaaaatt ttattcagag ggtatatcac acattaaacg     8340
ttcttattaa catgaaaaag ggatagaaaa taccatgaaa ccacttacag aaagcaagta     8400
tggcaatcct ctgtcctttg tcttgggaga aagttttggc caagagacaa tttaggcaaa    8460
aaagagaatt tactgaagaa aaacagagag caaatagttt atttagagag acagtgtact    8520
ctggaagata aggcagagcg ggctgctgat agagaatgag ccagcggccc gagaaatgtg    8580
cactgagttt ttatgatatt gcactttttc ttggagttcc cacctctgtt ttaagtctcc    8640 acctttttt ctttctctag tttttctgct tcagccttaa gtccctgcct tttccccaca     8700
tagtttccag cccaggctgt gggaccctcc cttaacacac acatgggccc agtgtttgat    8760
aggaattcta cctaatggct gcattgctca ttactgccac cccaggaagg ttgtatggtg    8820
gtcaaatcta tacttactgt acctgcatct ctcttagaaa tttctccttt gctctcaccc    8880
ctattatcag catgcagcta gctacattct gacaggttaa cttcagagtg agtgaatact    8940
gggtgtctta aggggctttg ttctggcata ggtatttacc ctaatctctg ttcgtatcta    9000
gcatgtgtgc tttgggtggt ctctggggtg tgagattttc cagaactccc ttttctcagg    9060
ggctgcccct cctgcttctg tctagctatc tgcctactct aaagttagta ttagtatgaa    9120
agcttttatg aaaaacattt ttttccaaga aaagggaggc atttttatact ggtgaaataa   9180 ggtgttcaat gacaacacat aacaactgta aattgtatgc acctaataaa atagcttttaa  9240 agtatttgaa gcaaaactgt ctcttttagc agaattaaaa agagaaataa tcaatccata    9300
atcatataca cagatattaa tacaactctc ttattaactg agtgaatgac atggagaaaa    9360
aagagtatac atacaaatac gtgaaaacca tgattaacaa aatcaatcca gtgacaccag    9420
gaacccaagc ctgaagggta gttgcttgag tatgcattca tggatgaacg catccaatga    9480
atcatcacag gaacaaacaa ttgaggcctt cgtttatgta tttctaactg atgttaagtt    9540
tttccttcct attctgtgag tagaggtgga tcc                                 9573
```

<210> SEQ ID NO 169
<211> LENGTH: 1180
<212> TYPE: DNA
<213> ORGANISM: Homo sapiens

<400> SEQUENCE: 169

```
ggagcggcgg cccctgagag gaagcggcga agatggccat gaacattttc cggctgactg       60
gggacctgtc ccacctggcg gccatcgtca tcctgctgct gaagatctgg aagacgcgct     120
cctgcgccgg tatttctggg aaaagccagc ttctgtttgc actggtcttc acaactcgtt    180
acctggatct ttttacttca tttatttcat tgtataacac atctatgaag gttatctacc     240
```

-continued

| | |
|---|---|
| ttgcctgctc ctatgccaca gtgtacctga tctacctgaa atttaaggca acctacgatg | 300 |
| gaaatcatga taccttccga gtggagtttc tggtggtccc tgtgggaggc ctctcatttt | 360 |
| tagttaatca cgatttctct cctcttgaga tcctctggac cttctccatc tacctggagt | 420 |
| ccgtggctat ccttccgcag ctgtttatga tcagcaagac tggggaggcc gagaccatca | 480 |
| ccacccacta cctgttcttc ctgggcctct atcgtgcttt gtatcttgtc aactggatct | 540 |
| ggcgcttcta ctttgagggc ttctttgacc tcattgctgt ggtggccggc gtagtccaga | 600 |
| ccatcctata ctgtgacttc ttctacttgt acattacaaa agtactcaag ggaaagaagc | 660 |
| tcagtttgcc agcataagtt gccaaagacc atcaccagca tctgtccttc agggtgctcg | 720 |
| gacagaattc ttaccacagc aaaggcataa gatgcttgat acggaaaatc agaaacttaa | 780 |
| ctcttttgtt gcagatagtc atcagtggct ctgtaaaaac gcagaggaaa agagccagaa | 840 |
| ggtttctgtt taatgcatct tgccttatct ttttttatta ctgtgtacaa agattttttt | 900 |
| acacaaagaa acttaatgct gtattaataa attcagtgtg tagcttcaat tgggatagtt | 960 |
| ccaaaagtga agattttgtg aggaataagt gcaaattttt tttttatttt aaaaaattct | 1020 |
| ttgaaactct taagtctttg tgtctgcaat gaaattgtac tccttgacag ttgatagatt | 1080 |
| atgtattctt ccatccctca aacttgcatt ccactatatt tatttttggg caaaagatga | 1140 |
| gctgtatttg tttgaaatct gagacactat gttcaattgg | 1180 |

<210> SEQ ID NO 170
<211> LENGTH: 1267
<212> TYPE: DNA
<213> ORGANISM: Homo sapiens

<400> SEQUENCE: 170

| | |
|---|---|
| cagcgagcgg ctgcagcggg gccgtgacca gcagccagcg ggaggcggcg gcgagtcggt | 60 |
| gagcagctgg gaagagcaga accggggcgg agcacctgca ggcgcgggcg gcggccccac | 120 |
| catggcgatt cgcaagaaaa gcaccaagag ccccccagtg ctgagccacg aattcgtcct | 180 |
| gcagaatcac gcggacatcg tctcctgtgt ggcgatggtc ttcctgctgg ggctcatgtt | 240 |
| tgagataacg gcaaaagctt ctatcatttt tgttactctt cagtacaatg tcaccctccc | 300 |
| agcaacagaa gaacaagcta ctgaatcagt gtcccttat tactatggca tcaaagattt | 360 |
| ggctactgtt ttcttctaca tgctagtggc gataattatt catgccgtaa ttcaagagta | 420 |
| tatgttggat aaaattaaca ggcgaatgca cttctccaaa acaaaacaca gcaagtttaa | 480 |
| tgaatctggt cagcttagtg cgttctacct ttttgcctgt gtttggggca cattcattct | 540 |
| catctctgaa aactacatct cagacccaac tatcttatgg agggcttatc cccataacct | 600 |
| gatgacattt caaatgaagt ttttctacat atcacagctg gcttactggc ttcatgcttt | 660 |
| tcctgaactc tacttccaga aaaccaaaaa agaagatatt cctcgtcagc ttgtctacat | 720 |
| tggtcttac ctcttccaca ttgctggagc ttaccttttg aacttgaatc atctaggact | 780 |
| tgttcttctg gtgctacatt attttgttga atttcttttc cacatttccc gcctgtttta | 840 |
| ttttagcaat gaaaagtatc agaaaggatt ttctctgtgg gcagttcttt ttgttttggg | 900 |
| aagacttctg actttaattc tttcagtact gactgttggt tttggccttg caagagcaga | 960 |
| aaatcagaaa ctggatttca gtactggaaa cttcaatgtg ttagctgtta aatcgctgt | 1020 |
| tctggcatcc atttgcgtta ctcaggcatt tatgatgtgg aagttcatta attttcagct | 1080 |
| tcgaaggtgg agggaacatt ctgcttttca ggcaccagct gtgaagaaga aaccaacagt | 1140 |
| aactaaaggc agatcttcta aaaaggaac agaaaatggt gtgaatggaa cattaacttc | 1200 |

```
aaatgtagca gactctcccc ggaataaaaa agagaaatct tcataatgaa ttataaacta      1260
attgatt                                                                1267

<210> SEQ ID NO 171
<211> LENGTH: 520
<212> TYPE: DNA
<213> ORGANISM: Homo sapiens
<220> FEATURE:
<221> NAME/KEY: misc_feature
<222> LOCATION: (1)...(520)
<223> OTHER INFORMATION: n = A,T,C or G

<400> SEQUENCE: 171
aatccaagat cttttttttt tttttttttt tttttttttt ttttcagtt acacttttcc        60 ttgctttaat attttttgtc tttttctgct tttgaaatga gctctcaatt acaaaatacc      120
aaactacact caaaagaggg tgtanaaaaa gccagccatt ggcncagcat gganaagccc      180
acaagtaagg acagatagca gcagcaggng gcaagaggtg ggaggtgact gaagcagngg      240
ttacaaatgt tcacaggaag ctaaaactat ccaacaggtt gngccctaat gttagcncag      300
gttanactag ttactacctt gctaggnggc ctcagngngt tcanattnta cgcagcaata      360
caatttnttc cagttaanag ttcttgactt gcaccgatca cagcatggtt gaagggtact      420
ggaccagtct tgttagtttt tcaaaatgct gtcgtaaacc tgatanatgt attgagagac      480
ttcaggagct ntacncttca gtgacagcgt gtaattgggg                            520

<210> SEQ ID NO 172
<211> LENGTH: 1653
<212> TYPE: DNA
<213> ORGANISM: Homo sapiens

<400> SEQUENCE: 172
gcggccgcag ttttttttt tttttttttt ttttttagc caaacagatt ggtcattatt         60
gtacacatag ctggaaggga ggggtggtcc cggggtaagg acagggctgc ccaatatttg      120
gggggaggaa gggactcttc ttccaaatgg gcttgtccgg gaaccggggt cccggggagc      180
tgggcgcctg gtccacatgg accccctcca cctccccaca tacgctgtgg aagaagggca      240
ggagtgagaa atgctggggg aggacgaccc tttggtctga gatgtggagg tgatcataac      300
agttcccgcc cgctggctgt tttgttgact ttggagaggc cttcccggaa cccagagtcc      360
gtcattactt gctccatctg aacatcctcc tcgtcctcct ggggcagctg caggtacggg      420
ttgttccctg tgggctggaa cttgtagccc gtgagcacga agaaggccag ggtggagccc      480
tccaccaaga gctggtacag ccactgccac tgaaagggca cagccacctg cagcaggatg      540
gcgatgatgc gggtgaagta gacgtagcag atgaccatga catagtaatg ccggaacagc      600
ttcagcttgg ccaggttcac tgccaccttc ccgtctgtgc cagacgcatc ctggagatgc      660
cggatggacc agactacggg gaacaggatg gcaccacagc agatgaggtc caccaggaac      720
aaaatctcct tccacagcac gtagtcgctg gcgccttcct cgcgggactc gatgatgatg      780
taggccacgt tggccaggac ctgcatgggg atcacgatcc caaagacctt cttctcctta      840
tccgacagga cgtacttgat gaaggccag cctgagccaa tcagggcgat ggtgatgaag      900
aggagggcgc ccttcagcag gtgtgcgatg tagtacatga cggcaaggcc ttcgatgggg      960
tggccctggc tgttgatgaa gtagtagttg atgctgtgga agaggagaga gatgctcttg     1020
gtgaaggcca aggccgccat gagccagtgg atcttgaaga cgctgtacgt gttcctgcag     1080
```

```
aggatggaca cccagaagat gccagcggcc aggaagcagg cggacatgac catgtagagc    1140
ttgaaaaggg gcatctccgc tgccgacagg aagccatcgg ggttcttctc ccggatcatc    1200
accgtgatgt cgaatggatg ctcctttcct ggcactgaat tgttgcagtt gtggaagttc    1260
aggctgtact ggccttcttc cgcctgagag ccgatcacca cgtggaaact gaagttgtag    1320
gagttgttga ggtggctcag gcccaacacc aggtccttgt ccttcccact aggaccctga    1380
atcactgcgg gtgttgactt gggcttgctg gctgcagagg tccctccgcc atccaccttg    1440
cgggggactg tggcctgtgg cttcgggagc cctggtttgg agggtgcttc cgggaggagc    1500
ccgggaaaga taaacaacgt cttctgctct ccatacttcc gcacctggac ctgcagatcc    1560
ttggtgttga tgaggaacag gaccaggaaa ctgctactgt ttttctggag agggcagtcc    1620
tggaaatccc gggttggcct cgtgcccgaa ttc                                 1653

<210> SEQ ID NO 173
<211> LENGTH: 532
<212> TYPE: DNA
<213> ORGANISM: Homo sapiens
<220> FEATURE:
<221> NAME/KEY: misc_feature
<222> LOCATION: (1)...(532)
<223> OTHER INFORMATION: n = A,T,C or G

<400> SEQUENCE: 173
aggcccaaaa cgagaacatn naananccgt tttttccnca naaaagccnt tttnanaaag     60
cacagcaaga cnngnctgcg gacacacagg aggcacacgg acagcccgcc aaccagagag    120
ggagacgaag gccagcgagg ctctcacagg ccagcgnggc tcncacaggg cagcgcatcn    180
canaacccct ggcccccctc gngccaaggc tggccnagn caggccacgc ccacgccgcc    240
ntangacaaa tagaggccgg agccaaggag gnggcaacag agcagggca aggaaggnan    300 ccncaggttc ngataangac ccngcaaatc ccaccccacc ctcaggcacc nccggcnaag    360
gggaccggan accccaggna aggaggnacc caggagggcc gnggnaaccc tagggctgac    420
gaaacnagct ccgacaagcc aggccacngg gaggnacctc aggatggaaa agatgctgga    480
ggcnnagntg gcatcangaa gccgggagcc ccacgggggc aaaaggggag gg            532

<210> SEQ ID NO 174
<211> LENGTH: 1246
<212> TYPE: DNA
<213> ORGANISM: Homo sapiens

<400> SEQUENCE: 174
ctcgaggcca agaattcggc acgagagact tgctaggaag aaatgcagag ccagcctgtg     60
ctgcccactt tcagagttga actctttaag cccttgtgag tgggcttcac cagctactgc    120
agaggcattt tgcatttgtc tgtgtcaaga agttcacctt ctcaagccag tgaaatacag    180
acttaattcg tcatgactga acgaatttgt ttatttccca ttaggtttag tggagctaca    240
cattaatatg tatcgcccta gagcaagagc tgtgttccag gaaccagatc acgattttta    300
gccatggaac aatatatccc atgggagaag acctttcagt gtgaactgtt ctattttgt     360 gttataattt aaacttcgat ttcctcatag tcctttaagt tgacatttct gcttactgct    420
actggatttt tgctgcagaa atatatcagt ggcccacatt aaacatacca gttggatcat    480
gataagcaaa atgaaagaaa taatgattaa gggaaaatta agtgactgtg ttacactgct    540
tctcccatgc cagagaataa actctttcaa gcatcatctt tgaagagtcg tgtggtgtga    600 attggttttgt gtacattaga atgtatgcac acatccatgg acactcagga tatagttggc    660
```

```
ctaataatcg gggcatgggt aaaacttatg aaaatttcct catgctgaat tgtaattttt    720
tcttacctgt aaagtaaaat ttagatcaat tccatgtctt tgttaagtac agggatttaa    780
tatattttga atataatggg tatgttctaa atttgaactt tgagaggcaa tactgttgga    840
attatgtgga ttctaactca ttttaacaag gtagcctgac ctgcataaga tcacttgaat    900
gttaggtttc atagaactat actaatcttc tcacaaaagg tctataaaat acagtcgttg    960
aaaaaaattt tgtatcaaaa tgtttggaaa attagaagct tctccttaac ctgtattgat   1020
actgacttga attattttct aaattaaga gccgtatacc tacctgtaag tcttttcaca    1080
tatcatttaa acttttgttt gtattattac tgatttacag cttagttatt aattttctt   1140 tataagaatg ccgtcgatgt gcatactttt atgtttttca gaaaagggtg tgtttggatg   1200
aaagtaaaaa aaaaaaaaaa aaaagatct ttaattaagc ggccgc                   1246
```

<210> SEQ ID NO 175
<211> LENGTH: 1223
<212> TYPE: DNA
<213> ORGANISM: Homo sapiens

<400> SEQUENCE: 175

```
ctcgaggcca agaattcggc acgaggccag caagtgtttt acaggtgcct tggattaaaa     60
caaaattgat tttaaaattt ttatgtaagt cattgtgtct atgatgccac ttttaaaagg    120
aaaatgcaat tgcgtaatgg cttatatcct tatttaatgt acctatttgt gttctaataa    180
ttgtttgaat gttttattca gcttaaaact ttaccatgaa gtcataaaca gtaaacaatg    240
ttttgttatg tattaagggg atatcagtgt ttctcaaagt atgatccatg gaccatctgg    300
gtcatggcgc ctggtttcag acaacctgaa tcaaatctta ggggtggggc tttgggatgt    360
cattgttcaa taggcacctc aggagattct gagcacacca atgtttgaga accactaaaa    420
tgaggagtgg gaaaaaaaaa ataggtgttt tgttaattta gagctgagct gagaagataa    480
tatattttta ttgtcaatga cattaacaga tatgcactga ttcttttata cctacaattt    540
acttaatgtt cctttttatta aaacgcgtgg ttcatgagca actacagact gaatccagat    600
tattacctgt tgctttcagt attttcgtga tggcttttaa tcttatgaaa tcatcttgag    660
atcattcatg gtcaagccat gaaaactccc atcttcaagc ctgcctgcta aagcttcttt    720
gccttcctga ttgtgattat ggtaacaatt tatatcagac agttgtactt tttgataact    780
tagggaaaac agaaatgact tgaacaaggg attgcctgcc tcactgcatt gcagagatac    840
aatttctgta aagaacacaa atagcagttg tgaatattaa ggtgtgatta tcttcccctg    900
tccatgtgct tattgaaaga agatagtgaa caaatgatta tattgaggat ttttttaatt    960
tataagatct aatgtgaaat ccacacttgg aacttttag atctgtctgt tgcttgttta   1020
atatatttct tttatgacat tacttaaagt ttaaaagggt tttctatcca ctgtcaattt   1080
caattggata acattttgtc aagttttttt tttcctgatt atttgatgct agctggaatt   1140
caagaaatgg cattgacctt attcaaataa agaaatattt tagtaaaaaa aaaaaaaaa    1200 aaaaaaaaaa aaaaggcggc cgc                                           1223
```

<210> SEQ ID NO 176
<211> LENGTH: 2780
<212> TYPE: DNA
<213> ORGANISM: Homo sapiens

<400> SEQUENCE: 176

-continued

```
gtgggcggac cgcgcggctg gaggtgtgag gatccgaacc caggggtggg gggtggaggc    60
ggctcctgcg atcgaagggg acttgagact caccggccgc acgccatgag ggccctgtgg   120
gtgctgggcc tctgctgcgt cctgctgacc ttcgggtcgg tcagagctga cgatgaagtt   180
gatgtggatg gtacagtaga agaggatctg ggtaaaagta gagaaggatc aaggacggat   240
gatgaagtag tacagagaga ggaagaagct attcagttgg atggattaaa tgcatcacaa   300
ataagagaac ttagagagaa gtcggaaaag tttgccttcc aagccgaagt taacagaatg   360
atgaaactta tcatcaattc attgtataaa aataaagaga ttttcctgag agaactgatt   420
tcaaatgctt ctgatgcttt agataagata aggctaatat cactgactga tgaaaatgct   480
ctttctggaa atgaggaact aacagtcaaa attaagtgtg ataaggagaa gaacctgctg   540
catgtcacag acaccggtgt aggaatgacc agagaagagt tggttaaaaa ccttggtacc   600
atagccaaat ctgggacaag cgagttttta aacaaaatga ctgaagcaca ggaagatggc   660
cagtcaactt ctgaattgat tggccagttt ggtgtcggtt tctattccgc cttccttgta   720
gcagataagg ttattgtcac ttcaaaacac aacaacgata cccagcacat ctgggagtct   780
gactccaatg aattttctgt aattgctgac ccaagaggaa acactctagg acggggaacg   840
acaattaccc ttgtcttaaa agaagaagca tctgattacc ttgaattgga tacaattaaa   900
aatctcgtca aaaaatattc acagttcata aactttccta tttatgtatg gagcagcaag   960
actgaaactg ttgaggagcc catggaggaa gaagaagcag ccaaagaaga gaaagaagaa  1020
tctgatgatg aagctgcagt agaggaagaa gaagaagaaa agaaaccaaa gactaaaaaa  1080
gttgaaaaaa ctgtctggga ctgggaactt atgaatgata tcaaaccaat atggcagaga  1140
ccatcaaaag aagtagaaga agatgaatac aaagctttct acaaatcatt ttcaaaggaa  1200
agtgatgacc ccatggctta tattcacttt actgctgaag gggaagttac cttcaaatca  1260
attttatttg tacccacatc tgctccacgt ggtctgtttg acgaatatgg atctaaaaag  1320
agcgattaca ttaagctcta tgtgcgccgt gtattcatca cagacgactt ccatgatatg  1380
atgcctaaat acctcaattt tgtcaagggt gtggtggact cagatgatct ccccttgaat  1440
gtttcccgcg agactcttca gcaacataaa ctgcttaagg tgattaggaa gaagcttgtt  1500
cgtaaaacgc tggacatgat caagaagatt gctgatgata aatacaatga tacttttttgg  1560 aaagaatttg gtaccaacat caagcttggt gtgattgaag accactcgaa tcgaacacgt  1620
cttgctaaac ttcttaggtt ccagtcttct catcatccaa ctgacattac tagcctagac  1680
cagtatgtgg aaagaatgaa ggaaaaacaa gacaaaatct acttcatggc tgggtccagc  1740
agaaaagagg ctgaatcttc tccatttgtt gagcgacttc tgaaaaaggg ctatgaagtt  1800
atttacctca cagaacctgt ggatgaatac tgtattcagg cccttcccga atttgatggg  1860
aagaggttcc agaatgttgc caaggaagga gtgaagttcg atgaaagtga gaaaactaag  1920
gagagtcgtg aagcagttga gaaagaattt gagcctctgc tgaattggat gaaagataaa  1980
gcccttaagg acaagattga aaaggctgtg gtgtctcagc gcctgacaga atctccgtgt  2040
gctttggtgg ccagccagta cggatggtct ggcaacatgg agagaatcat gaaagcacaa  2100
gcgtaccaaa cggcaaggga catctctaca aattactatg cgagtcagaa gaaaacattt  2160
gaaattaatc ccagacaccc gctgatcaga gacatgcttc gacgaattaa ggaagatgaa  2220
gatgataaaa cagttttgga tcttgctgtg gttttgtttg aaacagcaac gcttcggtca  2280
gggtatcttt taccagacac taaagcatat ggagatagaa tagaaagaat gcttcgcctc  2340
agtttgaaca ttgaccctga tgcaaaggtg gaagaagagc ccgaagaaga acctgaagag  2400
```

| acagcagaag acacaacaga agacacagag caagacgaag atgaagaaat ggatgtggga | 2460 |
| acagatgaag aagaagaaac agcaaaggaa tctacagctg aaaaagatga attgtaaatt | 2520 |
| atactctcac catttggatc ctgtgtggag agggaatgtg aaatttacat catttctttt | 2580 |
| tgggagagac ttgttttgga tgcccctaa tccccttctc ccctgcactg taaaatgtgg | 2640 |
| gattatgggt cacaggaaaa agtgggtttt ttagttgaat tttttttaac attcctcatg | 2700 |
| aatgtaaatt tgtactattt aactgactat tcttgatgta aaatcttgtc atgtgtataa | 2760 |
| aaataaaaaa gatcccaaat | 2780 |

<210> SEQ ID NO 177
<211> LENGTH: 998
<212> TYPE: DNA
<213> ORGANISM: Homo sapiens
<220> FEATURE:
<221> NAME/KEY: misc_feature
<222> LOCATION: (1)...(998)
<223> OTHER INFORMATION: n = A,T,C or G

<400> SEQUENCE: 177

| gataacccca tcttgtatac ctgtggtgac caacatggag gccttctcat cagaacattt | 60 |
| caacttagag atctatcgcc aaaatctgca gaccaagcag ttggggaaag taattttgtt | 120 |
| tgccgaagtg acccccacaa cgatgcgtct cctggatggg ctgatgtttc agacaccgca | 180 |
| ggaaatgggc ttaatagtga tcgcggcccg gcagaccgag gcaaaggac ggggagggaa | 240 |
| tgtgtggctg agccctgtgg gatgtgctct ttctactctg ctcatctcca ttccactgag | 300 |
| atcccagctg ggacagagga tcccgttgt ccagcatctg atgtccgtgg ctgtngtggg | 360 |
| aagcagtgag gtccattccc gagtattcag gatattcaac tttacggagt gnaagtgggc | 420 |
| ccaacggtna tttatttaca gtggacctca tgaagatcng gcggattctg ggttaactca | 480 |
| acantcatgg ggaggaaaca tttatatact tatttgggtg ttggatttaa tgtggantaa | 540 |
| cagttaacct taccatttgc atcaacgacc ttatnacaag tgtcacaaga atgttcttac | 600 |
| agttcagtac ctccccagat gcttacaaac agtgatagca tacctctaac tcaccactgg | 660 |
| cctgggcgca agagcatatt ttggtttgtt ttttcataga ctagggtaa aggtctgcac | 720 |
| tactaagaaa atatctgaat tttcccattg tcatttccat gtaaaaactc cccttgacaa | 780 |
| taaacgtaag tccaagccac agaggggaga gcaatttccc acctgtggga gggctttccc | 840 |
| taaactaaat tttctacttc ttaaccatct atcccagagc ctcttcaaac accaaagaaa | 900 |
| acgacaacaa aacaaaccta aaaacaaaca ggaaacacag ganaaaggaa caaaggnctt | 960 |
| taaccaaatg anttgggagg gaaaggaaaa tttcacct | 998 |

<210> SEQ ID NO 178
<211> LENGTH: 2780
<212> TYPE: DNA
<213> ORGANISM: Homo sapiens

<400> SEQUENCE: 178

| gtgggcggac cgcgcggctg gaggtgtgag gatccgaacc caggggtggg gggtggaggc | 60 |
| ggctcctgcg atcgaagggg acttgagact caccggccgc acgccatgag ggccctgtgg | 120 |
| gtgctgggcc tctgctgcgt cctgctgacc ttcgggtcgg tcagagctga cgatgaagtt | 180 |
| gatgtggat gtacagtaga agaggatctg ggtaaaagta gagaaggatc aaggacggat | 240 |
| gatgaagtag tacagagaga ggaagaagct attcagttgg atggattaaa tgcatcacaa | 300 |

```
ataagagaac ttagagagaa gtcggaaaag tttgccttcc aagccgaagt taacagaatg    360
atgaaactta tcatcaattc attgtataaa aataaagaga ttttcctgag agaactgatt    420
tcaaatgctt ctgatgcttt agataagata aggctaatat cactgactga tgaaaatgct    480
ctttctggaa atgaggaact aacagtcaaa attaagtgtg ataaggagaa gaacctgctg    540
catgtcacag acaccggtgt aggaatgacc agagaagagt tggttaaaaa ccttggtacc    600
atagccaaat ctgggacaag cgagtttta aacaaaatga ctgaagcaca ggaagatggc    660
cagtcaactt ctgaattgat tggccagttt ggtgtcggtt tctattccgc cttccttgta    720
gcagataagg ttattgtcac ttcaaaacac aacaacgata cccagcacat ctgggagtct    780
gactccaatg aattttctgt aattgctgac caagaggaa acactctagg acggggaacg    840
acaattaccc ttgtcttaaa agaagaagca tctgattacc ttgaattgga tacaattaaa    900
aatctcgtca aaaatattc acagttcata aactttccta tttatgtatg gagcagcaag    960
actgaaactg ttgaggagcc catggaggaa gaagaagcag ccaaagaaga gaaagaagaa   1020
tctgatgatg aagctgcagt agaggaagaa gaagaagaaa agaaaccaaa gactaaaaaa   1080
gttgaaaaaa ctgtctggga ctgggaactt atgaatgata tcaaaccaat atggcagaga   1140
ccatcaaaag aagtagaaga agatgaatac aaagctttct acaaatcatt ttcaaaggaa   1200
agtgatgacc ccatggctta tattcacttt actgctgaag gggaagttac cttcaaatca   1260
attttatttg tacccacatc tgctccacgt ggtctgtttg acgaatatgg atctaaaaag   1320
agcgattaca ttaagctcta tgtgcgccgt gtattcatca cagacgactt ccatgatatg   1380
atgcctaaat acctcaattt tgtcaagggt gtggtggact cagatgatct ccccttgaat   1440
gtttcccgcg agactcttca gcaacataaa ctgcttaagt tgattaggaa gaagcttgtt   1500
cgtaaaacgc tggacatgat caagaagatt gctgatgata aatacaatga tacttttggg   1560
aaagaatttg gtaccaacat caagcttggt gtgattgaag accactcgaa tcgaacacgt   1620
cttgctaaac ttcttaggtt ccagtcttct catcatccaa ctgacattac tagcctagac   1680
cagtatgtgg aaagaatgaa ggaaaaacaa gacaaaatct acttcatggc tgggtccagc   1740
agaaaagagg ctgaatcttc tccatttgtt gagcgacttc tgaaaaaggg ctatgaagtt   1800
atttacctca cagaacctgt ggatgaatac tgtattcagg cccttcccga atttgatggg   1860
aagaggttcc agaatgttgc caaggaagga gtgaagttcg atgaaagtga gaaaactaag   1920
gagagtcgtg aagcagttga aaagaatttt gagcctctgc tgaattggat gaaagataaa   1980
gcccttaagg acaagattga aaaggctgtg gtgtctcagc gcctgacaga atctccgtgt   2040
gctttggtgg ccagccagta cggatggtct ggcaacatgg agagaatcat gaaagcacaa   2100
gcgtaccaaa cgggcaagga catctctaca aattactatg cgagtcagaa gaaaacattt   2160
gaaattaatc ccagacaccc gctgatcaga gacatgcttc gacgaattaa ggaagatgaa   2220
gatgataaaa cagttttgga tcttgctgtg gttttgtttg aaacagcaac gcttcggtca   2280
gggtatcttt taccagacac taaagcatat ggagatagaa tagaaagaat gcttcgcctc   2340
agtttgaaca ttgaccctga tgcaaaggtg gaagaagagc ccgaagaaga acctgaagag   2400
acagcagaag acacaacaga agacacagag caagacgaag atgaagaaat ggatgtggga   2460
acagatgaag aagaagaaac agcaaaggaa tctacagctg aaaagatga attgtaaatt   2520 atactctcac catttggatc ctgtgtggag agggaatgtg aaatttacat catttctttt   2580
tgggagagac ttgttttgga tgcccctaa tccccttctc ccctgcactg taaaatgtgg   2640
gattatgggt cacaggaaaa agtgggtttt ttagttgaat ttttttaac attcctcatg   2700
```

```
aatgtaaatt tgtactattt aactgactat tcttgatgta aaatcttgtc atgtgtataa    2760
aaataaaaaa gatcccaaat                                               2780
```

<210> SEQ ID NO 179
<211> LENGTH: 2475
<212> TYPE: DNA
<213> ORGANISM: Homo sapiens

<400> SEQUENCE: 179

```
ccggaggagt ccgagaggaa gcggaggcgc gagctggagg cggcggctcc cgtcggcctc      60
cggcaggact gagcgctggg aggccggaag gcgggcgcgc acggcggaga ggcgggcggg     120
aggccggagc atattaatga aaagtgccat aaactgaaaa accaaacatg agggtagcag     180
gtgctgcaaa gttggtggta gctgtggcag tgttttact gacattttat gttatttctc      240
aagtatttga aataaaaatg gatgcaagtt taggaaatct atttgcaaga tcagcattgg     300
acacagctgc acgttctaca aagcctccca gatataagtg tgggatctca aaagcttgcc     360
ctgagaagca ttttgctttt aaaatggcaa gtggagcagc caacgtggtg ggacccaaaa     420
tctgcctgga agataatgtt ttaatgagtg gtgttaagaa taatgttgga agagggatca     480
atgttgcctt ggcaaatgga aaaacaggag aagtattaga cactaaatat tttgacatgt     540
ggggaggaga tgtggcacca tttattgagt ttctgaaggc catacaagat ggaacaatag     600
ttttaatggg aacatacgat gatggagcaa ccaaactcaa tgatgaggca cggcggctca     660
ttgctgattt ggggagcaca tctattacta atcttggttt tagagacaac tgggtcttct     720
gtggtgggaa gggcattaag acaaaaagcc ctttttgaaca gcacataaag aacaataagg     780
atacaaacaa atatgaagga tggcctgaag ttgtagaaat ggaaggatgc atcccccaga     840
agcaagacta atgaaatgt ggagagaatt gaagaaagcg cactttcact cttaatggga     900
gagctataaa tggcagagct atgtgtaaat attttaagag catgcagcca tcttggtgtg     960
tgcatgagta ttgtctcttt tgatatcagg attatttatt gctaacgtaa atagatagca    1020
ttgtaaataa tcatcacaat gatcaaatca ctgaaccatg tctccgcaca tttccctaaa    1080
agtacaatgt ttagactgct atggtaatac atatttaaa ttctaaaagc atacacaatg     1140
tgtaactgaa tggtttgtga aaaatatatt gatatatata ctagttgcta tgaaaatatc    1200
atggaataat agggattta gggtggatac tttattttct tttatgtttc tatatgttgc     1260
gttgtgatga cattatcttt taaattaaaa agagatttgg ctagttgtgt gtgtaatgtt    1320
actttacagt ccgactctcc tgatgtacct cttttcatga tctttttctt tccttcccaa    1380
gaaactgagg aatgtttaat atgaaaacat acatcggata tgtgaaaagc acaacaaaat    1440
tcttaatgta cacagtaaaa aagtaaatat ataaatgtag atggcattta ggaccacagc    1500
ttgctggatt tgtgttagct atgggaataa cttgattttg tataagctat ttagagtgag    1560
gctggaggtg gcagcttcac agaactggag aaccaggcca agtcccctcc ccaacctaat    1620
taggtcattc aggacagcta agtcagtata tttagagcaa tactagcata cgttttctt     1680 aattgttatc agcattgacc aagtggtttg gaaggaggca tgctttaata tcacaataat    1740
tttgatttgt aaaccaagaa attaatcctg tgtttatcta acttcataat agcaattatt    1800
gcccgaagct atagtggcat atttacaaaa gttcttatta ctgggcggac tgataacatt    1860
taaaaaataa ttgtgtttga ccccaaatga ctttataccc aattctacat aaaaatatag    1920
aagatctatc ttttttttgtt accttcagat gttcactaaa taactcagtt tttaagcaga    1980
```

-continued

| | |
|---|---|
| agttttcagg gcattaaata tatgttgtgt atgaagtatc tcaaactgga acataaattt | 2040 |
| agtgatcaaa ctgccattca cagtgtaagg cagcacttaa atttcgaacc taaagtttag | 2100 |
| atgcattgta taaaaaaacc taaaagcagt atctgttatt tagctgtaaa ccaagttgga | 2160 |
| agctattcgg ataatttctt aaatattgat gaactttgga gtactgtttc ttccttcaaa | 2220 |
| ctgaatgtaa ttaattcatg aataaatgca ccttatatgt ttaaacaatc tttgtatact | 2280 |
| tttgggattt ttggtgctta tgctaaat cacattcagc atgtgtattt tgacatttaa | 2340 |
| aatacttccc tcaattctgt aaattaaaag aatagttatt ttacagttcc agggattgtg | 2400 |
| aaataaatgt tgcagttttt taaaataatg aaaataaata ctcttggttt tgctttgtga | 2460 |
| aaaaaaaaaa aaaaa | 2475 |

<210> SEQ ID NO 180
<211> LENGTH: 823
<212> TYPE: DNA
<213> ORGANISM: Homo sapiens
<220> FEATURE:
<221> NAME/KEY: misc_feature
<222> LOCATION: (1)...(823)
<223> OTHER INFORMATION: n = A,T,C or G

<400> SEQUENCE: 180

| | |
|---|---|
| gctggagaaa ggaatgtgct catcaccagt gccctccctt acgtcaacaa tgtcccccac | 60 |
| cttgggaaca tcattggttg tgtgctcagt gccgatgtct tgccaggta ctctcgcctc | 120 |
| cgccagtgga acaccctcta tctgtgtggg acagatgagt atggtacagc aacagagacc | 180 |
| aaggctctgg gaggagggac taaccccca ggagatctgc gacaagtacc acatcatcca | 240 |
| tgctgacatc taccgctggt ttaacatttc ngtttgatat ttttggtcgc accaccactc | 300 |
| cacagcagga ccaaaatcac ccaggacatt ttccagcagt tgctgaaacg aggttttgtg | 360 |
| ctgcaagata ctgtgagaga ttcgtacatt tatttattac tgtccctatc tattaaagtg | 420 |
| actttctatg agccaaggtc ttttacttt tcttcttgcc tttagggct tcaggggtt | 480 |
| tcccctcagc tacagccaac tgtttcttta gatccaagag tttcgccacc tccgcagcaa | 540 |
| cctcgttctt gtctgccttt tgtgctttca gttctcggac aatgtttcct tgttttgtca | 600 |
| cttcatccat cagcgcttgt atctgctgtg gcttggctgt tgtaacagtc tctacaactg | 660 |
| ctggcttcgg ggacgttttt gcctggcccc ctccaaagcg ctgccttaaa ctttcaatct | 720 |
| ggtcattttc caattttggg aacaagggac tgactgtgcc aatctggtgt cctgctggta | 780 |
| aggtacacag gaagtttgtc agcaggatac tgcaggctgg gag | 823 |

<210> SEQ ID NO 181
<211> LENGTH: 415
<212> TYPE: DNA
<213> ORGANISM: Homo sapiens
<220> FEATURE:
<221> NAME/KEY: misc_feature
<222> LOCATION: (1)...(415)
<223> OTHER INFORMATION: n = A,T,C or G

<400> SEQUENCE: 181

| | |
|---|---|
| tttttttttt ttatggatgc actgttacat gtttatttag cgaaggtgac ttggaaaagg | 60 |
| agattcacat acttccactg tatcctccgg gtaagttttc cttctcttct gtanatgtct | 120 |
| ccatgttaca gtcaactata aacatggct catgttcact ctgggcttcg ccttcagagg | 180 |
| agtttgatat tttggaagtg gtacctttgt tctgtgtgct tttcagacca accgcttctt | 240 |
| tcatttcttc aaggcttnct tccaaaggag ttaaatcatc atcatgtcct tttggaagag | 300 |

```
cagggtcctc aatggtgtaa gaaaagccat ttccctntgg gcatgcgtct tctttcccag      360
cctgtctaca acaccttagg gcttcttcag gggcagaagt cacgcaactt gaagt          415
```

<210> SEQ ID NO 182
<211> LENGTH: 1601
<212> TYPE: DNA
<213> ORGANISM: Homo sapiens

<400> SEQUENCE: 182

```
gcggccgctt aattaaagat cttttttttt tttttttttt tttttcaca aataaaccaa       60 ctttaataga tattattttg tatttatata gtgccttctt caagaaccct aaatgcttta      120
cagacattat ctctaattaa tccccacaac aaccctgtga ggtaggtatt actcccattt      180
tacaagacag ggagactgaa gcacagagag gttaagtgac ttgcccaagg tcacacagtt      240
aaattcactg aagagccagg acatgagcgc tttagcctcc cagctcccag ccaaatacct      300
catgatagaa tctttaataa aaagtgtttt taaagaaagt atcaagagta gttatgttat      360
gaaaatgagg tctttctact gccatcaagg aaagaaaaaa ccctatactg atggttagag      420
gccccaagac ccatataata caacatttcc ctctttccct gttcccaagc ctcctggttc      480
ctgtcttaaa taatcttttta aaggtaaaat ttccaagaca gaagccatgt gacttaagaa      540
gtgggactta atttagaata tttactttta gttacaataa tttatagaaa tttttattcc      600
aatatacaaa atatgggaca gccatcccaa caatcatgta catagttaca cggcaatcag      660
ccaccactta caacttacac cagccccgca ttttaatcac agtcaaccaa catacaacct      720
cacgatgctt tcttcatggg tcacttttct tacttactat acctgtattt ttcccccaac      780
cctgacccta tacgttttaa aagtacattt agtttctgat aaacttcaaa acattttact      840
tagatccagc tgcattaaga agaaaaagta aatgtaaaac tgtcacccca caatccctcc      900
cctgacaaat catactatga agtacggtgt agatgtgaac aagtatgtga ttaccaggaa      960
ctcaacacat acactagaac ttgctttaat atgaaattta acttggcttt tacggcatgt     1020
ttttttttaa tgcaaaaatg taaaaacaaa cacaacatag tatttcaatg ctgtaccttt     1080
atgcaaatga cttcatctat cttttcttaaa catgttgata tagctaatgt taaaactgac     1140
acagcttcac tttcctcttt ttctctgtac cgaaagctgc agaaatacag ctttaattcc     1200
aagacaattt ggtttaagcc ttcaaaataa aaagagtgca tccacttcca ctgccctgac     1260
tttccccaca ctgttgattg tgattctctg tggcatgttg gtagatcagg ctggcttata     1320
tataatttgt acaaaacacc tctagccagg gtaaggcttt aggaactatc ttaaaaagaa     1380
acttgtcaaa atacttttttg atattttgta caaatactaa atattataat tttctcccag     1440
aacatccgtt taagcagccc aattaagtga ctctgttaaa ggtctgctta tggaaaaaat     1500
aggtgaagtc atttcctgag ccaaaagata cagataataa atgttaataa tagcagcaga     1560
ctaaaaaatt cctttttgtt gttttccctc gtgccgaatt c                        1601
```

<210> SEQ ID NO 183
<211> LENGTH: 1056
<212> TYPE: DNA
<213> ORGANISM: Homo sapiens

<400> SEQUENCE: 183

```
ctcgaggcca agaattcggc acgaggagtc atcagatatt ttagccacct acacaaaagc       60
aaactgcatt tttaaaaatc tttctgagat gggagaaaat gtattctcct ttcctatacc      120
```

```
gctctcccaa caaaaaaaca actagttagt tctactaatt agaaacttgc tgtacttttt      180
cttttctttt aggggtcaag gaccctcttt atagctacca tttgcctaca ataaattatt      240
gcagcagttt gcaatactaa atatttttt atagactttta tattttttcct tttgataaag     300
ggatgctgca tagtagagtt ggtgtaatta aactatctca gccgtttccc tgctttccct      360
tctgctccat atgcctcatt gtccttccag ggagctcttt taatcttaaa gttctacatt      420
tcatgctctt agtcaaattc tgttaccttt ttaataactc ttcccactgc atatttccat      480
cttgaattgg tggttctaaa ttctgaaact gtagttgaga tacagctatt taatatttct      540
gggagatgtg catccctctt ctttgtggtt gcccaaggtt gttttgcgta actgagactc      600
cttgatatgc ttcagagaat ttaggcaaac actggccatg gccgtgggag tactgggagt      660
aaaataaaaa tatcgaggta tagactagca tccacataga gcacttgaac ctcctttgta      720
cctgtttggg gaaaaagtat aatgagtgta ctaccaatct aactaagatt attatagtct      780
ggttgtttga ataccatttt ttttctcctt ttgtgttttt cccactttcc aatgtactca      840
agaaaattga acaaatgtaa tggatcaatt taaaatattt tatttcttaa agccttttt      900
tgcctgttgt aatgtgcagg acccttctcc tttcatggga gagacaggta gttacctgaa      960
tataggttga aaaggttatg taaaaagaaa ttataataaa agggatactt tgcttttcaa     1020
aaaaaaaaaa aaaaaaaaaa aaattggtgc ggccgc                              1056
```

<210> SEQ ID NO 184
<211> LENGTH: 1215
<212> TYPE: DNA
<213> ORGANISM: Homo sapiens

<400> SEQUENCE: 184

```
gaattcggca cgaggaggtg aaggacccag aggacaaggt catcctggcc cggcagtatg       60
gctccgaggg caggttcact ttcacttccc atacccctgg tgagcaccag atctgtcttc      120
actccaattc caccaagttc tccctctttg ctggaggcat gctgagagtt cacctggaca      180
tccaggtagg tgaacatgcc aatgactatg cagaaattgc tgctaaagac aagttgagtg      240
agttgcagct acgagtgcga cagctggtgg aacaagtgga gcagatccag aaagagcaga      300
actaccagcg gtggcgagag gagcgattcc ggcagaccag tgagagcacc aaccagcggg      360
tgctgtggtg gtccattctg cagaccctca tcctcgtggc catcggtgtc tggcagatgc      420
ggcacctcaa gagcttcttt gaagccaaga agcttgtgta gctgtcccag gcgtcacaac      480
ccatcctccc aggctggggg agaaaggacc tcctggaact gacttcttct gtcaggagga      540
ctggttttcca gccataccctg ttctggaagg gagaggggct ggaggcaccc acaggcacaa      600
gctgaaggca gcagcttggc taatactgag caggtagtgg ggcaaattcc tgccctctct      660
ctctggcctc tgggccgttt ggtagtaatc acccagggc tggtaaagcc cctcctcttg       720
gcacctcaga atcacagtgt tactgatcag ggatgtgagg ctgctgttgg gggtggggg       780
aggggaatgg gcaggcaagc cagtcttctg tcttccttttg ctaacttagg gttttgagca      840
ggttggggta tggtgcctgt catacccacc tgccacctg ggaacctcac tgttctctct       900
ttcagcctag acctgctgat ccagggtgtg tgtgagttga gggtgggtgg aggggttttgc     960
agtgtgggaa tgtggccctg cagttgacct gagctgcttc acatggttgt ccattctggg     1020
gcttaaagaa ctgggaccag accaagtaga ggccttggtg ctggttgggg tggggcctgc    1080
agagtcttag ttactgattt cattttcaat aaatgtaggt ttgttacatg agtttcccaa    1140
ttaaaaaaaa aatgacttct tgtccagtga aaaaaaaaaa aaaaaaaaaa aaaaaaaaa     1200
```

```
aattggtgcg gccgc                                                       1215
```

<210> SEQ ID NO 185
<211> LENGTH: 836
<212> TYPE: DNA
<213> ORGANISM: Homo sapiens

<400> SEQUENCE: 185

```
ctcgaggcca agtattcggc acgaggggca agtctactgc gggctggtcc gggctcctca       60
ggttcagacc cgaccgttat ccagtcggtt cgtggagagg agaggtgcac tttacaggtc      120
cctgatgaac caagagaacc ctccaccata tccaggccct ggtccaacgg ccccataccc      180
accttatcca ccacaaccaa tgggtccagg acctatgggg ggaccctacc cacctcctca      240
agggtacccc taccaaggat acccacagta cggctggcag ggtggacctc aggagcctcc      300
taaaaccaca gtgtatgtgg tagaagacca agaagagat gagctaggac catccacctg       360
cctcacagcc tgctggacgg ctctctgttg ctgctgtctc tgggacatgc tcacctgacc      420
agaccagccc agccgtcctg tcctgccagc tctgctgcca cctctgacag gtgtgcctgc      480
ccccatctct tctgattgct gttaacaaat gactagcttt gcacagacac ctctaccttc      540
agcactatgg gattctagat taatgggggt tgctactgtt taattcagtg acttgatctt      600
tttaatgtcc aaaatccatt tcttattgat ctttaaagat gtgctaaatg actttttgg       660
ccaaaggctt agttgtgaaa aatataattt ttaaattata cattcaaggt agtggccaaa      720
tgtaacacat caatcatgga atgatttctc tgctaacagc cgcctgtatg tttcaataaa      780
tttgtccaaa gctcaaaaaa aaaaaaaaaa aaaaaaaaaa aaattggtgc ggccgc          836
```

<210> SEQ ID NO 186
<211> LENGTH: 495
<212> TYPE: DNA
<213> ORGANISM: Homo sapiens

<400> SEQUENCE: 186

```
gcggccgcat ctttttttt tttttttttt tttttttttt tttttttttt tttttttttt       60
ttcaataaat acatgctgat ttattacagg gataagatgg tttcttgggg gatagattca      120
agaggagttg agaatgtttt attcatttac aatgtcccct tcctggaagg gtggacagca      180
agatttagga caagctaaaa tcatccccta tttaaaaaaa aaaaaaaaaa aaaagtcacc      240
agcaagtagt cccgggtggg aggtgggagc agaataaaaa aaaatctgca atgattccta      300
attgttttc aatacagaag cttgggaagg ggtttctgcc agtttcatga ggaaggcaca       360
acttccaggt agtgttgggg aagggtatga ggtcctatgc aggctggcct cttatcccac      420
agatgccaag atgatgtcta ctggcagctc ctccaaactt ctggctgtcc ctcgtgccga      480
attcttggcc tcgag                                                       495
```

<210> SEQ ID NO 187
<211> LENGTH: 525
<212> TYPE: DNA
<213> ORGANISM: Homo sapiens
<220> FEATURE:
<221> NAME/KEY: misc_feature
<222> LOCATION: (1)...(525)
<223> OTHER INFORMATION: n = A,T,C or G

<400> SEQUENCE: 187

```
tccttttttt tttttttttt aggtgattac aacagctgat ttttatttt cttnttgatt        60
```

-continued

| | |
|---|---|
| ctcttctaca gttttcaaat tctctacaat gaacatgtac ttcttttaa tatcaaaaga | 120 |
| caaaagaatt ggtacgtaaa agaacatcc ttcccatctt caaggtcaag attgaacgct | 180 |
| gactcctgca ggaagtcttc caggattccc aggcaggaat gatggctccc tgtccctgta | 240 |
| gctccaggag ttcttgcttc acgcacgcct cacataccag actgaatgtt ggcaggagga | 300 |
| gtgaccaggt cggtcatctg tgtccctacc acctacaaca ggccagcaat ctaccgtgt | 360 |
| gtgtttgttg gacagaatta accatgatgg gcggccgagg gcgcctggag ctatttgggg | 420 |
| gcttggagag aacctcttag gagagtgtca ggccctaggc cagtgtcacc agaggaggtc | 480 |
| agtctcagtc cttggagtgg tgggatggaa accagacggg actgg | 525 |

<210> SEQ ID NO 188
<211> LENGTH: 2274
<212> TYPE: DNA
<213> ORGANISM: Homo sapiens

<400> SEQUENCE: 188

| | |
|---|---|
| gcggccgcac ttttttttt tttttttttt tttttttttt tttcacaacg cctatttatt | 60 |
| ccccacacgt cacgccctgc accccggtg ggcttggcac acacctcacc gccatgaacg | 120 |
| gctgcagggc cgcggtggcc cccgttccta ctgctaccta cgatacacgg tactgcgcct | 180 |
| acctcacaga cggccaggag ccagggagcc ccaggatgct ccgactgaca accctgctgc | 240 |
| tgggaccacg gcgccgtggg ctcgtctgcc acccccaggc ctcaggaacc cagacaggct | 300 |
| gcccgctgtc cggctctccg gctgctttcc tggtggctgt tttagggcca aggtgggtgg | 360 |
| cacctgaggt gtcccgtggc ctccacccag cacaggaggg gtaagcttcc ctgggggggcc | 420 |
| ccgggcccat gaaacatcca ggacagaagg acagcaggat gggacacaga cagaaacggc | 480 |
| ccagctgcct tccctgtgcc cggggctaag gcggccggga cagaaggtca tgatgtcgcc | 540 |
| cctggctctc agtcgcgagg accagaaaat gagggtggga ggaggggaaa catgtctgtc | 600 |
| aacatgccca actggagaaa agtcacagaa actggtccta tgcacccagg acggctcctg | 660 |
| agccacggag gcgtggggtg accgcagccg tctcttaggt gtctgccact aaagagttcc | 720 |
| tcatgcaaac acacatggcc cgcggtgccc aggccgcagc tggcagtgag ctcttccgag | 780 |
| caggcacagg gccggggtgg ccggggaggtc gactcggaaa gaggcttctc acagacggga | 840 |
| gagttcctgc agacagacca cgggatgggg ggcgggggct gtaaaaggct ttggaagcca | 900 |
| cacgatccgc cacacggctg aacgtgaaac ctgccacttc tctgagagcg gcccgggagc | 960 |
| accccaggat tctagaaaac actcaagtga ccgagctttc tggggggctgg aagggaggtc | 1020 |
| gctgctggtc tgtgctcagc ttgctggctc tcgtttcaag aagggtctgg gggctgtaag | 1080 |
| ggagttacaa aaagggagtg gaggagggca gagataaaag gggaaaatcc atcttgacat | 1140 |
| gcaggtccga ggtctctctc ttcccctctc tcaggcagtc caacaggagg aagtggcaga | 1200 |
| caaccagaag gcttccttcg ggtcggccag ggaaggacgc ggtcacaccg ggagcaggca | 1260 |
| gcgtcactcc tgctggtcgt cgttgctggc gctgggcgtc cgactccgga tctggctcct | 1320 |
| gagctgctct atcaactctg ggttctgctg ctgcatctgc tgggcaaact gctggcccgc | 1380 |
| ctggatgagg ctggccaggt cgttctgcga ggggctggtg ccgggagttc caagggggtt | 1440 |
| gttgccaccc gaaatcatgc cggacatgag ctgctgaatc tggggattgt tcattaggtt | 1500 |
| cgaagccatg ctcatgaagc cagggttgtt cagcaggccg gcgatgtcga agctgcccac | 1560 |
| gcctcccgtg gggctggggg cctccgcag cttcagctcc gctatcttga ggttggactt | 1620 |
| gtatgtctcg ttgtcggggt ccagctccag cgccttcttg tagtaagcca cggcctccac | 1680 |

```
gtgcttgttg aggctggaga gcgccaggcc catcctgccg taggccttgc tgtaggccgg      1740
gtcaatgcag atggcccgct cacagtcctg caccgcgcct gcgtagttgc cgagtttgct      1800
gtaggctgcg gctctgttgc agaaatagac ggcgttggct gggttgagct cgatggcttt      1860
tccgtagaaa tgcacggcag cttcaaagtt ttccactttc atctgctcgt ttccttcggt      1920
tttgaggcgc tctgcctctg ctgagtcctc ctcggaaggc ggggttcgcg ctgggctcct      1980
caggtcctgc ggcatctcct tgcccgtggc agccgcttca aatatctccg gcagagtctg      2040
agggagcgca aggtcactgt cttctaccgt caccccaaac gcagtctcca ggcactggat      2100
ggcgacttcc aagctctcct gagcatcgga cgagaggccc ccgtgccgga gctggtcatg      2160
caggaactgg atgatggcgt aggccaggcg cttcttgttg tccatcttga gcccagaaga      2220
ggtgatacct ctcaggcgac cgatccccga cccaccgacc ctcgtgccga attc            2274
```

<210> SEQ ID NO 189
<211> LENGTH: 2373
<212> TYPE: DNA
<213> ORGANISM: Homo sapiens

<400> SEQUENCE: 189

```
gcacgagcgg ttctgagcat tagtttgaga actcgttccc gaatgtgctt tcctccctct        60
cccctgccca cctcaagttt aataaataag gttgtacttt tcttactata aaataaatgt       120
ctgtaactgc tgtgcactgc tgtaaacttg ttagagaaaa aaataacctg catgtgggct       180
cctcagttat tgagttttg tgatcctatc tcagtctggg ggggaacatt ctcaagaggt       240
gaaatacaga aagcctttt ttcttgatct ttcccgaga ttcaaatctc cgattcccat        300
ttgggggcaa gtttttttct tcaccttcaa tatgagaatt cagcgaactt gaaagaaaaa       360
tcatctgtga gttccttcag gttctcactc atagtcatga tccttcagag ggaatatgca       420
ctggcgagtt taaagtaagg gctatgatat tgatggtcc caaagtacgg cagctgcaaa       480
aagtagtgga aggaaattgt ctacgtgtct tggaaaaatt agttaggaat ttggatgggt       540
aaaaggtacc cttgccttac tccatcttat tttcttagcc ccctttgagt gttttaactg       600
gtttcatgtc ctagtaggaa gtgcattctc catcctcatc ctctgccctc ccaggaagtc       660
agtgattgtc ttttgggct tcccctccaa aggaccttct gcagtggaag tgccacatcc       720
agttcttttc ttttgttgct gctgtgttta gataattgaa gagatctttg tgccacacag       780
gatttttttt ttttttaaga aaacctata gatgaaaaat tactaatgaa actgtgtgta       840
cgtgtctgtg cgtgcaacat aaaaatacag tagcacctaa ggagcttgaa tcttggttcc       900
tgtaaaattt caaattgatg tggtattaat aaaaaaaaaa aaaaaaaact cgctcgtgcc       960
gaattcggca cgaggaacaa cctgtgtgca tgcttttga gtatattaat caggggatc      1020 tccatgagtt cctcatcatg agatccccac actctgatgt tggctgcagc agtgatgaag      1080
atgggactgt gaaatccagc ctggaccacg gagattttct gcacattgca attcagattg      1140
cagctggcat ggaatacctg tctagtcact tctttgtcca caaggacctt gcagctcgca      1200
atattttaat cggagagcaa cttcatgtaa agatttcaga cttggggctt ccagagaaa      1260 tttactccgc tgattactac agggtccaga gtaagtcctt gctgcccatt cgctggatgc      1320
cccctgaagc catcatgtat ggcaaattct cttctgattc agatatctgg tcctttgggg      1380
ttgtcttgtg ggagattttc agttttggac tccagccata ttatggattc agtaaccagg      1440
aagtgattga gatggtgaga aaacggcagc tcttaccatg ctctgaagac tgcccaccca      1500
```

-continued

| | |
|---|---|
| gaatgtacag cctcatgaca gagtgctgga atgagattcc ttctaggaga ccaagattta | 1560 |
| aagatattca cgtccggctt cggtcctggg agggactctc aagtcacaca agctctacta | 1620 |
| ctccttcagg gggaaatgcc accacacaga caacctccct cagtgccagc ccagtgagta | 1680 |
| atctcagtaa ccccagatat cctaattaca tgttcccgag ccagggtatt acaccacagg | 1740 |
| gccagattgc tggtttcatt ggcccgccaa tacctcagaa ccagcgattc attcccatca | 1800 |
| atggataccc aatacctcct ggatatgcag cgtttccagc tgcccactac cagccaacag | 1860 |
| gtcctcccag agtgattcag cactgccacc tcccaagagt cggtcccca agcagtgcca | 1920 |
| gtgggtcgac tagcactggc catgtgacta gcttgccctc atcaggatcc aatcaggaag | 1980 |
| caaatattcc tttactacca cacatgtcaa ttccaaatca tcctggtgga atgggtatca | 2040 |
| ccgtttttgg caacaaatct caaaaaccct acaaaattga ctcaaagcaa gcatctttac | 2100 |
| taggagacgc caatattcat ggacacaccg aatctatgat ttctgcagaa ctgtaaaatg | 2160 |
| cacaactttt gtaaatgtgg tatacaggac aaactagacg gccgtagaaa agatttatat | 2220 |
| tcaaatgttt ttattaaagt aaggttctca tttagcagac atcgcaacaa gtaccttctg | 2280 |
| tgaagtttca ctgtgtctta ccaagcagga cagacactcg gccagaaaaa aaaaaaaaaa | 2340 |
| aaaaaactcg aggggggcc cgtacccgat cgc | 2373 |

<210> SEQ ID NO 190
<211> LENGTH: 566
<212> TYPE: DNA
<213> ORGANISM: Homo sapiens
<220> FEATURE:
<221> NAME/KEY: misc_feature
<222> LOCATION: (1)...(566)
<223> OTHER INFORMATION: n = A,T,C or G

<400> SEQUENCE: 190

| | |
|---|---|
| agggantaag cttgcggccg cttaattaaa naanatttag cgtaaaatta cacttaaaca | 60 |
| ttatcagctg ctgctgggaa aaaatggaca aattgcccag gcagccacat tagaagaaga | 120 |
| aagtcattng aatacagnta tatacttatt tttattgaga cacatcttgc tgngtcaccc | 180 |
| agggttttgc tctgttgcca cagcttactg cagccgtgac ccaggctcaa gtgatccctc | 240 |
| ccacctcagg ccctctccc cgaccagtag ccgagactac aggcaggcac agactggcac | 300 |
| caccacactc ggctaatttt tttttttga ggcagggtct cactatgttg tccaggctgg | 360 |
| tcttgaactc ctgagctcaa gtgatcctct naccttggct tccaaagtgc tgggattaca | 420 |
| gacaagtcat ggcanctggc tgagtacagt tattcancat aagcataaca aatacagaat | 480 |
| ggcagcccag ttcctttgnt aatgaaatng taagggggtgt actagggcaa gctggccctg | 540 |
| attatgtcac atgagtttgg tttaga | 566 |

<210> SEQ ID NO 191
<211> LENGTH: 775
<212> TYPE: DNA
<213> ORGANISM: Homo sapiens

<400> SEQUENCE: 191

| | |
|---|---|
| gaattcggca cgaggcagga actccaatgt atcttgtgat ttttccagaa ggtacaaggt | 60 |
| ataatccaga gcaaacaaaa gtcctttcag ctagtcaggc atttgctgcc caacgtggcc | 120 |
| ttgcagtatt aaaacatgtg ctaacaccac gaataaaggc aactcacgtt gcttttgatt | 180 |
| gcatgaagaa ttatttagat gcaatttatg atgttacggg ggtttatgaa gggaaagacg | 240 |
| atggagggca gcgaagagag tcaccgacca tgacggaatt tctctgcaaa gaatgtccaa | 300 |

-continued

```
aaattcatat tcacattgat cgtatcgaca aaaaagatgt cccagaagaa caagaacata      360
tgagaagatg gctgcatgaa cgtttcgaaa tcaaagataa gatgcttata gaattttatg      420
agtcaccaga tccagaaaga agaaaaagat ttcctgggaa aagtgttaat tccaaattaa      480
gtatcaagaa gactttacca tcaatgttga tcttaagtgg tttgactgca ggcatgctta      540
tgaccgatgc tggaaggaag ctgtatgtga acacctggat atatggaacc ctacttggct      600
gcctgtgggt tactattaaa gcatagacaa gtagctgtct ccagacagtg ggatgtgcta      660
cattgtctat ttttggcggc tgcacatgac atcaaattgt ttcctgaatt tattaaggag      720
tgtaaataaa gccttgttga ttgaaaaaaa aaaaaaaaaa aaaaaaggcg gccgc           775
```